United States Patent
Yu

(10) Patent No.: US 11,186,563 B2
(45) Date of Patent: Nov. 30, 2021

(54) PD(II)-CATALYZED ENANTIOSELECTIVE β-METHYLENE C(SP³)—H BOND ACTIVATION

(71) Applicant: The Scripps Research Institute, La Jolla, CA (US)

(72) Inventor: Jin-Quan Yu, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 212 days.

(21) Appl. No.: 16/086,535

(22) PCT Filed: Mar. 20, 2017

(86) PCT No.: PCT/US2017/023229
§ 371 (c)(1),
(2) Date: Sep. 19, 2018

(87) PCT Pub. No.: WO2017/165304
PCT Pub. Date: Sep. 28, 2017

(65) Prior Publication Data
US 2019/0315710 A1 Oct. 17, 2019

Related U.S. Application Data

(60) Provisional application No. 62/447,217, filed on Jan. 17, 2017, provisional application No. 62/311,039, filed on Mar. 21, 2016.

(51) Int. Cl.
| | | |
|---|---|---|
| *C07B 53/00* | (2006.01) | |
| *C07D 401/06* | (2006.01) | |
| *C07D 209/48* | (2006.01) | |
| *C07D 213/06* | (2006.01) | |
| *C07D 215/12* | (2006.01) | |
| *C07D 263/10* | (2006.01) | |
| *C07D 413/06* | (2006.01) | |
| *C07D 491/048* | (2006.01) | |
| *B01J 31/18* | (2006.01) | |

(52) U.S. Cl.
CPC .......... *C07D 401/06* (2013.01); *B01J 31/181* (2013.01); *C07B 53/00* (2013.01); *C07D 209/48* (2013.01); *C07D 213/06* (2013.01); *C07D 215/12* (2013.01); *C07D 263/10* (2013.01); *C07D 413/06* (2013.01); *C07D 491/048* (2013.01); *B01J 2531/004* (2013.01); *B01J 2531/824* (2013.01); *C07B 2200/07* (2013.01)

(58) Field of Classification Search
CPC .. C07D 401/06; C07D 413/06; C07D 263/10; C07D 215/12; C07D 209/48; C07D 491/048; C07D 213/06; C07B 53/00; C07B 2200/07; B01J 31/181; B01J 2531/824; B01J 2531/004
See application file for complete search history.

(56) References Cited

PUBLICATIONS

WO 2017/165304 Search Report.
WO 2017/165304 Written Opinion.
Gao et al., *Angew. Chem. Int. Ed.* 2015, 54:11956-11960.
Zhang et al., *Org. Biomol. Chem.*, 2016, 14, 5511-5515.
Zhang et al., *Org. Biomol. Chem.*, 2016, 14, 5511-5515, Supplemental Information.
Engle et al., *J Org Chem*, Sep. 20, 2013;78(18):8927-8955.
He et al., *Science*, Mar. 14, 2014 ;(343):1216-1220.
Chen et al., *Science*, Sep. 2, 2016;(353):1023-1027.
Wu et al., *Science*, Feb. 3, 2017;(355):499-503.
Xu et al., *Sci China Chem*, 2017, 60:165-166 (published online Dec. 26, 2016).

*Primary Examiner* — John Mabry
(74) *Attorney, Agent, or Firm* — Husch Blackwell LLP

(57) ABSTRACT

Chiral acetyl-protected aminoethyl quinoline (APAQ), pyridine and imazoline ligands are disclosed that enable Pd (II)-catalyzed enantioselective arylation or heteroarylation of ubiquitous prochiral β-methylene C—H bonds of aliphatic amides offers an alternative disconnection for constructing β-chiral centers. Systematic tuning of the ligand structure reveals that a six-membered instead of a five-membered chelation of these types of ligands with the Pd(II) is important for accelerating the C(sp³)-H activation thereby achieving enantioselectivity for quinoline and pyridine ligands.

35 Claims, No Drawings

PD(II)-CATALYZED ENANTIOSELECTIVE β-METHYLENE C(SP³)—H BOND ACTIVATION

CROSS-REFERENCE TO RELATED APPLICATION

This application claims priority of provisional application Ser. No. 62/311,039 filed on Mar. 21, 2016, and provisional application Ser. No. 62/447,217 filed on Jan. 17, 2017, both of whose disclosures are incorporated herein by reference.

STATEMENT OF GOVERNMENT LICENSE RIGHTS

This invention was made with government support under grant numbers GM102265 and GM084019 awarded by the National Institutes of Health. The government has certain rights in the invention.

TECHNICAL FIELD

The present invention relates to a method for the preparation of β-arylated and β-heteroarylated carboxylic acid derivatives, and more particularly to a method for the Pd(II)-catalyzed insertion of an aryl or heteroaryl substituent at the β-carbon of a protected carboxylic acid substrate in a high yield and with high diastereoselectivity.

BACKGROUND ART

Enantioselective functionalization of prochiral C—H bonds can potentially lead to a broad range of asymmetric reactions for preparing chiral compounds. Despite extensive efforts, the scope and efficiency of enantioselective C(sp³)-H activation reactions are far from being adequate for broad applications in asymmetric synthesis [Giri et al., *Chem. Soc. Rev.* 38, 3242-3272 (2009)]. Enantioselective carbene and nitrene insertions into C(sp³)-H bonds have been demonstrated in both diastereoselective and enantioselective fashion [Doyle et al., *Chem. Rev.* 110, 704-724 (2010); Reddy et al., *Org. Lett.* 8, 5013-5016 (2006); Liang et al., *Angew. Chem. Int. Ed.* 45, 4641-4644 (2006); Zalatan et al., *J. Am. Chem. Soc.* 130, 9220-9221 (2008); and Milczek et al., *Angew. Chem. Int. Ed.* 47, 6825-6828 (2008)].

However, asymmetric C(sp³)-H activation reactions via metal insertion are largely limited to the desymmetrization of C—H bonds located on two different carbon centers. For example, desymmetrizations of cyclopropyl and cyclobutyl C—H bonds have been achieved with Pd(II) catalysts and chiral mono-protected amino acid ligands [Shi et al., *Angew. Chem. Int. Ed.* 47, 4882-4886 (2008); Wasa et al., *J. Am. Chem. Soc.* 133, 19598-19601 (2011); Xiao et al., *J. Am. Chem. Soc.* 136, 8138-8142 (2014); and Chan et al., *J. Am. Chem. Soc.* 137, 2042-2046 (2015)]. Desymmetrization of prochiral C—H bonds has also been achieved through a Pd(0)-catalyzed intramolecular arylation as demonstrated in a series of pioneering studies [Nakanishi et al., *Angew. Chem. Int. Ed.* 50, 7438-7441 (2011); Anas et al., *Chem. Comm.* 47, 11483-11485 (2011); Martin et al., *Chem. Eur. J.* 18, 4480-4484 (2012); and Saget et al., *Angew. Chem. Inc. Ed.* 51, 2238-2242 (2012)] (Scheme 1, below).

Scheme 1
Desymmetrization of prochiral C(sp³)—H bonds on the two different carbon centers

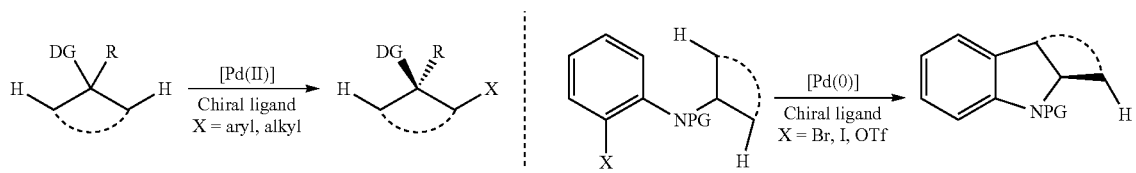

In Scheme 1, and in Schemes 2, and 3 hereinafter: DG=directing group; PG=protecting group; OTf=trifluoromethanesulfonate; Ar=aryl group; Ac=acetyl group; Et=ethyl group; and Bu=butyl group.

However, an efficient chiral metal catalyst capable of enantioselective insertion into ubiquitous methylene C—H bonds residing on the same carbon center has not been developed thus far. An effort to achieve such a process using a bidentate 8-aminoquinoline directing group and chiral phosphoric amide has afforded varied enantiomeric ratios (er) (ranging from 74:26 to 91:9) with benzyl C—H bonds and poor er (63:37) with alkyl C—H bonds [Yan et al., *Org. Lett.* 17, 2458-2461 (2015)]. Recently, a transient chiral directing group has also been shown to perform enantioselective C—H arylation of benzylic C—H bonds [Zhang et al., *Science* 351, 252-256 (2016)].

Although solutions for achieving site selectivity with each C—H bond in a given molecule remain elusive, selective activation of a single C—H bond at a strategic site with a particular distal relationship to an existing functional group could provide a broadly useful synthetic disconnection. When considering retrosynthetic disconnections for the asymmetric synthesis of β-functionalized chiral carboxylic acids or amides, one immediately considers α,β-unsaturated esters or amides as building blocks which can be transformed to the desired products in the forward sense using state of the art conjugate addition reactions. Notably, Rh(I)-catalyzed asymmetric conjugate addition of α,β-unsaturated ketones with aryl boronic acids has afforded an elegant method for the preparation of chiral β-arylated compounds [Berthon et al., "Rhodium- and Palladium-Catalyzed Asymmetric Conjugate Additions." In *Catalytic Asymmetric Conjugate Reactions* A. Cordova, Eds. (Wiley, 2010), pp. 1-67; and Paquin et al., *J. Am. Chem. Soc.* 127, 10850-10851 (2005). It was therefore envisioned that enantioselective arylation of methylene C—H bonds at the n-position of amides through Pd(II) insertion could provide an alternative disconnection to these highly valuable synthons starting from saturated aliphatic acids (Scheme 2, below).

Scheme 2

Two synthetic disconnections

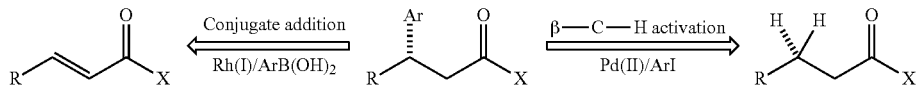

In early efforts, the inventor and coworkers adopted a chiral auxiliary approach to gain insight into stereoselective Pd insertion into β-C(sp³)-H bonds [Giri et al., *Angew. Chem. Int. Ed.* 44, 2112-2115 (2005)]. However, development of an enantioselective version of these diastereoselective β-C—H iodination and acetoxylation reactions has not been successful due to the lack of an appropriate ligand that can match the strongly coordinating oxazoline directing group [Engle et al., *J. Org. Chem.* 78, 8927-8955 (2013)]. Employing a weakly coordinating amide directing group in combination with chiral mono-protected amino acid ligands (MPAA) has led to desymmetrization of methyl, cyclopropyl and cyclobutyl C—H bonds (Scheme 1) at two different carbon centers [Wasa et al., *J. Am. Chem. Soc.* 133, 19598-19601 (2011); and Xiao et al., *J. Am. Chem. Soc.* 136, 8138-8142 (2014)]. Unfortunately, MPAA ligands have proven ineffective in promoting palladium insertion into β-methylene C—H bonds.

In another aspect, it is understood that nature constructs a myriad of natural products through the enantioselective β-C—H hydroxylation of isobutyric acid [Goodhue et al., *Biotechnol. Bioeng.* 13, 203-214 (1971); Hasegawa et al., *J. Ferment. Technol.* 59, 203-208 (1981)]; further, this process has been adapted for the industrial preparation of the Roche ester, which has served as an invaluable source of α-center chirality in the synthesis of complex molecules [Bode et al., *Angew. Chem. Int. Ed.* 40, 2082-2085 (2001); Paterson et al., *Angew. Chem. Int. Ed.* 43, 4629-4633 (2004); Lawhorn et al., *J. Am. Chem. Soc.* 128, 16720-16732 (2006); Feng et al., *J. Am. Chem. Soc.* 138, 5467-5478 (2016)].

Inspired by the bulk preparation of the Roche ester and the central role of α-chiral centers in retrosynthetic analysis (Corey et al. Eds., *Enantioselective Chemical Synthesis: Methods, Logic and Practice* (Direct Book Publishing, Dallas, Tex., 2010)), the inventor and co-workers have long sought to develop methodologies that desymmetrizes the isopropyl group of isobutyric acid derivatives through transition metal catalyzed C—H functionalization, in turn expanding the existing chiral pool.

Although enantioselective β-methylene C—H arylation has recently been realized [Chen et al., *Science* 353, 1023-1027 (2016)], and is discussed herein after, desymmetrization of isopropyl groups is a fundamentally different challenge. This challenge is reflected in an analysis of the steric environment associated with respective C—H insertion intermediates.

In methylene C—H activation, steric differentiation between a bulky alkyl group and a methylene C—H bond is required, whereas in the desymmetrization of isopropyl moieties differentiation between the alpha-hydrogen atom and relatively small alpha-methyl groups of an isopropyl group is required. This latter differentiation by a transition metal catalyst is challenging due to (A) the small difference in size of methyl vs. alpha C—H bonds and (B) when attempting to desymmetrize isopropyl groups, the prochiral center (the alpha carbon) is not directly interacting with the ligated transition metal catalyst, as is the case with methylene C—H activation. Consequently, the chiral center being generated is further away from the chiral center of the catalyst, making chiral recognition significantly more challenging.

To date, intermolecular desymmetrization of isopropyl groups has only been possible with substrates containing large α-substituents, which serves to amplify the chiral recognition in the transition state [Giri et al., *Angew. Chem. Int. Ed.* 44, 2112-2115 (2005); Giri et al., *Angew. Chem. Int. Ed.* 44, 7420-7424 (2005); Xiao et al., *J. Am. Chem. Soc.* 136, 8138-8142 (2014); He et al., *Angew. Chem. Int. Ed.* 54, 15840-15844 (2015)]. Related studies on desymmetrization of α-dialkyl groups via C—H activation from other laboratories have been limited to intramolecular Pd(0)-catalyzed C—H arylations [Nakanishi et al., *Angew. Chem. Int. Ed.* 50, 7438-7441 (2011); Anas et al., *Chem. Comm.* (*Camb.*) 47, 11483-11485 (2011); Martin et al., *Chem. Eur. J.* 18, 4480-4484 (2012); Saget et al., *Angew. Chem. Int. Ed.* 51, 2238-2242 (2012); Larionov et al., *Chem. Sci.* 4, 1995-2005 (2013); Holstein et al., *ACS Catal.* 5, 4300-4308 (2015); Murai et al., *J. Org. Chem.* 80, 5407-5414 (2015); Yang et al., *Chem. Sci.* advance article, DOI: 10.1039/C6SC04006C; Holstein et al., *Angew. Chem. Int. Ed.* 55, 2805-2809 (2016)].

An inspiring formal enantioselective intermolecular β-arylation of isobutyric esters has been demonstrated with moderate enantioselectivity (67:33-77:23 er) [Renaudat et al., *Angew. Chem. Int. Ed.* 49, 7261-7265 (2010)]. In this reaction, α-lithiation preceeds α-palladation followed by β-hydride elimination to give the corresponding olefin intermediate. Subsequent enantioselective carbopalladation of the double bond, rather than chiral recognition of geminal methyl groups, is responsible for chiral induction.

As discussed in detail hereinafter, chiral acetyl-protected aminoethyl quinoline (APAQ) ligands and similarly structured oxazolines and pyridines are prepared and are used that enable Pd(II)-catalyzed enantioselective arylation of β-methylene C—H bonds of aliphatic amides with an enantiometric ratio (er) reaching up to 96:4 and yield as high as 94% (Scheme 3, below). A wide range of simple aliphatic amides Scheme 3
Differentiating methylene C(sp³)—H bond
on the same carbon center

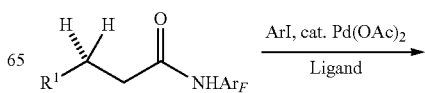

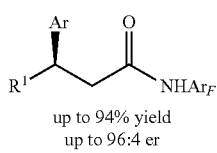

up to 94% yield
up to 96:4 er

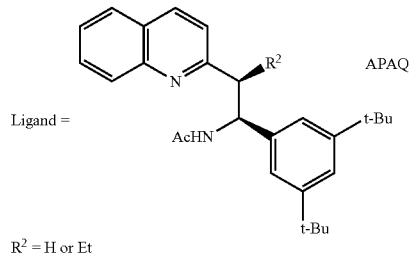

R¹: alkyl, aryl
Ar$_F$ = 4-(CF$_3$)C$_6$F$_4$

Ligand = APAQ

R² = H or Et as well as aryl iodide coupling partners are compatible with this reaction.

The design of these new chiral ligands merges the key structural motifs of previous quinoline and acetyl-protected amino acid ligands that are known to promote C(sp³)-H activation [Wasa et al., *J. Am. Chem. Soc.* 134, 18570-18572 (2012); and Chan et al., *Nat. Chem.* 6, 146-150 (2014)]. Strikingly, the adoption of a six-membered chelation of the APAQ ligand with the Pd(II) is important for accelerating the C(sp³)-H activation thereby controlling the stereoselectivity. In contrast, the use of acetyl-protected aminomethyl quinoline coordinating with Pd(II) via five-membered chelation is completely inactive in this reaction.

SUMMARY OF THE INVENTION

A chiral ligand compound (L) that corresponds in structure to Formula A is contemplated. In Formula A:

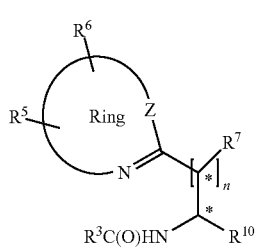

A

R³ is a C$_1$-C$_4$ alkyl group or a fluoro-substituted benzoyl group; the depicted cyclic moiety (Ring) on which R⁵ and R⁶ can be substituents is a cyclic ring structure containing one ring or two fused rings that each contains 5 or 6 atoms in the ring; Z is oxygen (O), or CH when part of a double bond; R⁵ and R⁶ are the same or different and are independently selected from the group consisting of a hydrido, halogen other than iodo, straight chain, branched chain and cyclic C$_1$-C$_7$ hydrocarbyl, C$_1$-C$_7$ hydrocarbyloxy, carboxy C$_1$-C$_6$ hydrocarbyl, trifluoromethyl, C$_1$-C$_6$ hydrocarboyl, nitro, C$_1$-C$_6$ hydrocarbylthiooxy, and a cyano group, or a benzyl group whose ring is substituted by 1 through 5 fluoro groups; R⁷ is a straight chain, branched chain or cyclic C$_1$-C$_7$ hydrocarbyl group, or a C$_1$-C$_7$ hydrocarbyloxy group; "n" is zero or one, such that when n is zero, the carbon atom bearing R⁷ and R⁷ itself are absent, and the depicted Ring is bonded directly to the carbon atom bearing the R³C(O)HN group; R¹⁰ is a straight chain, branched chain or cyclic C$_1$-C$_7$ hydrocarbyl group, or a C$_1$-C$_7$ hydrocarbyloxy group that is unsubstituted or when R¹⁰ is a cyclic C$_5$-C$_7$ hydrocarbyl group (preferably phenyl or benzyl), or a C$_5$-C$_7$ hydrocarbyloxy group substituted with one or two substituent groups R⁸ and R⁹ that are the same or different and are independently selected from the group consisting of straight chain, branched chain and cyclic C$_1$-C$_7$ hydrocarbyl group, and a C$_1$-C$_7$ hydrocarbyloxy group; and an atom with an adjacent asterisk is chiral.

In some preferred embodiments where n is one, and Z is CH, a compound of Formula A corresponds in structure to Formula A1 or A2

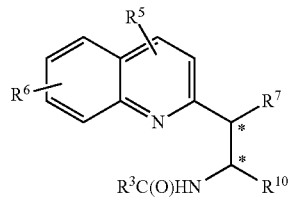

A-1

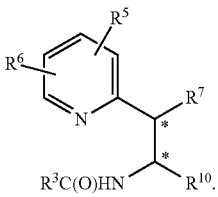

A-2

In other embodiments, where n is one, and Z is oxygen, a compound of Formula A corresponds in structure to Formula A3, or where n is zero, and Z is oxygen, such a compound corresponds in structure to Formula A4

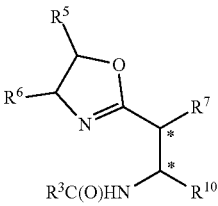

A-3

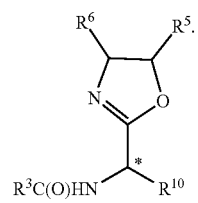

A-4

Compounds of Formula A-1 and Formula A-4 are particularly preferred.

In further additional independent preferences, R³C(O) is preferably acetyl. R⁷ is a straight chain C$_1$-C$_3$ hydrocarbyl group, or a C$_1$-C$_3$ hydrocarbyloxy group. When ring R is quinolinyl or pyridinyl, R¹⁰ is preferably a phenyl or a benzyl group whose ring structure can contain two substituent C$_1$-C$_5$ hydrocarbyl groups, R⁸ and R⁹, that are the same substituent, and are bonded a) in the 3- and 5-positions of the ring or b) in the 2- and 6-positions of the ring; $R^8$ and $R^9$ are both preferably t-butyl; and $R^7$ and $R^{10}$ phenyl ring are in a syn or an anti relationship.

A method for carrying out a Pd(II)-catalyzed chiral insertion of an aryl or heteroaryl substituent into a C—H bond at a β-carbon of a protected prochiral carboxylic acid substrate to provide an insertion product whose enantiomeric ratio (er) is greater for one enantiomer than the other (a chiral product) is also contemplated. That method comprises the steps of: a) heating a reaction mixture containing a solvent having dispersed or dissolved therein (i) a protected prochiral carboxylic acid substrate molecule of Formula I, (ii) an excess of an

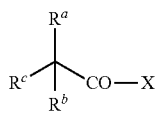
I aromatic or heteroaromatic iodide reactant relative to the substrate, (iii) a catalytic amount of a Pd(II) catalyst, (iv) a chiral acyl-protected ligand (L) of Formula A (above) present in an amount of about 5 to about 20 mole percent based on the amount of protected carboxylic acid substrate molecule of Formula I, and (v) an excess of silver compound oxidant relative to said protected carboxylic acid substrate at a temperature of about 70° to about 120° C. in a sealed pressure vessel. The reaction mixture is maintained for a time and at a temperature sufficient to carry out the insertion reaction and form an insertion product whose enantiomeric ratio (er) is greater for one enantiomer than the other.

In a molecule of Formula I i) $R^a$ is hydrogen (H; hydrido), a protected amino group (NPG), or a $C_1$-$C_6$ hydrocarbyl straight or branched chain substituent, and one or two of $R^b$ and $R^c$ is hydrido. Illustrative amino protecting groups (NPGs) are discussed hereinafter. When other than hydrido, a $R^b$ and $R^c$ group is a $C_1$-$C_{13}$ hydrocarbyl straight or branched chain or cyclic aliphatic group; or a (methyl)$C_6$-$C_{10}$ aromatic or heteroaromatic group containing up to three heteroatoms that can each be nitrogen, or can be two nitrogens and an oxygen. Illustrative substituents include (methyl)phenyl (benzyl), 1- or 2-(methylnaphthyl), 3-(methyl)pyridinyl, 2-(methyl)purinyl and the like. The ring of a (methyl)$C_6$-$C_{10}$ aromatic or heteroaromatic group is unsubstituted or substituted with up to three substituents that are independently selected from one or more of the group consisting of halogen (fluoro, chloro and bromo; i.e., other than iodo), $C_1$-$C_6$ hydrocarbyl, $C_1$-$C_6$ hydrocarbyloxy, carboxy $C_1$-$C_6$ hydrocarbyl, trifluoromethyl, $C_1$-$C_6$ hydrocarboyl, $C_1$-$C_6$ hydrocarbyl carboxylate, nitro, $C_1$-$C_6$ hydrocarbylthiooxy, cyano and protected amino.

An X of a molecule of Formula I is a $NHR^2$ group, in which $R^2$ is a perfluorinated p-tolyl group [4-($CF_3$)$C_6F_4$]], OH, or —O—$C_1$-$C_{12}$ hydrocarbyl group so that X is NH[4-($CF_3$)$C_6F_4$], NOH or NH—O—$C_1$-$C_{12}$, or more preferably a NH—O—$C_1$-$C_6$ hydrocarbyl group.

Preferred protected carboxylic acid substrate molecules of Formula I include those in which both $R^a$ are $R^b$ hydrido (hydrogen) so that a protected prochiral carboxylic acid substrate molecule of Formula I corresponds in structure to a compound of Formula Ia, below, in which $R^c$ and X

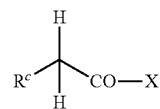
Ia are as defined previously.

In another embodiment, a protected prochiral carboxylic acid substrate molecule of Formula I corresponds in structure to a compound of Formula Ib, below, in which X, $R^b$ and $R^c$ are as previously defined, but $R^b$ and $R^c$ are preferably a $C_1$-$C_{13}$ hydrocarbyl straight or branched chain or cyclic aliphatic group, and more preferably the same $C_1$-$C_6$ aliphatic group.

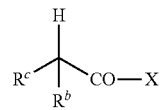
Ib

In yet another embodiment, a protected prochiral carboxylic acid substrate molecule of Formula I corresponds in structure to a compound of Formula Ic, below, in which X, $R^b$ and $R^c$ are as

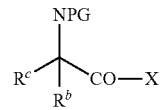
Ic previously defined, and $R^b$ and $R^c$ are preferably the same $C_1$-$C_6$ aliphatic group.

The aromatic or heteroaromatic iodide reactant is otherwise unsubstituted, or contains up to three substituents in addition to the iodo group. The additional substituents are independently selected from one or more of the group consisting of halogen other than iodo, $C_1$-$C_6$ hydrocarbyl, $C_1$-$C_6$ hydrocarbyloxy [—O-hydrocarbyl), trifluoromethyl], trifluoromethoxy, $C_1$-$C_6$ hydrocarboyl [—C(O)hydrocarbyl], $C_1$-$C_6$ hydrocarbyl carboxylate [—C(O)O-hydrocarbyl], hydrocarbylthiooxy, nitro, cyano, methylene dioxy, $C_2$-$C_6$ vicinyl dioxy alkyl such as a 3,4-(α,β-ethylenedioxy) group (Compound 2u, below) or 4,5-(γ,δ-hexylenedioxy), and a $C_1$-$C_6$ hydrocarbyl di-$C_1$-$C_6$ alkyl phosphonate group.

The before-discussed independent preferences for the ligand of Formula A are applicable to the use of that compound in a contemplated method.

The thereby produced insertion product whose enantiomeric ratio (er) is greater for one enantiomer than the other can be recovered by standard organic chemical means, or can be further reacted without recovery or purification. Recovery prior to further reaction is usually preferred.

The present invention has several benefits and advantages.

One benefit is that aromatic or heteroaromatic beta-insertion products can be prepared in protected carboxylic acid substrate molecules in high enantiomeric ratios, exceeding 90 percent, of some insertion products.

An advantage of the invention is that the yield of insertion product can also be relatively high, exceeding 80 percent for some products.

Another benefit of the invention is the chiral ligand that directs the stereospecificity of the insertion reaction.

Another advantage of the invention is that high enantiomeric ratios of insertion products of both enantiomers can be obtained by appropriate selection of the chiral ligand.

Yet another benefit of the invention is that the chiral ligand can often be recovered and reused.

Still further benefits and advantages will be apparent to the skilled worker from the description that follows.

Definitions

The following commonly used organic chemical abbreviations and symbols are sometimes used herein: *=chiral atom; PG=protecting group; min=minute(s); h=hour(s); rt=room temperature; Ph=phenyl, Ac=acetyl; Ms-methanesulfonyl; Ts=toluenesulfonyl; Tf=trifluoromethanesulfonyl; Me=methyl; MeO=methoxy; $Ar_F$=2,3,5,6-tetrafluoro-4-(trifluoromethyl); $Ar_FNH_2$=2,3,5,6-tetrafluoro-4-(trifluoromethyl)aniline;

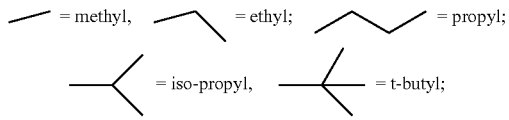

and the like as are well known. Additional organic chemical abbreviations include the following: MeOH-methanol; EtOH=ethanol; iPrOH=iso-propanol; THF=tetrahydrofuran; DME=dimethoxyethane; HMPA=hexamethylphosphoramide; $Et_3N$=triethylamine; HFIP=hexafluoro-2-propanol; $Ac_2O$=acetic anhydride; DCC=dicyclohexylcarbodiimide; TBAF=tetrabutylammonium fluoride; DEAD=diethyl azocarboxylate; EtOAc=ethyl acetate; DMAF=4-(dimethylamino)pyridine; Ac-Phe-OH=N— acetyl phenylalanine; M-CPBA=meta-chloropropoxybenzoic acid; n-BuLi=n-butyl lithium; Ac=acetyl; Bn=benzyl; Cbz=(benzyloxy)carbonyl; Boc-tert-butyloxycarbonyl; Fmoc=fluorenylmethyloxycarbonyl; and TBS=tert-butyl-dimethylsilyloxy.

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

The word "prochiral" is used herein to mean a molecule in which an achiral center can be converted to a chiral center in a single step. Thus, an achiral molecule is contemplated as is a molecule having one or more chiral centers as well as an achiral center, the latter of which can be converted to an additional chiral center in one step.

The words "ortho", "meta" and "para" are used in their usual manner to describe benzenoid compounds that are substituted "1-2", "1-3" and "1-4", respectively. Where an iodo group is present on an aromatic or heteroaromatic reactant, the compound and numbering system is usually based on the iodo substituent at the 1-position of a ring or ring system.

The word "hydrocarbyl" is used herein as a short hand term for a non-aromatic group that includes straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter.

Where a specific aliphatic hydrocarbyl substituent group is intended, that group is recited; i.e., $C_1$-$C_4$ alkyl, methyl or hexenyl. Exemplary hydrocarbyl groups contain a chain of 1 to about 7 carbon atoms, and preferably 1 to about 4 carbon atoms.

A particularly preferred hydrocarbyl group is an alkyl group. Consequently, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, iso-amyl, hexyl, octyl and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of alkynyl radicals include ethynyl, 2-propynyl, 3-propynyl, decynyl, 1-butynyl, 2-butynyl, 3-butynyl, and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, n-propoxy, isopropoxy, allyloxy, n-butoxy, iso-butoxy, sec-butoxy, tert-butoxy, cyclohexenyloxy groups and the like. On the other hand, a hydrocarbyl group containing a —C(O)O-functionality is referred to as a hydrocarboyl (acyl) group inasmuch as there is no ambiguity in using that suffix. Exemplary hydrocarboyl and hydrocarboyloxy groups include acyl and acyloxy groups, respectively, such as acetyl and acetoxy, acryloyl and acryloyloxy.

As a skilled worker will understand, a substituent that cannot exist such as a $C_1$ alkenyl group is not intended to be encompassed by the word "hydrocarbyl", although such substituents with two or more carbon atoms are intended.

A "carboxyl" substituent is a —C(O)OH group. A $C_1$-$C_6$ hydrocarbyl carboxylate is a $C_1$-$C_6$ hydrocarbyl ester of a carboxyl group [—C(=O)—O—$C_1$-$C_6$ hydrocarbyl].

The term "aryl", alone or in combination, means a phenyl or naphthyl or other aromatic radical. An aryl group can be carbocyclic, containing only carbon atoms in the ring(s) or heterocyclic as a heteroaryl group discussed hereinafter. A "heteroaryl" group is an aromatic heterocyclic ring substituent that preferably contains one, or two, up to three or four, atoms in the ring other than carbon. Those heteroatoms can be nitrogen, sulfur or oxygen. A heteroaryl group can contain a single 5- or 6-membered ring or a fused ring system having two 6-membered rings or a 5- and a 6-membered ring. Exemplary heteroaryl groups include 6-membered ring substituents such as pyridyl, pyrazyl, pyrimidinyl, and pyridazinyl; 5-membered ring substituents such as 1,3, 5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2, 5-, or 1,3,4-oxadiazolyl and isothiazolyl groups; 6-/5-membered fused ring substituents such as benzothiofuranyl, isobenzothiofuranyl, benzisoxazolyl, benzoxazolyl, purinyl and anthranilyl groups; and 6-/6-membered fused rings such as 1,2-, 1,4-, 2,3- and 2,1-benzopyronyl, quinolinyl, isoquinolinyl, cinnolinyl, quinazolinyl, and 1,4-benzoxazinyl groups.

The term "halogen" means fluorine, chlorine or bromine. The term perfluorohydrocarbyl means a hydrocarbyl group wherein each hydrogen is replaced by a fluorine atom. Examples of such perfluorohydrocarbyl groups, in addition to trifluoromethyl, which is preferred, are perfluorobutyl, perfluoroisopropyl, perfluorododecyl and perfluorodecyl.

The terms "amino-protecting group" and "amine-protecting group" as used herein refer to one or more selectively removable substituents on the amino group commonly employed to block or protect the amino functionality. Illustrative amine protecting groups are those used in solid phase peptide syntheses.

Examples of such amine-protecting groups include the formyl ("For") group, the trityl group ("Trt"), the phthalimido group ("Phth"), the trichloroacetyl group, the chloroacetyl, bromoacetyl, and iodoacetyl groups. Urethane blocking groups, such as t-butoxy-carbonyl ("Boc"), 2-(4-biphenylyl)propyl-(2)oxycarbonyl ("Bpoc"), 2-phenylpropyl(2)oxycarbonyl ("Poc"), 2-(4-xenyl)-isopropoxycarbonyl, 1,1-diphenyl-ethyl(1)oxycarbonyl, 1,1-diphenylpropyl(1)-oxycarbonyl, 2-(3,5-dimethoxyphenyl) propyl(2)oxycarbonyl ("Ddz"), 2-(p-5-toluyl)-propyl(2) oxycarbonyl, cyclopentanyl-oxycarbonyl, 1-methylcyclopentanyloxycarbonyl, cyclohexanyloxycarbonyl, 1-methylcyclohexanyl-oxycarbonyl, 2-methylcyclohexanyloxycarbonyl, 2-(4-toluylsulfonyl)ethoxycarbonyl, 2-(methyl-sulfonyl)-ethoxycarbonyl, 2-(triphenylphosphino)-ethoxy-carbonyl, 9-fluoroenylmethoxycarbonyl ("Fmoc"), 2-(trimethyl-silyl)ethoxycarbonyl, allyloxycarbonyl, 1-(trimethyl-silylmethyl)prop-1-enyloxycarbonyl, 5-benzisoxalyl-methoxycarbonyl, 4-acetoxybenzyloxycarbonyl, 2,2,2-trichloro-ethoxycarbonyl, 2-ethynyl(2) propoxy-carbonyl, cyclopropylmethoxycarbonyl, isobornyloxycarbonyl, 1-piperidyloxycarbornyl, benzyloxycarbonyl ("Z"), 4-phenylbenzyloxycarbonyl, 2-methylbenzyloxy-carbonyl, α-2,4,5,4-tetramethylbenzyloxycarbonyl ("Tmz"), 4-methoxybenzyloxycarbonyl, 4-fluorobenzyl-oxycarbonyl, 4-chlorobenzyloxycarbonyl, 3-chloro-benzyloxycarbonyl, 2-chlorobenzyloxycarbonyl, dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxy-carbonyl, and the like, the benzoylmethylsulfonyl group, dithiasuccinoyl ("Dts') group, the 2-(nitro)-phenylsulfenyl group ("Nps'), the 2- or 4-nitrophenylsulfonyl ("Nos") group, 4-toluenesulfonyl ("Ts"), the diphenylphosphine oxide group, and like amino-protecting groups.

The species of amine-protecting group employed is usually not critical so long as the derivatized amino group is stable to the conditions of the subsequent reactions and can be removed at the appropriate point without disrupting the remainder of the compound. A preferred amine-protecting group is a $C_1$-$C_5$ acyl group or a phthaloyl group.

Both the ligand and the Formula I reactant contain amido groups whose nitrogen atoms are protected from reaction during the insertion reaction, but are removable for later synthetic procedures if desired. Ligand amido protecting groups are preferably a $C_1$-$C_5$ acyl group or a di-, tri- or pentafluorobenzoyl group. The amido nitrogen atom of a reactant compound preferably has a previously discussed perfluorinated p-tolyl group [4-($CF_3$)$C_6F_4$; or $AR_F$ group], OH, or —O—$C_1$-$C_{12}$ hydrocarbyl group so that X is NH[4-($CF_3$)$C_6F_4$], NOH or NH—O—$C_1$-$C_{12}$, with NH-ARE and NH—$OCH_3$ being preferred X groups.

Further examples of amino-protecting groups embraced to by the above term are well known in organic synthesis and the peptide art and are described by, for example: T. W. Greene and P. G. M. Wuts, *Protective Groups in Organic Synthesis*, 2nd ed., John Wiley and Sons, New York. N.Y., Chapter 7, 1991; M. Bodanzsky, Principles of Peptide Synthesis, 1st and 2nd revised ed., Springer-Verlag, New York, N.Y., 1984 and 1993; and Stewart and Young, *Solid Phase Peptide Synthesis*, 2nd ed., Pierce Chemical Co, Rockford, Ill. 1984.

The related term "protected amino" or "protected amine" defines an amino group substituted with an amino-protecting group discussed above.

The terms "hydroxy-protecting group" and "hydroxyl-protecting group" refer to readily cleavable groups bonded to hydroxyl groups, such as the tetrahydropyranyl, 2-methoxyprop-2-yl, 1-ethoxyeth-1-yl, methoxymethyl, methylthiomethyl, β-methoxyethoxymethyl, t-butyl, t-amyl, trityl, 4-methoxytrityl, 4,4'-dimethoxytrityl, 4,4',4"-trimethoxytrityl, benzyl, allyl, trimethylsilyl ("TMS"), t-butyldiphenylsilyl ("TBDPS"), (t-butyl)dimethylsilyl ("TBS" or "TBDMS"), triisopropylsilyl ("TIPS"), and 2,2,2-trichloro-ethoxycarbonyl groups, and the like. Ester groups such as $C_1$-$C_6$-hydrocarboyl esters such as acetate ("OAc"), propionate and hexanoate are also useful, as is a benzyl ether ("Bn") group. The species of hydroxyl-protecting groups is also usually not critical so long as the derivatized (protected) hydroxyl group is stable to the conditions of subsequent reaction(s) and the protecting group can be removed at the appropriate point without disrupting the remainder of the compound.

Further examples of hydroxy-protecting groups are described by C. B. Reese and E Haslam, *Protective Groups in Organic Chemistry*, J. G. W. McOmie Ed., Plenum Press, New York, N.Y., Chapters 3 and 4, 1973, and T. W. Greene and P. G. M. Wuts, *Protective Groups in Organic Synthesis*, 2nd ed., John Wiley and Sons, New York, N.Y., Chapters 2 and 3, 1991.

DETAILED DESCRIPTION

In accordance with a contemplated method, a reaction mixture is provided that contains (i) a prochiral protected substrate molecule I (below),

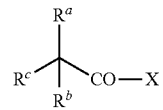

whose substituents are discussed below, (ii) an excess of an aromatic or heteroaromatic iodide reactant, (iii) a Pd(II) catalyst, (iv) a chiral protected ligand (L) such as a protected aminoethyl quinoline (APAQ) ligand that is preferred, a protected aminoethyl pyridine (APAP) or a chiral mono-protected aminomethyl oxazoline (MPAO), and (v) a silver compound oxidant dissolved or dispersed in a solvent at the temperature and pressure of use. The reaction mixture is sealed in an appropriate vessel and the contents heated to a temperature of about 80 to about 120° C. for a time period sufficient for the reaction to progress to a desired extent of formation of an arylated or heteroarylated product. That product can be recovered, or maintained in the reacted reaction mixture and further reacted or recovered at a later time.

After the reacted reaction mixture has cooled sufficiently for safety, a second amount of each of the same or different iodide reactant, catalyst, ligand and silver oxidant can be added, the vessel resealed and again heated and maintained at an elevated temperature as before to provide a second product that contains two of the same or different aryl or heteroaryl substituents. That second product is typically purified and recovered.

In a molecule of Formula I i) $R^a$ is hydrogen (H; hydrido), a protected amino group (NPG), or a $C_1$-$C_6$ hydrocarbyl straight or branched chain substituent, and one or two of $R^b$ and $R^c$ is hydrido. Illustrative amino protecting groups (NPGs) are discussed hereinafter. When other than hydrido, a $R^b$ and $R^c$ group is a $C_1$-$C_{13}$ hydrocarbyl straight or branched chain or cyclic aliphatic group; or a (methyl)$C_6$-$C_{10}$ aromatic or heteroaromatic group containing up to three heteroatoms that can each be nitrogen, or can be two nitrogens and an oxygen. Illustrative substituents include (methyl)phenyl (benzyl), 1- or 2-(methylnaphthyl), 3-(methyl)pyridinyl, 2-(methyl)purinyl and the like. The ring of a (methyl)$C_6$-$C_{10}$ aromatic or heteroaromatic group is unsubstituted or substituted with up to three substituents that are independently selected from one or more of the group consisting of halogen (fluoro, chloro and bromo; i.e., other than iodo), $C_1$-$C_6$ hydrocarbyl, $C_1$-$C_6$ hydrocarbyloxy, carboxy $C_1$-$C_6$ hydrocarbyl, trifluoromethyl, $C_1$-$C_6$ hydrocarboyl, $C_1$-$C_6$ hydrocarbyl carboxylate, nitro, $C_1$-$C_6$ hydrocarbylthiooxy, cyano and protected amino.

An X of a molecule of Formula I is a $NHR^2$ group, in which $R^2$ is a perfluorinated p-tolyl group [4-($CF_3$)$C_6F_4$], OH, or —O—$C_1$-$C_{12}$ hydrocarbyl group so that X is NH[4-($CF_3$)$C_6F_4$], NOH or NH—O—$C_1$-$C_{12}$, or more preferably a NH—O—$C_1$-$C_6$ hydrocarbyl group.

Preferred protected carboxylic acid substrate molecules of Formula I include those in which both $R^a$ are $R^b$ hydrido (hydrogen) so that a protected prochiral carboxylic acid substrate molecule of Formula I corresponds in structure to a compound of Formula Ia, below, in which $R^c$ and X

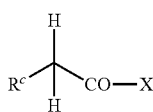

Ia are as defined previously.

In another embodiment, a protected prochiral carboxylic acid substrate molecule of Formula I corresponds in structure to a compound of Formula Ib, below, in which X, $R^b$ and $R^c$ are as previously defined, but $R^b$ and $R^c$ are preferably a $C_1$-$C_{13}$ hydrocarbyl straight or branched chain or cyclic aliphatic group, and more preferably the same $C_1$-$C_6$ aliphatic group.

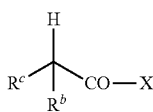

Ib

In yet another embodiment, a protected prochiral carboxylic acid substrate molecule of Formula I corresponds in structure to a compound of Formula Ic, below, in which X, $R^b$ and $R^c$ are as

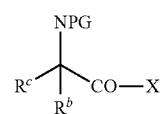

Ic previously defined, and $R^b$ and $R^c$ are preferably the same $C_1$-$C_6$ aliphatic group.

The aromatic or heteroaromatic iodide reactant is otherwise unsubstituted, or contains up to three substituents in addition to the iodo group. The additional substituents are independently selected from one or more of the group consisting of halogen other than iodo, $C_1$-$C_6$ hydrocarbyl, $C_1$-$C_6$ hydrocarbyloxy [—O-hydrocarbyl], trifluoromethyl, trifluoromethoxy, $C_1$-$C_6$ hydrocarboyl [—C(O)hydrocarbyl], $C_1$-$C_6$ hydrocarbyl carboxylate [—C(O)O-hydrocarbyl], hydrocarbylthiooxy, nitro, cyano, methylene dioxy, $C_2$-$C_6$ vicinyl dioxy alkyl such as a 3,4-(α,β-ethylenedioxy) group (Compound 2u, below) or 4,5-(γ,δ-hexylenedioxy), and a $C_1$-$C_6$ hydrocarbyl di-$C_1$-$C_6$ alkyl phosphonate group.

The before-discussed independent preferences for the ligand of Formula A are applicable to the use of that compound in a contemplated method.

The thereby produced insertion product whose enantiomeric ratio (er) is greater for one enantiomer than the other can be recovered by standard organic chemical means, or can be further reacted without recovery or purification. Recovery prior to further reaction is usually preferred.

In a substrate molecule of Formula I, i) R and $R^1$ can both be hydrogen (hydrido), and at least one of R and $R^1$ must be hydrido. When other than hydrido, a R or $R^1$ group is a $C_1$-$C_{12}$ hydrocarbyl straight or branched chain or cyclic aliphatic group; or a $C_6$-$C_{10}$ aromatic or heteroaromatic group containing up to three heteroatoms that can each be nitrogen, oxygen or sulfur. When other than hydrido, an R or $R^1$ group is unsubstituted or substituted with up to three substituents that are independently selected from one or more of the group consisting of halogen (fluoro, chloro and bromo; i.e., other than iodo), $C_1$-$C_6$ hydrocarbyl, $C_1$-$C_6$ hydrocarbyloxy, carboxy $C_1$-$C_6$ hydrocarbyl, trifluoromethyl, $C_1$-$C_6$ hydrocarboyl, $C_1$-$C_6$ hydrocarbyl carboxylate, nitro, $C_1$-$C_6$ hydrocarbylthiooxy, cyano and protected amino; and (ii) X is $NHR^2$ group, in which $R^2$ is a perfluorinated p-tolyl group that is usually abbreviated $Ar_F$ and has the chemical formula 4-($CF_3$)$C_6F_4$, so that X is NH[4-($CF_3$)$C_6F_4$]. When $R^2$ is OH, yields of the desired arylated or heteroarylated product are less satisfactory. Yields are good when $R^2$ is a NH—O—$C_1$-$C_{12}$ hydrocarbyl group, and particularly a NH—O—$C_1$-$C_6$ hydrocarbyl group, such as a methyl or t-butyl group.

A substrate molecule of Formula I is preferably present in the reaction mixture (pre-reaction) at about 0.05 to about 0.2 molar, and preferably at about 0.1 to about 0.15 molar.

Aromatic and heteroaromatic iodides are the co-reactants in a contemplated arylation or heteroarylation reaction. The iodide reactant is typically utilized in excess over the molar amount of the protected carboxylic acid substrate molecule (substrate) of Formula I.

A contemplated aromatic iodide (ArI) or heteroaromatic iodide (HetArI) is present in the reaction mixture in excess over the amount of the substrate of Formula I. That excess is typically about 2 to about 4 equivalents per equivalent of substrate of Formula I, and preferably about 2.5 to about 3 equivalents per substrate equivalent.

A contemplated aromatic or heteroaromatic iodide can be otherwise unsubstituted, or contain up to three substituents in addition to the iodo group. Contemplated substituents are independently selected from one or more of the group consisting of halogen (fluoro, chloro, and bromo), $C_1$-$C_6$ hydrocarbyl, preferably $C_1$-$C_6$ alkyl, $C_1$-$C_6$ hydrocarbyloxy [—O-hydrocarbyl], preferably $C_1$-$C_6$ alkoxy, trifluoromethyl, trifluoromethoxy, $C_1$-$C_6$ hydrocarboyl [—C(O)hydrocarbyl], preferably $C_1$-$C_6$ acyl, $C_1$-$C_6$ hydrocarbyl carboxylate [—C(O)O-hydrocarbyl], hydrocarbylthiooxy, nitro, cyano, methylene dioxy, $C_2$-$C_6$ vicinyl dioxy alkyl such as a 3,4-(α,β-ethylenedioxy) group (Compound 2u, below) or 4,5-(γ,δ-hexylenedioxy), and $C_1$-$C_6$ hydrocarbyl di-$C_1$-$C_6$ alkyl phosphonate.

Illustrative iodide-substituted aryl rings are phenyl and naphthyl that is optionally substituted as discussed above. An illustrative iodide-substituted heteroaryl ring compound includes an aromatic monocyclic or bicyclic heterocycle that contains one or more ring atoms that are other than carbon and is optionally substituted as defined above.

A "heteroaryl" group preferably contains one, two, three or four (up to four) ring atoms other than carbon (heteroatoms). Those heteroatoms can be nitrogen, sulfur or oxygen. A heteroaryl group can contain a single 5- or 6-membered ring or a fused ring system having two 6-membered rings or a combination of two 5- and 6-membered rings. Exemplary heteroaryl groups include 6-membered ring substituents such as pyridyl, pyrazyl, pyrimidinyl, and pyridazinyl; 5-membered ring substituents such as 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl groups; 6-/5-membered fused ring substituents such as benzothiofuranyl, isobenzothiofuranyl, benzisoxazolyl, benzoxazolyl, purinyl and anthranilyl groups; and 6-/6-membered fused rings such as 1,2-, 1,4-, 2,3- and 2,1-benzopyronyl, quinolinyl, isoquinolinyl, cinnolinyl, quinazolinyl, a $C_1$-$C_4$ alkyl 4-oxo-4H-chromenecarboxylate and 1,4-benzoxazinyl groups. When an iodide-substituted heteroaryl group contains a ring —NH— group, it is preferred that that nitrogen atom be present as a $C_1$-$C_8$ carboxamide, sulfonamide, or be otherwise substituted with a removable nitrogen protecting group, as have been discussed previously.

A contemplated chiral ligand, L, can have the general structural Formula A shown below.

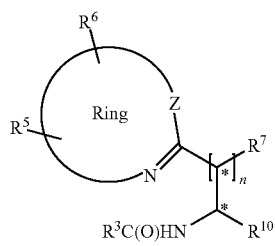

A

In a ligand of Formula A:

$R^3$ is a $C_1$-$C_4$ alkyl group, and preferably a $C_1$ group so that $R^3C(O)$ is an acetyl group, or a fluoro-substituted benzoyl group, preferably containing two fluoro substituents at the 2- and 6-positions of the benzoyl ring, although up to five fluoro substituents can be present on the benzoyl ring.

The depicted cyclic moiety (Ring) on which $R^5$ and $R^6$ can be substituents is a cyclic ring structure containing one ring or two fused rings that each contains 5 or 6 atoms in the ring; $R^5$ and $R^6$ are the same or different and are independently selected from the group consisting of hydrido (H), halogen (fluoro, chloro and bromo; i.e., other than iodo), straight chain, branched chain and cyclic $C_1$-$C_7$ hydrocarbyl, including phenyl and benzyl, $C_1$-$C_7$ hydrocarbyloxy, carboxy $C_1$-$C_6$ hydrocarbyl, trifluoromethyl, $C_1$-$C_6$ hydrocarboyl, nitro, $C_1$-$C_6$ hydrocarbylthiooxy, and cyano, or a benzyl group whose ring is substituted by 1 through five fluoro groups.

The depicted cyclic moiety (Ring) on which $R^5$ and $R^6$ can be substituents is a cyclic ring structure containing one ring or two fused rings that each contains 5 or 6 atoms in the ring. The Ring moiety can be aromatic, but need not be so. The ring member, X, is oxygen (O) or CH when part of a double bond.

$R^7$ is straight chain, branched chain and cyclic $C_1$-$C_7$ hydrocarbyl, including phenyl and benzyl, or $C_1$-$C_7$ hydrocarbyloxy.

"n" is zero or one, such that when n is zero, the carbon atom bearing $R^7$ and $R^7$ are absent, and the depicted Ring is bonded directly to the carbon atom bearing the $R^3C(O)HN$ group. It is preferred that n be zero when Z is oxygen, and n is preferably one when Z is CH or $CH_2$.

$R^{10}$ is a straight chain, branched chain or cyclic $C_1$-$C_7$ hydrocarbyl group, or a $C_1$-$C_7$ hydrocarbyloxy group that is unsubstituted or when $R^{10}$ is a cyclic $C_5$-$C_7$ hydrocarbyl group (preferably phenyl or benzyl), or a $C_5$-$C_7$ hydrocarbyloxy group substituted with one or two substituent groups $R^8$ and $R^9$ that are the same or different and are independently selected from the group consisting of straight chain, branched chain and cyclic $C_1$-$C_7$ hydrocarbyl group, and a $C_1$-$C_7$ hydrocarbyloxy group. In some embodiments, it is preferred that $R^{10}$ be a straight chain or branched chain $C_1$-$C_6$ hydrocarbyl group.

Atoms with adjacent asterisks are chiral.

A preferred ligand, L, where n is one and Z is CH is illustrated by a compound of Formula A-1 or

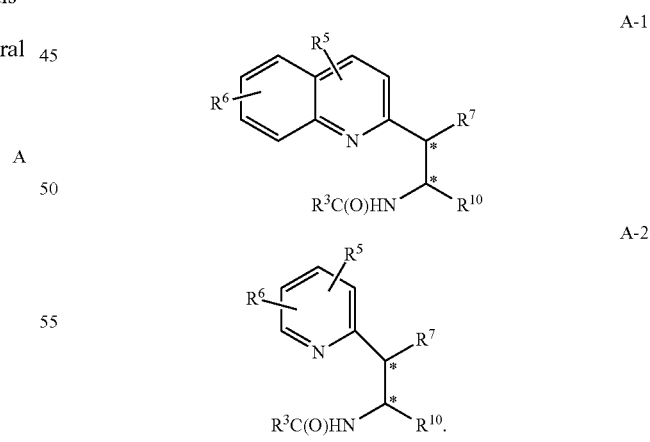

A-2. It is preferred that $R^5$ and $R^6$ be hydrido in a ligand of Formulas A-1 or A-2.

In other embodiments, where n is one, and Z is oxygen, a compound of Formula A corresponds in structure to Formula A-3, or where n is zero, and Z is oxygen, such a compound corresponds in structure to Formula A-4

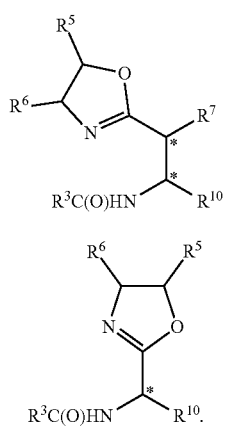

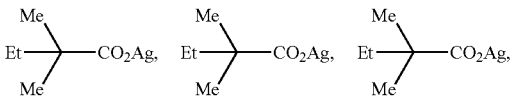

and Ag$_2$CO$_3$. Ag(OAc) is a preferred oxidant and is used illustratively herein.

A contemplated reaction is carried out with the ingredients dissolved or dispersed in a solvent and with agitation as can be provided at laboratory scale by the use of a magnetic stir bar. Additional means of agitation such as shaking can also be utilized. Exemplary solvents include $^t$BuCO$_2$Me, hexafluoroisopropanol (HFIP), $^t$BuCN, $^t$BuOMe, t-amyl OH, $^t$Bu(C=O)Me, n-hexane, C$_6$F$_6$, toluene, dichloromethane (DCM), and 1,2-dichloroethane (DCE). DCE, t-amylOH and HFIP are preferred among these materials.

A contemplated method is preferably carried out under anhydrous conditions. A bench-scale reaction using about 0.05 to about 0.10 mmoles of reactive substrate and appropriate amounts of other ingredients is typically carried out in about 0.5 to about 3 mL of solvent. Larger quantities can be readily scaled from those proportions.

A reaction mixture formed in carrying out a method of the invention is maintained at a temperature of about 30° to about 120° C., and preferably at a temperature of about 35° to about 110° C., for a time period sufficient to carry out the electrophilic insertion and form a reaction product. More preferably, that temperature is about 600 to about 100° C. Reaction times are typically about 15 to about 80 hours, with times of about 18-50 hours being usual.

A contemplated reaction is preferably carried out in a sealed reaction vessel, so the pressure under which the ingredients are maintained is mostly that created by the solvent used, with some contribution from the reactants, at the reaction temperature. Upon completion of the reaction, the desired product can be recovered by usual work-up procedures, or can be left in situ and reacted further as desired.

Results

Guided by an overarching goal of developing ligand-accelerated enantioselective C—H activation of weakly coordinating substrates, electron-deficient amide substrate 1 (below) was used and its effects of It is preferred that at least R$^6$, depicted as being adjacent to the ring nitrogen in Formulas A-3 and A-4 be a benzyl group that is preferably unsubstituted or substituted at ring positions 2- and 6- by fluoro groups. Compounds of Formula A-1 and Formula A-4 are particularly preferred.

The substituent groups R$^5$ through R$^{10}$, X and the asterisks for a compound of each of Formulas A1-A4 are as defined before for a compound of Formula A.

In further additional independent preferences, R$^3$C(O) is preferably acetyl. R$^7$ is a straight chain C$_1$-C$_3$ hydrocarbyl group, or a C$_1$-C$_3$ hydrocarbyloxy group. When Ring R is quinolinyl or pyridinyl, R$^{10}$ is preferably a phenyl or a benzyl group whose ring structure can contain two substituent C$_1$-C$_5$ hydrocarbyl groups, R$^8$ and R$^9$, that are the same substituent, and are bonded a) in the 3- and 5-positions of the ring or b) in the 2- and 6-positions of the ring; R$^8$ and R$^9$ are both preferably t-butyl; and R$^7$ and R$^{10}$ phenyl ring are in a syn or an anti relationship.

A contemplated ligand, L, is used in a reaction in an amount that is about 5 to about 20 mole percent. More preferably, the ligand, L, is present at about 8 to about 17 mole percent based on the amount of substrate. The iodo group-containing reactant is typically present in excess over the amount of prochiral substrate. That excess is preferably about 2 to about 3 equivalents to 1 equivalent of the prochiral substrate.

Useful Pd(II) catalysts are well known in the art. Exemplary catalysts include PdCl$_2$, Pd(TFA)$_2$, Pd(Piv)$_2$, [PdCl(C$_3$H$_5$)]$_2$, PdCl$_2$(PPh$_3$), Pd(PPh$_3$)$_4$, Pd$_2$(dba)$_3$, [PdCl(MeCN)$_2$], [Pd(OTf)$_2$·4MeCN], and [Pd(BF$_4$)$_2$·4MeCN]. Of these catalysts, Pd(TFA)$_2$, Pd(Piv)$_2$ and Pd(OAc)$_2$ are presently preferred. Palladium acetate [Pd(OAc)$_2$] is used illustratively herein. A contemplated catalyst is utilized in a catalytic amount. That amount is typically about 5 to about 20 mole percent based on the moles of reactive substrate, and more preferably about 10 to about 15 mole percent. The catalyst and ligand can be used at relative ratios of about 5:1 to about 1:5 catalyst to ligand. More usual amounts are about 1:2 to about 1:1 catalyst to ligand. For quinolone ligands, the catalyst and ligand are typically utilized at about the same mole percentage, e.g., within about 2 percent of each other (±2%), with the percentage based on the moles of substrate.

A contemplated method utilizes an excess, about 1.5 to about 5 equivalents (moles) of an oxidant per mole of reactive substrate, and preferably about 2 to about 4 equivalents of oxidant. A silver oxidant is typically used, although oxygen and other mild oxidants can also be used. Illustrative catalysts include Ag(Piv), Ag(OAc), Ag$_2$O, AqTFA, AgOTf,

1

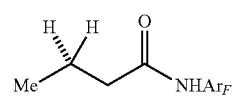

Ar$_F$ = 4-(CF$_3$)C$_6$F$_4$ chiral ligands evaluated on the extensively studied C—H arylation reaction [Zaitsev et al., *J. Am. Chem. Soc.* 127, 13154-13155 (2005); Reddy et al., *Org. Lett.* 8, 3391-3394 (2006); and Feng et al., *Angew. Chem. Int. Ed.* 49, 958-961 (2010)]. Following the previous finding that quinoline and pyridine ligands can accelerate C(sp$^3$)-H activation [He et al., *Angew. Chem. Int. Ed.* 55, 785-789 (2016)] (Table 1, below, L1-L3), a number of corresponding chiral ligands were prepared, including L4, L5 and their activity under standard reaction conditions was examined. Chiral carbon atoms are illustrated by an asterisk (*) adjacent to the chiral atom in the structural formulas that follow.

TABLE 1*

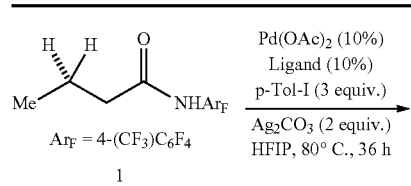

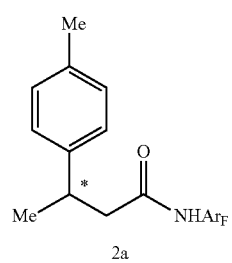
2a

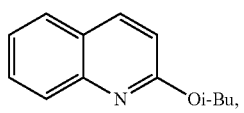
L1
58%

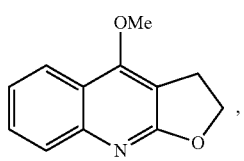
L2
60%

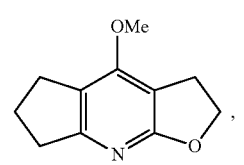
L3
62%

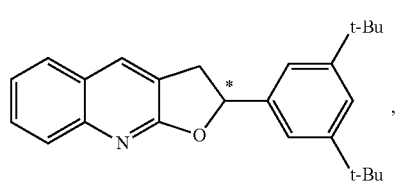
L4
53% yield
50:50 er

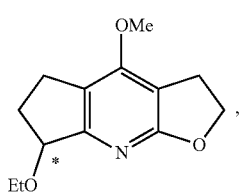
L5
28% yield
50:50 er

TABLE 1*-continued

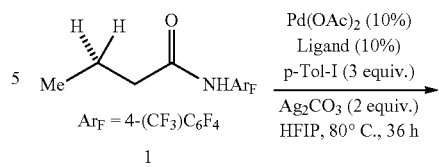

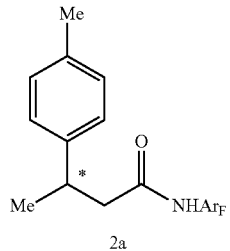
2a

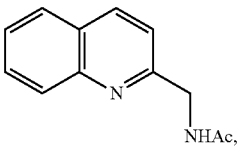
L6
N.R.

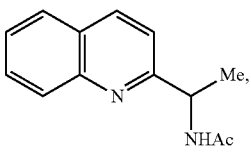
L7
N.R.

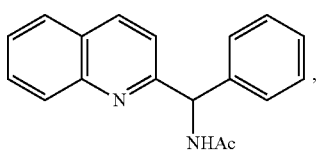
L8
N.R.

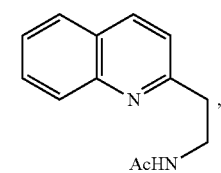
L9
46%

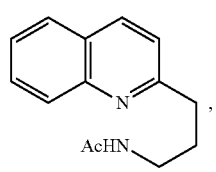
L10
58%

*The yields were determined $^1$H NMR analysis of the crude product using $CH_2Br_2$ as an internal standard. Enantiomeric ratios (er) were determined by chiral high-performance liquid chromatography. The absolute configurations of L13, L21, L35 and L40b, hereinafter, were determined by X-ray crystallography.
HFIP = hexafluoro-2-propanol;
Me = methyl group;
Pr = propyl group;
Bn = benzyl group;
Ph = phenyl group.

Unfortunately, these monodentate chiral ligands do not exert significant influence on the stereochemistry of the Pd insertion step.

Considering the effectiveness of bidentate mono-protected amino acid ligands (MPAA) in controlling the stereochemistry of Pd-catalyzed desymmetrization of prochiral cyclopropyl and cyclobutyl C—H bond on two different carbon centers, bidentate ligands were developed incorporating structural motifs from both quinoline and MPAA ligands. The crucial role of the NHAc moiety of MPAA ligands in the C—H cleavage step, identified by experimental and computational studies [Cheng et al., *J. Am. Chem. Soc.* 136, 894-897 (2014)] prompted development of acetyl-protected aminomethyl quinoline ligands that incorporate this coordinating moiety.

Disappointingly, such ligands L6-L8, resulted in a complete loss of reactivity (N.R.). It was reasoned that the five-membered bidentate chelation with Pd(II) could result in the formation of a stable, but inactive palladium complex tetra-coordinated with two ligands. As such, acetyl-protected aminoethyl quinoline (APAQ) and aminopropyl quinoline ligands were prepared that coordinate with Pd(II) via six- and seven-membered chelate structures, respectively (L9, L10), both of which should have significantly reduced binding constants compared to the corresponding five-membered chelate (L9, L10, Table 1). Remarkably, such subtle modification restored the reactivity with L9 and L10, thus offering a novel bidentate ligand scaffold for further development.

Although aminopropyl quinoline L10 is more reactive than aminoethyl quinoline L9, the latter scaffold was focused upon due to its synthetic accessibility. A series of chiral acetyl-protected aminoethyl quinoline ligands was prepared from 2-methylquinoline and optically pure sulfinyl imines using Ellman's highly efficient asymmetric imine addition reaction [Robak et al., *Chem. Rev.* 110, 3600-3740 (2010)].

It was initially found that ligand L11 containing an α-methyl group at the chiral center enhanced the reactivity significantly (75% yield), albeit giving poor enantioselectivity (47:53 er) See, Table 2. The α-methyl group was then replaced with various alkyl groups and only the sterically bulky isopropyl group was found to give significantly improved er reaching 27:73, but with diminished yield (L16).

TABLE 2

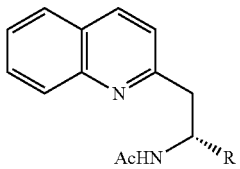

L11, R = Me, 75% yield, 47:53 er
L12, R = Et, 68% yield, 41:59 er
L13, R = n-Pr, 66% yield, 41:59 er
L14, R = i-Bu, 65% yield, 43:57 er
L15, R = Bn, 51% yield, 44:56 er
L16, R = i-Pr, 40% yield, 27:73 er
L17, R = Ph, 76% yield, 29:71 er Although further tuning of the alkyl substitution proved less promising, the result obtained with the α-phenyl substitution in L17 provided an encouraging lead for ligand optimization (76% yield, 29:71 er). With L17 in hand, various protecting groups were surveyed on the amino group (see Scheme 4, below). Replacing the methyl group in the acetyl protecting group by more hindered alkyls or phenyls decreased the yields significantly. Other types of protecting groups such as carbamates and sulfonyls are completely inactive.

Scheme 4*

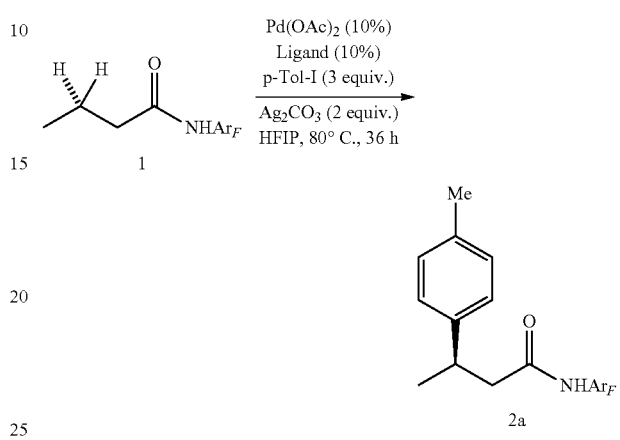

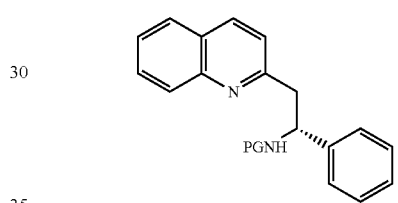

L17-1, PG = SOt-Bu, N.R.
L42, PG = Ms, N.R.
L43, PG = Ts, N.R.
L44, PG = CO$_2$Me, N.R.
L45, PG = CO$_2$Et, N.R.
L46, PG = CO$_2$i-Bu, N.R.
L47, PG = Boc, N.R.
L48, PG = Cbz, N.R.
L49, PG = Fmoc, N.R.

L50, PG = COCF$_3$, N.R.
L51, PG = COCH$_2$F, N.R.
L17, PG = COCH$_3$, 76% yield, 29:71 dr
L52, PG = COEt, 60% yield, 31:69 er
L53, PG = COi-Pr, 20% yield, 48:52 er
L54, PG = COi-Bu, 52% yield, 28:72 er
L55, PG = COt-Bu, trace
L56, PG = R = COPh, n.r.
L57, R = COBn, N.R.

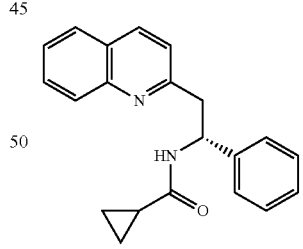

L58, N.R.

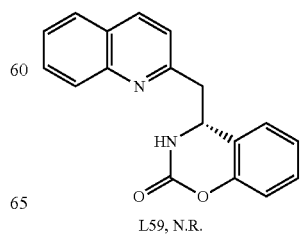

L59, N.R.

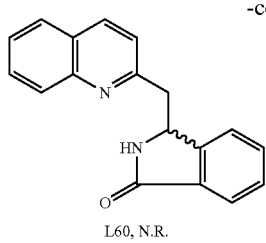

L60, N.R.

*The yields were determined by $^1$H NMR analysis of the crude product using $CH_2Br_2$ as an internal standard. Enantiomeric ratios (er) were determined by chiral high-performance liquid chromatography. N.R., no reaction.

A number of APAQ ligands (L18-33) with a range of steric and electronic variation on the α-phenyl ring. The steric effect was found to be predominant as indicated by the drastically improved yield and enantioselectivity obtained with ligand L32 bearing the sterically hindered 3,5-di-tert-butylphenyl group (85% yield, 19:81 er). See, Table 3, below.

TABLE 3

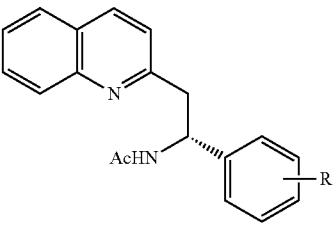

L18, R = 2-F, 85% yield, 25:75 er
L19, R = 2-Cl, 75% yield 27:73 er
L20, R = 2-Me, 62% yield, 28:72 er
L21, R = 2-CF$_3$, 85% yield, 29:71 er
L22, R = 3-Me, 45% yield, 30:70 er
L23, R = 3-t-Bu, 65% yield, 28:72 er
L24, R = 4-OMe, 75% Yield: 30:70 er
L25, R = 4-CF$_3$, 85% yield, 28:72 er
L26, R = 2,6-F, 80% yield, 31:69 er
L27, R = 2,6-Cl, 72% yield, 24:76 er
L28, R = 2,6-Me, 60% yield, 20:80 er
L29, R = 2,6-OMe, 62% yield, 20:80 er
L30, R = 3,5-Me, 88% yield, 30:70 er
L31, R = 3,5-CF$_3$, 60% yield, 25:75 er
L32, R = 3,5-t-Bu, 85% yield, 19:81 er
L33, R = 3,5-Ph, 82% yield, 26:74 er At this point of optimization, it was decided to introduce a second chiral center at the benzylic position, hoping to further improve the enantioselectivity. Because the origin of the stereoselectivity is believed to derive from creating a less hindered face on the square planar palladium complex [Shi et al., *Angew. Chem. Int. Ed.* 47, 4882-4886 (2008); Wasa et al., *J. Am. Chem. Soc.* 133, 19598-19601 (2011); Xiao et al., *J. Am. Chem. Soc.* 136, 8138-8142 (2014); and Chan et al., *J. Am. Chem. Soc.* 137, 2042-2046 (2015)], the variations of syn-APAQ ligands in which both substituents point upwards or downwards upon chelating with Pd(II) were focused upon.

The introduction of a methyl group at the benzylic position (L34) afforded a significant improvement in enantioselectivity (90:10 er), while maintaining the high yield. A slightly more bulky ethyl group (L35) further improved the enantioselectivity to 92.5:7.5 er. Further increasing steric hindrance at the benzylic position decreased both yield and enantioselectivity (L36-39). To obtain insight into the stereochemical model of this unprecedented enantioselective palladium insertion process, the anti-APAQ ligands (L40a, L41) were also tested. See, Table 4.

TABLE 4

Ligands

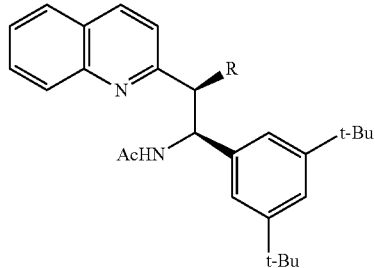

L34, R = Me, 86%, 90:10 er
L35, R = Et, 82%, 92.5:7.5 er
L36, R = n-Pr, 71%, 90.5:9.5 er
L37, R = i-Pr, 48%, 78:22 er
L38, R = OMe, 69%, 84:16 er
L39, R = Bn, 75%, 88:12 er

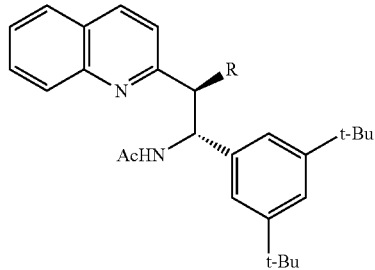

L40a, 13% yield, 31:69 er

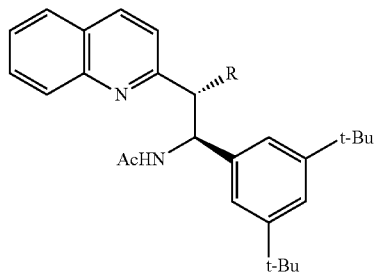

L41a, 15% yield, 68:32 er

Although both yield and enantioselectivity dropped significantly with these two anti-ligands, the reversal of chiral induction by altering the absolute configuration at the α-position suggests that the chiral center adjacent to the amino group dictates enantioselection (see Table 5).

TABLE 5*

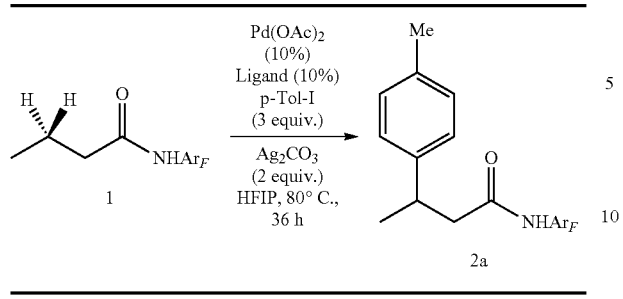
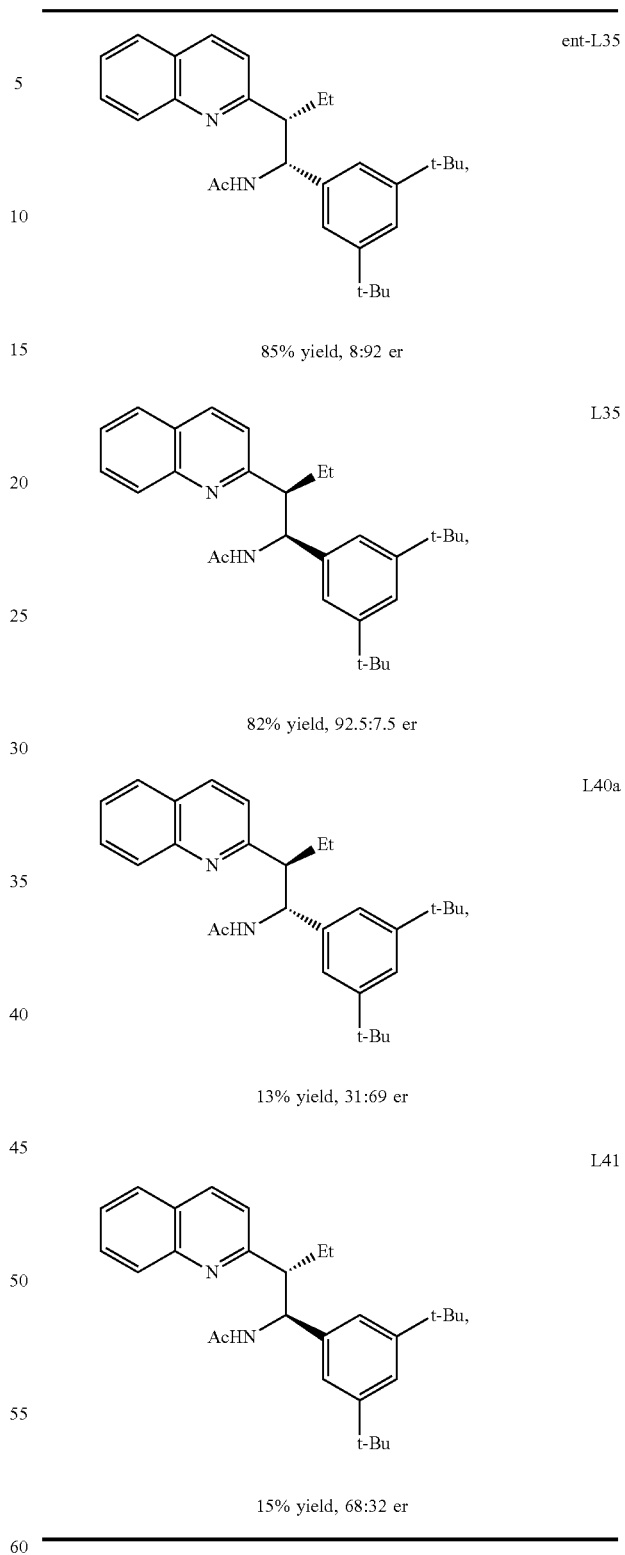

*The yields were determined by $^1$H NMR analysis of the crude product using $CH_2Br_2$ as an internal standard. Enantiomeric ratios (er) were determined by chiral high-performance liquid chromatography.

With the optimal ligand L35 in hand, the reaction conditions were further optimized for the arylation of 2a and improved the enantioselectivity to 95:5 er (see Table 6, entry 21).

TABLE 6*

Reaction scheme: substrate 1 (MeCH(H)(H)C(O)NHAr$_F$) with Pd(OAc)$_2$ (x), L35 (y), p-Tol-I (w equiv.), Ag$_2$CO$_3$ (z equiv.), HFIP, 80 °C, 36 h → product 2a.

| Entry | Pd(x) | L35 (y) | Ag$_2$CO$_3$ (z) | ArI (w) | M (mol/L) | Yield | er |
|---|---|---|---|---|---|---|---|
| 1 | 10% | 5% | 2.0 | 3.0 | 0.1 | 78% | 85.5:14.5 |
| 2 | 10% | 8% | 2.0 | 3.0 | 0.1 | 80% | 86.5:13.5 |
| 3 | 10% | 10% | 2.0 | 3.0 | 0.1 | 82% | 87.5:12.5 |
| 4 | 10% | 12% | 2.0 | 3.0 | 0.1 | 82% | 88.5:11.5 |
| 5 | 10% | 15% | 2.0 | 3.0 | 0.1 | 70% | 89.5:10.5 |
| 6 | 10% | 20% | 2.0 | 3.0 | 0.1 | 76% | 90:10 |
| 7 | 10% | 10% | 0.5 | 3.0 | 0.1 | 45% | 95:5 |
| 8 | 10% | 10% | 1.0 | 3.0 | 0.1 | 65% | 94:6 |
| 9 | 10% | 10% | 1.5 | 3.0 | 0.1 | 78% | 93:7 |
| 10 | 10% | 10% | 2.5 | 3.0 | 0.1 | 85% | 93.5:6.5 |
| 11 | 10% | 10% | 3.0 | 3.0 | 0.1 | 84% | 92:8 |
| 12 | 10% | 10% | 2.0 | 3.0 | 0.2 | 81% | 87:13 |
| 13 | 10% | 10% | 2.0 | 3.0 | 0.13 | 85% | 90:10 |
| 14 | 10% | 10% | 2.0 | 3.0 | 0.067 | 72% | 93.6:6.5 |
| 15 | 10% | 10% | 2.0 | 3.0 | 0.05 | 56% | 94:6 |
| 16 | 5% | 10% | 2.0 | 3.0 | 0.1 | 54% | 87:13 |
| 17 | 15% | 10% | 2.0 | 3.0 | 0.1 | 85% | 94.5:5.5 |
| 18 | 20% | 10% | 2.0 | 3.0 | 0.1 | 82% | 95:5 |
| 19 | 10% | 12% | 1.5 | 2.0 | 0.1 | 71% | 95.5:4.5 |
| 20 | 10% | 12% | 1.5 | 2.5 | 0.1 | 76% | 96:4 |
| 21 | 10% | 12% | 1.75 | 2.5 | 0.1 | 83% | 95:5 |

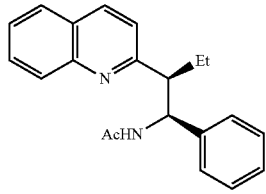

L35

*The yields were determined by $^1$H NMR analysis of the crude product using CH$_2$Br$_2$ as an internal standard. Enantiomeric ratios (er) were determined by chiral high-performance liquid chromatography.

The scope of aryl iodides for this enantioselective β-C—H arylation (Table 7, below) was next surveyed. Simple phenyl iodide and electron-rich aryl iodides containing methyl and methoxy groups afforded excellent enantioselectivity (2a-f) with the exception of o-methoxyphenyl iodide (2 g, 89:11 er). The absolute configuration of the arylated product 2a was determined to be (R) by X-ray crystallographic analysis, which is consistent with a stereochemical model based on steric repulsion. Electron-deficient aryl iodides bearing trifluoromethoxy, fluoro, chloro, bromo, and iodo substituents were also compatible, providing consistently high enantioselectivity (2h-m), although the yield dropped to 45% with trifluoromethyl substitution (2n). Other electron-withdrawing functional groups including ketones, ester and phosphonates are also compatible, affording the desired enantioselectivity and good yields (2o-s). Disubstituted aryl iodides also proved to be suitable coupling partners (2t-v).

TABLE 7

Reaction: 1 with Pd(OAc)$_2$ (10%), L35 (12%), ArI (2.5 equiv.), Ag$_2$CO$_3$ (1.75 equiv.), HFIP, 80 °C, 36 h. Ar$_F$ = 4-(CF$_3$)C$_5$F$_4$ → product 2.

2a: 78% yield, 95:5 er (p-Me-C$_6$H$_4$)

2b: 89% yield, 95:5 er (C$_6$H$_5$)

2c: 71% yield, 96:4 er (m-Me-C$_6$H$_4$)

2d: 64% yield, 95.5:4.5 er (4-CH$_2$OMe-C$_6$H$_4$)

2e: 83% yield, 95:5 er (p-OMe-C$_6$H$_4$)

TABLE 7-continued

| ID | Product | Yield / er |
|---|---|---|
| 2f | 3-MeO-C6H4-CH(Me)-CH2-C(O)-NHAr_F | 78% yield 96:4 er |
| 2g | 2-MeO-C6H4-CH(Me)-CH2-C(O)-NHAr_F | 57% yield 89:11 er |
| 2h | 4-OCF3-C6H4-CH(Me)-CH2-C(O)-NHAr_F | 57% yield 94:6 er |
| 2i | 3-F-C6H4-CH(Me)-CH2-C(O)-NHAr_F | 58% yield 95:5 er |
| 2j | 4-F-C6H4-CH(Me)-CH2-C(O)-NHAr_F | 84% yield 94:6 er |
| 2k | 4-Cl-C6H4-CH(Me)-CH2-C(O)-NHAr_F | 67% yield 95:5 er |
| 2l | 4-Br-C6H4-CH(Me)-CH2-C(O)-NHAr_F | 56% yield 95:5 er |
| 2m | 3-I-C6H4-CH(Me)-CH2-C(O)-NHAr_F | 50% yield 96:4 er |
| 2n | 4-CF3-C6H4-CH(Me)-CH2-C(O)-NHAr_F | 45% yield 94:6 er |
| 2o | 4-C(O)Me-C6H4-CH(Me)-CH2-C(O)-NHAr_F | 64% yield 96:4 er |
| 2p | 4-CO2Me-C6H4-CH(Me)-CH2-C(O)-NHAr_F | 78% yield 95.5:4.5 er |
| 2q | 3-CO2Me-C6H4-CH(Me)-CH2-C(O)-NHAr_F | 62% yield 96:4 er |

TABLE 7-continued

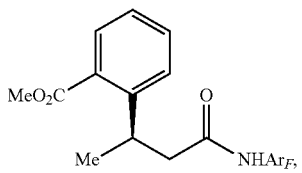

2r

79% yield 90:10 er

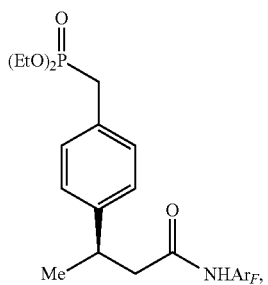

2s

60% yield 93.5:6.5 er

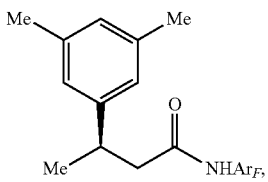

2t

61% yield 94:6 er

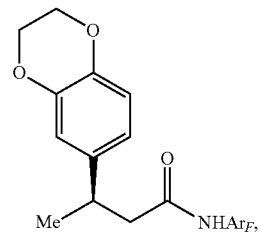

2u

58% yield 96:4 er

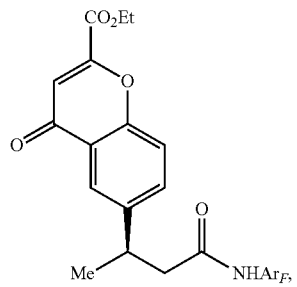

2v

56% yield 92:8 er

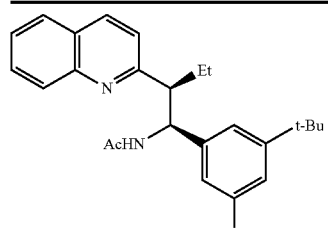

L35

Isolated yield of purified compounds. The absolute configuration was determined by X-ray crystallography.

It was pleasant to find that this protocol for enantioselective arylation of methylene C—H bonds was also applicable to other aliphatic amides (Table 8, below). Thus, aliphatic amides with various chain lengths were well tolerated with excellent enantioselectivity and high yields (4a-d).

TABLE 8

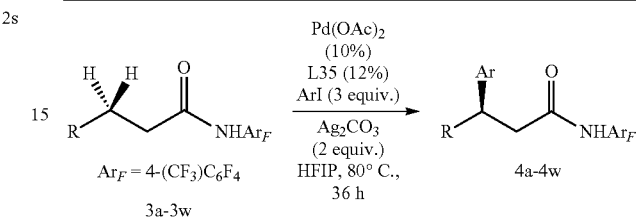

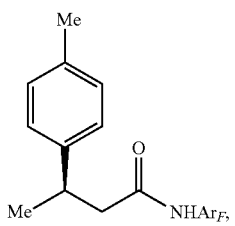

2a

78% yield 95:5 er

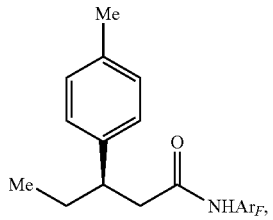

4a

78% yield 93.5:6.5 er

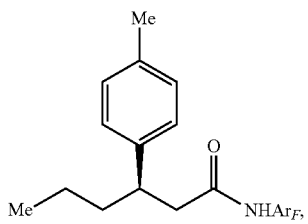

4b

83% yield 95:5 er

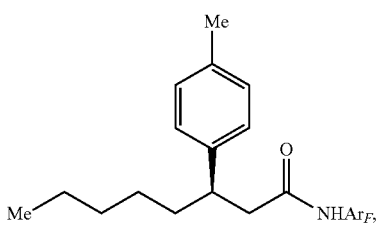

4c

80% yield 94:6 er

TABLE 8-continued
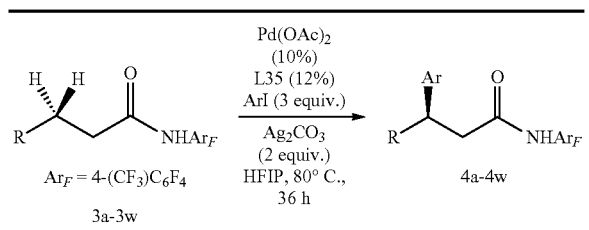
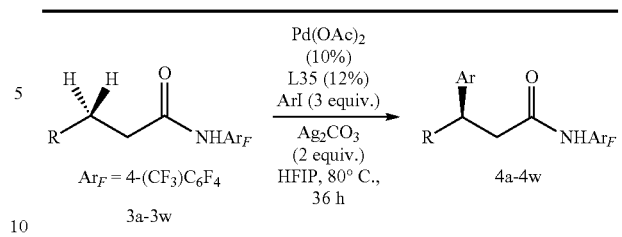
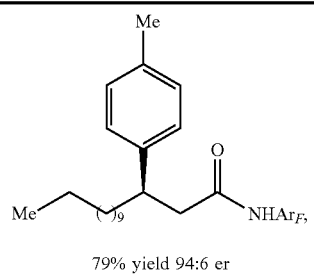
4d
79% yield 94:6 er
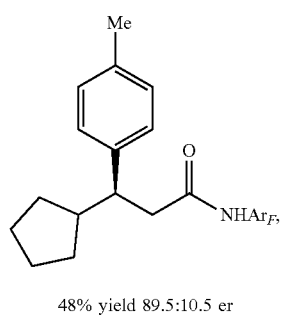
4e
48% yield 89.5:10.5 er
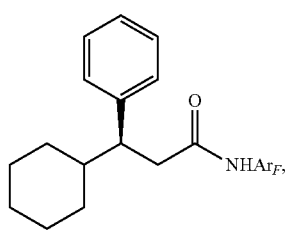
4f
56% yield 93.5:6.5 er
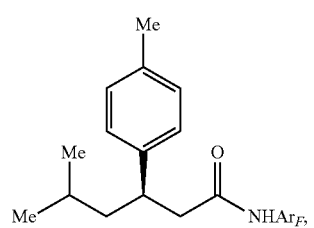
4g
71% yield 95:5 er
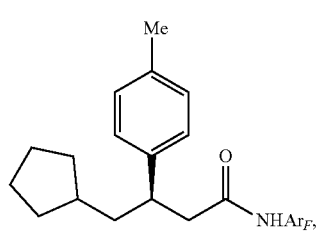
4h
72% yield 94:6 er
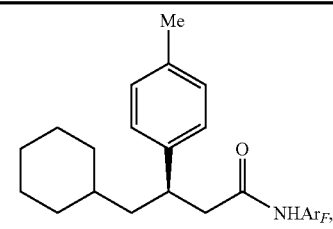
4i
74% yield 95:5 er
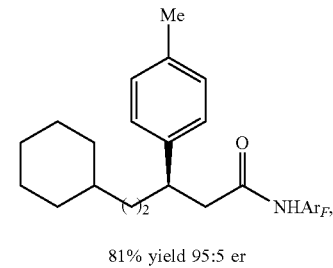
4j
81% yield 95:5 er
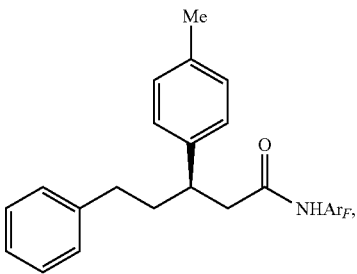
4k
72% yield 90:10 er
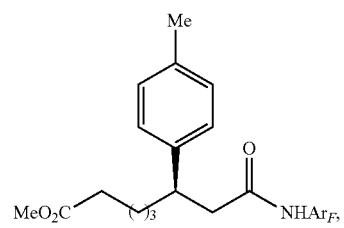
4l
60% yield 95:5 er
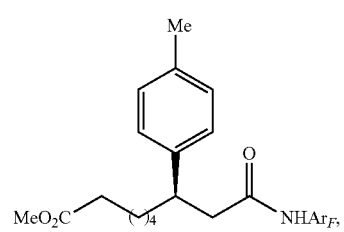
4m
68% yield 95:5 er TABLE 8-continued
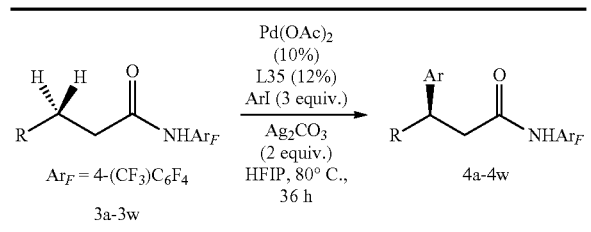
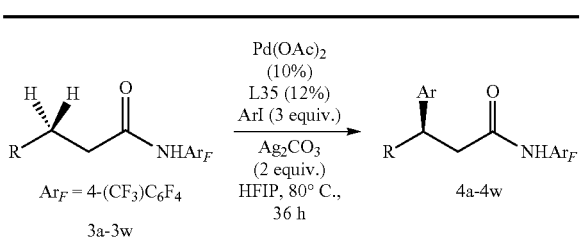
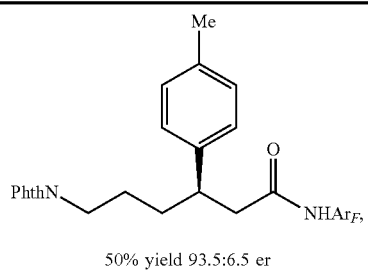
4n
50% yield 93.5:6.5 er
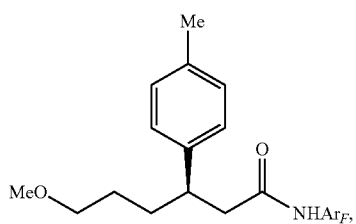
4o
40% yield 95.5:4.5 er
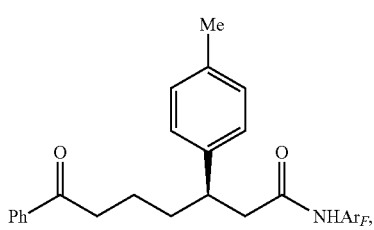
4p
35% yield 94:6 er
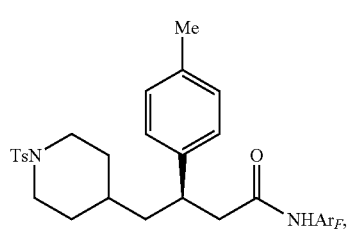
4q
68% yield 95:5 er
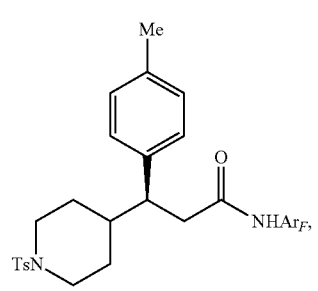
4r
37% yield 96:4 er
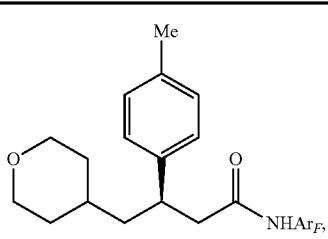
4s
57% yield 93:7 er
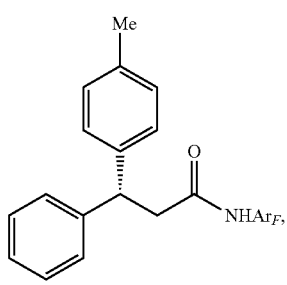
4t*
85% yield 87:13 er
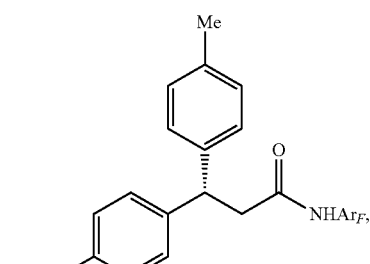
4u*
87% yield 92.5:7.5 er
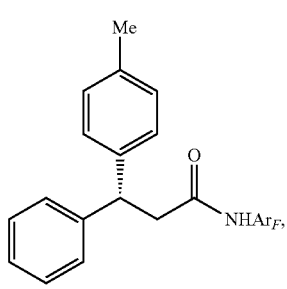
4t*
85% yield 87:13 er

TABLE 8-continued

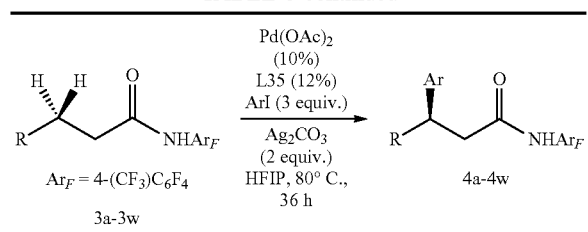

87% yield 92.5:7.5 er

[Structure of L35: quinoline with Et and AcHN substituents on carbon attached to 3,5-di-tert-butylphenyl]

L35

*Isolated yield of purified compound. The absolute configuration was determined by X-ray.
**Compounds 4t-4w were obtained using 1.5 equiv. Ag$_2$CO$_3$, 2.5 equiv. aryl iodide and L32 as ligand.
Phth = phthalimido group;
Ts = toluenasulfonyl.

As is seen from the data of Table 8, substrates containing sterically hindered alkyl groups at the β-position (cyclopentyl, cyclohexyl) provided good enantioselectivity, but gave lower yields (4e, 4f). Isopropyl, cyclopentyl, cyclohexyl and cyclohexylmethyl at the γ-positions are well tolerated, affording satisfactory yields and enantioselectivity (4 g-j). Phenyl, ester, amino, ether and ketone functionalities at δ- and ε-positions consistently afforded high enantioselectivity (4k-p). However, lower yields were obtained with the ether and ketone substrates (4o, 4p).

Piperidine at the γ-position afforded good yield and high enantioselectivity (4q), whereas the presence of piperidine at the β-position gave lower yield (4r). The presence of tetrahydropyran motif at the γ-position is also well tolerated, affording synthetically useful yield and enantioselectivity (4s).

Interestingly, arylation of benzylic C—H with 3t using ligand L35 provided poor yield and enantioselectivity (38% yield, 68:32 er). Switching to ligand L32 improved both yield and enantioselectivity significantly (4t). β-Phenyl groups containing both electron-withdrawing and -donating groups were also compatible with this reaction (4u-4w), thus demonstrating that this ligand scaffold is also applicable to enantioselective activation of benzylic C—H bonds.

In summary, a chiral bidentate acetyl protected aminoethyl quinoline ligand scaffold is found to enable enantioselective arylation of β-methylene C—H bonds through palladium catalysis.

As was noted previously, a contemplated ligand can be a quinolone, which is preferred, a pyridine or a imidazoline. Studies with imidazoline ligands of Formula A-4 are shown below.

[Reaction scheme: isobutyric amide + PhI with 10 mol % Pd(MeCN)$_2$Cl$_2$, 20 mol % L, 2.0 equiv. Ag$_2$CO$_3$, 2 equiv. NaTFA, Toluene, 60° C., N$_2$, 72 h, giving α-methyl-β-phenyl product; 72% yield, 97:3 er]

[Ligand L structure: t-Bu-substituted AcHN oxazoline with benzyl group]

[Second reaction: phthalimido-protected α-methyl substrate with Weinreb amide + 4-iodotoluene (3 eq), 10 mol % Pd(MeCN)$_2$Cl$_2$, 20 mol % L, Ag$_2$CO$_3$ (2 eq), t-Bu—OH, 60° C.; product 0.1 mmol scale: 50% yield, mono/di = 6/1; 95:5 er]

[Ligand L: isobutyl-substituted AcHN oxazoline with benzyl group]

Use of chiral mono-protected aminomethyl oxazoline (MPAO) ligands such as those shown above enable Pd(II)-catalyzed enantioselective β-arylation, -alkenylation, and -alkynylation of isobutyric amides, as is disclosed hereinafter. The remaining α-methyl group can then undergo further C—H functionalizations to afford greater product diversity.

Using a chiral benzoyl-protected aminomethyl oxazoline ligand, desymmetrization of 2-aminoisobutyric acid-derived amide (5) is also showcased to provide straightforward access to a wide range of enantioenriched α,α-dialkyl α-amino acids that may be used as building blocks for peptide based drug synthesis [Venkatraman et al., Chem. Rev. 101, 3131-3152 (2001); Sagan et al., Curr. Med. Chem. 11, 2799-2822 (2004)]. Systematic ligand modification suggests that the additional interaction of the chiral center on the oxazoline ring with the substrate is of import to the successful desymmetrization of isopropyl groups.

Early efforts of the inventor and co-workers to desymmetrize isopropyl groups of isobutyric acid-derived substrates focused on the use of chiral auxiliaries [Giri et al., Angew. Chem. Int. Ed. 44, 2112-2115 (2005); Giri et al., Angew. Chem. Int. Ed. 44, 7420-7424 (2005)]. These studies, through isolation of well-defined chiral C—H insertion intermediates and computational analysis [Musaev et al., J. Am. Chem. Soc. 134, 1690-1698 (2012); Giri et al., J. Am. Chem. Soc. 134, 14118-14126 (2012)], improved understanding of how chiral differentiation of α-gem-dimethyl groups can potentially be achieved.

The difficulty of desymmetrizing the gem-dimethyl groups in isobutyric acid-derived substrates is demonstrated by the fact that even when employing a bulky oxazoline as a chiral auxiliary, no diastereoselectivity is obtained [Giri et al., Angew. Chem. Int. Ed. 44, 2112-2115 (2005)]. Furthermore, desymmetrization of α-dimethyl groups using a chiral amino acid-derived ligands is only successful (90:10 er) when the α-hydrogen atom is replaced by an extremely bulky α-tert-butyl group [Xiao et al., J. Am. Chem. Soc. 136, 8138-8142 (2014)]. The use of chiral phosphoric acid ligands has also failed to give enantioselectivity for the desymmetrization of the gem-dimethyl groups in isobutyric acid-derived substrates [Engle et al., J. Org. Chem. 78, 8927-8955 (2013); Yan et al., Org. Lett. 17, 2458-2461 (2015); Jain et al., Nat. Chem. 134, 14118-14126 (2016); Wang et al., Angew. Chem. Int. Ed. 55, 15387-15391 (2016)].

The development of a bisdentate chiral acetyl-protected aminoethyl quinoline (APAQ, e.g., L35) ligand for enantioselective methylene C—H activation prompted testing whether these ligands would prove useful for the desymmetrization of isopropyl groups in isobutyric acid-derived amides [Chen et al., Science 353, 1023-1027 (2016)]. With isobutyric amide substrate 3, L35 gave nearly racemic products. Furthermore, extensive modification of APAQ ligands did not lead to a noticeable improvement in enantiomeric ratio (er) with this group of substrate.

This result highlights the difference between the desymmetrization of isopropyl groups and the enantioselective methylene C—H activation. To amplify steric interactions between substrates and catalysts, the quinoline motif was replaced with an oxazoline moiety thereby enabling introduction of additional chiral bias to the catalyst. L63—consisting of an achiral oxazoline moiety, a bulky isopropyl stereocenter (derived from valine), and an N-acetyl-protected amine—failed to achieve significant stereoinduction. Further, the chiral oxazoline-ligand L64 derived from N-acetyl glycine—and consequently lacking a stereocenter on the ligand backbone—also failed to afford enantioenriched products.

Intriguingly, the combination of the two chiral centers at C-4 on the oxazoline and the side chain in L82 afforded a promising er of 85:15. Increasing the steric bulkiness on the side chain (i.e. from isopropyl to tert-butyl, L61) further improved the selectivity to 98:2 er. The synergistic effect of these two relative stereocenters is evident from the complete loss of enantioselectivity when the absolute stereochemistry of one of the chiral centers is reversed as shown in L83. These results are shown with greater detail in Table 9, below.

TABLE 9

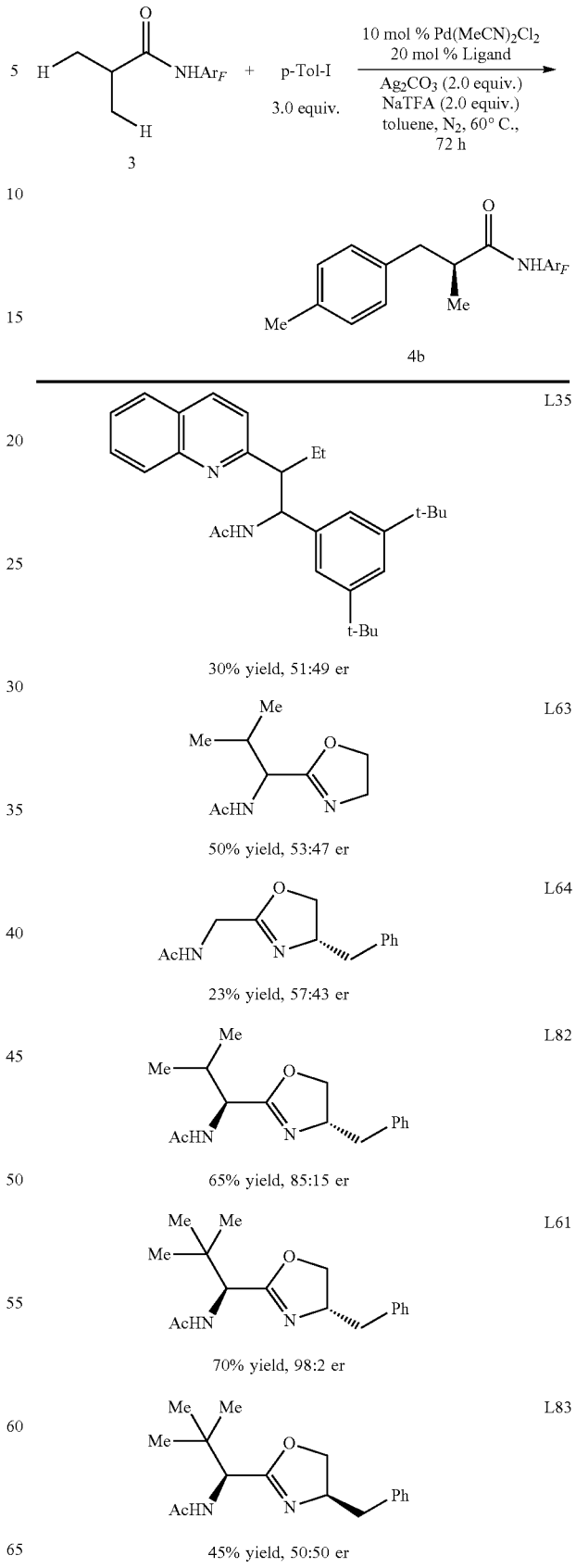

Although full rationalizations of the observed chiral induction require extensive computational and kinetic analysis, the absolute configuration of the product and the observed influence of each chiral center on the ligands are consistent with the steric interactions. It is proposed that the N-acetyl group on the coordinating nitrogen is oriented on the top face of the palladium square plane due to the steric repulsion with the chiral center on the side chain. The 4-benzyl group on the oxazoline ring further shields the top face of intermediate. These combined steric interactions may reinforce the orientation of the α-methyl group in the intermediate, thereby establishing the stereochemistry of the C—H cleavage step.

With the optimized chiral ligand and conditions in hand, we screened the enantioselective β-C—H arylation of isobutyric amide 3 with a wide range of aryl iodides. para-Substituents on the aryl iodides ranging from electron-donating (OMe, NBnBoc) to electron-withdrawing (halides, $CF_3$, keto and nitro) groups are tolerated, providing enantioselectivity up to 98:2 er (4a-q). The scope of meta-substituted aryl iodides is also broad and enantiomeric ratios greater than 94:6 (4r-ab) were obtained. Of interest, the above scope of ortho-, meta- and para-substituted aryl iodides features either halogens (as in 4l-4n, 4u-4w and 4ah) or reactive groups (phosphonate moiety as in 4i and aldehyde functionality as in 4aa and 4ae) that can serve as useful synthetic handles for subsequent chemical manipulation. Several heteroaryl iodides, including thiophene, benzothiophene and indole moieties are also compatible, affording products with high enantioselectivity in synthetically useful yields (4al-ap). The simplicity of deprotecting the amide auxiliary using $BF_3.Et_2O$ was also demonstrated with product 4q without erosion in enantioselectivity. These results are detailed in Table 10, below.

TABLE 10

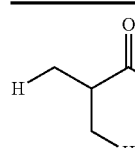

| X = H | 4a, 68% yield, 98:2 er |
| --- | --- |
| Me | 4b, 70% yield, 98:2 er |
| OMe | 4c, 70% yield, 96:4 er |
| $OCF_3$ | 4d, 62% yield, 97:3 er |
| Ph | 4e, 65% yield, 93:7 er |
| OTBS | 4f, 62% yield, 94:6 er |
| $CH_2OTBS$ | 4g, 53% yield, 96:4 er |
| $CH_2OBn$ | 4h, 50% yield, 94:6 er |
| $CH_2PO(OEt)_2$ | 4i, 75% yield, 93:7 er* |
| X = NBnBoc | 4j, 60% yield, 94:6 er |
| F | 4k, 68% yield, 96:4 er |
| Cl | 4l, 73% yield, 97:3 er |
| Br | 4m, 60% yield, 96:4 er |
| I | 4n, 63% yield, 98:2 er* |
| $CF_3$ | 4o, 57% yield, 97:3 er |
| COMe | 4p, 80% yield, 95:5 er* |
| $NO_2$ | 4q, 71% yield, 98:2 er |

TABLE 10-continued

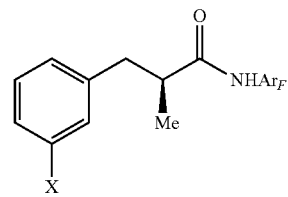

| X = Me | 4r, 62% yield, 95:5 er |
| --- | --- |
| OMe | 4s, 67% yield, 96:4 er |
| F | 4t, 65% yield, 95:5 er |
| Cl | 4u, 70% yield, 96:4 er |
| Br | 4v, 68% yield, 94:6 er |
| I | 4w, 55% yield, 96:4 er |
| X = $CF_3$ | 4x, 60% yield, 96:4 er* |
| COMe | 4y, 76% yield, 96:4 er* |
| $NO_2$ | 4z, 72% yield, 99:1 er* |
| CHO | 4aa, 78% yield, 94:6 er* |
| $CO_2Me$ | 4ab, 62% yield, 97:3 er |

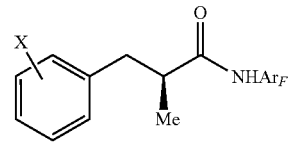

| X = 2-F | 4ac, 50% yield, 91:9 er* |
| --- | --- |
| 2-$CO_2Me$ | 4ad, 85% yield, 93:7 er* |
| 2-CHO | 4ae, 45% yield, 93:7 er* |
| 3,4-OMe | 4af, 72% yield, 94:6 er |
| 3,4,5-F | 4ag, 58% yield, 95:5 er |
| 3-Br-5-F | 4ah, 63% yield, 92:8 er |

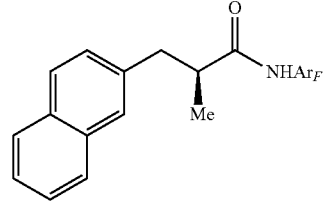

4ai, 50% yield, 98:2 er

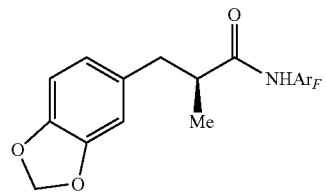

4aj, 52% yield, 97:3 er

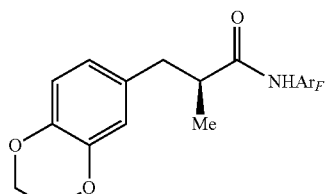

2ak, 54% yield, 94.5:5.5 er

TABLE 10-continued

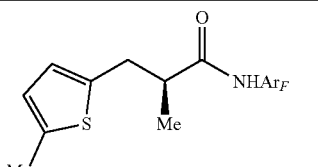

2al, 47% yield, 95:5 er

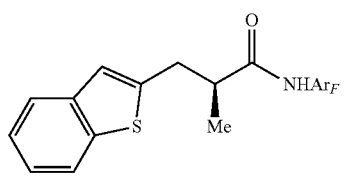

2am, 60% yield, 98:2 er

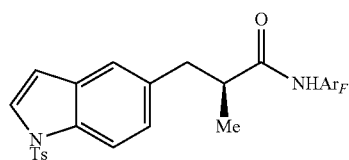

2an, 45% yield, 93:7 er*

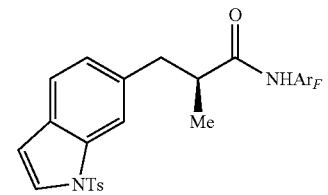

2ao, 60% yield, 92:8 er*

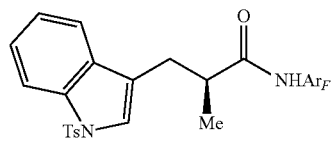

2ap, 45% yield, 90:10 er*

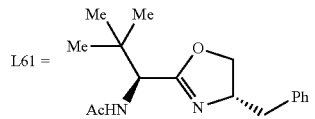 [SMILES: CC(=O)N[C@H](C1=N[C@@H](Cc2ccccc2)CO1)C(C)(C)C]

L61 =

For each entry number, data are reported as isolated yield.
* = 10 mol % L89, Ar—I, Ag$_2$CO$_3$, toluene, 50° C. 72 hours.
† = 96 hours.
Ar$_F$ = 4-(CF$_3$) C$_6$F$_4$;
p-Tol-I = para-tolyl iodide; equiv. = equivalent;
Et = ethyl group; Ph = phenyl group;
Ac = acetyl group; Ar(Het) = (hetero)aryl group;
TBS = tert-butyldimethylsilyl group;
Bn = benzyl group; Boc = tert-butyloxycarbonyl group;
Ts = tosyl group; Phth = phthalimido group;
HFIP = hexafluoro-2-propanol.

The unique pharmacological and conformational properties of α,α-disubstituted α-amino acids display in peptide drug molecules [Venkatraman et al., *Chem. Rev.* 101, 3131-3152 (2001); Sagan et al., *Curr. Med. Chem.* 11, 2799-2822 (2004)] prompted application to N-phthaloyl-protected 2-amino-isobutyric acid derivatives. However, the analogous amide substrate prepared by condensing the N-Phth-protected-2-aminoisobutyric acid with 2,3,5,6-tetrafluoro-4-(trifluoromethyl)aniline is not reactive under these conditions, presumably due to the steric bulkiness of this substrate which may prevent coordination. To reduce the steric hindrance of the substrate, the N-methoxy amide 7 of N-phthaloyl-protected 2-amino-isobutyric acid was prepared [Chen et al., *J. Am. Chem. Soc.* 137, 3338-3351 (2015); Zhu et al., *Angew. Chem. Int. Ed.* 55, 10578-10599 (2016)].

Although 7 showed substantial decomposition under the conditions established for substrate 3, find milder conditions were found that permitted the β-arylation to proceed at 35° C. Although ligand L61 gave satisfactory enantioselectivity (91:9 er), the yield remained low despite extensive optimizations (about 40% yield).

MPAO ligands were thereafter screened. Although modification of the oxazoline ring and the amino acid side chain afforded only moderate improvement in yields, replacement of the N-acetyl moiety by an ortho-difluorobenzoyl group (L100) increased the yield of 8b to 75%, while maintaining high enantioselectivity (96:4 er). C—H coupling with a variety of aryl iodides afforded difficult-to-access enantioenriched α,α-disubstituted α-amino acids containing chiral α-quaternary centers (8a-r).

The facile conversion of the N-methoxy amide auxiliary to an ester renders this method easy to use [Chen et al., *J. Am. Chem. Soc.* 137, 3338-3351 (2015)]. In gram scale, both the N-methoxy amide auxiliary and the phthaloyl (phth) protecting group were removed and converted the Fmoc-protected amino acid to be used in peptide drug discovery program.

These results using an amino- and carboxy-protected 2-aminobutyric acid as the substrate are shown in Table 11, below.

TABLE 11

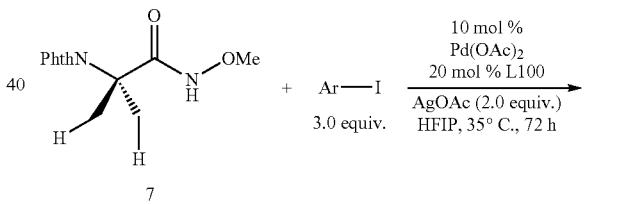

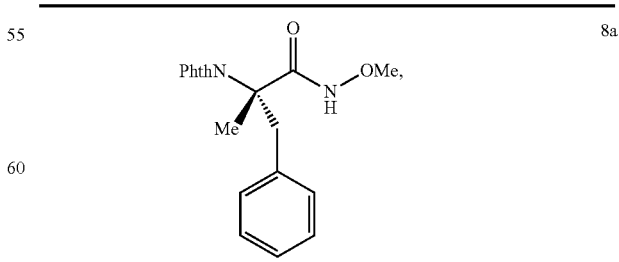

84% yield, 97:3 er

TABLE 11-continued
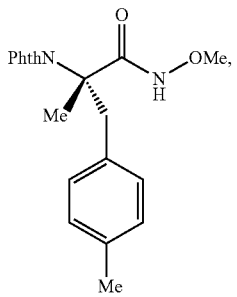
8b
75% yield, 96:4 er
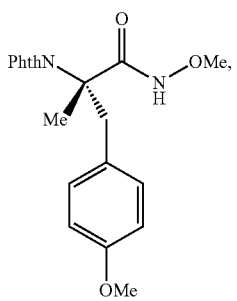
8c
68% yield, 96:2 er
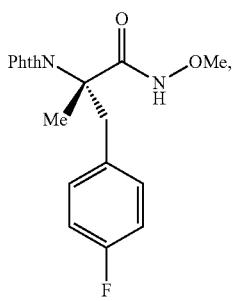
8d
66% yield, 97:3 er
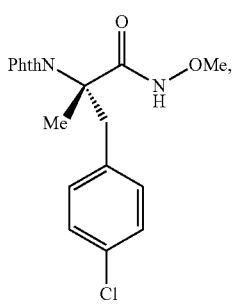
8e
70% yield, 94:6 er†
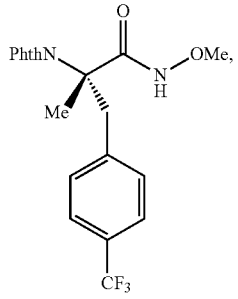
8f
66% yield, 95:5 er
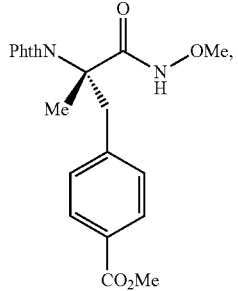
8g
70% yield, 95:5 er
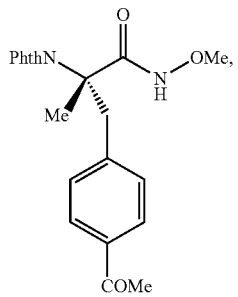
8h
73% yield, 96:4 er
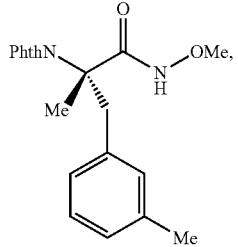
8i
70% yield, 97:3 er
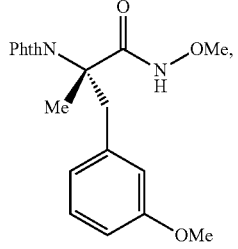
8j
79% yield, 96:4 er TABLE 11-continued

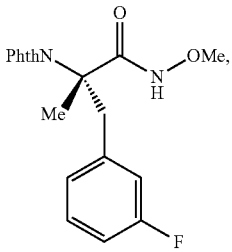

65% yield, 96:4 er

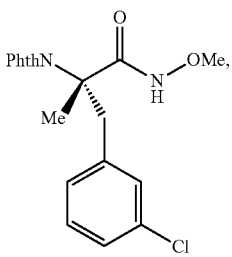

64% yield, 95:5 er

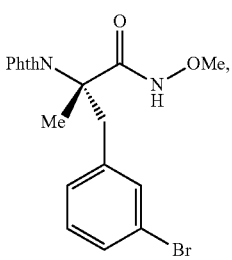

69% yield, 95:5 er†

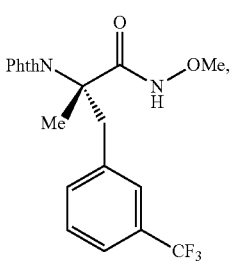

72% yield, 94.5:5.5 er

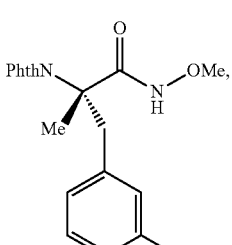

74% yield, 96:4 er

TABLE 11-continued

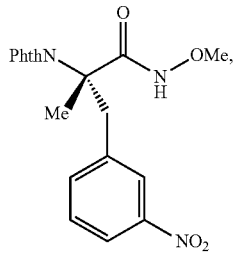

8p

68% yield, 93:7 er

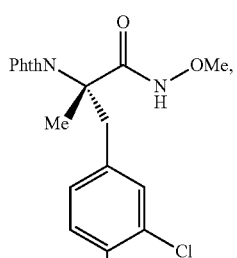

8q

67% yield, 94:6 er†

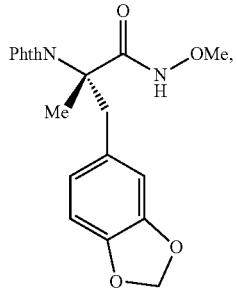

8r

70% yield, 95:5 er

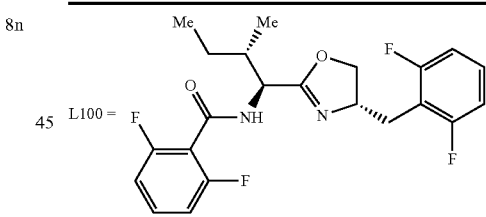

† = 96 hours.

One potential advantage of an organometallic approach to enantioselective functionalizations of C(sp$^3$)-H bonds is that the metallated intermediate can undergo reactivity with various coupling partners. Unfortunately, Pd-catalyzed enantioselective C(sp$^3$)-H activation reactions have been limited to arylation thus far. To fully realize the potential of asymmetric metal insertion processes, enantioselective C—H alkenylation, and alkynylation reactions of 3 were develoed.

β-Styrenylation of amide 3 using chiral ligand 61 afforded 88:12 er in the products. The use of L89 containing an additional chiral center at C-5 improved the enantioselectivity to 94:6 er.

Several (E)-styrenyl iodides are compatible coupling partners (9a-s) including the disubstituted (E)-styrenyl iodide (9t). The use of other simple (E)-alkenyl iodides also gave good enantioselectivity, albeit in lower yields (5u, 5v). Upon minor alteration of reaction conditions, use of L89 has also permitted the enantioselective β-alkynylation to proceed in 94.5:5.5 er (10). These results are shown in Table 12 below.

TABLE 12

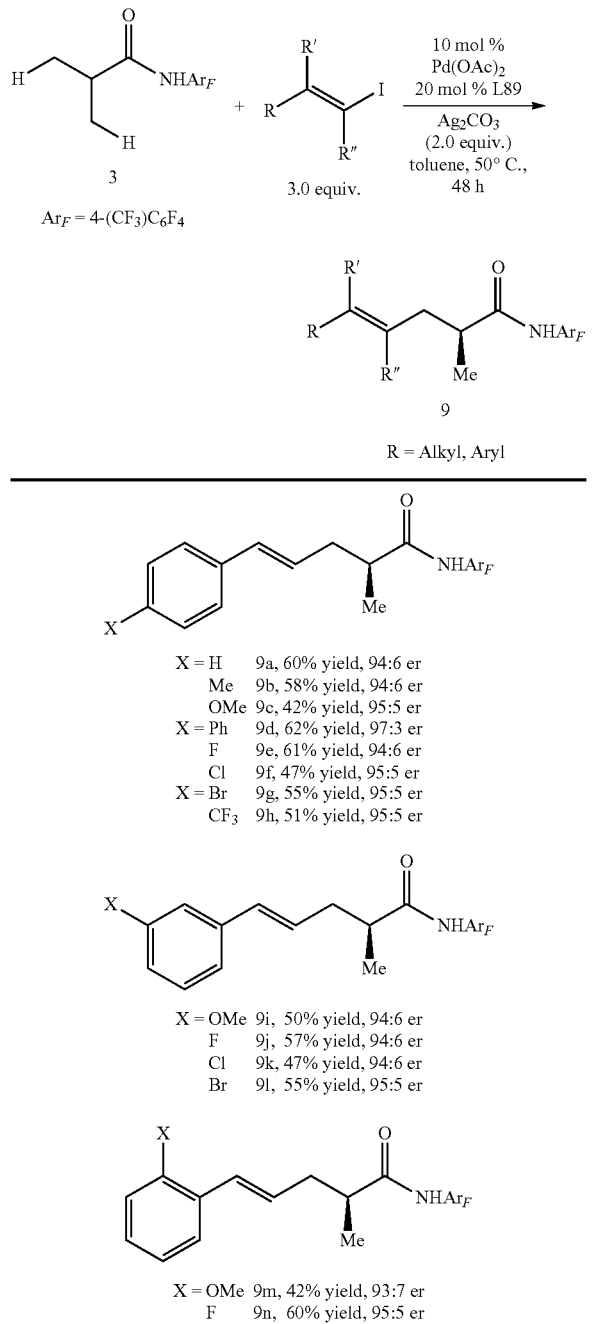

TABLE 12-continued

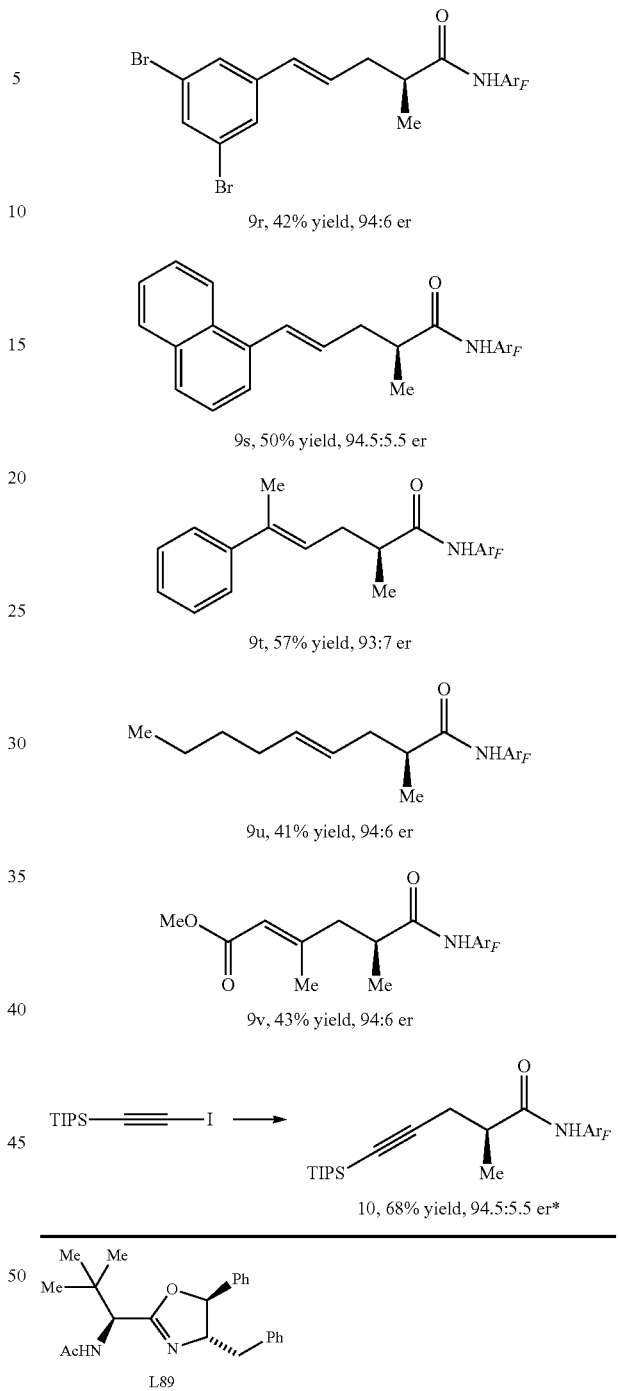

For each entry number, data are reported as isolated yield.
*10 mol % Pd(MeCN)$_2$Cl$_2$ was used instead of Pd(OAc)$_2$.
NaOAc was used as the additive.
TIPS = triisopropylsilyl.

To further broaden the diversity of the chiral centers accessed through these three enantioselective transformations, subsequent diverse β-functionalizations of the remaining methyl group were performed including arylation (11a-f), alkynylation (12), alkylation (13), bromination (14), and borylation (15). Thus, the sequential C—H functionalizations of the isopropyl groups with a wide range of coupling partners afford a myriad of α-chiral carboxylic acids. These results are shown in Table 13, below.

TABLE 13
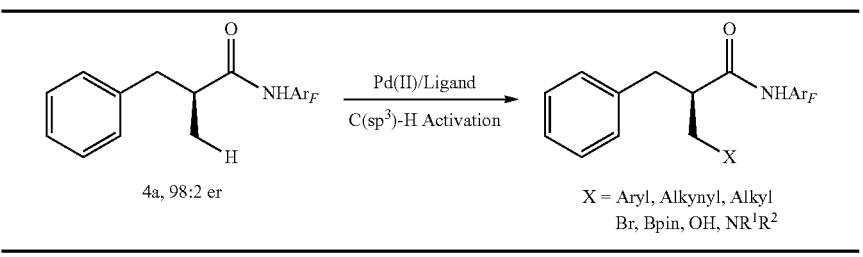
4a, 98:2 er
X = Aryl, Alkynyl, Alkyl
Br, Bpin, OH, NR¹R²
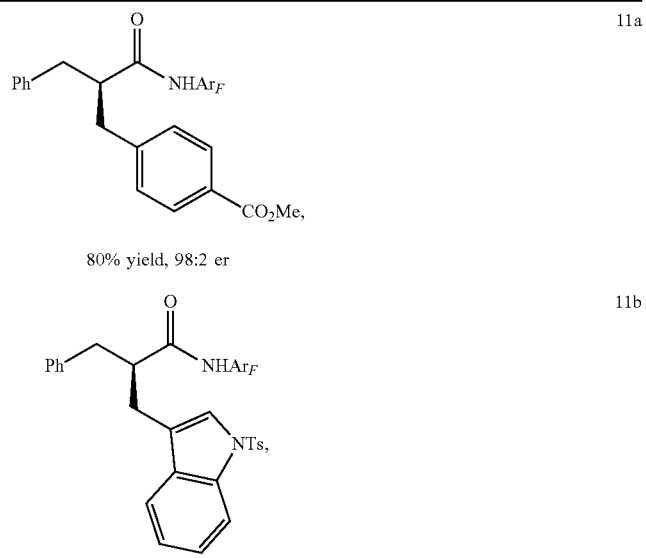
11a
80% yield, 98:2 er
11b
56% yield, 98:2 er
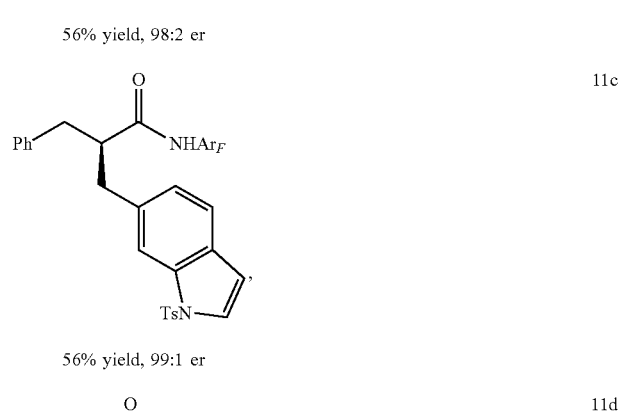
11c
56% yield, 99:1 er
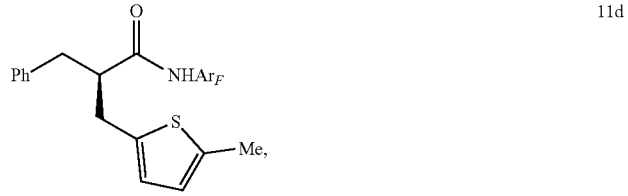
11d
63% yield, 98:2 er
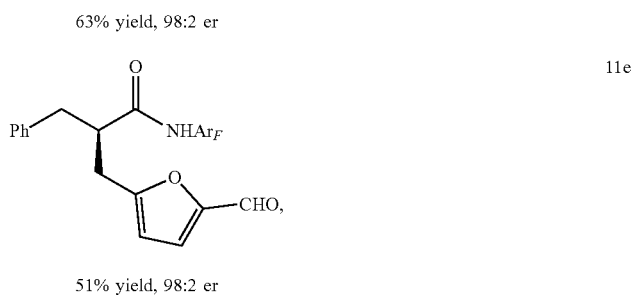
11e
51% yield, 98:2 er TABLE 13-continued
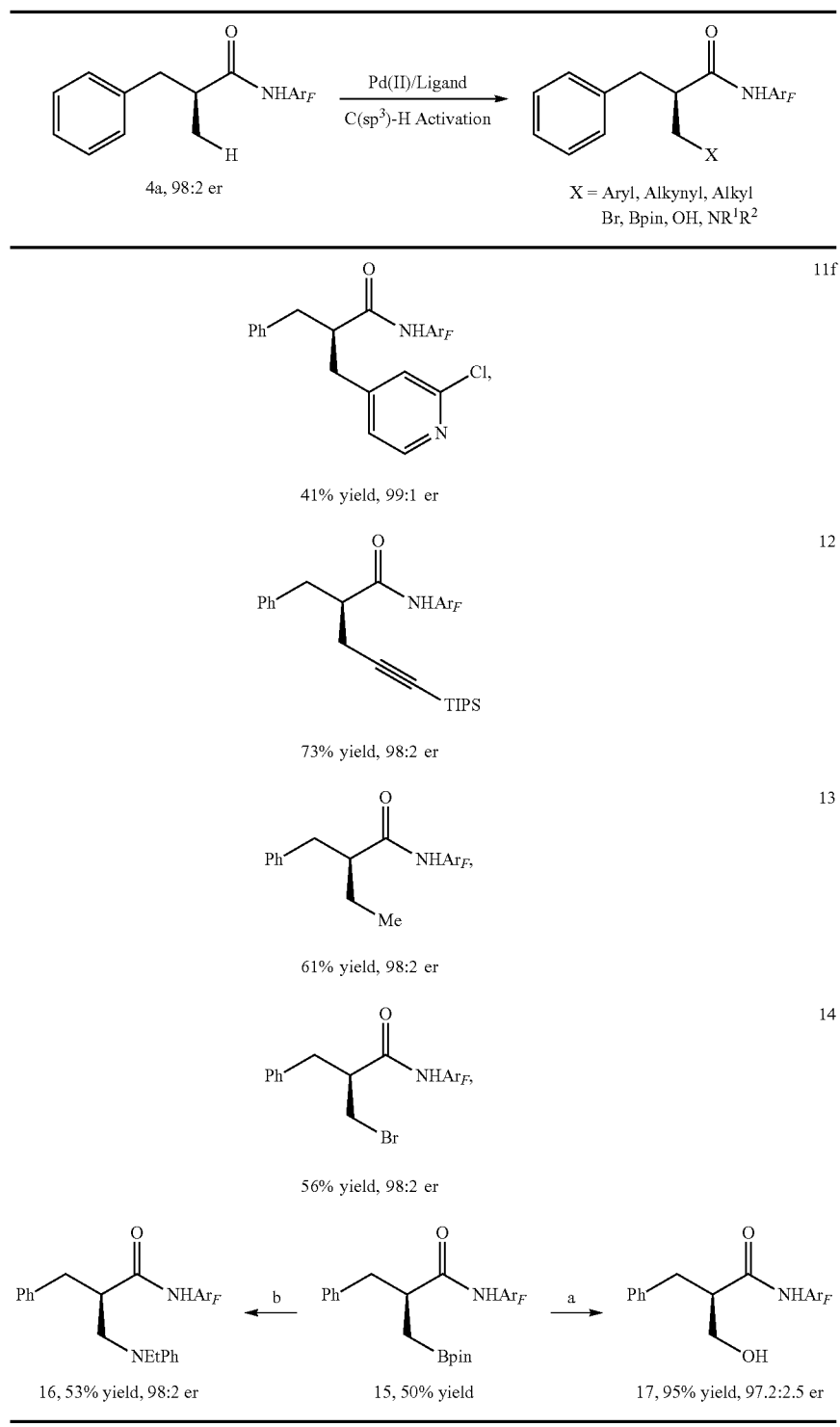
$Ar_F$ 4-$(CF_3)C_6F_4$;
Et = ethyl group; Ph = phenyl group;
Ts = tosyl group;
Bpin = pinacolyl boronate group,
aq. = aqueous; rt. = room temperature.
For each entry number, data are reported as isolated yield.
Reagents and conditions:
a $H_2O_2$, aq. buffer (pH = 7), THF, rt.
b 10 mol % Cu(OAc)$_2$, NMEtPh, Ag$_2$CO$_3$, toluene, 100° C.

Materials and Methods
General Information

Solvents were obtained from Sigma-Aldrich, Alfa-Aesar, Oakwood and Acros, and were used directly without further purification. Pd(CH$_3$CN)$_4$(OTf)$_2$ was synthesized from Pd(OAc)$_2$ (Strem Chemicals 46-1781) and trifluoromethanesulfonic acid (Acros 169890500) in acetonitrile [Drent et al., *J. Organomet. Chem.* 1991, 417:235]. Bis(pinacolato)diboron was purchased from Matrix Scientific (101787-966). Carboxylic acids or carboxylic acid chlorides and 2,3,5,6-tetrafluoro-4-(trifluoromethyl)aniline were obtained from the commercial sources or synthesized following literature procedures, and used to prepare the corresponding amides.

Analytical thin layer chromatography was performed on 0.25 mm silica gel 60-F$_{254}$. Visualization was carried out with UV light and Vogel's permanganate.

$^1$H NMR spectra were recorded on Bruker DRX-600 instrument (400 MHz or 600 MHz). Chemical shifts were quoted in parts per million (ppm) referenced to 0.0 ppm for tetramethylsilane. The following abbreviations (or combinations thereof) were used to explain multiplicities: s=singlet, d=doublet, t=triplet, q=quartet, sep=septet, m=multiplet, br=broad. Coupling constants, J, were reported in Hertz unit (Hz). $^{13}$C NMR spectra were recorded on Bruker DRX-600 instrument (150 MHz), and were fully decoupled by broad band proton decoupling. Chemical shifts were reported in ppm referenced to the center line of a triplet at 77.0 ppm of chloroform-d or the center line of a multiplet at 29.8 ppm of acetone-d$_6$. In the $^{13}$C NMR analysis, peaks that correspond to those of the polyfluoroarylamide auxiliary appeared as nearly invisible, complex sets of multiplets; they are omitted in the following spectroscopic analysis. $^{19}$F NMR spectra were recorded on Bruker AMX-400 instrument (376 MHz).

Melting points were recorded on a Fisher-Johns 12-144 melting point apparatus. High-resolution mass spectra (HRMS) were recorded on an Agilent Mass spectrometer using ESI-TOF (electrospray ionization-time of flight). Enantiomeric excesses values (er) were determined on a Hitachi LaChrom Elite® HPLC system using commercially available chiral columns. Optical rotation data were obtained on a Perkin-Elmer 341 polarimeter.

Substrate Preparation

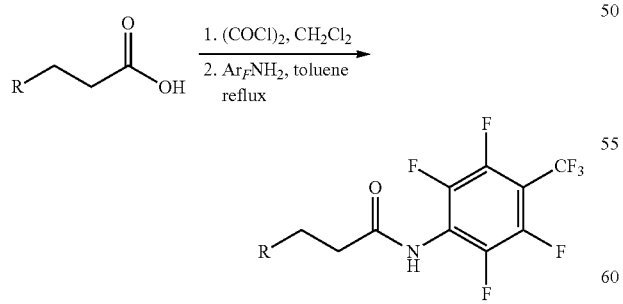

General Procedure for the Preparation of Amides

An acid chloride (1 equiv.), prepared from the corresponding carboxylic acid and oxalyl chloride, was added to a vigorously stirred solution of 2,3,5,6-tetrafluoro-4-(trifluoromethyl)aniline (Ar$_F$NH$_2$) (1.1 equiv.) in toluene (1 M). The reaction mixture was stirred for 12 hours under reflux, and then cooled at room temperature. The product mixture was concentrated under vacuum and was recrystallized from ethyl acetate/hexane to give the desired amide. In the $^{13}$C NMR analysis, peaks that correspond to those of the polyfluoroarylamide auxiliary appeared as nearly invisible, complex sets of multiplets; they are omitted in the following spectroscopic analysis.

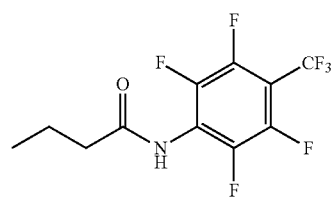 [SMILES: CCCC(=O)Nc1c(F)c(F)c(C(F)(F)F)c(F)c1F]

N-(2,3,5,6-tetrafluoro-4-(trifluoromethyl)phenyl)
butyramide (1)

$^1$H NMR (600 MHz, CDCl$_3$) δ 6.99 (br s, 1H), 2.47 (t, J=7.4 Hz, 2H), 1.83-1.76 (m, 2H), 1.04 (t, J=7.4 Hz, 3H).

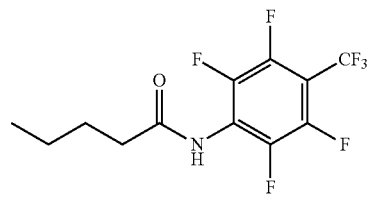 [SMILES: CCCCC(=O)Nc1c(F)c(F)c(C(F)(F)F)c(F)c1F]

N-(2,3,5,6-tetrafluoro-4-(trifluoromethyl)phenyl)
pentanamide (3a)

$^1$H NMR (600 MHz, CDCl$_3$) δ 7.07 (br s, 1H), 2.48 (t, J=7.8 Hz, 2H), 1.75-1.71 (m, 2H), 1.45-1.41 (m, 2H), 0.96 (t, J=7.4 Hz, 3H); $^{13}$C NMR (150 MHz, CDCl$_3$) δ 170.79, 36.09, 27.34, 22.13, 13.68.

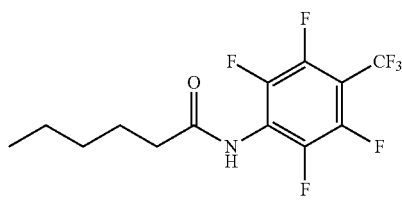 [SMILES: CCCCCC(=O)Nc1c(F)c(F)c(C(F)(F)F)c(F)c1F]

N-(2,3,5,6-tetrafluoro-4-(trifluoromethyl)phenyl)
hexanamide (3b)

$^1$H NMR (600 MHz, CDCl$_3$) δ 7.17 (br s, 1H), 2.48 (t, J=7.8 Hz, 2H), 1.76-1.73 (m, 2H), 1.38-1.35 (m, 4H), 0.92 (t, J=7.4 Hz, 3H); $^{13}$C NMR (150 MHz, CDCl$_3$) δ 170.92, 36.32, 31.17, 25.01, 22.31, 13.83.

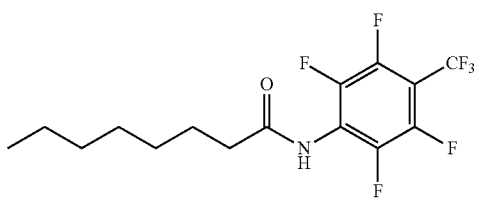

N-(2,3,5,6-tetrafluoro-4-(trifluoromethyl)phenyl) octanamide (3c)

¹H NMR (600 MHz, CDCl₃) δ 7.11 (br s, 1H), 2.48 (t, J=7.8 Hz, 2H), 1.77-1.72 (m, 2H), 1.41-1.26 (m, 8H), 0.90-0.88 (m, 3H); ¹³C NMR (150 MHz, CDCl₃) δ 170.85, 36.38, 31.61, 28.99, 28.92, 25.33, 22.56, 14.01.

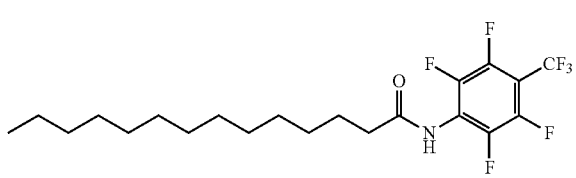 [SMILES: CCCCCCCCCCCCCC(=O)Nc1c(F)c(F)c(C(F)(F)F)c(F)c1F]

N-(2,3,5,6-tetrafluoro-4-(trifluoromethyl)phenyl) tetradecanamide (3d)

¹H NMR (600 MHz, CDCl₃) δ 7.00 (br s, 1H), 2.48 (t, J=7.5 Hz, 2H), 1.75-1.73 (m, 2H), 1.40-1.24 (m, 20H), 0.88 (t, J=7.0 Hz, 3H); ¹³C NMR (150 MHz, CDCl₃) δ 170.72, 36.41, 31.91, 29.63, 29.62, 29.56, 29.43, 29.35, 29.26, 29.25, 29.04, 25.33, 22.68, 14.10.

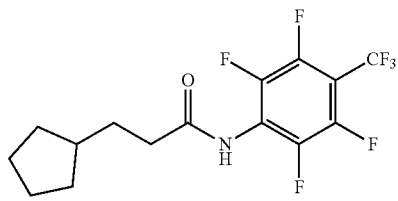 [SMILES: O=C(CCC1CCCC1)Nc1c(F)c(F)c(C(F)(F)F)c(F)c1F]

3-cyclopentyl-N-(2,3,5,6-tetrafluoro-4-(trifluoromethyl)phenyl)propanamide (3e)

¹H NMR (600 MHz, CDCl₃) δ 7.20 (br s, 1H), 2.49 (t, J=7.9 Hz, 2H), 1.84-1.74 (m, 5H), 1.65-1.61 (m, 2H), 1.58-1.35 (m, 2H), 1.15-1.11 (m, 2H); ¹³C NMR (150 MHz, CDCl₃) δ 171.03, 39.57, 35.69, 32.41, 31.48, 25.10.

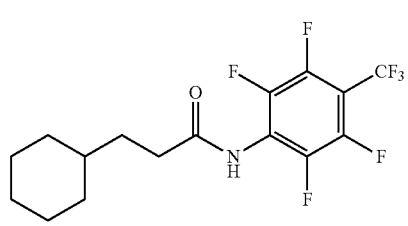 [SMILES: O=C(CCC1CCCCC1)Nc1c(F)c(F)c(C(F)(F)F)c(F)c1F]

3-cyclohexyl-N-(2,3,5,6-tetrafluoro-4-(trifluoromethyl)phenyl)propanamide (3f)

¹H NMR (600 MHz, CDCl₃) δ 6.96 (br s, 1H), 2.49 (t, J=7.9 Hz, 2H), 1.75-1.63 (m, 7H), 1.33-1.14 (m, 4H), 0.97-0.91 (m, 2H); ¹³C NMR (150 MHz, CDCl₃) δ 170.94, 37.19, 33.96, 32.99, 32.62, 26.42, 26.15.

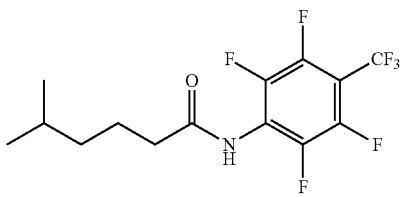 [SMILES: CC(C)CCCC(=O)Nc1c(F)c(F)c(C(F)(F)F)c(F)c1F]

5-methyl-N-(2,3,5,6-tetrafluoro-4-(trifluoromethyl)phenyl)hexanamide (3 g)

¹H NMR (600 MHz, CDCl₃) δ 7.12 (br s, 1H), 2.46 (t, J=7.5 Hz, 2H), 1.75-1.73 (m, 2H), 1.62-1.57 (m, 1H), 1.29-1.25 (m, 2H), 0.91 (d, J=6.7 Hz, 6H); ¹³C NMR (150 MHz, CDCl₃) δ 170.83, 38.21, 36.58, 27.79, 23.20, 22.41.

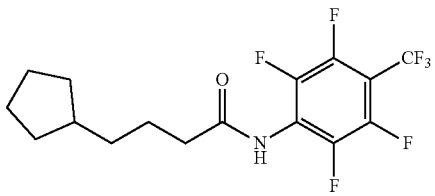 [SMILES: O=C(CCCC1CCCC1)Nc1c(F)c(F)c(C(F)(F)F)c(F)c1F]

4-cyclopentyl-N-(2,3,5,6-tetrafluoro-4-(trifluoromethyl)phenyl)butanamide (3h)

¹H NMR (600 MHz, CDCl₃) δ 6.98 (br s, 1H), 2.48 (t, J=7.5 Hz, 2H), 1.80-1.74 (m, 5H), 1.65-1.47 (m, 4H), 1.42-1.38 (m, 2H), 1.12-1.06 (m, 2H); ¹³C NMR (150 MHz, CDCl₃) δ 170.68, 39.82, 36.64, 35.51, 32.60, 25.13, 24.55.

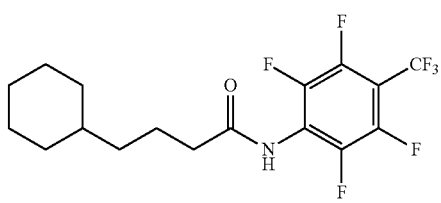 [SMILES: O=C(CCCC1CCCCC1)Nc1c(F)c(F)c(C(F)(F)F)c(F)c1F]

4-cyclohexyl-N-(2,3,5,6-tetrafluoro-4-(trifluoromethyl)phenyl) butanamide (3i)

¹H NMR (600 MHz, CDCl₃) δ 6.98 (br s, 1H), 2.46 (t, J=7.5 Hz, 2H), 1.80-1.63 (m, 7H), 1.29-1.11 (m, 6H), 0.93-0.86 (m, 2H); ¹³C NMR (150 MHz, CDCl₃) δ 170.71, 37.39, 36.78, 36.69, 33.22, 26.60, 26.29, 22.75.

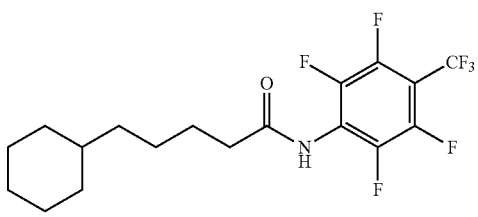 [SMILES: O=C(CCCCC1CCCCC1)Nc1c(F)c(F)c(C(F)(F)F)c(F)c1F]

5-cyclohexyl-N-(2,3,5,6-tetrafluoro-4-(trifluoromethyl)phenyl)pentanamide (3j)

$^1$H NMR (600 MHz, CDCl$_3$) δ 7.19 (br s, 1H), 2.47 (t, J=7.5 Hz, 2H), 1.74-1.62 (m, 7H), 1.42-1.36 (m, 2H), 1.25-1.11 (m, 6H), 0.91-0.83 (m, 2H); $^{13}$C NMR (150 MHz, CDCl$_3$) δ 170.94, 37.45, 37.07, 36.38, 33.33, 26.66, 26.35, 26.28, 25.64.

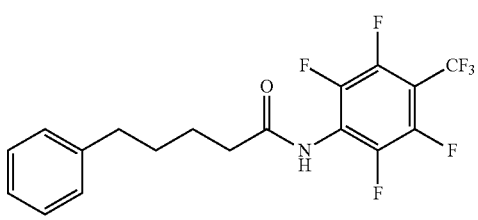 [SMILES: O=C(CCCCc1ccccc1)Nc1c(F)c(F)c(C(F)(F)F)c(F)c1F]

5-phenyl-N-(2,3,5,6-tetrafluoro-4-(trifluoromethyl)phenyl) pentanamide (3k)

$^1$H NMR (600 MHz, CDCl$_3$) δ 7.30-7.27 (m, 2H), 7.20-7.17 (m, 3H), 6.99 (s, 1H), 2.67 (t, J=7.4 Hz, 2H), 2.48 (t, J=7.3 Hz, 2H), 1.82-1.70 (m, 4H); $^{13}$C NMR (150 MHz, CDCl$_3$) δ 170.47, 141.79, 128.39, 128.36, 125.92, 36.15, 35.55, 30.68, 24.85.

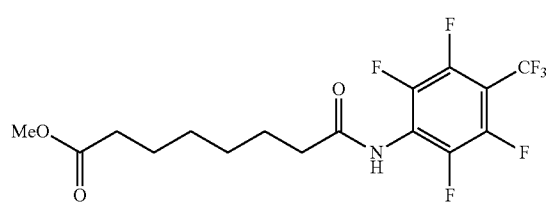 [SMILES: COC(=O)CCCCCCC(=O)Nc1c(F)c(F)c(C(F)(F)F)c(F)c1F]

Methyl 8-oxo-8-((2,3,5,6-tetrafluoro-4-(trifluoromethyl)phenyl)amino)octanoate (3l)

$^1$H NMR (600 MHz, CDCl$_3$) δ 7.54 (br s, 1H), 3.67 (s, 3H), 2.48 (t, J=7.5 Hz, 2H), 2.33 (t, J=7.4 Hz, 2H), 1.79-1.72 (m, 2H), 1.67-1.62 (m, 2H), 1.44-1.33 (m, 4H). $^{13}$C NMR (150 MHz, CDCl$_3$) δ 174.39, 170.94, 51.54, 35.97, 33.82, 28.47, 28.40, 24.98, 24.52.

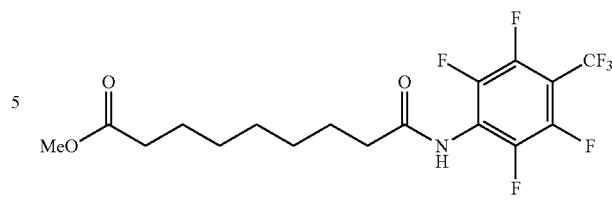

Methyl 9-oxo-9-((2,3,5,6-tetrafluoro-4-(trifluoromethyl)phenyl)amino)nonanoate (3m)

$^1$H NMR (600 MHz, CDCl$_3$) δ 7.29 (br s, 1H), 3.67 (s, 3H), 2.48 (t, J=7.5 Hz, 2H), 2.32 (t, J=7.4 Hz, 2H), 1.79-1.71 (m, 2H), 1.65-1.61 (m, 2H), 1.43-1.31 (m, 6H); $^{13}$C NMR (150 MHz, CDCl$_3$) δ 174.40, 170.78, 51.50, 36.20, 33.95, 28.72, 28.70, 28.62, 25.11, 24.69.

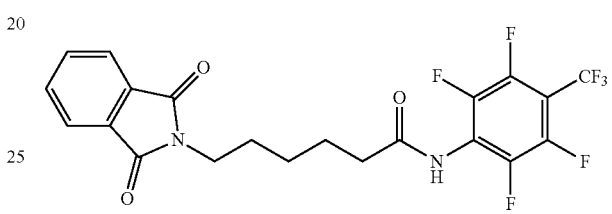

6-(1,3-dioxoisoindolin-2-yl)-N-(2,3,5,6-tetrafluoro-4-(trifluoromethyl)phenyl)hexanamide (3n)

$^1$H NMR (600 MHz, CDCl$_3$) δ 7.82 (dd, J$_1$=3.1 Hz, J$_2$=5.4 Hz, 2H), 7.71 (dd, J$_1$=3.0 Hz, J$_2$=5.5 Hz, 2H), 7.26 (br s, 1H), 3.72 (t, J=7.1 Hz, 2H), 2.50 (t, J=7.4 Hz, 2H), 1.86-1.81 (m, 2H), 1.78-1.73 (m, 2H), 1.49-1.44 (m, 2H); $^{13}$C NMR (150 MHz, CDCl$_3$) δ 170.41, 168.54, 133.98, 132.01, 123.17, 37.41, 35.98, 27.97, 25.85, 24.54.

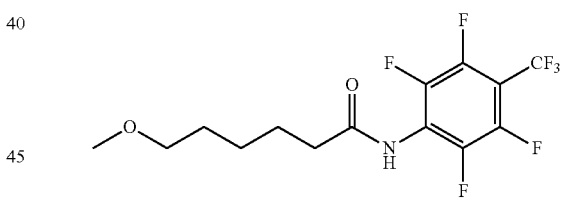

6-Methoxy-N-(2,3,5,6-tetrafluoro-4-(trifluoromethyl)phenyl)hexanamide (3o)

$^1$H NMR (600 MHz, CDCl$_3$) δ 7.63 (br s, 1H), 3.41 (t, J=6.4 Hz, 2H), 3.34 (s, 3H), 2.48 (t, J=7.4 Hz, 2H), 1.79-1.74 (m, 2H), 1.65-1.60 (m, 2H), 1.49-1.44 (m, 2H); $^{13}$C NMR (150 MHz, CDCl$_3$) δ 171.00, 72.49, 58.48, 36.01, 29.04, 25.55, 25.05.

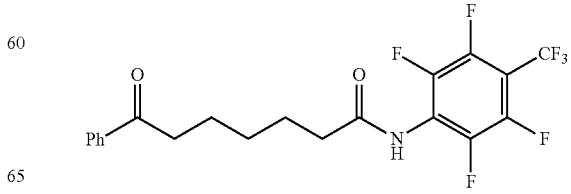

N-(2,3,5,6-tetrafluoro-4-(trifluoromethyl)phenyl)
pentanamide (3p)

$^1$H NMR (600 MHz, CDCl$_3$) δ 7.96-7.91 (m, 2H), 7.58-7.55 (m, 1H), 7.48-7.45 (m, 2H), 7.31 (br s, 1H), 3.03 (t, J=7.0 Hz, 2H), 2.54 (t, J=7.3 Hz, 2H), 1.85-1.79 (m, 4H), 1.53-1.48 (m, 2H); $^{13}$C NMR (150 MHz, CDCl$_3$) δ 200.48, 170.68, 136.85, 133.15, 128.62, 128.00, 38.05, 35.84, 28.33, 25.05, 23.23.

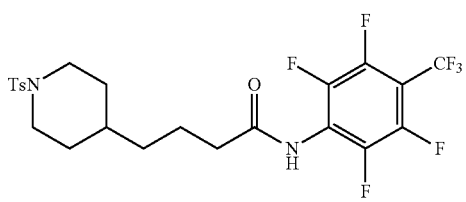 [SMILES: Cc1ccc(S(=O)(=O)N2CCC(CCCC(=O)Nc3c(F)c(F)c(C(F)(F)F)c(F)c3F)CC2)cc1]

N-(2,3,5,6-tetrafluoro-4-(trifluoromethyl)phenyl)-4-(1-tosylpiperidin-4-yl) butanamide (3q)

$^1$H NMR (600 MHz, CDCl$_3$) δ 7.61-7.58 (m, 3H), 7.33-7.30 (m, 2H), 3.75-3.71 (m, 2H), 2.45-2.43 (m, 5H), 2.23-2.17 (m, 2H), 1.76-1.66 (m, 4H), 1.32-1.24 (m, 4H), 1.23-1.15 (m, 1H); $^{13}$C NMR (150 MHz, CDCl$_3$) δ 170.78, 143.62, 132.81, 129.60, 127.58, 46.39, 36.14, 35.39, 34.91, 31.36, 22.34, 21.46.

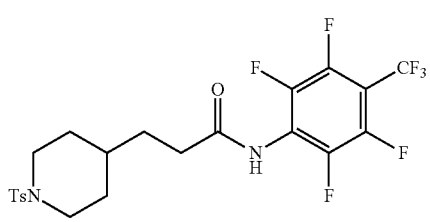 [SMILES: Cc1ccc(S(=O)(=O)N2CCC(CCC(=O)Nc3c(F)c(F)c(C(F)(F)F)c(F)c3F)CC2)cc1]

N-(2,3,5,6-tetrafluoro-4-(trifluoromethyl)phenyl)-3-(1-tosylpiperidin-4-yl)propanamide (3r)

$^1$H NMR (600 MHz, CDCl$_3$) δ 7.61 (d, J=8.0 Hz, 2H), 7.50 (br s, 1H), 7.32 (d, J=7.9 Hz, 2H), 3.77-3.75 (m, 2H), 2.48-2.44 (m, 2H), 2.42 (s, 3H), 2.24-2.20 (m, 2H), 1.78-1.75 (m, 2H), 1.71-1.65 (m, 2H), 1.37-1.26 (m, 3H); $^{13}$C NMR (150 MHz, CDCl$_3$) δ 170.55, 143.72, 132.75, 129.66, 127.58, 46.30, 34.37, 33.08, 31.14, 31.09, 21.49.

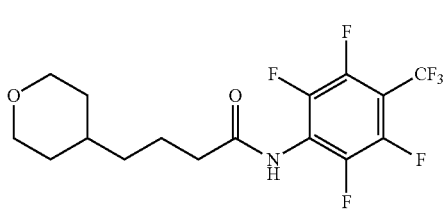 [SMILES: O=C(CCCC1CCOCC1)Nc1c(F)c(F)c(C(F)(F)F)c(F)c1F]

N-(2,3,5,6-tetrafluoro-4-(trifluoromethyl)phenyl)-4-(tetrahydro-2H-pyran-4-yl) butanamide (3s)

$^1$H NMR (600 MHz, CDCl$_3$) δ 7.54 (br s, 1H), 3.97-3.94 (m, 2H), 3.38 (dt, J$_1$=2.1 Hz, J$_2$=11.9 Hz, 2H), 2.47 (t, J=7.4 Hz, 2H), 1.79-1.74 (m, 2H), 1.63-1.60 (m, 2H), 1.54-1.48 (m, 1H), 1.35-1.22 (m, 4H); $^{13}$C NMR (150 MHz, CDCl$_3$) δ 170.74, 67.99, 36.27, 36.23, 34.76, 32.95, 22.16.

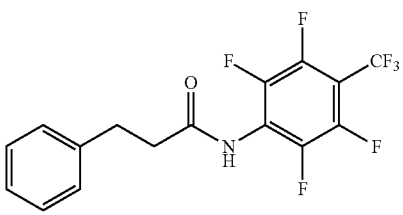 [SMILES: O=C(CCc1ccccc1)Nc1c(F)c(F)c(C(F)(F)F)c(F)c1F]

3-phenyl-N-(2,3,5,6-tetrafluoro-4-(trifluoromethyl)phenyl)propanamide (3t)

$^1$H NMR (600 MHz, CDCl$_3$) δ 7.34-7.30 (m, 2H), 7.26-7.23 (m, 3H), 3.07 (t, J=7.4 Hz, 2H), 2.79 (t, J=7.5 Hz, 2H).

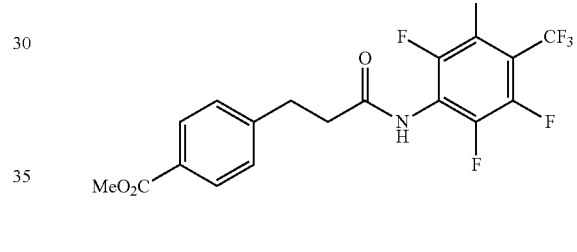

Methyl 4-(3-oxo-3-((2,3,5,6-tetrafluoro-4-(trifluoromethyl)phenyl)amino)propyl)benzoate (3u)

$^1$H NMR (600 MHz, CDCl$_3$) δ 7.98 (d, J=8.3 Hz, 2H), 7.30 (d, J=8.3 Hz, 2H), 6.99 (br s, 1H), 3.91 (s, 3H), 3.13 (t, J=7.4 Hz, 2H), 2.81 (t, J=7.4 Hz, 2H); $^{13}$C NMR (150 MHz, CDCl$_3$) δ 169.29, 166.97, 145.27, 130.05, 128.61, 128.43, 52.11, 37.53, 31.02.

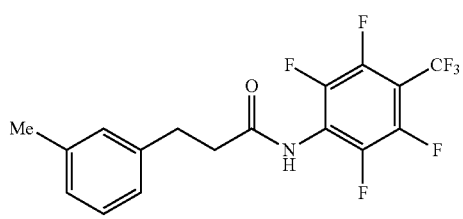 [SMILES: Cc1cccc(CCC(=O)Nc2c(F)c(F)c(C(F)(F)F)c(F)c2F)c1]

N-(2,3,5,6-tetrafluoro-4-(trifluoromethyl)phenyl)-3-(m-tolyl)propanamide (3v)

$^1$H NMR (600 MHz, CDCl$_3$) δ 7.21 (t, J=7.8 Hz, 1H), 7.06-7.03 (m, 3H), 6.88 (br s, 1H), 3.03 (t, J$_1$=7.4 Hz, 2H), 2.78 (t, J=7.4 Hz, 2H), 2.34 (s, 3H); $^{13}$C NMR (150 MHz, CDCl$_3$) δ 169.88, 139.68, 138.48, 129.12, 128.69, 127.43, 125.25, 38.18, 31.17, 21.34.

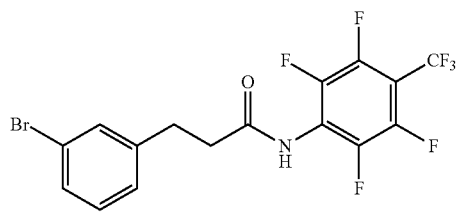 [SMILES: O=C(CCc1cccc(Br)c1)Nc1c(F)c(F)c(C(F)(F)F)c(F)c1F]
3-(3-bromophenyl)-N-(2,3,5,6-tetrafluoro-4-(trifluoromethyl)phenyl)propanamide (3w)
$^1$H NMR (600 MHz, CDCl$_3$) δ 7.40-7.39 (m, 1H), 7.38-7.36 (m, 1H), 7.20-7.16 (m, 2H), 6.92 (br s, 1H), 3.04 (t, J=7.4 Hz, 2H), 2.78 (t, J=7.5 Hz, 2H); $^{13}$C NMR (150 MHz, CDCl$_3$) δ 169.33, 142.11, 131.36, 130.29, 129.82, 127.08, 122.73, 37.73, 30.69.
Ligand Preparation
Ligand L2 [Geissman et al., *J. Org. Chem.* 24, 41-43 (1959)], L3 (bromide L5-1) [Wang et al., *Nature* 519, 334-338 (2015)], L6 [Jordan et al., *Hetercycles* 33, 657-671 (1992)], and L9 [Hervé et al., WIPO WO2014/140184 A1 (2014)] were prepared following the literature procedure.
Synthesis of ligand L4:
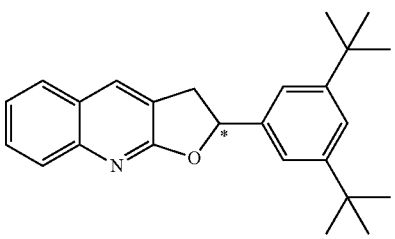 [SMILES: CC(C)(C)c1cc(C2Cc3cc4ccccc4nc3O2)cc(C(C)(C)C)c1]
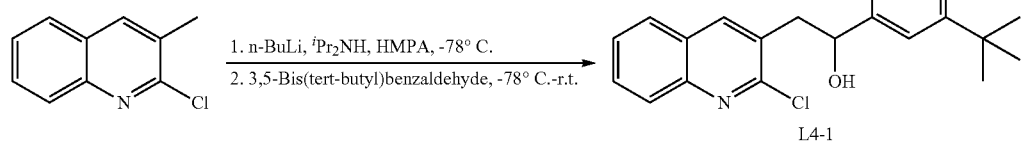
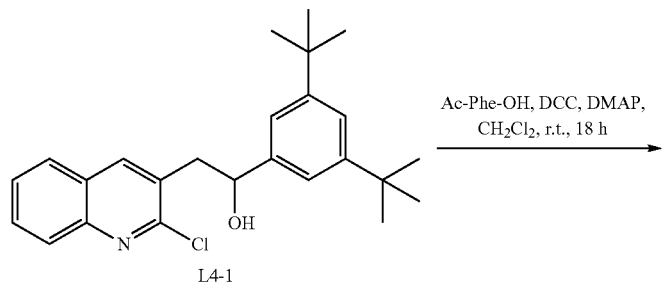
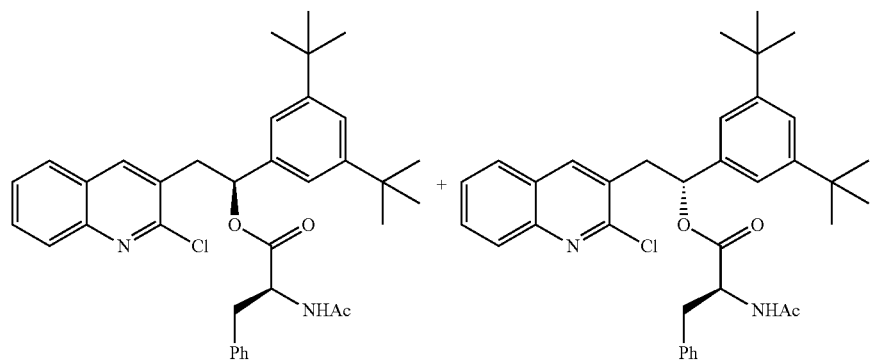
L4-2a & L4-2b

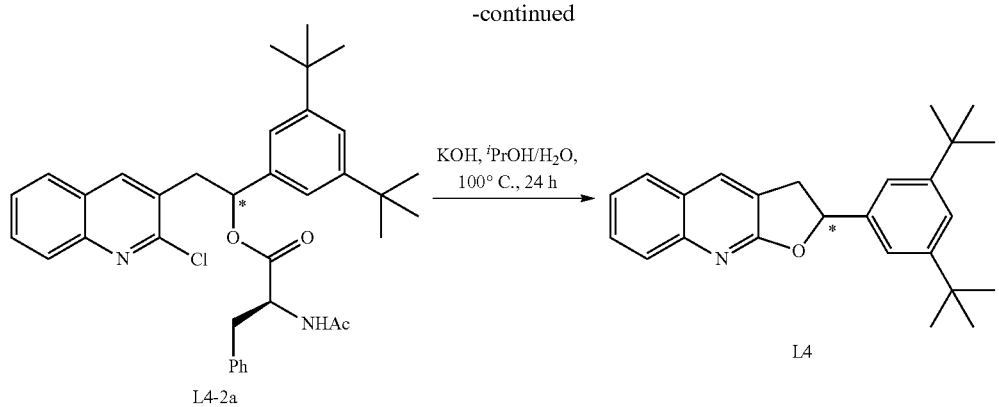

Synthesis of L4-1:

To a solution of diisopropylamine (1.01 g, 1.4 mL, 10 mmol) in 10 ml of THF at −78° C. under nitrogen was added n-butyllithium (2.5 M in hexanes, 4 mL, 10 mmol) dropwise. After 30 minutes, to this solution was added HMPA (1.79 g, 1.74 mL, 10 mmol). The resulting solution was treated with 2-chloro-3-methylquinoline (1.78 g, 10 mmol) in THF (10 mL) to afford a red solution, which was stirred for 30 minutes. To this mixture was added 3,5-bis(tert-butyl) benzaldehyde (1.09 g, 5 mmol) in THF (10 mL) at −78° C. After one hour at −78° C., the reaction mixture was quenched with saturated aqueous NH$_4$Cl solution and treated with 30 ml of diethyl ether, and the product was extracted with three 20-ml portions of diethyl ether. The combined extracts were washed with water, dried over anhydrous MgSO$_4$, and concentrated under vacuum. Flash chromatography (eluent: dichloromethane) afforded the alcohol L4-1 (1.40 g, 71?; yield) as a yellow foam. $^1$H NMR (600 MHz, CDCl$_3$) δ 8.02-8.00 (m, 1H), 7.96 (s, 1H), 7.73 (dd, J$_1$=1.3 Hz, J$_2$=8.1 Hz, 1H), 7.71-7.68 (m, 1H), 7.55-7.52 (m, 1H), 7.39 (t, J=1.8 Hz, 1H), 7.24 (d, J=1.8 Hz, 2H), 5.16 (t, J=6.6 Hz, 1H), 3.33 (dd, J$_1$=3.7 Hz, J$_2$=6.6 Hz, 2H), 1.32 (s, 18H); $^{13}$C NMR (150 MHz, CDCl$_3$) δ 151.41, 151.08, 146.62, 142.73, 139.71, 130.35, 129.87, 128.09, 127.31, 127.13, 126.92, 121.91, 119.85, 73.65, 43.37, 34.88, 31.42.

Synthesis of L4-2a and L4-2b:

To a mixture of Ac-Phe-OH (311 mg, 1.5 mmol), DMAP (183 mg, 1.5 mmol) and DCC (309 mg, 1.5 mmol) in CH$_2$Cl$_2$ (10 mL) was added alcohol L4-1 (300 mg, 0.75 mmol). The mixture was stirred at room temperature for 18 hours. The resulting suspension was filtered using a funnel filled with Celite® to give a clear solution. After removing the solvent under vacuum, the crude products were separated by preparative TLC (eluent: dichloromethane/acetone=10/1) to afford two diastereomeric esters: L4-2a (white solid, less polar, 197 mg, 45% yield) and L4-2b (white solid, more polar, 189 mg, 43% yield). L4-2a: $^1$H NMR (400 MHz, CDCl$_3$) δ 0.98-7.96 (m, 1H), 7.79 (s, 1H), 7.70-7.63 (m, 2H), 7.51-7.47 (m, 1H), 7.34 (t, J=1.8 Hz, 1H), 7.10-7.04 (m, 5H), 6.78 (dd, J$_1$=2.0 Hz, J$_2$=7.3 Hz, 2H), 6.10 (dd, J$_1$=5.7 Hz, J$_2$=8.4 Hz, 1H), 5.91 (d, J=7.9 Hz, 1H), 4.91 (dt, J$_1$=5.9 Hz, J$_z$=7.9 Hz, 1H), 3.50 (dd, J=8.4 Hz, J$_2$=14.1 Hz, 1H), 3.27 (dd, J; =5.7 Hz, J$_2$=14.1 Hz, 1H), 3.05 (dd, J, =6.5 Hz, J$_2$=13.8 Hz, 1H), 2.95 (dd, J$_1$=5.5 Hz, J$_2$=13.8 Hz, 1H), 1.88 (d, J=1.0 Hz, 3H), 1.25 (s, 18H); $^{13}$C NMR (100 MHz, CDCl$_3$) δ 170.77, 169.29, 151.09, 151.04, 146.72, 139.68, 137.86, 135.40, 130.19, 128.91, 128.76, 128.27, 128.12, 127.13, 127.08, 126.94, 126.87, 122.41, 120.28, 76.81, 53.06, 40.53, 37.80, 34.76, 31.29, 22.96. L4-2b: $^1$H NMR (400 MHz, CDCl$_3$) δ 7.98-7.95 (m, 1H), 7.80 (s, 1H), 7.72-7.65 (m, 2H), 7.54-7.49 (m, 1H), 7.41 (dt, J$_1$=1.1 Hz, J$_2$=1.9 Hz, 1H), 7.19 (d, J=1.8 Hz, 2H), 7.08-7.00 (m, 3H), 6.74-6.71 (m, 2H), 6.21 (dd, J=8.4, 5.1 Hz, 1H), 5.79 (d, J=8.0 Hz, 1H), 4.98-4.76 (m, 1H), 3.51 (dd, J$_1$=8.4 Hz, J$_2$=14.3 Hz, 1H), 3.42 (dd, J$_1$=5.2 Hz, J$_2$=14.3 Hz, 1H), 3.11 (dd, J, =6.0 Hz, J$_2$=13.9 Hz, 1H), 2.96 (dd, J$_1$=5.2 Hz, J$_2$=13.9 Hz, 1H), 1.81 (s, 3H), 1.28 (d, J=0.7 Hz, 18H); $^{13}$C NMR (100 MHz, CDCl$_3$) δ 170.65, 169.36, 151.20, 146.66, 139.42, 137.59, 135.26, 130.09, 129.21, 128.74, 128.22, 128.06, 127.22, 127.11, 127.02, 126.82, 122.54, 120.87, 76.49, 52.74, 40.19, 37.33, 34.82, 31.36, 22.90.

Synthesis of L4:

A mixture of ester L4-2a (210 mg, 0.36 mmol) and KOH (100 mg, 1.8 mmol) in isopropanol (7 mL) and H2O (7 mL) was heated to 100° C. for 24 hours. The mixture was cooled to room temperature before the solvents were removed under vacuum. To the residue was added saturated aqueous NH$_4$Cl solution and treated with 10 ml of diethyl ether, and the product was extracted with three 10-ml portions of diethyl ether. The combined extracts were washed with water, dried over anhydrous MgSO$_4$, and concentrated under vacuum. Flash chromatography (eluent: ethyl acetate/hexanes=1/10) afforded the product L4 (100 mg, 77% yield) as a white solid.

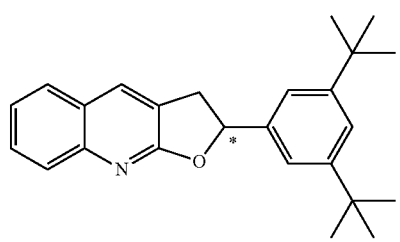

2-(3,5-di-tert-butylphenyl)-2,3-dihydrofuro-(2,3-b] quinolone (L4)

$^1$H NMR (600 MHz, CDCl$_3$) δ 7.90 (dd, J$_1$=1.1 Hz, J$_2$=8.5 Hz, 1H), 7.87 (d, J=1.7 Hz, 1H), 7.69 (dd, J$_1$=1.4 Hz, J$_2$=8.1 Hz, 1H), 7.61-7.59 (m, 1H), 7.42 (t, J=1.8 Hz, 1H), 7.39-7.36 (m, 1H), 7.30 (d, J=1.8 Hz, 2H), 5.91 (t, J=8.5 Hz, 1H), 3.82-3.77 (m, 1H), 3.40-3.36 (m, 1H), 1.33 (s, 18H).

¹³C NMR (150 MHz, CDCl₃) δ 151.25, 147.03, 139.85, 132.65, 129.08, 127.53, 127.26, 123.99, 122.29, 122.00, 119.63, 82.76, 36.59, 34.94, 31.43. HRMS (ESI-TOF) Calcd for C₂₅H₃₀NO [M+H]⁺: 360.2322; found: 360.2323.
The absolute stereochemistry was not assigned.

Synthesis of ligand L5:

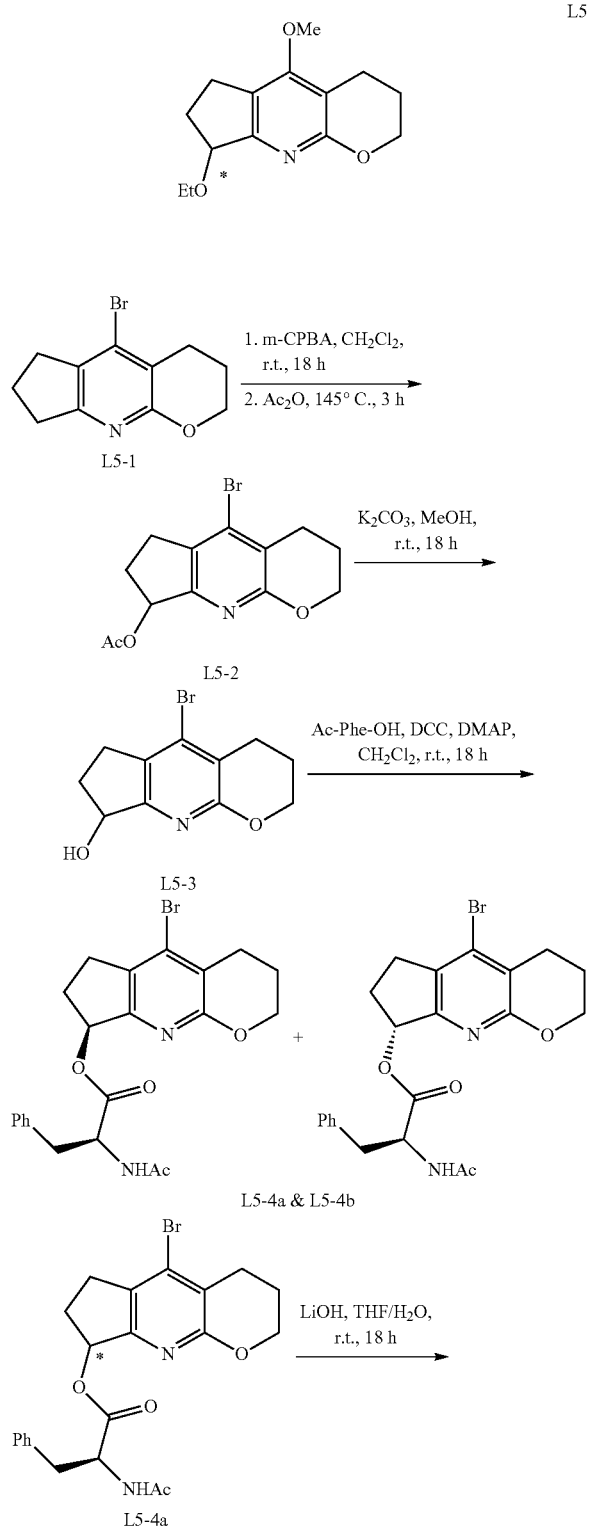

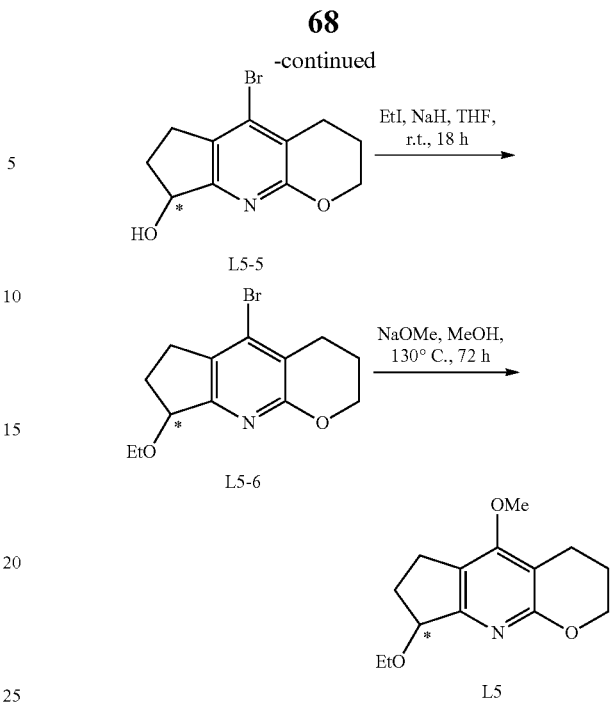

Synthesis of L5-2:

A mixture of bromide L5-1 [Wang et al., Nature 519, 334-338 (2015)] (5.08 g, 20 mmol) and 3-chloroperoxybenzoic acid (6.40 g, 77% max) in CH₂Cl₂ (150 mL) was stirred at room temperature overnight (about 18 hours). To the resulting reaction mixture was added water (150 mL), NaHCO₃ (13 g) and Na₂CO₃ (1.5 g) subsequently. The aqueous phase was washed with CH₂Cl₂ (2×100 mL), and organic phase was combined and dried with anhydrous MgSO₄. After removal of the solvent under vacuum, the crude product was transferred to a round-bottom flask, to which was added acetic anhydride (20 mL). The mixture was refluxed for one hour with an oil bath (145-150° C.). The acetic anhydride was removed by vacuum evaporation, and the residue was dissolved in CH₂Cl₂ (50 mL) and then water (50 mL), NaHCO₁ (1.5 g) and Na₂CO₃ (2.5 g) were added subsequently. The aqueous phase was washed with CH₂Cl₂ (3×30 mL), and the organic phase was combined and dried over anhydrous MgSO₄. The solvent was evaporated under vacuum, leaving a brown sticky oil. The crude product was purified by flash chromatography (eluent: ethyl acetate/hexanes=1/1) to afford the acetate L5-2 as a yellow solid (4.80 g, 77% yield). ¹H NMR (400 MHz, CDCl₃) δ 6.06-6.02 (m, 1H), 4.31-4.28 (m, 2H), 2.98 (m, 1H), 2.87-2.71 (m, 3H), 2.84-2.76 (m, 1H), 2.08 (s, 3H), 2.07-1.99 (m, 3H); ¹³C NMR (100 MHz, CDCl₃) δ 170.56, 161.78, 156.19, 134.80, 132.04, 117.50, 77.80, 67.02, 30.10, 28.88, 25.74, 21.64, 21.16.

Synthesis of L5-3:

To a mixture of the acetate L5-2 (4.80 g, 15.38 mmol) and K₂CO₃ (4.35 g, 30.77 mmol) was added MeOH (80 mL) and H₂O (80 mL). The mixture was stirred at room temperature overnight (about 18 hours). The solvent was removed under vacuum. The residue was dissolved in CH₂Cl₂ (50 mL) and water (50 mL) was added. The aqueous phase was washed with CH₂Cl₂ (3×30 mL), and the organic phase was combined and dried over anhydrous MgSO₄. The solvent was evaporated under vacuum to give the crude product, which was purified by flash chromatography (eluent:ethyl acetate/hexanes=1/2 to 1/1) to afford the alcohol L5-3 as a yellow solid (3.55 g, 85% yield). $^1$H NMR (400 MHz, CDCl$_3$)) δ 5.20-5.16 (m, 1H), 4.32-4.26 (m, 2H), 3.01-2.93 (m, 1H), 2.78-2.69 (m, 3H), 2.55-2.46 (m, 1H), 2.09-1.98 (m, 3H); $^{13}$C NMR (100 MHz, CDCl$_3$) δ 161.52, 160.70, 135.11, 130.75, 116.38, 75.18, 67.08, 31.80, 28.53, 25.61, 21.69.

Synthesis of L5-4a and L5-4b:

To a mixture of Ac-Phe-OH (4.35 g, 21 mmol), DMAP (2.56 g, 21 mmol) and DCC (4.33 g, 21 mmol) in CH$_2$Cl$_2$ (50 mL) was added alcohol L5-3 (1.89 g, 7 mmol). The mixture was stirred at room temperature for 18 hours. The resulting suspension was filtered using a funnel filled with Celite® to give a clear solution. After removing the solvent under vacuum, the crude products were separated by flash chromatography (eluent:ethyl acetate/CH$_2$Cl$_2$=1/1) to afford two diastereomeric esters: L5-4a (white solid, less polar, 1.32 g, 41% yield) and L5-4b (white solid, more polar, 1.29 g, 40% yield).

L5-4a: $^1$H NMR (400 MHz, CDCl$_3$) δ 7.32-7.25 (m, 2H), 7.24-7.16 (m, 3H), 6.13 (dd, J$_1$=3.8 Hz, J$_2$ 7.5 Hz, 1H), 5.93 (d, J=7.9 Hz, 1H), 4.86 (dt, J$_1$=5.8 Hz, J$_2$=7.8 Hz, 1i), 4.33-4.29 (m, 2H), 3.19 (dd, J$_1$=5.5 Hz, J$_2$=14.0 Hz, 1H), 3.08 (dd, J$_1$=5.9 Hz, J$_2$=14.0 Hz, 1H), 3.04-2.94 (m, 1H), 2.87-2.76 (m, 3H), 2.60-2.51 (m, 1H), 2.06 (dt, J$_1$=3.6 Hz, J$_2$=6.6 Hz, 3H), 1.96 (s, 3H); $^{13}$C NMR (100 MHz, CDCl$_3$) δ 171.06, 169.58, 161.82, 155.68, 135.81, 134.79, 132.46, 129.59, 128.43, 126.90, 117.86, 79.06, 67.07, 53.10, 37.58, 29.83, 28.99, 25.84, 23.12, 21.67.

L5-4b: $^1$H NMR (400 MHz, CDCl$_3$) δ 7.28-7.19 (m, 3H), 7.15-7.13 (m, 2H), 6.30 (d, J=7.7 Hz, 1H), 6.07 (dd, J=4.0 Hz, J$_2$=7.5 Hz, 1H), 4.90 (q, J=6.4 Hz, 1H), 4.28 (t, J=5.2 Hz, 2H), 3.17-3.07 (m, 2H), 2.94-2.87 (m, 1H), 2.81-2.73 (m, 3H), 2.53-2.43 (m, 1H), 2.05-1.99 (m, 2H), 1.96 (s, 3H), 1.92-1.84 (m, 18). $^{13}$C NMR (100 MHz, CDCl$_3$) δ 170.93, 169.26, 161.55, 155.26, 135.89, 134.53, 132.02, 129.19, 128.15, 126.69, 117.65, 78.65, 66.84, 53.08, 37.70, 29.44, 28.72, 25.55, 22.88, 21.39.

Synthesis of L5:

To a solution of lithium hydroxide monohydrate (28 mg, 0.66 mmol) in THF (2 mL) and H$_2$O (2 mL) was added ester L5-4a (100 mg, 0.22 mmol). The mixture was stirred overnight (about 18 hours) at room temperature. Aqueous NH$_4$Cl solution was added to the mixture and CH$_2$Cl$_2$ was used for extraction. After removing the solvent under vacuum, the crude products were separated by flash chromatography (eluent:ethyl acetate/hexanes=1/1) to afford the alcohol product L5-5 (48 mg, 80% yield), which has identical $^1$H and $^{13}$C NMR spectra as those of the racemic compound L5-3.

To a solution of alcohol L5-5 (122 mg, 0.45 mmol) in anhydrous THF (3 mL) was added NaH (54 mg, 60% w/w in mineral oil, 1.35 mmol) at 0° C. The suspension was stirred for 30 minutes before EtI (350 mg, 0.18 mL, 2.25 mmol) was added. The mixture was allowed to warm to room temperature and stirred overnight (about 18 hours). Aqueous NH$_4$Cl solution was added to the mixture and CH$_2$Cl$_2$ was used for extraction. After removing the solvent under vacuum, the crude product L5-6 was directly used for the next step without further purification.

To a solution of the crude bromide L5-6 in MeOH (2 mL) was added NaOMe (178 mg, 3.3 mmol) at room temperature. The tube was sealed and heated to 130° C. for 72 hours. The reaction mixture was allowed to cool down to room temperature before it was poured into a saturated aqueous NH$_4$Cl$_2$ solution. The aqueous phase was extracted with CH$_2$Cl$_2$ and the combined organic phase was dried over anhydrous MgSO$_4$. After filtration and removal of the organic solvent under vacuum, the crude product was subjected to preparative TLC separation (eluent:ethyl acetate/hexanes=1/3) to give the ether L5 as a light yellow oil (75 mg, 67% yield over two steps).

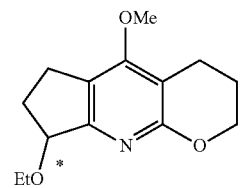 [SMILES: CCOC1CCc2c1nc1c(c2OC)CCCO1]

8-ethoxy-5-methoxy-2,3,4,6,7,8-hexahydrocyclopenta[b]pyrano[3,2-e]pyridine (L5)

$^1$H NMR (600 MHz, CDCl$_3$) δ 4.58 (dd, J$_1$=3.0 Hz, J$_2$=6.9 Hz, 1H), 4.26-4.19 (m, 2H), 3.97 (s, 3H), 3.88-3.82 (m, 1H), 3.65 (dq, J$_1$=7.0 Hz, J$_1$=9.4 Hz, 1H), 3.25-3.20 (m, 1H), 2.97-2.91 (m, 1H), 2.62 (q, J=6.4 Hz, 2H), 2.26-2.20 (m, 1H), 2.09-2.04 (m, 1H), 1.93-1.89 (m, 2H), 1.18 (t, J=7.0 Hz, 3H); $^{13}$C NMR (150 MHz, CDCl$_3$) δ 162.41, 161.86, 161.64, 117.03, 106.08, 81.55, 66.69, 64.82, 58.40, 30.94, 30.92, 27.44, 21.37, 19.56, 15.39; HRMS (ESI-TOF) Calcd for C$_{14}$H$_{10}$NO$_3$ [M+H]$^+$: 250.1438; found: 250.1434.

The absolute stereochemistry was not assigned.

Synthesis of Ligand L6

[Jordan et al., *Hetercycles* 33, 657-671. (1992)]

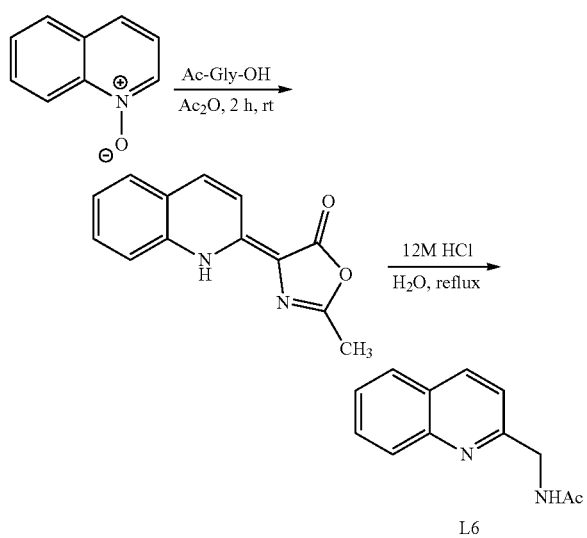

N-(quinolin-2-ylmethyl)acetamide (L6)

Gray solid $^1$H NMR (600 MHz, CDCl$_3$) δ 8.14 (d, J=8.4 Hz, 1H), 8.06 (dd, J$_1$=1.0 Hz, J$_1$=8.3 Hz, 1H), 7.82 (dd, J$_1$=1.4 Hz, J$_1$=8.2 Hz, 1H), 7.75-7.72 (m, 1H), 7.56-7.54 (m, 1H), 7.34 (d, J=8.4 Hz, 1H), 7.16 (br s, 1H), 4.75 (d, J=4.5 Hz, 2H), 2.16 (s, 3H); $^{13}$C NMR (150 MHz, CDCl$_3$) δ 169.75, 155.58, 146.79, 136.43, 129.35, 128.28, 127.26, 126.92, 126.00, 119.58, 44.54, 22.86.

Synthesis of Ligand L7:

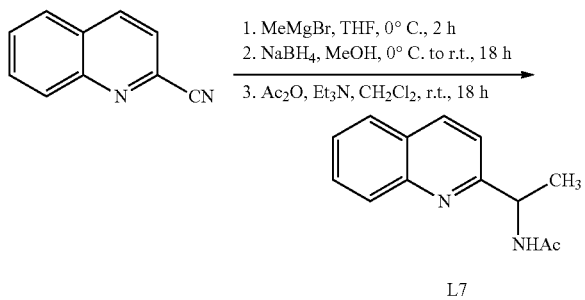

To a solution of 2-cyanoquinoline (308 mg, 2 mmol) in THF (5 mL) at 0° C. was added MeMgBr solution (3M in ether, 0.73 mL, 2.2 mmol) dropwise. After the mixture was stirred at 0° C. for 2 hours, NaBH$_4$ (91 mg, 2.4 mmol) was added followed by MeOH (5 mL). The mixture was stirred overnight (about 18 hours) at room temperature. The reaction was then quenched with aq. NH$_4$Cl solution and extracted with CH$_2$Cl$_2$. The combined extracts were washed with water, dried over anhydrous MgSO$_4$, and concentrated under vacuum. The resulting crude amine was dissolved in CH$_2$Cl$_2$ (3 mL). To the solution was added Ac$_2$O (612 mg, 0.58 mL, 6 mmol) and Et$_3$N (606 mg, 0.91 mL, 6 mmol). The mixture was stirred at room temperature for 18 hours. After the solvent was removed by vacuum, the crude product was purified by preparative thin layer chromatography (eluent:ethyl acetate/hexanes=1:2) to give L7 as a white solid (80 mg, 19% yield over three steps).

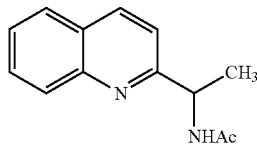 [SMILES: CC(=O)NC(C)c1ccc2ccccc2n1]

N-(1-(quinolin-2-yl)ethyl)acetamide (L7)

$^1$H NMR (600 MHz, CDCl$_3$) δ 8.14 (dd, J$_1$=0.8 Hz, J$_2$=8.5 Hz, 1H), 8.07-8.06 (m, 1H), 7.82 (dd, J=1.4 Hz, J$_2$=8.0 Hz, 1H), 7.74-7.71 (m, 1H), 7.55-7.53 (m, 1H), 7.43 (br s, 1H), 7.33 (d, J=8.4 Hz, 1H), 5.30-5.25 (m, 1H), 2.12 (s, 3H), 1.55 (d, J=6.8 Hz, 3H); $^{13}$C NMR (150 MHz, CDCl$_3$) δ 169.36, 160.78, 147.04, 136.86, 129.56, 128.69, 127.53, 127.18, 126.23, 119.52, 50.08, 23.44, 22.48; HRMS (ESI-TOF) Calcd for C$_{13}$H$_{15}$N$_2$O [M+H]$^+$: 215.1179; found: 215.1175.

Synthesis of Ligand L8:

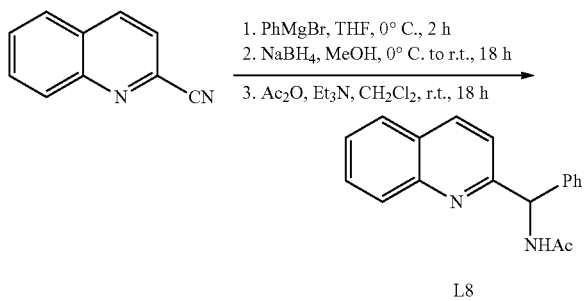

To a solution of 2-cyanoquinoline (308 mg, 2 mmol) in THF (5 mL) at 0° C. was added PhMgBr solution (lM in THF, 2.2 mL, 2.2 mmol) dropwise. After the mixture was stirred at 0° C. for 2 hours, NaBH$_4$ (91 mg, 2.4 mmol) was added followed by MeOH (5 mL). The mixture was stirred overnight (about 18 hours) at room temperature. The reaction was then quenched with aq. NH$_4$Cl solution and extracted with CH$_2$Cl$_2$. The combined extracts were washed with water, dried over anhydrous MgSO$_4$, and concentrated under vacuum. The resulting crude amine was dissolved in CH$_2$Cl$_2$ (3 mL). To the solution was added Ac$_2$O (612 mg, 0.58 mL, 6 mmol) and Et$_3$N (606 mg, 0.91 mL, 6 mmol). The mixture was stirred at room temperature for 18 hours. After the solvent was removed by vacuum, the crude product was purified by preparative thin layer chromatography (eluent:ethyl acetate/hexanes=1/2) to give L8 as a yellow solid (95 mg, 17% yield over three steps).

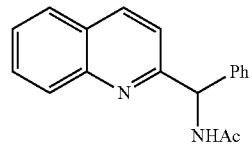 [SMILES: CC(=O)NC(c1ccccc1)c1ccc2ccccc2n1]

N-(phenyl (quinolin-2-yl)methyl)acetamide (L8)

$^1$H NMR (600 MHz, CDCl$_3$) δ 8.20-8.10 (m, 2H), 8.04 (dd, J$_1$=0.8 Hz, J$_2$=8.5 Hz, 1H), 7.78 (dd, J$_1$=1.4 Hz, J$_2$=8.2 Hz, 1H), 7.76-7.73 (m, 1H), 7.55-7.52 (m, 1H), 7.42-7.38 (m, 2H), 7.28 (dd, J$_1$=6.9 Hz, J$_2$=8.4 Hz, 2H), 7.25 (d, J=8.5 Hz, 1H), 7.23-7.20 (m, 1H), 6.28 (d, J=6.7 Hz, 1H), 2.13 (s, 3H); $^{13}$C NMR (150 MHz, CDCl$_3$) δ 169.23, 158.34, 146.80, 141.64, 136.86, 129.69, 128.92, 128.54, 127.77, 127.59, 127.49, 127.23, 126.50, 120.69, 57.76, 23.43; HRMS (ESI-TOF) Calcd for C$_{18}$H$_{17}$N$_2$O [M+H]$^+$: 277.1336; found: 277.1328.

Synthesis of Ligand L9 (32):

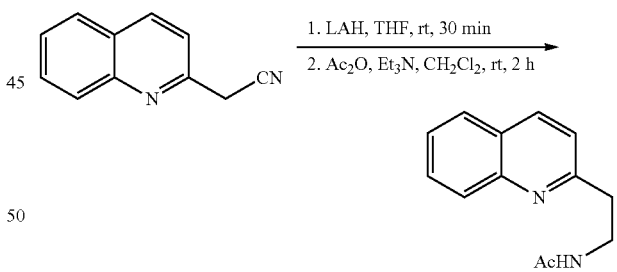

N-(2-(quinolin-2-yl)ethyl)acetamide (L9)

Gray solid. $^1$H NMR (600 MHz, CDCl$_3$) δ 8.10 (dd, J$_1$=0.8 Hz, J$_2$=8.4 Hz, 1H), 8.03-8.02 (m, 1H), 7.80 (dd, J$_1$=1.4 Hz, J$_2$=8.1 Hz, 1H), 7.73-7.69 (m, 1H), 7.53-7.51 (m, 1H), 7.30 (d, J=8.4 Hz, 1H), 6.64 (br s, 1H), 3.81-3.78 (m, 2H), 3.19-3.16 (m, 2H), 1.95 (s, 3H); $^{13}$C NMR (150 MHz, CDCl$_3$) δ 169.98, 160.15, 147.65, 136.61, 129.59, 128.80, 127.63, 126.85, 126.09, 121.79, 38.17, 37.50, 23.45; HRMS (ESI-TOF) Calcd for C$_{13}$H$_{15}$N$_2$O [M+H]$^+$: 215.1179; found: 215.1182.

Synthesis of Ligand L10:

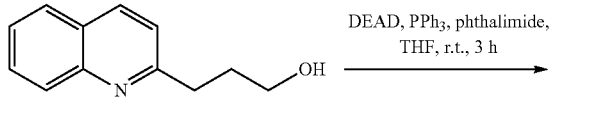

L10-1

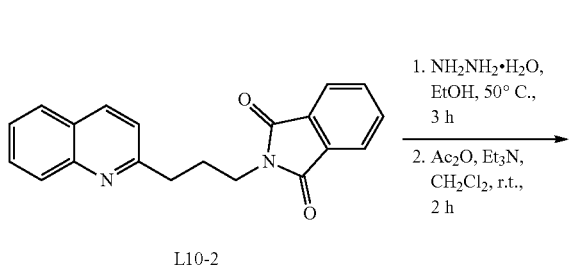

L10-2

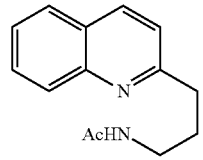 [SMILES: CC(=O)NCCCc1ccc2ccccc2n1]

N-(3-(quinolin-2-yl)propyl)acetamide (L10)

$^1$H NMR (400 MHz, CDCl$_3$) δ 8.06 (d, J=8.4 Hz, 1H), 8.01 (d, J=8.6 Hz, 1H), 7.77 (d, J=8.1 Hz, 1H), 7.68 (t, J=7.7 Hz, 1H), 7.49 (t, J=7.5 Hz, 1H), 7.28 (d, J=8.8 Hz, 1H), 6.75 (br s, 1H), 3.36-3.32 (m, 2H), 3.04 (t, J=7.3 Hz, 2H), 2.10-2.01 (m, 2H), 1.94 (s, 3H); $^{13}$C NMR (100 MHz, CDCl$_3$) δ 170.16, 161.77, 147.49, 136.48, 129.45, 128.31, 127.48, 126.62, 125.81, 121.41, 39.28, 36.28, 28.48, 23.14; HRMS (ESI-TOF) Calcd for C$_{14}$H$_{17}$N$_2$O [M+H]$^+$: 229.1335; found: 229.1337.

General Procedure for the Synthesis of L11-L33

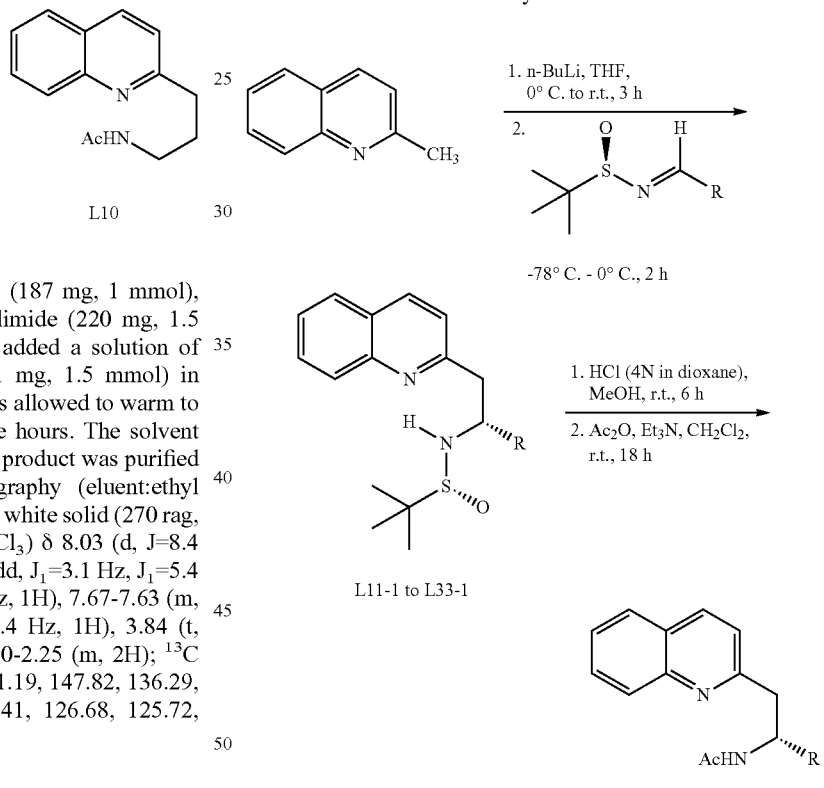

L11-1 to L33-1

L11-L33

To a mixture of alcohol L10-1 (33) (187 mg, 1 mmol), PPh$_3$ (393 mg, 1.5 mmol) and phthalimide (220 mg, 1.5 mmol) in THF (5 mL) at 0° C. was added a solution of diethyl azodicarboxylate (DEAD, 361 mg, 1.5 mmol) in THF (5 mL) dropwise. The mixture was allowed to warm to room temperature and stirred for three hours. The solvent was removed by vacuum and the crude product was purified by preparative thin layer chromatography (eluent:ethyl acetate/hexanes=2/3) to give L10-2 as a white solid (270 rag, 85% yield). $^1$H NMR (600 MHz, CDCl$_3$) δ 8.03 (d, J=8.4 Hz, 1H), 7.98 (d, J=8.5 Hz, 1H), 7.78 (dd, J$_1$=3.1 Hz, J$_1$=5.4 Hz, 2H), 7.72 (dd, J$_1$=1.5 Hz, J$_2$=8.1 Hz, 1H), 7.67-7.63 (m, 3H), 7.46-7.43 (m, 1H), 7.30 (d, J=8.4 Hz, 1H), 3.84 (t, J=7.0 Hz, 2H), 3.06-3.04 (m, 2H), 2.30-2.25 (m, 2H); $^{13}$C NMR (150 MHz, CDCl$_3$) δ 168.34, 161.19, 147.82, 136.29, 133.77, 132.05, 129.32, 128.80, 127.41, 126.68, 125.72, 123.05, 121.26, 37.82, 36.39, 28.07.

For L10:

To a suspension of phthalimide L10-2 (150 mg, 0.47 mmol) in EtOH (3 mL) was added hydrazine hydrate (117 mg, 2.4 mmol) at room temperature. The mixture was heated to 50° C. and stirred for three hours. Removal of the solvent and extra hydrazine afforded a white solid. To the solid was added CH$_2$Cl$_2$ and filtered. The filtrate was concentrated and CH$_2$Cl$_2$ (5 mL) was added to the flask. To the solution was added Ac$_2$O (153 mg, 0.15 mL, 1.5 mmol) and Et$_3$N (152 mg, 0.23 mL, 1.5 mmol). The mixture was stirred at room temperature for 18 hours. After removing the solvent, the resulting mixture was filtered and the solid was washed with CH$_2$Cl$_2$. The filtrate was condensed under vacuum and purified by preparative TLC (eluent: methanol/CH$_2$Cl$_2$=1/20) to give L10 as a light brown oil (80 mg, 61% yield over two steps) which became a solid upon standing.

Synthesis of tert-Butanesulfinyl Amines L11-1 to -L33-1 [Liu et al., *J. Org. Chem.* 64, 1278-1284 (1999)]

To a solution of 2-methylquinoline (643 mg, 0.6 mL, 4.5 mmol) in anhydrous THF (5 mL) at 0° C. was added n-butyllithium (2.5 M in hexanes, 1.8 mL, 4.5 mmol) dropwise. The resulting solution was allowed to warm to room temperature gradually and stirred for three hours. Then the mixture was cooled down to −78° C., to which the enantiomerically pure tert-butanesulfinyl imine (3 mmol) in anhydrous THF (5 mL) was added dropwise. The resulting mixture was allowed to warm to 0° C. over two hours, and then treated with saturated aqueous NH$_4$Cl solution. The product was extracted with dichloromethane. The combined extracts were washed with water, dried over anhydrous MgSO$_4$, and concentrated under vacuum. The sulfinyl amine was purified by column chromatography (eluent:ethyl acetate/hexanes=1/3)

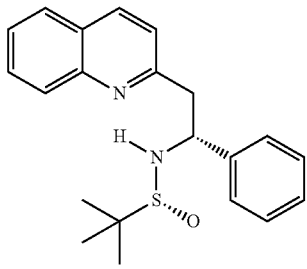

(R)-1-tert-butyl-1-($\lambda^1$-oxidanyl)-N-(1-phenyl-2-(quinolin-2-yl)ethyl)-$\lambda^3$-sulfanamine (L17-1)

Yellow foam. $^1$H NMR (500 MHz, CDCl$_3$) δ 8.03 (dd, J$_1$=1.2 Hz, J$_2$=8.4 Hz, 1H), 7.99 (d, J=8.4 Hz, 1H), 7.76 (d, J=8.0 Hz, 1H), 7.70 (ddd, J$_1$=1.5 Hz, J$_2$=6.9 Hz, J$_1$=8.4 Hz, 1H), 7.50 (ddd, J$_1$=1.2 Hz, J$_2$=6.9 Hz, J; =8.1 Hz, 1H), 7.39 (dd, J$_1$=1.5 Hz, J$_2$=7.1 Hz, 2H), 7.30 (t, J=7.2 Hz, 2H), 7.26-7.22 (m, 1H), 7.11 (d, J=8.4 Hz, 1H), 5.02 (dt, J$_1$=5.3 Hz, J$_2$=8.0 Hz, 1H), 4.81 (d, J=5.1 Hz, 1H), 3.59 (dd, J$_1$=8.1 Hz, J$_2$=14.2 Hz, 1H), 3.43 (dd, J$_1$=5.5 Hz, J$_2$=14.2 Hz, 1H), 1.10 (s, 9H); $^{13}$C NMR (125 MHz, CDCl$_3$) δ 158.82, 147.64, 141.84, 136.24, 129.53, 128.79, 128.53, 127.67, 127.53, 127.29, 126.77, 126.05, 122.23, 59.30, 56.10, 46.13, 22.47.

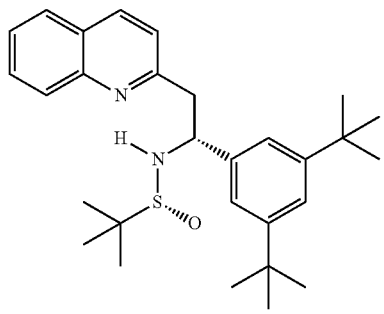

(R)-1-tert-butyl-N-(1-(3,5-di-tert-butylphenyl)-2-(quinolin-2-yl)ethyl)-1-($\lambda^1$-oxidanyl)-$\lambda^3$-sulfanamine (L32-1)

Yellow foam. $^1$H NMR (400 MHz, CDCl$_3$) δ 8.07 (dd, J$_1$=1.0 Hz, J$_1$=8.4 Hz, 2H), 7.82-7.73 (m, 2H), 7.57-7.53 (m, 1H), 7.34-7.32 (m, 2H), 7.26 (s, 1H), 7.16 (d, J=8.4 Hz, 1H), 5.06 (dt, J$_1$=5.2 Hz, J$_2$=9.1 Hz, 1H), 4.65 (d, J=4.5 Hz, 1H), 3.65 (dd, J$_1$=8.3 Hz, J$_2$=14.0 Hz, 1H), 3.48 (dd, J$_1$=5.5 Hz, J$_2$=14.0 Hz, 1H), 1.32 (s, 188H), 1.14 (s, 9H); $^{13}$C NMR (150 MHz, CDCl$_3$) δ 159.14, 150.80, 147.68, 140.95, 136.10, 129.48, 128.80, 127.48, 126.79, 126.00, 122.27, 121.55, 121.44, 59.64, 56.06, 46.57, 34.85, 31.41, 22.49. HRMS (ESI-TOF) Calcd for C$_{29}$H$_{41}$N$_2$OS [M+H]$^+$: 465.2934; found: 465.2934.

Synthesis of L11-L33

To a solution of tert-butanesulfinyl amine (1 equiv.) in MeOH at room temperature was added HCl solution (4N in dioxane, 4 equiv.). The mixture was stirred for 6 hours before the solvent was removed under vacuum. To the resulting foam was added CH$_2$Cl$_2$ and Et$_3$N (4 equiv.) at room temperature, followed by the addition of acetic anhydride (4 equiv.). The mixture was stirred overnight (about 18 hours) before it was treated with saturated aqueous Na$_2$CO$_3$ solution. The product was extracted with dichloromethane. The combined extracts were washed with water, dried over anhydrous MgSO$_4$, and concentrated under vacuum. Flash chromatography gave the ligand as a white solid or colorless oil.

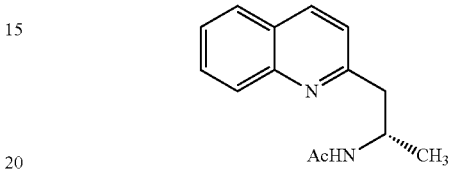

(S)—N-(1-(quinolin-2-yl)propan-2-yl)acetamide (L11)

White solid. $^1$H NMR (600 MHz, CDCl$_3$) δ 8.11 (d, J=8.4 Hz, 11i), 8.02 (d, J=8.5 Hz, 1H), 7.81 (d, J=8.1 Hz, 1H), 7.71 (t, J=7.7 Hz, 1H), 7.52 (t, J=7.5 Hz, 1H), 7.33 (d, J=8.4 Hz, 1H), 6.78 (br s, 1H), 4.47 (t, J=6.7 Hz, 1H), 3.19 (dd, J$_1$=5.3 Hz, J=14.0 Hz, 1H), 3.07 (dd, J$_1$=6.7 Hz, J$_2$=13.9 Hz, 1H), 1.92 (s, 3H), 1.21 (d, J=6.6 Hz, 3H); $^{13}$C NMR (150 MHz, CDCl$_3$) δ 169.32, 159.47, 147.56, 136.62, 129.62, 128.77, 127.65, 126.84, 126.12, 122.25, 45.33, 44.11, 23.57, 20.43; HRMS (ESI-TOF) Calcd for C$_{14}$H$_{17}$N$_2$O [M+H]$^+$: 229.1335; found: 229.1336.

The absolute stereochemistry was assigned by analogy to compound L13.

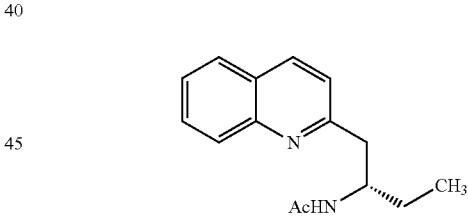

(S)—N-(1-(quinolin-2-yl)butan-2-yl)acetamide (L12)

White solid. $^1$H NMR (600 MHz, CDCl$_3$) δ 8.09 (d, J=8.4 Hz, 1H), 8.01-8.00 (m, 1H), 7.79 (dd, J; =1.4 Hz, J$_2$=8.1 Hz, 1H), 7.71-7.69 (m, 1H), 7.52-7.50 (m, 1H), 7.33 (d, J=8.4 Hz, 1H), 6.67 (d, J=8.5 Hz, 1H), 4.34-4.30 (m, 1H), 3.20 (dd, J$_1$=5.0 Hz, J$_2$=14.2 Hz, 1H), 3.08 (dd, J=7.1 Hz, J$_2$=14.1 Hz, 1H), 1.91 (s, 3H), 1.58-1.53 (m, 2H), 0.95 (t, J=7.4 Hz, 3H); $^{13}$C NMR (150 MHz, CDCl$_4$) δ 169.13, 159.24, 147.06, 136.16, 129.14, 128.25, 127.21, 126.37, 125.62, 121.70, 50.28, 41.53, 27.04, 23.09, 10.10; HRMS (ESI-TOF) Calcd for C$_{15}$H$_{19}$N$_2$O [M+H]+: 243.1492; found: 243.1489.

The absolute stereochemistry was assigned by analogy to compound L13.

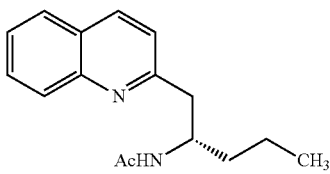 [SMILES: CCC[C@@H](Cc1ccc2ccccc2n1)NC(C)=O]

(S)—N-(1-(quinolin-2-yl)pentan-2-yl)acetamide (L13)

White solid, $[\alpha]_D^{20}$=−70.5 (c=0.89, CHCl$_3$). m.p.=129-131° C. $^1$H NMR (600 MHz, CDCl$_3$) δ 8.10-8.09 (m, 1H), 8.02-8.00 (m, 1H), 7.81-7.79 (m, 1H), 7.72-7.69 (m, 1H), 7.53-7.50 (m, 1H), 7.33 (d, J=8.4 Hz, 1H), 6.65 (d, J=8.6 Hz, 1H), 4.44-4.39 (m, 1H), 3.21 (dd, J$_1$=5.0 Hz, J$_2$=14.2 Hz, 1H), 3.07 (dd, J$_1$=6.9 Hz, J$_2$=14.2 Hz, 1H), 1.92 (s, 3H), 1.52-1.46 (m, 2H), 1.43-1.37 (m, 2H), 0.89 (t, J=7.2 Hz, 3H); $^{13}$C NMR (150 MHz, CDCl$_3$) δ 168.99, 159.29, 147.07, 136.12, 129.12, 128.30, 127.21, 126.37, 125.61, 121.74, 48.66, 42.03, 36.40, 23.11, 18.97, 13.50; HRMS (ESI-TOF) Calcd for C$_{16}$H$_{21}$N$_2$O [M+H]$^+$: 257.1648; found: 257.1647.

A suitable crystal of L13 for X-ray analysis was obtained using diffusion method from CHCl$_3$ and hexanes.

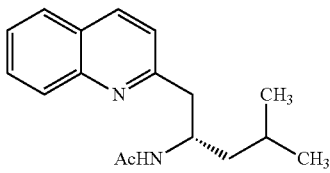 [SMILES: CC(=O)N[C@H](Cc1ccc2ccccc2n1)CC(C)C]

(S)—N-(4-methyl-1-(quinolin-2-yl)pentan-2-yl)acetamide (L14)

White solid. $^1$H NMR (400 MHz, CDCl$_3$) δ 8.13 (d, J=8.4 Hz, 1H), 8.05 (d, J=8.5 Hz, 1H), 7.80 (dd, J$_1$=1.4 Hz, J$_2$=8.2 Hz, 1H), 7.72-7.68 (m, 1H), 7.54-7.50 (m, 1H), 7.40 (d, J=8.4 Hz, 1H), 6.87 (d, J=9.2 Hz, 1H), 6.34 (br s, 1H), 4.54-4.46 (m, 1H), 3.20 (dd, J$_1$=4.8 Hz, J$_2$=13.8 Hz, 1H), 3.03 (dd, J=8.6 Hz, J$_2$=13.8 Hz, 1H), 2.12 (s, 3H), 1.72-1.65 (m, 1H), 1.50-1.43 (m, 1H), 1.37-1.30 (m, 1H), 0.93 (d, J=6.6 Hz, 6H); $^{13}$C NMR (100 MHz, CDCl$_3$) δ 169.87, 159.63, 146.52, 137.35, 129.90, 127.74, 127.49, 126.87, 126.29, 122.16, 47.71, 44.57, 42.95, 25.02, 23.06, 22.89, 22.36; HRMS (ESI-TOF) Calcd for C$_{17}$H$_{23}$N$_2$O [M+H]$^+$: 271.1805; found: 271.1796.

The absolute stereochemistry was assigned by analogy to compound L13.

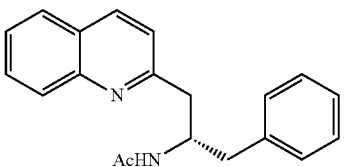 [SMILES: CC(=O)N[C@@H](Cc1ccccc1)Cc1ccc2ccccc2n1]

(S)—N-(1-phenyl-3-(quinolin-2-yl)propan-2-yl)acetamide (L15)

White solid. $^1$H NMR (600 MHz, CDCl$_3$) δ 8.09 (d, J=8.4 Hz, 1H), 8.03-8.01 (m, 1H), 7.81 (dd, J=1.4 Hz, J=8.2 Hz, 1H), 7.73-7.70 (m, 1H), 7.54-7.51 (m, 1H), 7.30 (dd, J$_1$=6.8 Hz, J$_2$=8.2 Hz, 2H), 7.25-7.20 (m, 4H), 7.00 (d, J=8.1 Hz, 1H), 4.64 (m, 1H), 3.17 (dd, J$_1$=4.9 Hz, J$_2$=14.5 Hz, 1H), 3.05 (dd, J$_1$=5.5 Hz, J$_2$=13.6 Hz, 1H), 2.98 (dd, J$_1$=7.2 Hz, J$_7$=14.5 Hz, 1H), 2.76 (dd, J$_1$=8.3 Hz, J$_2$=13.6 Hz, 1H), 1.91 (s, 3H); $^{13}$C NMR (150 MHz, CDCl$_3$) δ 169.48, 159.56, 147.48, 138.18, 136.61, 129.62, 129.47, 128.70, 128.43, 127.66, 126.81, 126.44, 126.14, 122.29, 50.64, 40.54, 40.14, 23.53; HRMS (ESI-TOF) Calcd for C$_{20}$H$_{21}$N$_2$O [M+H]$^+$: 305.1648; found: 305.1645.

The absolute stereochemistry was assigned by analogy to compound L13.

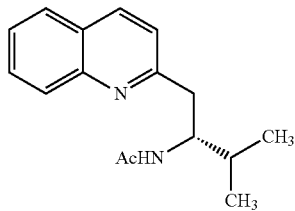 [SMILES: CC(=O)N[C@H](Cc1ccc2ccccc2n1)C(C)C]

(R)—N-(3-methyl-1-(quinolin-2-yl)butan-2-yl)acetamide (L16)

White solid. $^1$H NMR (600 MHz, CDCl$_3$) δ 8.11 (d, J=8.4 Hz, 1H), 8.00 (d, J=8.4 Hz, 1H), 7.81-7.80 (m, 1H), 7.72-7.70 (m, 1H), 7.54-7.51 (m, 1H), 7.37 (d, J=8.4 Hz, 1H), 6.49 (d, J=9.2 Hz, 1H), 4.43-4.39 (m, 1H), 4.27-4.22 (m, 1H), 3.21 (dd, J$_1$=4.2 Hz, J$_2$=14.2 Hz, 1H), 3.03 (dd, J$_1$=9.1 Hz, J$_2$=14.2 Hz, 1H), 1.88-1.84 (m, 4H), 0.99 (d, J=6.6 Hz, 3H), 0.98 (d, J=6.6 Hz, 3H); $^{13}$C NMR (150 MHz, CDCl$_3$) δ 170.06, 159.93, 137.01, 129.78, 128.19, 127.75, 126.86, 126.19, 121.93, 54.67, 40.02, 31.95, 23.28, 19.11, 18.58; HRMS (ESI-TOF) Calcd for C$_{16}$H$_{21}$N$_2$O [M+H]$^+$: 257.1648; found: 257.1650.

The absolute stereochemistry was assigned by analogy to compound L13.

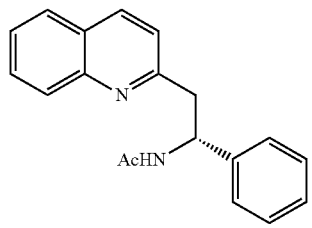 [SMILES: CC(=O)N[C@H](Cc1ccc2ccccc2n1)c1ccccc1]

(R)—N-(1-phenyl-2-(quinolin-2-yl)ethyl)acetamide (L17)

White solid. $^1$H NMR (600 MHz, CDCl$_3$) δ 8.05 (dd, J$_1$=1.0 Hz, J$_2$=8.4 Hz, 1H), 8.01 (dd, J$_1$=0.8 Hz, J$_2$=8.4 Hz, 1H), 7.78 (dd, J$_1$=1.3 Hz, J$_2$=8.0 Hz, 1H), 7.74-7.71 (m, 1H), 7.54-7.51 (m, 2H), 7.26-7.22 (m, 4H), 7.20-7.17 (m, 1H), 7.11 (d, J=8.4 Hz, 1H), 5.48 (dt, J$_1$=4.9 Hz, J$_2$=7.5 Hz, 1H), 3.49 (dd, J$_1$=4.9 Hz, J$_2$=14.0 Hz, 1H), 3.35 (dd, J$_1$=7.6 Hz, $J_2$=14.0 Hz, 1H), 1.97 (s, 3H). $^{13}$C NMR (150 MHz, CDCl$_3$) δ 168.89, 158.46, 147.00, 141.35, 136.18, 129.24, 128.25, 127.96, 127.25, 126.66, 126.42, 125.81, 125.77, 121.77, 52.69, 43.83, 22.96; HRMS (ESI-TOF) Calcd for C$_{19}$H$_{19}$N$_2$O [M+H]$^+$: 291.1492; found: 291.1491.

The absolute stereochemistry was assigned by analogy to compound L21.

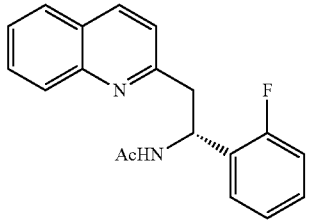 [SMILES: CC(=O)N[C@H](Cc1ccc2ccccc2n1)c1ccccc1F]

(R)—N-(1-(2-fluorophenyl)-2-(quinolin-2-yl)ethyl)acetamide (L18)

White solid. $^1$H NMR (600 MHz, CDCl$_3$) δ 8.03 (d, J=8.5 Hz, 1H), 7.95 (d, J=8.4 Hz, 1H), 7.75-7.67 (m, 3H), 7.49-7.46 (m, 1H), 7.14-7.06 (m, 3H), 7.01-6.97 (m, 1H), 6.90 (dt, $J_1$=1.2 Hz, $J_2$=7.5 Hz, 1H), 5.72 (dd, $J_1$=5.1 Hz, $J_2$=7.6 Hz, 1H), 3.45 (dd, $J_1$=5.2 Hz, $J_2$=14.0 Hz, 1H), 3.38 (dd, $J_1$=7.6 Hz, $J_2$=14.0 Hz, 1H), 1.95 (s, 3H); $^{13}$C NMR (150 MHz, CDCl$_3$) δ 169.24, 160.11 (d, $J_{FC}$=244.5 Hz), 158.51, 147.27, 136.46, 129.48, 128.58 (d, $J_{FC}$=4.5 Hz), 128.53, 128.50, 127.81 (d, $J_{FC}$=4.5 Hz), 127.51, 126.69, 126.03, 123.82 (d, $J_{FC}$=3 Hz), 121.87, 115.32 (d, $J_{FC}$=22.5 Hz), 48.49 (d, $J_{FC}$=1.5 Hz), 42.85 (d, $J_{FC}$=1.5 Hz), 23.08; HRMS (ESI-TOF) Calcd for C$_{19}$H$_{18}$FN$_2$O [M+H]$^+$: 309.1398; found: 309.1398.

The absolute stereochemistry was assigned by analogy to compound L21.

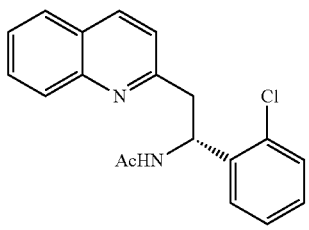 [SMILES: CC(=O)N[C@H](Cc1ccc2ccccc2n1)c1ccccc1C(F)(F)F]

(R)—N-(1-(2-chlorophenyl)-2-(quinolin-2-yl)ethyl)acetamide (L19)

White solid. $^1$H NMR (600 MHz, CDCl$_3$) δ 8.07-8.05 (m, 1H), 7.98 (d, J=8.3 Hz, 1H), 7.87 (d, J=6.9 Hz, 1H), 7.77 (dd, $J_1$=1.4 Hz, $J_2$=8.2 Hz, 1H), 7.73-7.70 (m, 1H), 7.53-7.50 (m, 1H), 7.34 (dd, $J_1$=1.2 Hz, $J_2$=7.9 Hz, 1H), 7.11-7.07 (m, 2H), 7.05-7.00 (m, 2H), 5.75 (dt, $J_1$=4.5 Hz, $J_2$=7.3 Hz, 1H), 3.49 (dd, $J_1$=4.5 Hz, $J_2$=14.0 Hz, 1H), 3.33 (dd, $J_1$=7.7 Hz, $J_2$=14.0 Hz, 1H), 1.97 (s, 3H). $^{13}$C NMR (150 MHz, CDCl$_3$) δ 169.25, 158.68, 147.27, 138.98, 136.65, 135.05, 132.21, 129.66, 129.64, 128.55, 128.14, 127.64, 127.09, 126.82, 126.66, 126.18, 122.08, 50.97, 41.94, 23.17; HRMS (ESI-TOF) Calcd for C$_{19}$H$_{18}$ClN$_2$O [M+H]$^+$: 325.1102; found: 325.1105.

The absolute stereochemistry was assigned by analogy to compound L21.

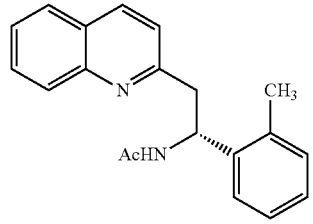

(R)—N-(2-(quinolin-2-yl)-1-(o-tolyl)ethyl)acetamide (L20)

White solid. $^1$H NMR (600 MHz, CDCl$_3$) δ 8.07 (d, J=8.5 Hz, 1H), 8.02 (d, J=8.4 Hz, 1H), 7.78 (dd, $J_1$=1.4 Hz, $J_2$=8.1 Hz, 1H), 7.74-7.71 (m, 1H), 7.54-7.51 (m, 1H), 7.31 (br s, 1H), 7.14-7.08 (m, 3H), 7.07-7.02 (m, 2H), 5.65 (dt, $J_1$=5.2 Hz, $J_2$=7.6 Hz, 1H), 3.40 (dd, $J_1$=5.2 Hz, $J_1$=13.8 Hz, 1H), 3.29 (dd, $J_1$=7.9 Hz, $J_2$=13.8 Hz, 1H), 2.49 (s, 3H), 1.92 (s, 3H). $^{13}$C NMR (150 MHz, CDCl$_3$) δ 169.12, 158.84, 147.39, 139.96, 136.63, 135.05, 130.53, 129.68, 128.62, 127.67, 126.99, 126.86, 126.19, 126.01, 125.25, 122.07, 49.83, 43.42, 23.23, 19.27. Calcd for C$_{20}$H$_{21}$N$_2$O [M+H]$^+$: 305.1648; found: 305.1647.

The absolute stereochemistry was assigned by analogy to compound L21.

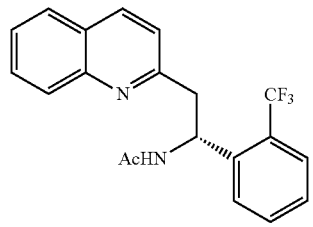

(R)—N-(2-(quinolin-2-yl)-1-(2-(trifluoromethyl)phenyl)ethyl)acetamide (L21)

White solid. $^1$H NMR (600 MHz, CDCl$_3$) δ 8.09-8.02 (m, 2H), 7.94 (d, J=5.8 Hz, 1H), 7.79 (dd, $J_1$=1.4 Hz, $J_2$=8.0 Hz, 1H), 7.74-7.71 (m, 1H), 7.65 (dd, $J_1$=1.4 Hz, $J_2$=7.8 Hz, 1H), 7.55-7.52 (m, 1H), 7.37-7.27 (m, 3H), 7.16 (d, J=8.4 Hz, 1H), 5.69 (dq, $J_1$=4.4 Hz, $J_2$=9.4 Hz, 1H), 3.45 (dd, $J_1$=4.1 Hz, $J_2$=14.0 Hz, 1H), 3.19 (dd, $J_1$=8.9 Hz, $J_2$=14.0 Hz, 1H), 1.90 (s, 3H); $^{13}$C NMR (150 MHz, CDCl$_3$) δ 169.40, 158.48, 147.25, 141.66 (q, $J_{FC}$=1.5 Hz), 136.98, 131.86, 129.76, 128.46, 127.70, 127.11, 127.05 (q, $J_{FC}$=30 Hz), 127.00, 126.91, 126.30, 126.02 (q, $J_{FC}$=6.0 Hz), 124.54 (q, $J_{FC}$=273 Hz), 122.01, 50.34 (q, $J_{FC}$=1.5 Hz), 44.44, 22.97; HRMS (ESI-TOF) Calcd for C$_{20}$H$_{18}$F$_3$N$_2$O [M+H]$^+$: 359.1365; found: 359.1366.

A suitable crystal of L21 for X-ray analysis was obtained using diffusion method from CHCl$_3$ and hexanes.

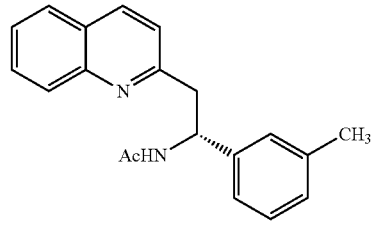 [SMILES: CC(=O)N[C@H](Cc1ccc2ccccc2n1)c1cccc(C)c1]

(R)—N-(2-(quinolin-2-yl)-1-(m-tolyl)ethyl)acetamide (L22)

White solid. $^1$H NMR (400 MHz, CDCl$_3$) δ 8.07 (d, J=8.4 Hz, 1H), 8.03 (d, J=8.4 Hz, 1H), 7.78 (d, J=8.1 Hz, 1H), 7.72 (t, J=7.7 Hz, 1H), 7.52 (t, J=7.5 Hz, 1H), 7.47 (d, J=7.7 Hz, 1H), 7.16 (d, J=8.3 Hz, 1H), 7.12 (d, J=7.5 Hz, 1H), 7.09 (s, 1H), 7.01 (t, J=8.6 Hz, 2H), 5.44 (q, J=7.5 Hz, 1H), 3.47 (dd, J$_1$=4.9 Hz, J$_2$=13.9 Hz, 1H), 3.35 (dd, J$_1$=8.0 Hz, J$_2$=13.9 Hz, 1H), 2.28 (s, 3H), 1.93 (s, 3H). $^{13}$C NMR (100 MHz, CDCl$_3$) δ 169.29, 158.87, 147.14, 141.72, 137.96, 136.76, 129.73, 128.43, 128.27, 127.88, 127.65, 127.11, 126.83, 126.23, 123.18, 122.13, 53.13, 44.30, 23.31, 21.39. HRMS (ESI-TOF) Calcd. for C$_{20}$H$_{21}$N$_2$O [M+H]$^+$: 305.1649; found: 305.1647.

The absolute stereochemistry was assigned by analogy to compound L21.

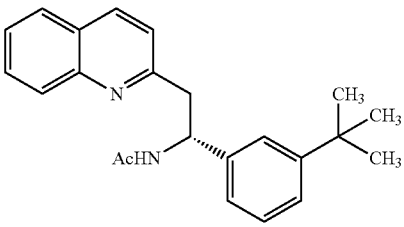 [SMILES: CC(=O)N[C@H](Cc1ccc2ccccc2n1)c1cccc(C(C)(C)C)c1]

(R)—N-(1-(3-(tert-butyl)phenyl)phenyl-2-(quinolin-2-yl)ethyl)acetamide (L23)

Yellow oil. $^1$H NMR (400 MHz, CDCl$_3$) δ 8.04 (d, J=8.5 Hz, 1H), 7.97 (d, J=8.4 Hz, 1H), 7.75 (d, J=8.1 Hz, 1H), 7.72-7.67 (m, 1H), 7.52-7.47 (m, 2H), 7.23-7.15 (m, 3H), 7.09 (dd, J$_1$=7.7 Hz, J$_2$=14.6 Hz, 2H), 5.51 (dt, J$_1$=4.8 Hz, J$_2$=7.7 Hz, 1H), 3.47 (dd, J$_1$=5.1 Hz, J$_2$=13.9 Hz, 1H), 3.35 (dd, J$_1$=7.6 Hz, J=13.8 Hz, 1H), 1.93 (s, 3H), 1.19 (s, 9H). $^{13}$C NMR (100 MHz, CDCl$_3$) δ 169.17, 158.97, 150.99, 147.38, 141.27, 136.34, 129.49, 128.57, 127.98, 127.52, 126.74, 126.02, 123.99, 123.36, 123.28, 122.10, 53.28, 44.55, 34.47, 31.14, 23.26. HRMS (ESI-TOF) Calcd for C$_{23}$H$_{27}$N$_2$O [M+H]$^+$: 347.2118; found: 347.2119.

The absolute stereochemistry was assigned by analogy to compound L21.

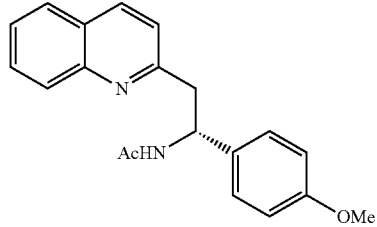 [SMILES: COc1ccc([C@@H](Cc2ccc3ccccc3n2)NC(C)=O)cc1]

(R)—N-(1-(4-methoxyphenyl)-2-(quinolin-2-yl)ethyl)acetamide (L24)

Yellow oil. $^1$H NMR (600 MHz, CDCl$_3$) δ 8.04 (d, J=8.4 Hz, 1H), 8.01 (d, J=8.4 Hz, 1H), 7.78 (dd, J$_1$=1.4 Hz, J$_2$=8.1 Hz, 1H), 7.73-7.70 (m, 1H), 7.53-7.50 (m, 1H), 7.44 (d, J=7.5 Hz, 1H), 7.16-7.14 (m, 2H), 7.13 (d, J=8.4 Hz, 1H), 6.79-6.76 (m, 2H), 5.44 (dt, J$_1$=5.1 Hz, J$_2$=7.5 Hz, 1H), 3.74 (s, 3H), 3.46 (dd, J=5.1 Hz, J$_2$=13.9 Hz, 1H), 3.34 (dd, J$_1$=7.6 Hz, J$_2$=14.0 Hz, 1H), 1.94 (s, 3H). $^{13}$C NMR (150 MHz, CDCl$_3$) δ 169.25, 159.00, 158.55, 147.41, 136.57, 133.95, 129.62, 128.65, 127.66, 127.42, 126.83, 126.15, 122.20, 113.76, 55.17, 52.57, 44.34, 23.37. HRMS (ESI-TOF) Calcd for C$_{20}$H$_{21}$N$_2$O$_2$[M+H]$^+$: 321.1598; found: 321.1593.

The absolute stereochemistry was assigned by analogy to compound L21.

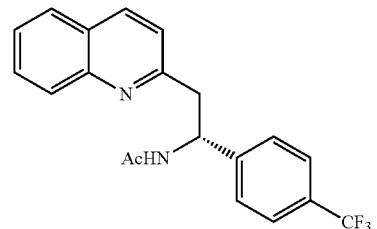

(R)—N-(2-(quinolin-2-yl)-1-(4-(trifluoromethyl)phenyl)ethyl)acetamide (L25)

$^1$H NMR (600 MHz, CDCl$_3$) δ 8.05 (d, J=8.6 Hz, 1H), 8.03 (d, J=8.4 Hz, 1H), 7.95 (d, J=6.9 Hz, 1H), 7.80 (dd, J$_1$=1.3 Hz, J$_2$=8.1 Hz, 1H), 7.75 (ddd, J$_1$=1.4 Hz, J$_1$=6.9 Hz, J$_2$=8.4 Hz, 1H), 7.55 (ddd, J$_1$=1.2 Hz, J$_1$=6.9 Hz, J$_1$=8.1 Hz, 1H), 7.49 (d, J=7.9 Hz, 2H), 7.33 (d, J=7.9 Hz, 2H), 7.06 (d, J=8.4 Hz, 1H), 5.49 (dt, J$_3$ 4.7 Hz, J$_2$=7.0 Hz, 1H), 3.51 (dd, J$_1$=4.8 Hz, J$_2$=14.2 Hz, 1H), 3.33 (dd, J$_1$=7.2 Hz, J=14.2 Hz, 1H), 2.02 (s, 3H); $^{13}$C NMR (150 MHz, CDCl$_3$) 169.55, 158.28, 147.34, 145.98 (q, J$_{FC}$=1.4 Hz), 136.96, 129.94, 129.28 (q, J$_{FC}$=32.3 Hz), 128.62, 127.76, 126.89, 126.57, 126.46, 125.37 (q, J$_{FC}$=3.8 Hz), 124.07 (q, J$_{FC}$=272.0 Hz), 122.19, 52.96, 43.56, 23.35; $^{19}$F NMR (375 MHz, CDCl$_3$) δ −62.7; HRMS (ESI-TOF) Calcd for C$_{20}$H$_{18}$F$_3$N$_2$O [M+H]$^+$ 359.1366, found 359.1364.

The absolute stereochemistry was assigned by analogy to compound L21.

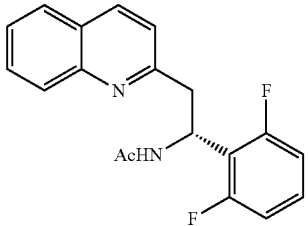 [SMILES: CC(=O)N[C@H](Cc1ccc2ccccc2n1)c1c(F)cccc1F]

(R)—N-(1-(2,6-difluorophenyl)-2-(quinolin-2-yl)ethyl)acetamide (L26)

White oil. $^1$H NMR (600 MHz, CDCl$_3$) δ 8.06 (d, J=8.4 Hz, 1H), 8.01 (dt, J$_1$=0.9 Hz, J$_2$=8.4 Hz, 1H), 7.77 (dd, J$_1$=1.4 Hz, J$_2$=8.2 Hz, 1H), 7.70-7.67 (m, 1H), 7.51-7.49 (m, 1H), 7.29 (d, J=8.4 Hz, 1H), 7.18-7.13 (m, 1H), 6.85-6.80 (m, 3H), 5.96 (dt, J$_1$=6.0 Hz, J$_2$=8.6 Hz, 1H), 3.51 (dd, J$_1$=8.8 Hz, J$_2$=13.7 Hz, 1H), 3.42 (dd, J$_1$=6.0 Hz, J$_2$=13.7 Hz, 1H), 1.88 (s, 3H); $^{13}$C NMR (150 MHz, CDCl$_3$) δ 169.28, 160.87 (dd, J$_{FC1}$=246 Hz, J$_{FC2}$=9 Hz), 157.92, 147.6:3, 136.67, 129.53, 128.97 (t, J$_{FC}$=10.5 Hz), 128.79, 127.57, 126.89, 126.15, 121.42, 117.33 (t, J$_{FC}$=16.5 Hz), 111.63 (dd, J$_{FC1}$=4.5 Hz, F$_{FC2}$=21.0 Hz), 44.70 (t, J$_{FC}$=1.5 Hz), 43.45, 23.12; HRMS (ESI-TOF) Calcd for C$_{19}$H$_{17}$F$_2$N$_2$O [M+H]$^+$: 667.4622; found: 667.4625.

The absolute stereochemistry was assigned by analogy to compound L21.

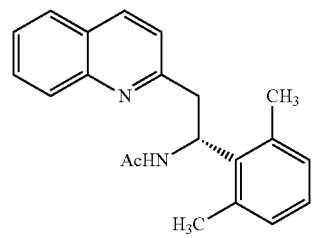

(R)—N-(1-(2,6-dimethylphenyl)-2-(quinolin-2-yl)ethyl)acetamide (L28)

White oil. $^1$H NMR (600 MHz, CDCl$_3$) δ 8.12 (d, J=8.4 Hz, 1H), 8.09 (d, J=8.5 Hz, 1H), 7.83 (d, J=8.1 Hz, 1H), 7.76-7.73 (m, 1H), 7.57-7.54 (m, 1H), 7.32 (d, J=8.3 Hz, 1H), 7.07 (dd, J$_1$=6.5 Hz, J$_2$=8.3 Hz, 1H), 7.01 (d, J=7.4 Hz, 2H), 6.81 (d, J=6.7 Hz, 1H), 5.80 (dt, J$_1$=6.0 Hz, J$_2$=10.9 Hz, 1H), 3.55 (dd, J$_1$=10.5 Hz, J$_2$=13.8 Hz, 1H), 3.36-3.32 (m, 1H), 2.53 (s, 6H), 1.86 (s, 3H); $^{13}$C NMR (150 MHz, CDCl$_3$) δ 169.32, 159.01, 147.55, 137.60, 136.99, 129.70, 128.64, 127.66, 127.04, 126.91, 126.21, 121.46, 51.01, 42.28, 22.96, 21.14; Calcd for C$_{22}$H$_{25}$N$_2$O [M+H]+: 333.1961; found: 333.1966.

The absolute stereochemistry was assigned by analogy to compound L21.

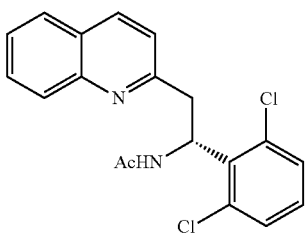 [SMILES: CC(=O)N[C@H](Cc1ccc2ccccc2n1)c1c(Cl)cccc1Cl]

(R)—N-(1-(2,6-dichlorophenyl)-2-(quinolin-2-yl)ethyl)acetamide (L27)

White solid. $^1$H NMR (600 MHz, CDCl$_3$) δ 8.11 (dd, J$_1$=0.8 Hz, J$_2$=8.4 Hz, 1H), 8.06 (dq, J$_1$=0.9 Hz, J$_1$=8.5 Hz, 1H), 7.80 (dd, J$_1$=1.4 Hz, J$_2$=8.1 Hz, 1H), 7.72-7.69 (m, 1H), 7.54-7.51 (m, 1H), 7.41 (d, J=8.4 Hz, 1H), 7.29 (d, J=8.0 Hz, 2H), 7.12 (t, J=8.0 Hz, 1H), 7.08 (d, J=8.1 Hz, 1H), 6.31-6.27 (m, 1H), 3.68 (dd, J$_1$=10.6 Hz, J$_2$=13.7 Hz, 1H), 3.41 (dd, J$_1$=5.2 Hz, J$_2$=13.7 Hz, 1H), 1.84 (s, 3H); $^{13}$C NMR (150 MHz, CDCl$_3$) δ 169.36, 158.09, 147.40, 137.03, 135.92, 129.63, 128.80, 128.53, 127.60, 126.95, 126.23, 121.40, 51.01, 41.25, 22.82; HRMS (ESI-TOF) Calcd for C$_{19}$H$_{17}$N$_2$O [M+H]$^+$: 359.0712; found: 359.0707.

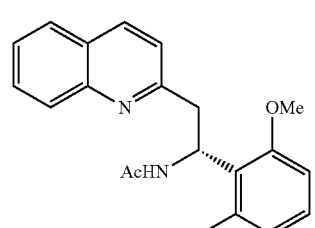

(R)—N-(1-(2,6-dimethoxyphenyl)-2-(quinolin-2-yl)ethyl)acetamide (L29)

White solid. $^1$H NMR (400 MHz, CDCl$_3$) δ 8.03-7.97 (m, 2H), 7.74 (dd, J$_1$=1.5 Hz, J$_2$=8.0 Hz, 1H), 7.65-7.61 (m, 1H), 7.47-7.41 (m, 2H), 7.15 (t, J=8.4 Hz, 1H), 7.05 (d, J=9.9 Hz, 1H), 6.50 (d, J=8.4 Hz, 2H), 6.34-6.28 (m, 1H), 3.73 (s, 6H), 3.47 (dd, J$_1$=8.7 Hz, J$_2$=13.2 Hz, 1H), 3.32 (dd, J$_1$=6.0 Hz, J$_2$=13.3 Hz, 1H), 1.82 (s, 3H); $^{13}$C NMR (100 MHz, CDCl$_3$) δ 168.72, 159.69, 157.85, 147.58, 135.65, 128.97, 128.75, 128.53, 127.43, 126.82, 125.60, 121.95, 117.04, 104.18, 55.74, 44.78, 44.31, 23.50; HRMS (ESI-TOF) Calcd for C$_{21}$H$_{23}$N$_2$O$_3$ [M+H]$^+$: 351.1703; found: 321.1693.

The absolute stereochemistry was assigned by analogy to compound L21.

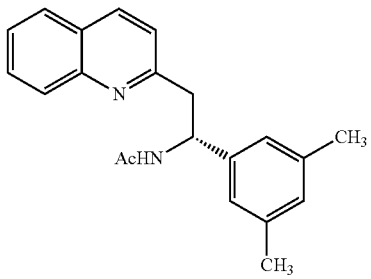 [SMILES: CC(=O)N[C@H](Cc1ccc2ccccc2n1)c1cc(C)cc(C)c1]

(R)—N-(1-(3,5-dimethylphenyl)-2-(quinolin-2-yl)ethyl)acetamide (L30)

White solid. $^1$H NMR (400 MHz, CDCl$_3$) δ 8.04 (t, J=9.4 Hz, 2H), 7.78 (d, J=8.1 Hz, 1H), 7.71 (t, J=7.7 Hz, 1H), 7.51 (t, J=7.5 Hz, 1H), 7.38-7.25 (m, 1H), 7.18 (d, J=8.3 Hz, 1H), 6.88 (s, 2H), 6.83 (s, 1H), 5.39 (dd, J$_1$=5.0 Hz, J$_2$=8.0 Hz, 1H), 3.44 (dd, J$_1$=4.9 Hz, J$_2$=13.8 Hz, 1H), 3.32 (dd, J$_1$=8.3 Hz, J$_2$=13.9 Hz, 1H), 2.24 (s, 6H), 1.92 (s, 3H); $^{13}$C NMR (100 MHz, CDCl$_3$) δ 169.27, 158.96, 147.42, 141.75, 137.83, 136.48, 129.55, 128.80, 128.62, 127.61, 126.81, 126.08, 124.08, 122.06, 53.16, 44.59, 23.31, 21.27; HRMS (ESI-TOF) Calcd for C$_{21}$H$_{23}$N$_2$O [M+H]$^+$: 319.1805; found: 319.1807.

The absolute stereochemistry was assigned by analogy to compound L21.

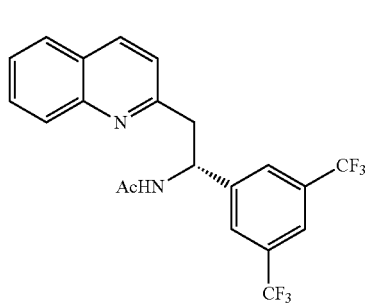 [SMILES: CC(=O)N[C@H](Cc1ccc2ccccc2n1)c1cc(C(F)(F)F)cc(C(F)(F)F)c1]

(R)—N-(1-(3,5-bis (trifluoromethyl)phenyl)-2-(quinolin-2-yl)ethyl)acetamide (L31)

White solid. $^1$H NMR (400 MHz, CDCl$_3$) δ 8.09-8.03 (m, 3H), 7.82-7.73 (m, 2H), 7.70-7.67 (m, 3H), 7.57-7.53 (m, 1H), 7.07 (d, J=8.4 Hz, 1H), 5.52 (dt, J$_1$=4.6 Hz, J$_2$=7.0 Hz, 1H), 3.54-3.49 (m, 1H), 3.35-3.29 (m, 1H), 2.03 (s, 3H). $^{13}$C NMR (150 MHz, CDCl$_3$) δ 169.84, 157.54, 147.37, 144.86, 137.17, 131.55 (q, J$_{FC}$=33 Hz), 130.12, 128.56, 127.75, 126.90, 126.78 (q, J$_{FC}$=36 Hz), 123.20 (q, J$_{FC}$=272 Hz), 121.96, 121.13 (q, J$_{FC}$=3 Hz), 109.97, 52.78, 43.35, 23.29; HRMS (ESI-TOF) Calcd for C$_{21}$H$_{17}$FN$_2$O [M+H]$^+$: 427.1240; found: 427.1233.

The absolute stereochemistry was assigned by analogy to compound L21.

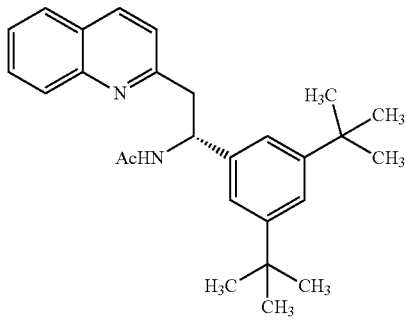 [SMILES: CC(=O)N[C@H](Cc1ccc2ccccc2n1)c1cc(C(C)(C)C)cc(C(C)(C)C)c1]

(R)—N-(1-(3,5-di-tert-butylphenyl)-2-(quinolin-2-yl)ethyl)acetamide (L32)

White foam, [α]$_D^{20}$=−93.2 (c=0.97, CHCl$_3$). $^1$H NMR (600 MHz, CDCl$_3$) δ 8.06-8.04 (m, 1H), 8.02-8.00 (m, 1H), 7.77 (dd, J$_1$=8.2 Hz, J$_2$=1.4 Hz, 1H), 7.73-7.70 (m, 1H), 7.52-7.50 (m, 1H), 7.25 (t, J=1.8 Hz, 1H), 7.17 (d, J=8.4 Hz, 1H), 7.08 (d, J=1.8 Hz, 2H), 5.53 (dd, J$_1$=4.9 Hz, J$_2$=8.1 Hz, 1H), 3.49 (dd, J$_1$=5.0 Hz, J$_2$=13.9 Hz, 1H), 3.37 (dd, J$_1$=8.2 Hz, J$_2$=13.9 Hz, 1H), 1.92 (s, 3H), 1.23 (s, 18H); $^{13}$C NMR (150 MHz, CDCl$_3$) δ 169.12, 159.22, 150.69, 147.46, 140.72, 136.44, 129.56, 128.61, 127.61, 126.86, 126.08, 122.15, 121.23, 120.66, 53.53, 44.89, 34.77, 31.38, 23.41. HRMS (ESI-TOF) Calcd for C$_{27}$H$_{35}$N$_2$O [M+H]$^+$: 403.2744; found: 403.2747.

The absolute stereochemistry was assigned by analogy to compound L32.

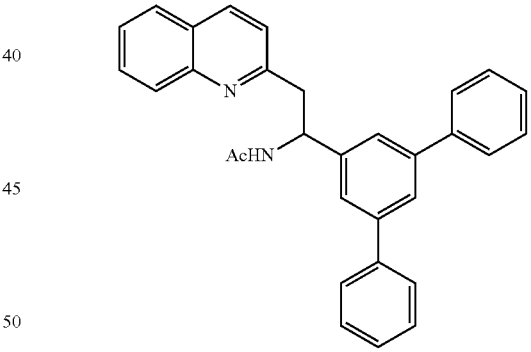

(R)—N-(1-([1,1':3',1"-terphenyl]-5'-yl)-2-(quinolin-2-yl)ethyl)acetamide (L33)

White foam. $^1$H NMR (400 MHz, CDCl$_3$) δ 8.1.0 (d, J=8.5 Hz, 1H), 8.06 (d, J=8.4 Hz, 1H), 7.82 (d, J=8.1 Hz, 1H), 7.78-7.73 (m, 2H), 7.61 (d, J=1.9 Hz, 1H), 7.57 (t, J=7.5 Hz, 1H), 7.48-7.46 (m, 3H), 7.41-7.31 (m, 7H), 7.18 (d, J=8.4 Hz, 1H), 5.64-5.59 (m, 1H), 3.59 (dd, J$_1$=4.7 Hz, J$_1$=14.0 Hz, 1H), 3.43 (dd, J$_1$=7.6 Hz, J$_2$=14.0 Hz, 1H), 1.99 (s, 3H); $^{13}$C NMR (125 MHz, CDCl$_3$) δ 169.43, 158.85, 147.37, 142.88, 141.76, 140.93, 136.64, 129.72, 128.61, 127.62, 127.29, 127.13, 126.86, 126.23, 124.96, 124.25, 122.30, 53.28, 44.30, 23.31; HRMS (ESI-TOF) Calcd for C$_{31}$H$_{27}$N$_2$O [M+H]$^+$: 443.2118; found: 443.2127.

The absolute stereochemistry was assigned by analogy to compound L32.

General Procedure for the Synthesis of L34-L39, L40a,

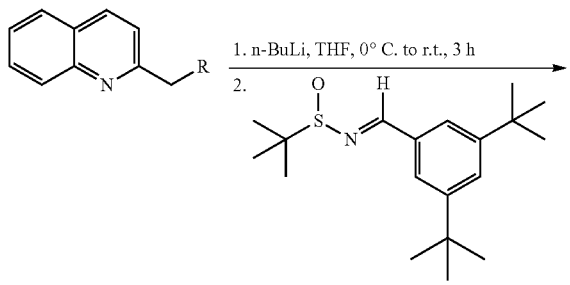

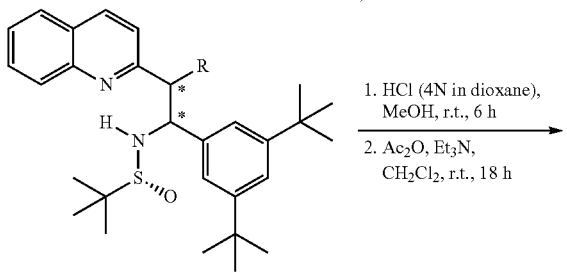

L34-1 to L39-1

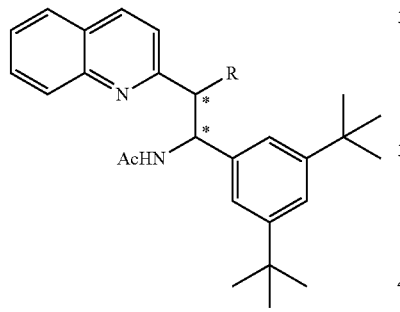

L34-L39, L40a, L41

Synthesis of tert-Butanesulfinyl Amines L35-1

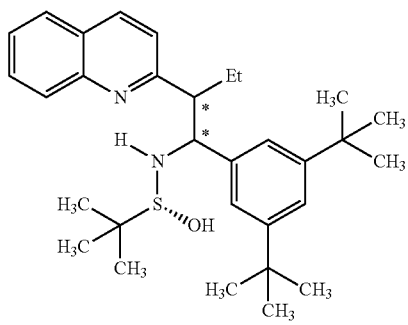

To a solution of 2-propylquinoline (4.45 g, 26 mmol, 1.3 equiv.) in anhydrous THF (30 mL) at 0° C. was added n-butyllithium (2.5 M in hexanes, 26 mmol, 16.25 mL, 1.3 equiv.) dropwise. The resulting solution was allowed to warm to room temperature gradually and stirred for three hours. Then the mixture was cooled down to −78° C., to which the tert-butanesulfinyl imine (6.44 g, 20 mmol, 1 equiv.) in anhydrous THF (30 mL) was added dropwise. The resulting mixture was allowed to warm to 0° C. over two hours, and then treated with a saturated aqueous NH$_4$Cl solution. The product was extracted with dichloromethane. The combined extracts were washed with water, dried over anhydrous MgSO$_4$, and concentrated under vacuum. Flash chromatography (eluent: ethyl acetate/hexanes=1/10 to 1/2) gave three fractions including L35-1b (the least polar compound, 3.52 g, 36% yield), L35-1c and L35-1d (a mixture of two diastereomers that could not be separated by column, 1.60 g, 16% yield) and L35-1a (the most polar compound, 2.30 g, 23% yield).

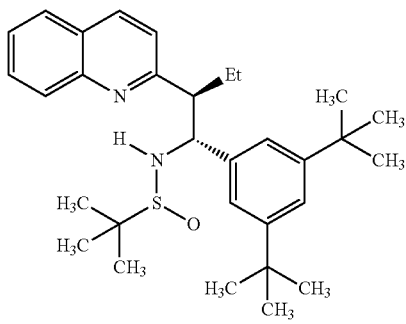

1-tert-butyl-N-((1R,2S)-1-(3,5-di-tert-butylphenyl)-2-(quinolin-2-yl)butyl)-1-($\lambda^1$-oxidanyl)-$\lambda^3$-sulfanamine (L35-1b)

$^1$H NMR (400 MHz, CDCl$_3$) δ 8.06 (dd, J$_1$=1.0 Hz, J$_1$=8.4 Hz, 1H), 7.88 (dd, J$_1$=0.8 Hz, J$_2$=8.5 Hz, 1H), 7.73-7.67 (m, 2H), 7.49-7.45 (m, 1H), 7.13 (t, J=1.8 Hz, 1H), 6.92 (d, J=1.8 Hz, 2H), 6.84 (d, J=8.4 Hz, 1H), 5.69 (d, J=8.1 Hz, 1H), 4.77 (dd, J$_1$=6.1 Hz, J$_2$=8.1 Hz, 1H), 3.19-3.13 (m, 1H), 2.04-1.96 (m, 1H), 1.95-1.85 (m, 1H), 1.14 (s, 18H), 1.10 (s, 9H), 0.82 (t, J=7.4 Hz, 3H); $^{13}$C NMR (100 MHz, CDCl$_3$) δ 162.86, 150.00, 147.39, 141.09, 135.74, 129.34, 128.79, 127.34, 126.88, 125.91, 122.62, 121.56, 120.42, 63.42, 56.89, 56.32, 34.57, 31.26, 26.29, 22.56, 12.13; HRMS (ESI-TOF) Calcd for C$_{31}$H$_{45}$N$_2$OS [M+H]$^+$: 493.3247; found: 493.3245.

The absolute stereochemistry was assigned by analogy to compound L40b.

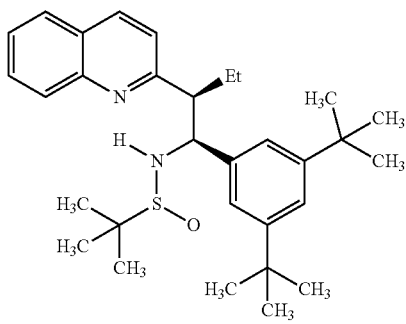

1-tert-butyl-N-((1,2S)-1-(3,5-di-tert-butylphenyl)-2-(quinolin-2-yl)butyl)-1-(λ¹-oxidanyl)-λ³-sulfanamine (L35-1a)

$^1$H NMR (400 MHz, CDCl$_3$) δ 8.07-7.99 (m, 1H), 8.00 (dd, J$_1$=0.8 Hz, J$_2$=8.5 Hz, 1H), 7.79-7.76 (m, 1H), 7.72-7.68 (m, 1H), 7.53-7.48 (m, 1H), 7.27 (dd, J$_1$=1.8 Hz, J$_2$=3.6 Hz, 1H), 7.03-7.01 (m, 3H), 6.15 (d, J=1.3 Hz, 1H), 4.87-4.85 (m, 1H), 3.18 (dt, J$_1$=3.9 Hz, J$_2$=11.0 Hz, 1H), 2.03 (dt, J$_1$=6.8 Hz, J$_2$=11.0 Hz, 1H), 1.86-1.79 (m, 1H), 1.32 (s, 9H), 1.26 (s, 18H), 0.71 (t, J=7.3 Hz, 3H); $^{13}$C NMR (100 MHz, CDCl$_3$) δ 162.46, 149.86, 147.40, 138.97, 136.06, 129.47, 128.88, 127.52, 127.09, 126.02, 122.78, 122.37, 120.99, 60.84, 55.94, 55.50, 34.70, 31.41, 23.03, 21.47, 12.24; HRMS (ESI-TOF) Calcd for C$_{31}$H$_{45}$N$_2$OS [M+H]$^+$: 493.3247; found: 493.3249.

The absolute stereochemistry was assigned by analogy to compound L35.

Synthesis of Ligand L40a and L40b

For L40b:

To a solution of tert-butanesulfinyl amine L35b (1.40 g, 2.84 mmol) in MeOH (10 mL) at room temperate was added HCl solution (4N in dioxane, 11.4 mmol, 2.84 mL). The mixture was stirred for 6 hours before the solvent was removed by vacuum. The crude oil was treated with saturated aqueous Na$_2$CO$_3$ solution and was extracted with dichloromethane. The combined extracts were washed with water, dried over anhydrous MgSO$_G$, and concentrated under vacuum. Flash chromatography (eluent: dichloromethane/methanol=20/1) gave the amine L40b (990 mg, 90% yield) as a pale yellow oil.

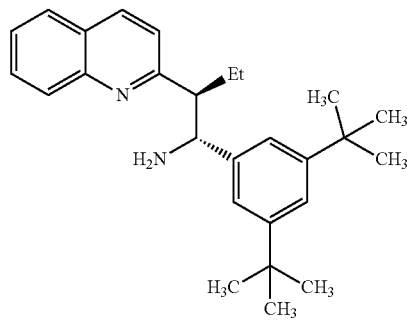 [SMILES: CC[C@H](c1ccc2ccccc2n1)[C@@H](N)c1cc(C(C)(C)C)cc(C(C)(C)C)c1]

(1R,2S)-1-(3,5-di-tert-butylphenyl)-2-(quinolin-2-yl)butan-1-amine (L40b)

$^1$H NMR (600 MHz, CDCl$_3$) δ 8.13 (d, J=8.5 Hz, 1H), 8.07 (d, J=8.5 Hz, 1H), 7.80 (d, J=8.1 Hz, 1H), 7.71 (t, J=7.7 Hz, 1H), 7.51 (t, J=7.5 Hz, 1H), 7.34-7.29 (m, 2H), 7.21 (s, 2H), 4.37 (d, J=9.0 Hz, 1H), 3.10 (dt, J$_1$=4.0 Hz, J$_2$=9.9 Hz, 1H), 1.78-1.73 (m, 1H), 1.59-1.54 (m, 1H), 1.32 (s, 18H), 0.65 (t, J=7.4 Hz, 3H); $^{13}$C NMR (150 MHz, CDCl$_3$) δ 164.03, 150.61, 148.03, 144.03, 135.91, 129.22, 129.15, 127.52, 127.08, 125.78, 122.01, 121.47, 120.95, 61.15, 58.37, 34.84, 31.51, 25.80, 12.04; HRMS (ESI-TOF) Calcd for C$_{27}$H$_{37}$N$_2$O [M+H]$^+$: 389.2951; found: 389.2949.

Preparation of HCl Salt of Amine L40b

To a solution of amine L40b (20 mg, 0.05 mmol) in a 5-mL vial was added HCl solution in Dioxane (4N, 0.1 mL, 0.4 mmol). The mixture was stirred at room temperature for 30 minutes. The solvent was removed under vacuum and small amount of CHCl$_3$ was added to the vial to dissolve the resulting salt. A suitable crystal for X-ray analysis was obtained using solvent evaporation method.

Synthesis of L40a

To a solution of tert-butanesulfinyl amine L35-1b (500 mg, 1 mmol) in MeOH (10 mL) at room temperature was added HCl solution (4N in dioxane, 4 mmol, 1 mL). The mixture was stirred for 6 hours before the solvent was removed by vacuum. To the resulting foam was added CH$_2$Cl$_2$ (10 mL) and Et$_3$N (405 mg, 4 mmol, 0.57 mL) at room temperature, followed by the addition of acetic anhydride (405 mg, 5 mmol, 0.38 mL). The mixture was stirred overnight (about 18 hours) before it was treated with saturated aqueous Na$_2$CO$_3$ solution. The product was extracted with dichloromethane. The combined extracts were washed with water, dried over anhydrous MgSO$_4$, and concentrated under vacuum. Flash chromatography (eluent:ethyl acetate/hexanes=1/3) gave the ligand L40a (323 mg, 75% yield) as a white solid, [α]$_D$=243.60 (c=0.74, CHCl$_3$).

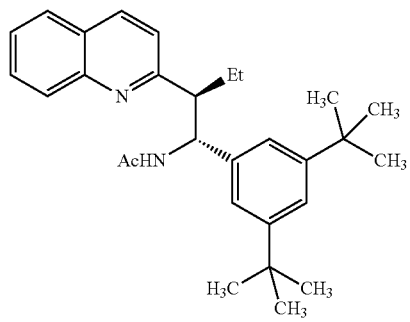 [SMILES: CC[C@H](c1ccc2ccccc2n1)[C@@H](NC(C)=O)c1cc(C(C)(C)C)cc(C(C)(C)C)c1]

N-((1R,2S)-1-(3,5-di-tert-butylphenyl)-2-(quinolin-2-yl)butyl)acetamide (L40a)

$^1$H NMR (400 MHz, CDCl$_3$) δ 8.41 (d, J=9.0 Hz, 1H), 8.13-8.11 (m, 1H), 8.04 (d, J=8.5 Hz, 1H), 7.79-7.72 (m, 2H), 7.54-7.50 (m, 1H), 7.20 (t, J=1.8 Hz, 1H), 7.16 (d, J=8.5 Hz, 1H), 6.99 (d, J=1.8 Hz, 2H), 5.39 (dd, J$_1$=7.5 Hz, J$_2$=9.0 Hz, 1H), 3.26-3.20 (m, 1H), 1.92-1.75 (m, 5H), 1.19 (s, 18H), 0.77 (t, J=7.4 Hz, 3H); $^{13}$C NMR (100 MHz, CDCl$_3$) δ 169.26, 163.36, 150.16, 146.88, 140.81, 136.37, 129.59, 128.20, 127.55, 126.97, 126.12, 122.36, 120.69, 120.55, 56.86, 54.94, 34.53, 31.22, 26.47, 23.34, 12.18; HRMS (ESI-TOF) Calcd for C$_{29}$H$_{39}$N$_2$O [M+H]$^+$: 431.3057; found: 431.3057.

The absolute stereochemistry was assigned by analogy to compound L40b.

Synthesis of L35

To a solution of tert-butanesulfinyl amine L35-1a (860 mg, 1.75 mmol) in MeOH (10 mL) at room temperate was added HCl solution (4N in dioxane, 7 mmol, 1.75 mL). The mixture was stirred for 6 hours before the solvent was removed by vacuum. To the resulting foam was added CH$_2$Cl$_2$ (10 mL) and Et$_3$N (710 mg, 7 mmol, 1 mL) at room temperature, followed by the addition of acetic anhydride (710 mg, 7 mmol, 0.67 mL).

The mixture was stirred overnight (about 18 hours) before it was treated with saturated aqueous Na$_2$CO$_3$ solution. The product was extracted with dichloromethane. The combined extracts were washed with water, dried over anhydrous MgSO$_4$, and concentrated under vacuum. Flash chromatography (eluent: ethyl acetate/hexanes=1:2) gave the ligand L35 (620 mg, 80% yield) as a white foam, [α]$_D^{20}$=−207.8

(c=0.96, CHCl₃). A suitable crystal of the HCl salt of L35 for X-ray analysis was obtained using diffusion method from CHCl₃ and hexanes.

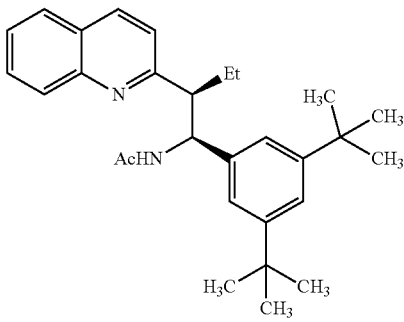 [SMILES: CC[C@H](c1ccc2ccccc2n1)[C@H](NC(C)=O)c1cc(C(C)(C)C)cc(C(C)(C)C)c1]

N-((1S,2S)-1-(3,5-di-tert-butylphenyl)-2-(quinolin-2-yl)butyl) acetamide (L35)

$^1$H NMR (600 MHz, CDCl₃) δ 8.06 (dd, $J_1$=1.0 Hz, $J_2$=8.4 Hz, 1H), 7.86 (d, J=8.4 Hz, 1H), 7.72-7.68 (m, 2H), 7.50-7.47 (m, 1H), 7.12-7.09 (m, 2H), 6.80 (d, J=8.5 Hz, 2H), 6.68 (d, J=1.8 Hz, 1H), 5.38 (dd, $J_1$=6.5 Hz, $J_2$=8.2 Hz, 1H), 3.35-3.31 (m, 1H), 2.04 (s, 3H), 1.93 (t, J=7.5 Hz, 2H), 1.09 (s, 18H), 0.90 (t, J=7.4 Hz, 3H); $^{13}$C NMR (150 MHz, CDCl₃) δ 169.03, 161.86, 149.85, 147.35, 138.61, 135.69, 129.33, 128.85, 127.35, 126.90, 126.03, 121.50, 121.03, 120.80, 57.35, 54.74, 34.52, 31.21, 23.90, 23.63, 12.17; HRMS (ESI-TOF) Calcd for C₂₉H₃₉N₂O (M+H)⁺: 431.3057; found: 431.3054.

Synthesis of Ligands L41 and Enantiomer of L35

To a solution of tert-butanesulfinyl amines L35-1c and L35-1d (320 mg, 0.65 mmol) in MeOH (5 mL) at room temperate was added HCl solution (4N in dioxane, 2.6 mmol, 0.65 mL). The mixture was stirred for 6 hours before the solvent was removed by vacuum. To the resulting foam was added CH₂Cl₂ (10 mL) and Et₃N (263 mg, 2.6 mmol, 0.37 mL) at room temperature, followed by the addition of acetic anhydride (263 mg, 2.6 mmol, 0.25 mL). The mixture was stirred overnight (about 18 hours) before it was treated with saturated aqueous Na₂CO₃ solution. The product was extracted with dichloromethane. The combined extracts were washed with water, dried over anhydrous MgSO₄, and concentrated under vacuum. Flash chromatography (eluent: ethyl acetate/hexanes=1/3 to 1/2) gave the ligand L41 (98 mg) and enantiomer of L35 (105 mg) as white solids.

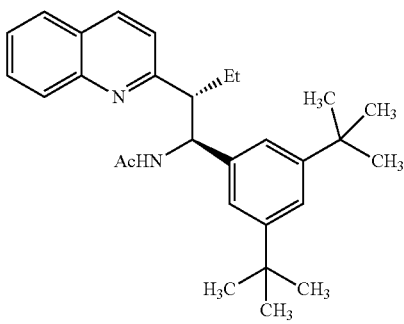 [SMILES: CC[C@@H](c1ccc2ccccc2n1)[C@H](NC(C)=O)c1cc(C(C)(C)C)cc(C(C)(C)C)c1]

N-((1S,2R)-1-(3,5-di-tert-butylphenyl)-2-(quinolin-2-yl)butyl)acetamide (L41)

$[α]_D^{20}$=−211.7 (c=0.685, CHCl₃). The $^1$H and $^{13}$C NMR spectrum data of L41 match those of its enantiomer L40a. HRMS (ESI-TOF) Calcd for C₂₉H₃₉N₂O [M+H]⁺: 431.3057; found: 431.3060.

The absolute stereochemistry was assigned by analogy to compound L40b.

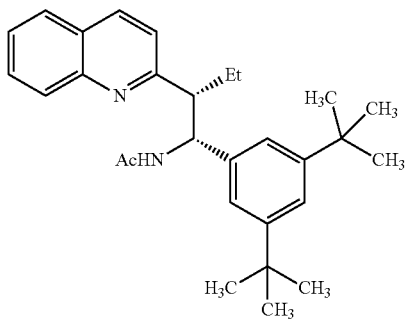 [SMILES: CC[C@@H](c1ccc2ccccc2n1)[C@@H](NC(C)=O)c1cc(C(C)(C)C)cc(C(C)(C)C)c1]

N-((1R,2R)-1-(3,5-di-tert-butylphenyl)-2-(quinolin-2-yl)butyl)acetamide (Enantiomer of L35)

$[α]_D^{20}$=201.6 (c=0.90, CHCl₃). The $^1$H and $^{13}$C NMR spectrum data of enantiomer of L35 match those of L35. HRMS (ESI-TOF) Calcd for C₂₉H₃₉N₂O [M+H]⁺: 431.3057; found: 431.3060.

The absolute stereochemistry was assigned by analogy to compound L35.

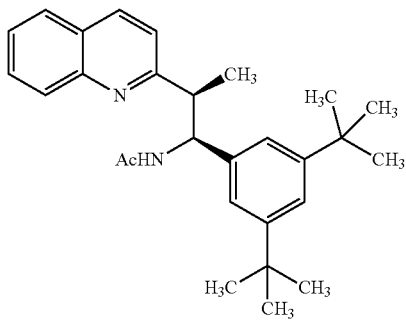 [SMILES: CC(=O)N[C@H](c1cc(C(C)(C)C)cc(C(C)(C)C)c1)[C@H](C)c1ccc2ccccc2n1]

N-((1S,2S)-1-(3,5-di-tert-butylphenyl)-2-(quinolin-2-yl)propyl)acetamide (L34)

Yellow oil. $^1$H NMR (600 MHz, CDCl₃) δ 8.06 (dd, $J_1$=1.0 Hz, $J_2$=8.4 Hz, 1H), 7.91 (d, J=8.4 Hz, 1H), 7.74-7.70 (m, 2H), 7.51-7.49 (m, 1H), 7.41 (d, J=8.2 Hz, 1H), 7.11 (t, J=1.8 Hz, 1H), 6.92 (d, J=8.5 Hz, 1H), 6.70 (d, J=1.8 Hz, 2H), 5.32 (dd, $J_1$=6.1 Hz, $J_2$=8.2 Hz, 1H), 3.62-3.58 (m, 1H), 2.06 (s, 3H), 1.44 (d, J=7.2 Hz, 3H), 1.09 (s, 18H); $^{13}$C NMR (150 MHz, CDCl₃) δ 169.01, 163.05, 149.88, 147.19, 138.43, 136.10, 129.49, 128.84, 127.41, 126.95, 126.09, 121.70, 120.87, 120.33, 58.40, 46.41, 34.55, 31.23, 23.70, 16.63; HRMS (ESI-TOF) Calcd for C₂₈H₃₇N₂O [M+H]⁺: 417.2900; found: 417.2898.

The absolute stereochemistry was assigned by analogy to compound L35.

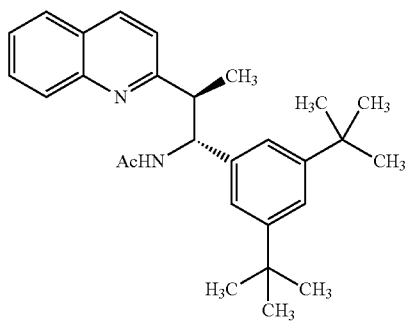 [SMILES: CC(=O)N[C@@H](c1cc(C(C)(C)C)cc(C(C)(C)C)c1)[C@H](C)c1ccc2ccccc2n1]

N-((1R,2S)-1-(3,5-di-tert-butylphenyl)-2-(quinolin-2-yl)propyl)acetamide (L34a)

Yellow oil. $^1$H NMR (600 MHz, CDCl$_3$) δ 8.09 (dd, $J_1$=5.8 Hz, $J_2$=8.9 Hz, 2H), 7.98 (d, J=8.4 Hz, 1H), 7.77-7.72 (m, 2H), 7.52 (t, J=7.3 Hz, 1H), 7.16 (s, 1H), 7.04 (d, J=8.4 Hz, 1H), 6.92 (d, J=1.9 Hz, 2H), 5.33 (dd, $J_1$=6.4 Hz, $J_2$=8.8 Hz, 1H), 3.46-3.41 (m, 1H), 1.95 (s, 3H), 1.44 (d, J=7.0 Hz, 3H), 1.15 (s, 18H); $^{13}$C NMR (150 MHz, CDCl$_3$) δ 169.36, 164.33, 150.36, 147.00, 140.76, 136.68, 129.64, 128.39, 127.63, 127.05, 126.16, 121.50, 120.86, 120.80, 58.34, 47.53, 34.67, 31.33, 23.45, 19.28; HRMS (ESI-TOF) Calcd for C$_{28}$H$_{37}$N$_2$O [M+H]$^+$: 417.2900; found: 417.2908.

The absolute stereochemistry was assigned by analogy to compound L40b.

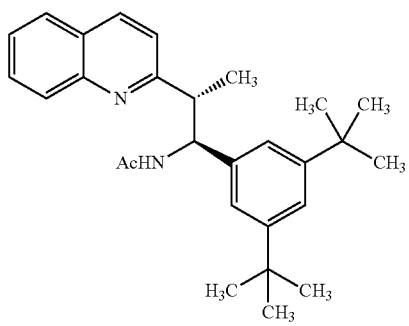 [SMILES: CC(=O)N[C@H](c1cc(C(C)(C)C)cc(C(C)(C)C)c1)[C@@H](C)c1ccc2ccccc2n1]

N-(1S,2R)-1-(3,5-di-tert-butylphenyl)-2-(quinolin-2-yl)propyl)acetamide (L34b)

Yellow oil. The $^1$H and $^{13}$C NMR spectrum data of L34b match those of its enantiomer L34a. HRMS (ESI-TOF) Calcd for C$_{28}$H$_{37}$N$_2$O [M+H]$^+$: 417.2900; found: 417.2909.

The absolute stereochemistry was assigned by analogy to compound L40b.

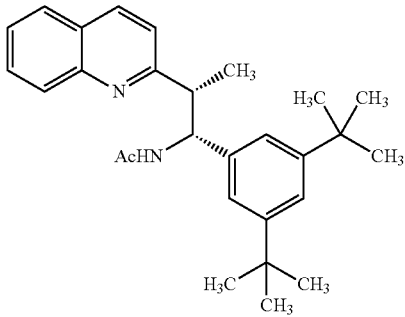 [SMILES: CC(=O)N[C@@H](c1cc(C(C)(C)C)cc(C(C)(C)C)c1)[C@@H](C)c1ccc2ccccc2n1]

N-((1R,2R)-1-(3,5-di-tert-butylphenyl)-2-(quinolin-2-yl)propyl)acetamide (L34c)

Yellow oil. The $^1$H and $^{13}$C NMR spectrum data of L34c match those of its enantiomer L34. HRMS (ESI-TOF) Calcd for C$_{28}$H$_{37}$N$_2$O [M+H]$^+$: 417.2900; found: 417.2908.

The absolute stereochemistry was assigned by analogy to compound L35.

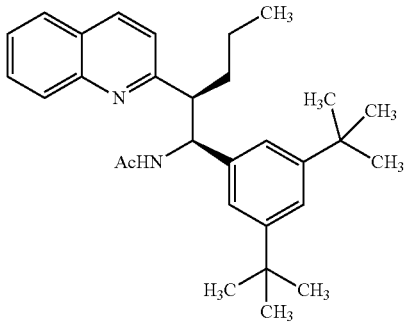 [SMILES: CCC[C@H](c1ccc2ccccc2n1)[C@H](NC(C)=O)c1cc(C(C)(C)C)cc(C(C)(C)C)c1]

N-((1S,2S)—N-(3,5-di-tert-butylphenyl)-2-(quinolin-2-yl)pentyl)acetamide (L36)

Yellow oil. $^1$H NMR (600 MHz, CDCl$_3$) δ 8.07-8.05 (m, 1H), 7.86 (d, J=8.4 Hz, 1H), 7.73-7.69 (m, 2H), 7.51-7.48 (m, 1H), 7.12-7.10 (m, 2H), 6.78 (d, J=8.5 Hz, 1H), 6.65 (d, J=1.8 Hz, 2H), 5.36 (dd, $J_1$=6.2 Hz, $J_2$=8.1 Hz, 1H), 3.42 (dt, $J_1$=5.8 Hz, $J_2$=9.6 Hz, 1H), 2.05 (S, 3H), 1.92-1.79 (m, 4H), 1.10 (s, 18H), 0.90 (t, J=7.4 Hz, 3H); $^{13}$C NMR (150 MHz, CDCl$_3$) δ 168.98, 162.10, 149.82, 147.38, 138.54, 135.65, 129.35, 128.95, 127.38, 126.93, 126.05, 121.55, 121.05, 120.82, 57.35, 52.56, 34.55, 32.97, 31.44, 31.24, 23.69, 14.20; HRMS (ESI-TOF) Calcd for C$_{30}$H$_{41}$N$_2$O [M+H]+: 445.3213; found: 445.3212.

The absolute stereochemistry was assigned by analogy to compound L35.

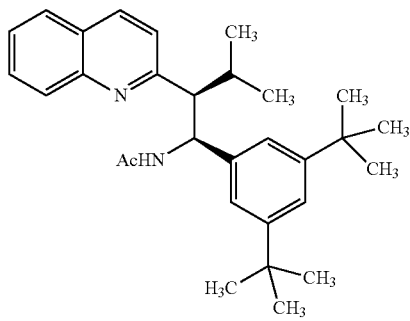 [SMILES: CC(=O)N[C@H](c1cc(C(C)(C)C)cc(C(C)(C)C)c1)[C@@H](c1ccc2ccccc2n1)C(C)C]

N-((1S,2S)-1-(3,5-di-tert-butylphenyl)-3-methyl-2-(quinolin-2-yl)butyl)acetamide (37)

Yellow oil. ¹H NMR (600 MHz, CDCl₃) δ 8.09 (dt, J₁=1.0 Hz, J₂=9.0 Hz, 1H), 7.77 (d, J=8.5 Hz, 1H), 7.72-7.70 (m, 2H), 7.51-7.49 (m, 1H), 7.10 (t, J=1.8 Hz, 1H), 6.85 (d, J=8.1 Hz, 1H), 6.66 (d, J=1.8 Hz, 2H), 6.55 (d, J=8.5 Hz, 1H), 5.67 (dd, J₁=6.0 Hz, J₂=8.2 Hz, 1H), 3.19 (dd, J₁=6.1 Hz, J₂=9.0 Hz, 1H), 2.21-2.15 (m, 1H), 2.02 (s, 3H), 1.29 (d, J=6.6 Hz, 3H), 1.09 (s, 18H), 0.88 (d, J=6.6 Hz, 3H); ¹³C NMR (150 MHz, CDCl₃) δ 168.74, 161.06, 149.75, 134.80, 129.26, 128.93, 127.32, 126.81, 126.12, 122.24, 121.53, 120.78, 60.16, 54.22, 34.54, 31.23, 27.75, 23.67, 21.73, 20.66; HRMS (ESI-TOF) Calcd for C₃₀H₄₁N₂O [M+H]⁺: 445.3213; found: 445.3218.

The absolute stereochemistry was assigned by analogy to compound L35.

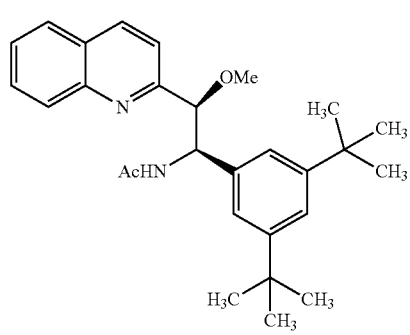

N-((1R,2S)-1-(3,5-di-tert-butylphenyl)-2-methoxy-2-(quinolin-2-yl)ethyl) acetamide (L38)

White solid. ¹H NMR (600 MHz, CDCl₃) δ 8.09-8.07 (m, 2H), 7.79 (dd, J₁=8.1 Hz, J₂=1.4 Hz, 1H), 7.73-7.70 (m, 1H), 7.54-7.52 (m, 1H), 7.34 (d, J=8.5 Hz, 1H), 7.27-7.25 (m, 1H), 7.07 (d, J=1.9 Hz, 2H), 6.90 (d, J=9.0 Hz, 1H), 5.49 (dd, J₁=3.1 Hz, J₂=9.1 Hz, 1H), 4.79 (d, J=3.1 Hz, 1H), 3.43 (s, 3H), 1.98 (s, 3H), 1.23 (s, 18H); ¹³C NMR (150 MHz, CDCl₃) δ 168.94, 160.00, 150.19, 147.49, 138.66, 136.37, 129.58, 129.06, 127.60, 126.44, 121.46, 121.19, 118.71, 86.39, 58.04, 56.62, 34.73, 31.39, 23.41; HRMS (ESI-TOF) Calcd for C₂₈H₃₇N₂O₂ [M+H]⁺: 433.2850; found: 433.2847.

The absolute stereochemistry was assigned by analogy to compound L35.

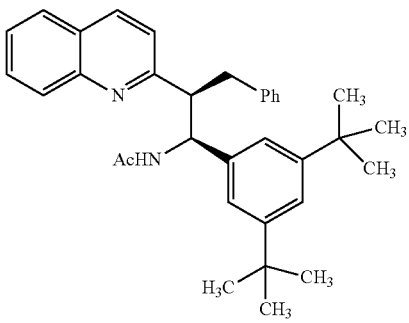 [SMILES: CC(=O)N[C@H](c1cc(C(C)(C)C)cc(C(C)(C)C)c1)[C@H](Cc1ccccc1)c1ccc2ccccc2n1]

N-((1S,2S)-1-(3,5-di-tert-butylphenyl)-3-phenyl-2-(quinolin-2-yl)propyl)acetamide (L39)

White solid. ¹H NMR (400 MHz, CDCl₃) δ 8.07 (d, J=8.5 Hz, 1H), 7.81 (d, J=8.5 Hz, 1H), 7.70 (t, J=7.6 Hz, 2H), 7.49 (t, J=7.4 Hz, 1H), 7.18-7.08 (m, 7H), 6.77 (d, J=8.5 Hz, 1H), 6.70 (d, J=1.8 Hz, 2H), 5.42 (t, J=7.3 Hz, 1H), 3.80 (dt, J₁=6.3 Hz, J₂=9.4 Hz, 1H), 3.31 (dd, J₁=9.2 Hz, J₂=14.2 Hz, 1H), 3.17 (dd, J₁=5.9 Hz, J₁=14.1 Hz, 1H), 2.03 (s, 3H), 1.00 (s, 18H); ¹³C NMR (100 MHz, CDCl₃) δ 169.56, 161.18, 150.15, 147.28, 139.55, 138.36, 135.73, 129.46, 128.90, 128.78, 128.33, 127.38, 126.89, 126.17, 126.09, 121.76, 121.51, 121.08, 57.61, 54.03, 36.82, 34.59, 31.22, 23.58; HRMS (ESI-TOF) Calcd for C₃₄H₄₁N₂O [M+H]⁺: 493.3214; found: 493.3215.

The absolute stereochemistry was assigned by analogy to compound L35.

General Procedure for the Synthesis of Ligand L42-L58:

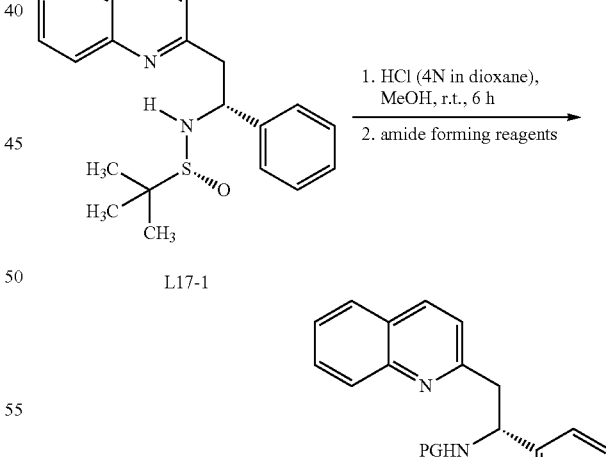

Generation of the Ligand from Sulfonamides L17-1

In an open flask at room temperature, HCl (4 M in dioxane) was added dropwise to a solution of the sulfinamide L17-1 in MeOH. When TLC indicated no starting material remaining, all volatiles were removed in vacuo.

Adding dry solvent to the intermediate under N$_2$-atmosphere gave a suspension, which turned into a solution upon addition of a base. At room temperature an anhydride or an acid chloride was added dropwise. When TLC indicated completion, the reaction mixture was quenched with brine and extracted with dichloromethane three times. The combined organic extracts were dried with Na$_2$SO$_4$ and the solvent was removed in vacuo. The residue was purified by preparative thin layer chromatography (pTLC) on SiO$_2$ with a combination of CH$_2$Cl$_2$ and EtOAc as eluent.

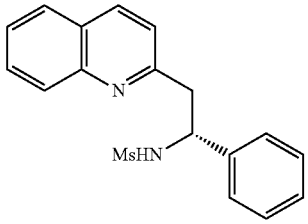

(R)—N-(1-phenyl-2-(quinolin-2-yl)ethyl)methanesulfonamide (L42)

White solid. $^1$H NMR (500 MHz, CDCl$_3$) δ 8.10 (d, J=8.5 Hz, 1H), 8.07 (d, J=8.4 Hz, 1H), 7.79 (d, J=8.1 Hz, 1H), 7.73 (dd, J$_1$=6.6 Hz, J$_2$=8.4 Hz, 1H), 7.54 (t, J=7.5 Hz, 1H), 7.38 (d, J=7.3 Hz, 2H), 7.33 (t, J=7.5 Hz, 2H), 7.28 (d, J=7.1 Hz, 1H), 7.21 (br s, 1H), 7.15 (d, J=8.3 Hz, 1H), 5.02 (dd, J$_1$=4.3 Hz, J$_2$=8.9 Hz, 1H), 3.41 (dd, J$_1$=4.3 Hz, J$_2$=14.4 Hz, 1H), 3.34 (dd, J$_1$=8.7 Hz, J$_2$=14.4 Hz, 1H), 2.50 (s, 3H); $^{13}$C NMR (125 MHz, CDCl$_3$) δ 158.24, 147.29, 141.12, 137.08, 129.99, 128.87, 128.70, 127.89, 127.57, 126.91, 126.50, 122.03, 57.73, 44.53, 41.70; HRMS (ESI-TOF) Calcd for C$_{18}$H$_{19}$N$_2$O$_2$S [M+H]$^+$ 327.1162, found 327.1157.

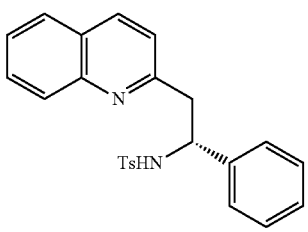

(R)-4-methyl-N-(1-phenyl-2-(quinolin-2-yl)ethyl) benzenesulfonamide (L43)

White solid. $^1$H NMR (600 MHz, CDCl$_3$) δ 8.09 (d, J=8.9 Hz, 1H), 7.94 (d, J=8.3 Hz, 1H), 7.75-7.78 (m, 2H), 7.56 (dt, J$_1$=1.2, J$_2$=7.8 Hz, 1H), 7.36 (d, J=8.3 Hz, 2H), 7.28 (dd, J$_1$=1.3 Hz, J$_2$=8.2 Hz, 2H), 7.24-7.17 (m, 4H), 7.01 (d, J=8.3 Hz, 1H), 6.83 (d, J=7.6 Hz, 2H), 4.66 (td, J$_1$=3.7 Hz, J$_2$=8.0 Hz, 1H), 3.24-3.17 (m, 2H), 2.24 (s, 3H); $^{13}$C NMR (150 MHz, CDCl$_3$) δ 158.11, 147.15, 142.43, 141.24, 137.08, 136.93, 129.97, 128.92, 128.34, 127.46, 127.35, 126.87, 126.81, 126.65, 126.46, 121.78, 109.95, 57.87, 44.71, 21.35; HRMS (ESI-TOF) Calcd for C$_{24}$H$_{23}$N$_2$O$_2$S [M+H]$^+$ 403.1475, found 403.1484.

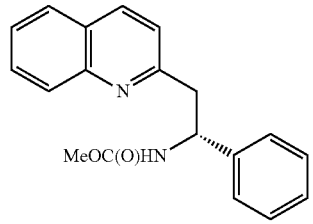

methyl (R)-(1-phenyl-2-(quinolin-2-yl)ethyl)carbamate (L44)

White solid. $^1$H NMR (500 MHz, CDCl$_3$) δ 8.08 (d, J=8.5 Hz, 1H), 7.99 (d, J=8.4 Hz, 1H), 7.76 (dd, J$_1$=1.4 Hz, J$_2$=8.2 Hz, 1H), 7.71 (ddd, J$_1$=1.4 Hz, J$_2$=6.8 Hz, J$_3$=8.4 Hz, 1H), 7.51 (ddd, J$_1$=1.1 Hz, J$_2$=6.8 Hz, J$_3$=:8.1 Hz, 1H), 7.23-7.27 (m, 4H), 7.21-7.17 (m, 1H), 7.07 (d, J=8.4 Hz, 1H), 6.58 (br s, 1H), 5.22 (br s, 1H), 3.57 (s, 3H), 3.47 (dd, J$_1$=5.0 Hz, J$_2$=14.0 Hz, 1H), 3.33 (dd, J$_1$=7.6 Hz, J$_2$=13.3 Hz, 1H); $^{13}$C NMR (125 MHz, CDCl$_3$) δ 158.58, 156.36, 147.58, 142.19, 136.45, 129.56, 128.98, 128.38, 127.53, 127.12, 126.81, 126.15, 122.05, 55.06, 51.97, 44.86, 29.68; HRMS (ESI-TOF) Calcd for C$_{19}$H$_{19}$N$_2$O$_2$ ([M+H]$^+$ 307.1441, found 307.1445.

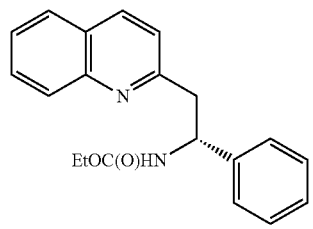

ethyl (R)-(1-phenyl-2-(quinolin-2-yl)ethyl)carbamate (L45)

White solid. $^1$H NMR (500 MHz, CDCl$_3$) δ 8.08 (d, J=8.5 Hz, 1H), 7.98 (d, J=8.3 Hz, 1H), 7.76 (dd, J$_1$=1.4 Hz, J$_2$=8.1 Hz, 1H), 7.71 (ddd, J$_1$=1.5 Hz, J$_2$=6.9 Hz, J$_3$=8.4 Hz, 1H), 7.50 (ddd, J$_1$=1.2 Hz, J$_2$=6.9 Hz, J$_3$=8.1 Hz, 1H), 7.25 (d, J=4.5 Hz, 4H), 7.21-7.17 (m, 1H), 7.07 (d, J=8.4 Hz, 1H), 6.43 (br s, 1H), 5.24 (br s, 1H), 4.00 (q, J=7.1 Hz, 2H), 3.47 (dd, J$_1$=5.1 Hz, J$_2$=14.0 Hz, 1H), 3.34 (dd, J$_1$=7.5 Hz, J=14.2 Hz, 1H), 1.15 (br s, 3H); $^{13}$C NMR (125 MHz, CDCl$_2$) δ 158.61, 155.98, 147.61, 142.26, 136.38, 129.51, 128.99, 128.36, 127.52, 127.08, 126.81, 126.18, 126.11, 122.06, 60.68, 54.92, 44.97, 29.67, 14.51; HRMS (ESI-TOF) Calcd. for C$_{20}$H$_{21}$N$_2$O$_2$ [M+H]$^+$ 321.1598, found 321.1599.

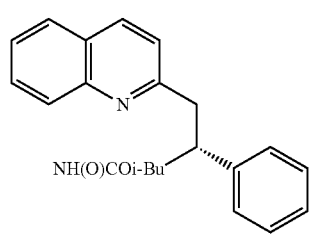

White solid. isobutyl (R)-(1-phenyl-2-(quinolin-2-yl)ethyl)carbamate (L46)

¹H NMR (500 MHz, CDCl₃) δ 8.08 (d, J=8.5 Hz, 1H), 7.99 (d, J=8.4 Hz, 1H), 7.76 (dd, J₁=1.3 Hz, J₂=8.2 Hz, 1H), 7.71 (ddd, J₁=1.4 Hz, J₂=6.8 Hz, J₃=8.4 Hz, 1H), 7.50 (ddd, J₁=1.2 Hz, J₂=6.9 Hz, J₃=8.1, Hz, 1H), 7.22-7.29 (m, 4H), 7.21-7.18 (m, 1H), 7.09 (br s, 1H), 6.41 (br s, 1H), 5.23 (br s, 1H), 3.74 (dd, J₁=6.7 Hz, J₂=10.1 Hz, 2H), 3.51-3.43 (m, 1H), 3.40-3.29 (m, 1H), 1.80 (br s, 1H), 0.83 (s, 6H); ¹³C NMR (125 MHz, CDCl₃) δ 158.64, 156.13, 147.60, 142.23, 136.41, 129.53, 128.95, 128.38, 127.52, 127.09, 126.82, 126.16, 126.12, 122.03, 70.88, 54.95, 45.00, 29.68, 27.91, 18.92; HRMS (ESI-TOF) Calcd. for C₂₂H₂₅N₂O₂ [M+H]⁺ 349.1911, found 349.1911.

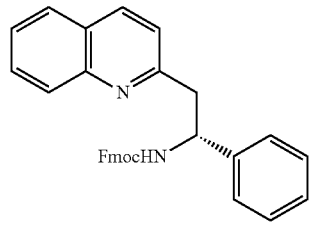

tert-butyl (R)-(1-phenyl-2-(quinolin-2-yl)-ethyl)-carbamate (L47)

White solid. ¹H-NMR (600 MHz, CDCl₃) δ 8.08 (d, J=8.4 Hz, 1H), 7.99 (d, J=8.4 Hz, 1H), 7.76 (dd, J₁=1.3 Hz, J₂=8.2 Hz, 1H), 7.71 (ddd, J₁=1.4 Hz, J₂=6.8 Hz, J₃=8.4 Hz, 1H), 7.50 (ddd, J₁=1.2 Hz, J₂=6.8 Hz, J₃=8.1 Hz, 1H), 7.25 (d, J=5.7 Hz, 4H), 7.20 (dt, J₁=3.2 Hz, J₂=5.6 Hz, 1H), 7.09 (d, J=8.4 Hz, 1H), 6.07 (br s, 1H), 5.21 (br s, 1H), 3.55-3.41 (m, 1H), 3.40-3.23 (m, 1H), 1.32 (s, 9H); ¹³C NMR (150 MHz, CDCl₃) δ 158.71, 155.21, 147.64, 142.39, 136.29, 129.46, 128.96, 128.36, 127.51, 127.01, 126.81, 126.17, 126.06, 122.08, 79.21, 54.55, 45.36, 28.23; HRMS (ESI-TOF) Calcd. for C₂₂H₂₅N₂O₂ [M+H]⁺ 349.1911, found 349.1917.

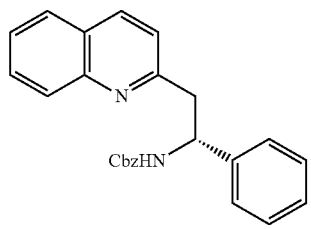

benzyl (R)-(1-phenyl-2-(quinolin-2-yl)ethyl)carbamate (L48)

White solid. ¹H NMR (600 MHz, CDCl₃) δ 8.06 (d, J=8.5 Hz, 1H), 7.97 (d, J=8.4 Hz, 1H), 7.75 (d, J=8.1 Hz, 1H), 7.70 (t, J=7.7 Hz, 1H), 7.50 (t, J=7.5 Hz, 1H), 7.14-7.35 (m, 10H), 7.07 (d, J=8.3 Hz, 1H), 6.58 (br s, 1H), 5.27 (d, J=7.9 Hz, 1H), 4.93-5.07 (m, 2H), 3.48 (dd, J₁=4.9 Hz, J₂=14.2 Hz, 1H), 3.28-3.39 (m, 1H); ¹³C NMR (150 MHz, CDCl₃) δ 158.50, 155.72, 147.56, 142.04, 136.62, 136.44, 129.55, 128.98, 128.40, 128.34, 127.87, 127.53, 127.15, 126.80, 126.18, 126.14, 122.04, 66.46, 55.04, 44.89; HRMS (ESI-TOF) Calcd. for C₂₅H₂₃N₂O₂ [M+H]⁺ 383.1754, found 383.1751.

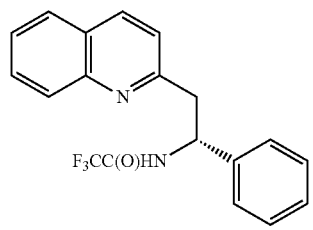

(9H-fluoren-9-yl)methyl (R)-(1-phenyl-2-(quinolin-2-yl)ethyl)carbamate (L49)

White foam. ¹H NMR (500 MHz, CDCl₃) δ 8.11 (d, J=8.4 Hz, 1H), 8.02 (d, J=8.4 Hz, 1H), 7.79-7.77 (m, 2H), 7.70 (t, J=7.2 Hz, 1H), 7.58 (t, J=7.5 Hz, 1H), 7.54-7.45 (m, 2H), 7.33 (t, J=7.5 Hz, 2H), 7.31-7.24 (m, 4H), 7.26-7.11 (m, 2H), 6.82 (br s, 1H), 5.21 (br s, 1H), 4.29 (t, J=9.2 Hz, 1H), 4.22 (t, J=8.8 Hz, 1H), 4.17-4.09 (m, 1H), 3.56-3.44 (m, 1H), 3.41-3.26 (m, 1H); ¹³C NMR (150 MHz, CDCl₃) δ 158.69, 155.73, 147.58, 143.94, 142.19, 141.19, 136.65, 129.69, 128.93, 128.49, 127.62, 127.50, 127.22, 126.93, 126.91, 126.24, 126.13, 125.08, 122.03, 119.83, 66.59, 55.17, 47.17, 44.79; HRMS (ESI-TOF) Calcd. for C₃₁H₃₆N₂O [M+H]⁺ 471.2067, found 471.2073.

(R)-2,2,2-trifluoro-N-(1-phenyl-2-(quinolin-2-yl)-ethyl)acetamide (L50)

White solid. ¹H NMR (500 MHz, CDCl₃) δ 10.30 (d, J=6.8 Hz, 1H), 8.04 (d, J=8.6 Hz, 1H), 8.01 (d, J=8.4 Hz, 1H), 7.78 (d, J=8.4 Hz, 1H), 7.76 (t, J=8.4 Hz, 1H), 7.55 (ddd, J₁=1.1 Hz, J₂=6.8 Hz, J₃=8.1 Hz, 1H), 7.13-7.23 (m, 3H), 7.11 (dd, J₁=1.7 Hz, J₂=7.8 Hz, 2H), 7.02 (d, J=8.3 Hz, 1H), 5.47 (q, J=5.6 Hz, 1H), 3.58 (dd, J₁=4.7 Hz, J₂=14.6 Hz, 1H), 3.36 (dd, J₁=5.5 Hz, J₂=14.6 Hz, 1H); ¹³C NMR (125 MHz, CDCl₃) δ 158.31, 156.45 (q, J_FC=36.6 Hz), 147.02, 139.93, 137.12, 130.14, 128.57, 128.51, 127.66, 127.49, 126.85, 126.58, 125.99, 122.49, 116.20 (d, J_FC=288.1 Hz), 53.40, 42.20; ¹⁹F-NMR (375 MHz, CDCl₃) δ −76.2; HRMS (ESI-TOF) Calcd. for C₁₉H₁₆F₃N₂O [M+H]⁺ 345.1209, found 345.1208.

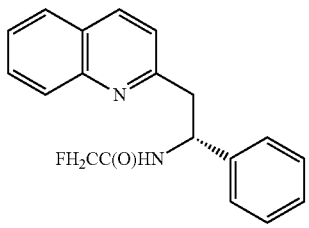

(R)-2-fluoro-N-(1-phenyl-2-(quinolin-2-yl)-ethyl) acetamide (L51)

White solid. $^1$H NMR (500 MHz, CDCl$_3$) δ 8.97 (d, J=6.5 Hz, 1H), 8.08 (d, J=8.5 Hz, 1H), 7.99 (d, J=8.4 Hz, 1H), 7.77 (dd, J$_1$=1.3 Hz, J$_2$=8.2 Hz, 1H), 7.72 (ddd, J$_1$=1.4 Hz, J$_2$=6.9 Hz, J$_3$=8.3 Hz, 1H), 7.52 (ddd, J$_1$=1.1 Hz, J$_2$=6.9 Hz, J$_3$=8.1 Hz, 1H), 7.12-7.25 (m, 5H), 7.05 (d, J=8.4 Hz, 1H), 5.57 (q, J=6.5 Hz, 1H), 4.79 (d, J$_1$=47.4 Hz, 2H), 3.55 (dd, J$_1$=4.9 Hz, J$_2$=14.2 Hz, 1H), 3.39 (dd, J$_1$=6.5 Hz, J$_2$=14.2 Hz, 1H); $^{13}$C NMR (125 MHz, CDCl$_3$) δ 166.97 (d, J$_{FC}$=17.3 Hz), 158.43, 147.40, 141.16, 136.62, 129.77, 128.87, 128.41, 127.53, 127.23, 126.78, 126.29, 126.21, 122.25, 80.37 (d, J$_{FC}$=186.3 Hz), 52.50, 43.63; $^{19}$F NMR (375 MHz, CDCl$_3$) δ −225.12; HRMS (ESI-TOF) Calcd. for C$_{19}$H$_{18}$FN$_2$O [M+H]$^+$ 309.1.398, found 309.1398.

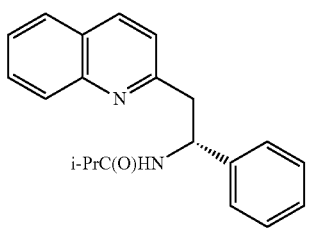

(R)—N-(1-phenyl-2-(quinolin-2-yl)ethyl)propionamide (L52)

White solid. $^1$H NMR (500 MHz, CDCl$_3$): δ 8.04 (dd, J$_1$=1.1 Hz, J$_2$=8.4 Hz, 1H), 8.01 (d, J=8.3 Hz, 1H), 7.78 (dd, J$_1$=1.4 Hz, J$_2$=8.1 Hz, 1H), 7.72 (ddd, J$_1$=1.9 Hz, J$_2$=6.5 Hz, J$_3$=8.4 Hz, 1H), 7.63 (d, J=7.3 Hz, 1H), 7.52 (ddd, J$_1$=1.2 Hz, J$_2$=6.9 Hz, J=8.1 Hz, 1H), 7.25-7.20 (m, 4H), 7.19-7.14 (m, 1H), 7.10 (d, J=8.4 Hz, 1H), 5.48 (dt, J$_1$=4.8 Hz, J$_2$=7.4 Hz, 1H), 3.50 (dd, J$_1$=4.8 Hz, J$_2$=14.0 Hz, 1H), 3.35 (dd, J$_1$=7.5 Hz, J$_2$=14.0 Hz, 1H), 2.25-2.20 (m, 2H), 1.11 (t, J=7.6 Hz, 3H); $^{13}$C NMR (125 MHz, CDCl$_3$): δ 172.98, 158.99, 147.40, 141.95, 136.61, 129.68, 128.63, 128.37, 127.69, 127.02, 126.84, 126.21, 126.19, 122.27, 52.92, 44.28, 29.82, 9.72; HRMS (ESI-TOF) Calcd. for C$_{20}$H$_{21}$N$_2$O, [M+H]$^+$ 305.1648, found 305.1652.

(R)—N-(1-phenyl-2-(quinolin-2-yl)ethyl)isobutyramide (L53)

White solid. $^1$H NMR (500 MHz, CDCl$_3$): δ 8.05 (d, J=8.4 Hz, 1H), 8.01 (d, J=8.4 Hz, 1H), 7.78 (d, J=8.0 Hz, 1H), 7.72 (ddd, J$_1$=1.4 Hz, J$_2$=7.0 Hz, J$_3$=8.4 Hz, 1H), 7.71 (d, J=7.6 Hz, 1H), 7.52 (ddd, J$_1$=0.9 Hz, J$_2$=7.0 Hz, J$_3$=8.0 Hz, 1H), 7.26-7.15 (m, 5H), 7.11 (d, J=8.4 Hz, 1H), 5.46 (dt, J$_1$=4.8 Hz, J$_2$=7.6 Hz, 1H), 3.50 (dd, J$_1$=4.8 Hz, J$_2$=14.0 Hz, 1H), 3.35 (dd, J$_1$=7.6 Hz, J$_2$=14.0 Hz, 1H), 2.42-2.36 (m, 1H), 1.12 (d, J=6.9 Hz, 3H), 1.06 (d, J=6.9 Hz, 3H); $^{13}$C NMR (125 MHz, CDCl$_3$) δ 176.08, 159.06, 147.37, 142.08, 136.62, 129.70, 128.59, 128.36, 127.70, 126.97, 126.84, 126.19, 126.13, 122.30, 52.75, 44.29, 35.66, 19.47; HRMS (ESI-TOF) Calcd. for C$_{21}$H$_{23}$N$_2$O [M+H]$^+$ 319.1805; found 319.1803.

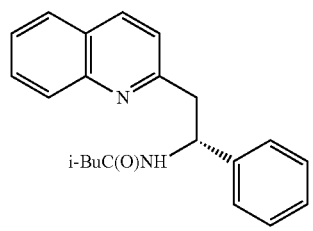

(R)-3-methy-N-(1-phenyl-2-(quinolin-2-yl)ethyl)-butanamide (L54)

White solid. $^1$H NMR (500 MHz, CDCl$_3$) δ 8.06 (d, J=8.4 Hz, 2H), 7.78 (d, J=8.2 Hz, 1H), 7.73 (t, J=7.8 Hz, 1H), 7.57 (d, J=7.8 Hz, 1H), 7.53 (t, J=7.6 Hz, 1H), 7.33-7.16 (m, 6H), 5.50 (dt, J$_1$=4.6 Hz, J$_2$=8.2 Hz, 1H), 3.48 (dd, J$_1$=4.8 Hz, J$_2$=14.0 Hz, 1H), 3.36 (dd, J$_1$=8.8 Hz, J$_2$=14.0 Hz, 1H), 2.05-1.90 (m, 1H), 1.05 (d, J=6.5 Hz, 2H), 0.74 (d, J=6.0 Hz, 3H), 0.66 (d, J=6.0 Hz, 3H); $^{13}$C NMR (125 MHz, CDCl$_3$) δ 171.87, 158.98, 147.15, 142.18, 136.98, 129.77, 128.42, 128.19, 127.67, 127.08, 126.90, 126.26, 122.02, 53.39, 53.07, 46.12, 44.43, 26.05, 22.26, 22.16; HRMS (ESI-TOF) Calcd. for C$_{22}$H$_{25}$N$_2$O [M+H]$^+$ 333.1961, found 333.1966.

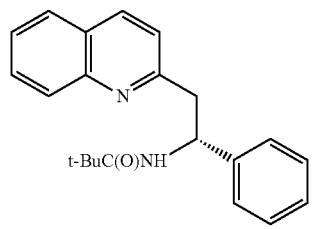

(R)—N-(1-phenyl-2-(quinolin-2-yl)ethyl)pivalamide (L55)

White solid. $^1$H-NMR (500 MHz, CDCl$_3$) δ 8.20 (d, J=6.8 Hz, 1H), 8.04 (d, J=8.5 Hz, 1H), 7.99 (d, J=8.4 Hz, 1H), 7.77 (dd, J$_1$=1.4 Hz, J$_2$=8.2 Hz, 1H), 7.73 (ddd, J$_1$=1.4 Hz, J$_2$=6.9 Hz, J$_3$=8.4 Hz, 1H), 7.52 (ddd, J$_1$=1.1 Hz, J$_2$=6.9 Hz, J$_3$=8.0 Hz, 1H), 7.23-7.18 (m, 2H), 7.17-7.12 (m, 3H), 7.04 (d, J=8.3 Hz, 1H), 5.40 (dt, J$_1$=4.6 Hz, J$_2$=6.9 Hz, 1H), 3.50 (dd, J$_1$=4.6 Hz, J$_2$=13.9 Hz, 1H), 3.32 (dd, J$_1$=7.1 Hz, J$_2$=13.9 Hz, 1H), 1.19 (s, 9H); $^{13}$C NMR (125 MHz, CDCl$_3$) δ

177.74, 159.16, 147.32, 142.22, 136.60, 129.73, 128.51, 128.28, 127.70, 126.83, 126.80, 126.17, 125.96, 122.44, 52.87, 44.15, 38.69, 27.53; HRMS (ESI-TOF) Calcd. for $C_{22}H_{25}N_2O$ [M+H]$^+$ 333.1961, found 333.1960.

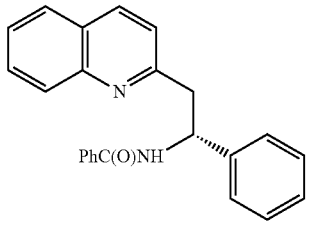

(R)—N-(1-phenyl-2-(quinolin-2-yl)ethyl)benzamide (L56)

White solid. $^1$H NMR (500 MHz, CDCl$_3$) δ 9.15 (d, J=6.8 Hz, 1H), 8.19 (d, J=8.4 Hz, 1H), 8.10 (d, J=8.4 Hz, 1H), 8.02 (dd, J$_1$=1.7 Hz, J$_2$=7.9 Hz, 2H), 7.87 (d, J=8.2 Hz, 1H), 7.84 (dd, J$_1$=6.9 Hz, J$_2$=8.4 Hz, 1H), 7.62 (d, J=7.7 Hz, 1H), 7.58 (d, J=7.0 Hz, 1H), 7.54 (t, J=7.4 Hz, 2H), 7.33 (d, J=7.1 Hz, 2H), 7.30 (t, J=7.5 Hz, 2H), 7.25 (t, J=6.9 Hz, 1H), 7.18 (d, J=8.4 Hz, 1H), 5.73 (q, J=6.4 Hz, 1H), 3.71 (dd, J$_1$=4.7 Hz, J$_2$=14.0 Hz, 1H), 3.53 (dd, J$_1$=6.7 Hz, J$_2$=14.1 Hz, 1H); $^{13}$C NMR (125 MHz, CDCl$_3$) δ 166.38, 159.15, 147.32, 141.85, 136.80, 134.63, 131.32, 129.86, 128.49, 128.43, 128.34, 127.77, 127.10, 127.00, 126.89, 126.27, 126.16, 122.57, 53.49, 43.92; HRMS (ESI-TOF) Calcd. for $C_{24}H_{21}N_2O$ [M+H]$^+$ 353.1648, found 353.1655.

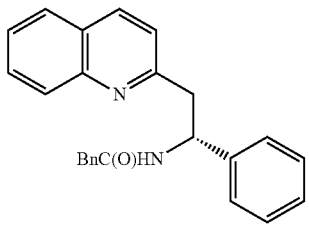

(R)-2-phenyl-N-(1-phenyl-2-(quinolin-2-yl)-ethyl)acetamide (L57)

White solid. $^1$H NMR (600 MHz, CDCl$_3$) δ 7.95 (d, J=8.3 Hz, 1H), 7.80 (dd, J$_1$=1.1 Hz, J$_2$=8.4 Hz, 1H), 7.75 (dd, J$_1$=1.5 Hz, J$_2$=8.2 Hz, 1H), 7.70 (ddd, J$_1$=1.5 Hz, J$_2$=6.8 Hz, J$_1$=8.4 Hz, 1H), 7.52 (ddd, J$_1$=1.2 Hz, J$_2$=6.8 Hz, J$_3$=8.0 Hz, 1H), 7.36 (d, J=7.6 Hz, 1H), 7.24-7.18 (m, 5H), 7.18-7.08 (m, 5H), 7.03 (d, J=8.4 Hz, 1H), 5.51 (dt, J$_1$=4.7 Hz, J$_2$=7.7 Hz, 1H), 3.53 (s, 2H), 3.44 (dd, J$_1$=4.8 Hz, J$_2$=14.2 Hz, 1H), 3.27 (dd, J$_1$=7.9 Hz, J$_2$=14.2 Hz, 1H); $^{13}$C NMR (150 MHz, CDCl$_3$) δ 170.28, 158.62, 147.33, 141.75, 136.47, 134.88, 129.40, 129.34, 128.96, 128.80, 128.33, 127.54, 127.09, 127.00, 126.75, 126.13, 121.97, 53.07, 44.25, 43.99; HRMS (ESI-TOF) Calcd. for $C_{25}H_{23}N_2O$ [M+H]$^+$ 367.1805, found 367.1803.

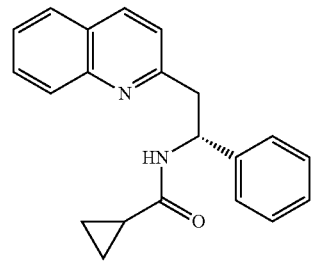 [SMILES: O=C(N[C@H](Cc1ccc2ccccc2n1)c1ccccc1)C1CC1]

(R)—N-(1-phenyl-2-(quinolin-2-yl)-ethyl)cyclopropanecarboxamide (L58)

White solid. $^1$H NMR (500 MHz, CDCl$_3$) δ 8.06 (d, J=8.5 Hz, 1H), 8.00 (d, J=8.4 Hz, 1H), 7.78 (dd, J$_1$=1.4 Hz, J$_2$=8.2 Hz, 1H), 7.73-7.69 (m, 4H), 7.52 (ddd, J$_1$=1.1 Hz, J$_2$=6.9 Hz, J$_3$=8.0 Hz, 1H), 7.25-7.20 (m, 4H), 7.18-7.15 (m, 1H), 7.10 (d, J=8.4 Hz, 1H), 5.49 (dt, J$_1$=5.0 Hz, J$_2$=7.3 Hz, 1H), 3.50 (dd, J$_1$=5.0 Hz, J$_2$=14.0 Hz, 1H), 3.37 (dd, J$_1$=7.4 Hz, J$_2$=14.0 Hz, 1H), 1.45-1.39 (m, 1H), 0.90-0.79 (m, 2H), 0.70-0.61 (m, 2H); $^{13}$C NMR (125 MHz, CDCl$_3$) δ 172.79, 159.01, 147.45, 141.98, 136.53, 129.60, 128.73, 128.36, 127.67, 127.00, 126.85, 126.26, 126.15, 122.28, 53.23, 44.36, 14.89, 7.03, 6.98; HRMS (ESI-TOF) Calcd. for $C_{21}H_2N_2O$ [M+H]$^+$ 317.1648; found 317.1649.

Synthesis Ligand of L59

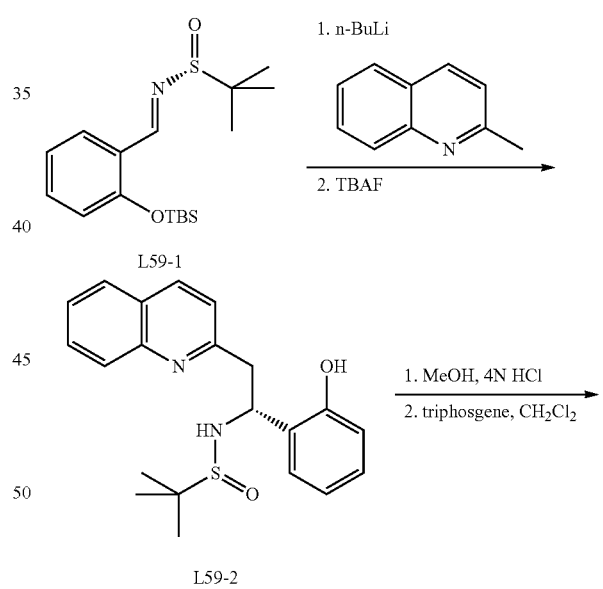

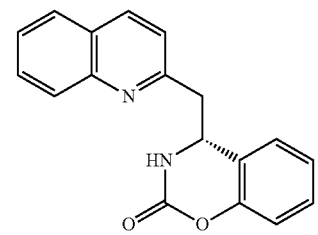 [SMILES: O=C1N[C@H](Cc2ccc3ccccc3n2)c2ccccc2O1]

L59

Synthesis of L59-2 n-Butyllithium (1.50 mL, 1.6 M solution in hexanes, 2.40 mmol) was added to quinaldine (0.35 mL, 2.59 mmol) in 20 mL THF. After 90 minutes, a solution of L59-1 (679 mg, 2.00 mmol) in THF (2.0 mL) was added at −78° C., leading the solution along the flask's interior walls. The dry ice was removed 90 minutes later and the solution was allowed to warm to rt for 5 hours. Aqueous workup gave 1.179 g crude product (d.r. about 1:10), which was subjected to preparative TLC (EtOAC/$CH_2Cl_2$=1/8, developed three times) to obtain of the TBS-protected sulfonamide (723 mg, 1.50 mmol, 75%). In an open flask, tetrabutylammonium fluoride (TBAF) (0.72 mL, 1 M in THF, 0.72 mmol) was added dropwise to a solution of TBS-protected sulfonamide (1.72 mg, 0.36 mmol) in THF (5 mL). After 45 minutes, the reaction mixture was diluted with $CH_2Cl_2$ (25 mL) and brine (50 mL). After phase separation, the aqueous phase was extracted with $CH_2Cl_2$ (3×5 mL). The combined organic extracts were dried with $Na_2SO_4$ and concentrated in vacuo to give a crude product, which was subjected to preparative TLC (EtOAc/$CH_2Cl_2$=1/1) to obtain L59-2 (122 mg, 93%). $^1$H NMR (500 MHz, $CDCl_3$) δ 10.11 (br s, 1H), 8.10 (d, J=8.5 Hz, 1H), 8.00 (d, J=8.4 Hz, 1H), 7.76 (dd, $J_1$=1.4 Hz, $J_2$=8.2 Hz, 1H), 7.71 (ddd, $J_1$=1.5 Hz, $J_2$=6.9 Hz, $J_3$=8.4 Hz, 1H), 7.50 (t, J=7.5 Hz, 1H), 7.17 (d, J=8.4 Hz, 1H), 7.08 (dd, $J_1$=1.6 Hz, $J_2$=7.5 Hz, 1H), 6.84 (dt, $J_1$=1.6 Hz, $J_2$=7.6 Hz, 1H), 6.67 (dt, $J_1$=1.1 Hz, $J_2$=7.4 Hz, 1H), 6.50 (d, J=8.0 Hz, 1H), 5.20 (d, J=7.9 Hz, 1H), 5.07 (q, J=7.6 Hz, 1H), 3.77 (dd, $J_1$=8.0 Hz, $J_2$=14.5 Hz, 1H), 3.46 (dd, $J_1$=6.8 Hz, $J_2$=14.5 Hz, 1H), 1.07 (s, 9H); $^{13}$C NMR (125 MHz, $CDCl_3$) δ 159.38, 154.97, 147.29, 136.32, 129.65, 128.90, 128.31, 127.89, 127.58, 127.52, 126.80, 126.05, 122.40, 119.32, 116.98, 59.46, 56.16, 45.09, 22.51.

Synthesis of L59

L59-2 (119 mg, 0.32 mmol) in MeOH (10 mL) was stirred with HCl (0.50 mL, 4 M solution in dioxane, 2 mmol) for 30 minutes. Under $N_2$-atmosphere the intermediate was dissolved in $CH_2Cl_2$ (5.0 mL) and pyridine (0.52 mL) and stirred with a solution of triphosgene (126 mg, 0.43 mmol) in $CH_2Cl_2$ (1.0 mL) for 4 hours, at which point the reaction mixture began to turn brown. After aqueous workup with sat. aq. $CuSO_4$ solution, the residue was subjected to preparative TLC (EtOAc/$CH_2Cl_2$=1/1) to give L59 as a yellow foam (22 mg, 23%).

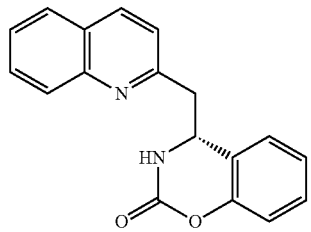

(R)-4-(quinolin-2-ylmethyl)-3,4-dihydro-2H-benzo[e][1,3]oxazin-2-one (L59)

$^1$H NMR (600 MHz, $CDCl_3$) δ 8.11 (d, J=8.4 Hz, 1H), 8.07 (d, J=8.4 Hz, 1H), 7.81 (dd, $J_1$=1.4 Hz, $J_2$=8.2 Hz, 1H), 7.74 (ddd, $J_1$=1.5 Hz, $J_2$=6.9 Hz, $J_3$=8.4 Hz, 1H), 7.55 (dt, $J_1$=1.2 Hz, $J_2$=6.8 Hz, $J_3$=7.4 Hz, 1H), 7.31 (dt, $J_1$=1.7 Hz, $J_2$=7.8 Hz, 1H), 7.21 (d, J=8.3 Hz, 2H), 7.16 (dt, $J_1$=1.2 Hz, $J_2$=7.4 Hz, 1H), 7.08 (dd, $J_1$=1.1 Hz, $J_2$=8.2 Hz, 1H), 7.04 (br s, 1H), 5.41 (dt, $J_1$=2.7 Hz, $J_2$=10.4 Hz), 3.49 (dd, $J_1$=3.2 Hz, $J_2$=16.4 Hz, 1H), 3.41 (dd, $J_1$=10.2 Hz, $J_2$=16.4 Hz, 1H); $^{13}$C NMR (150 MHz, $CDCl_3$) δ 157.52, 150.29, 149.66, 147.45, 136.88, 129.90, 129.13, 128.92, 127.60, 126.90, 126.51, 125.61, 124.39, 121.82, 120.55, 116.83, 51.64, 46.30; HRMS (ES-TOF) Calcd. for $C_{18}H_{14}N_2O_2$ [M+H]$^+$ 291.1128, found 291.1121.

Synthesis of Racemic Ligand L60

[Qian, et al., *J. Am. Chem. Soc.* 132, 3650-3651 (2010); and Hesp, et al., *Org. Lett.* 14, 2304-2307 (2012)]

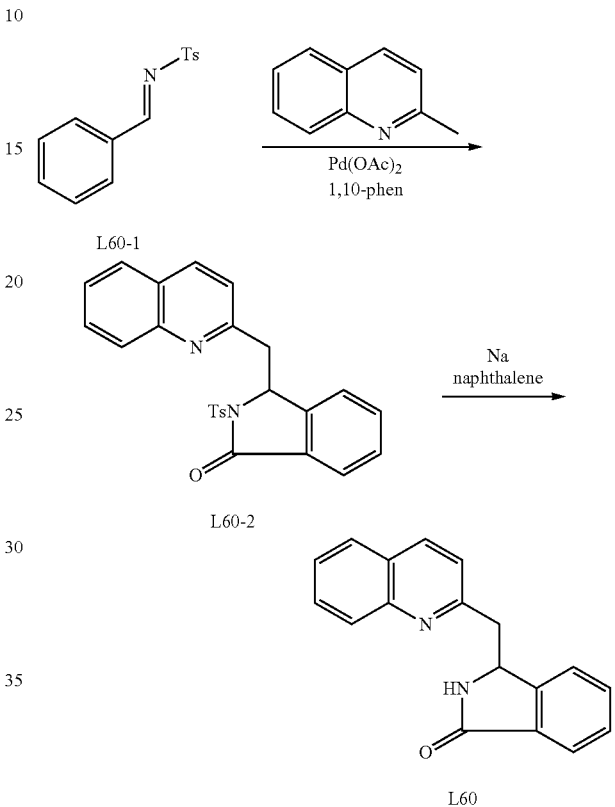

Under $N_2$-atmosphere Pd(OAc)$_2$ (2.8 mg, 0.13 mmol), 1,10-phenanthroline (1,10-phen; 3.4 mg, 0.19 mmol) and dry $CH_2Cl_2$ (1.0 mL) were added to a screw cap vial containing a stir bar, the mixture was kept stirring at 40° C. for 0.5 hours. After evaporating $CH_2Cl_2$, quinaldine (0.10 mL, 0.74 mmol), L60-1 (95 mg, 0.3 mmol), and dry THF (1.5 mL) were added to the vial. The mixture was kept stirring at 120° C. for 26 hours. The solvent was evaporated under reduced pressure and the residue was purified by pTLC (EtOAc/$CH_2Cl_2$=1/50) to give L60-2 (91 mg, 71%). $^1$H NMR (600 MHz, $CDCl_3$) δ 8.07 (d, J=8.3 Hz, 2H), 8.06 (d, J=8.4 Hz, 1H), 7.93 (dd, $J_1$=1.1 Hz, $J_2$=8.4 Hz, 1H), 7.78 (dd, $J_1$=1.4 Hz, $J_2$=8.0 Hz, 1H), 7.70 (d, J=7.4 Hz, 1H), 7.68 (ddd, $J_1$=1.5 Hz, $J_2$=6.9 Hz, $J_3$=8.4 Hz, 1H), 7.52 (ddd, $J_1$=1.2 Hz, $J_2$=6.9 Hz, $J_3$=8.1 Hz, 1H), 7.38 (dt, $J_1$=1.4 Hz, $J_2$=7.5 Hz, 1H), 7.35 (dt, $J_1$=1.1 Hz, $J_2$=7.4 Hz, 1H), 7.28 (dd, $J_1$=3.0 Hz, $J_2$=8.3 Hz, 3H), 6.99 (dd, $J_1$=1.0 Hz, $J_2$=7.6 Hz, 1H), 6.03 (dd, $J_1$=3.4 Hz, $J_2$=8.8 Hz, 1H), 4.31 (dd, $J_1$=3.4 Hz, $J_1$=14.6 Hz, 1H), 3.44 (dd, $J_1$=8.8 Hz, $J_2$=14.5 Hz, 1H), 2.38 (s, 3H); $^{13}$C NMR (150 MHz, $CDCl_3$) δ 166.67, 156.75, 147.62, 145.90, 144.97, 136.32, 135.95, 133.57, 129.51, 129.49, 129.26, 129.10, 128.70, 128.33, 127.51, 126.86, 126.27, 124.66, 123.70, 122.09, 61.39, 43.06, 21.61.

Under $N_2$-atmosphere finely chopped sodium metal (26.7 mg, 1.16 mmol) and naphthalene (170 mg, 1.33 mmol) were suspended in freshly dried and distilled DME (2.0 mL), and stirred for 2 hours at room temperature. Of this dark green solution 1.00 mL were added dropwise over 15 minutes to a solution of L60-2 (71 mg, 0.17 mmol) in DME (1.0 mL) at −78° C. under N$_2$-atmosphere. After the addition, the dark green color persisted for 3 minutes before the reaction mixture solidified. The green solid was overlaid with MeOH (1.0 mL) by dropwise addition and gently warmed to room temperature. The obtained orange solution was diluted with EtOAc (20 mL) and (brine 80 mL). After phase separation, the aqueous phase was extracted with EtOAc (3×5 mL). The combined organic extracts were dried with MgSO$_4$ and concentrated in vacuo. The residue was subjected to preparative TLC (EtOAc/CH$_2$Cl$_2$=1/3) to give L60 as a yellow foam (15 mg, 33%). Additionally, 14 mg (8%) of starting material L60-2 was recovered.

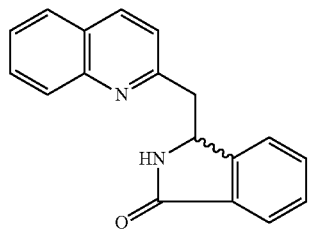 [SMILES: O=C1NC(Cc2ccc3ccccc3n2)c2ccccc21]

3-(quinolin-2-ylmethyl)isoindolin-1-one (L60)

$^1$H NMR (600 MHz, CDCl$_3$) δ 8.12 (dd, J=0.8 Hz, J$_1$=8.4 Hz, 1H), 8.08 (dd, J$_1$=1.0 Hz, J$_2$=8.4 Hz, 1H), 7.90 (dt, J$_1$=1.0 Hz, J$_2$=7.5 Hz, 1H), 7.82 (dd, J$_1$=1.4 Hz, J$_2$=8.1 Hz, 1H), 7.75 (ddd, J$_1$=1.4 Hz, J$_2$=6.9 Hz, J$_2$=8.4 Hz, 1H), 7.60 (dt, J$_1$=1.2 Hz, J$_2$=7.5 Hz, 1H), 7.55 (ddd, J$_1$=1.2 Hz, J$_2$=6.8 Hz, J$_3$=8.1 Hz, 1H), 7.51 (t, J=7.5 Hz, 1H), 7.49 (dd, J$_1$=0.9 Hz, J$_2$=7.5 Hz, 1H), 7.45 (br s, 1H), 7.28 (d, J=8.4 Hz, 1H), 5.30 (dd, J$_1$=3.4 Hz, J$_2$=10.6 Hz, 1H), 3.68 (dd, J$_1$=3.4 Hz, J$_2$=15.8 Hz, 1H), 3.09 (dd, J$_1$=10.6 Hz, J$_2$=15.8 Hz, 1H); $^{13}$C NMR (150 MHz, CDCl$_3$) δ 169.90, 158.35, 147.75, 147.18, 136.68, 132.29, 131.75, 129.85, 129.01, 128.34, 127.60, 126.93, 126.40, 124.01, 122.38, 121.65, 55.52, 43.03.

Syntheses of Pyridine and Imazoline Ligands with Two Chiral Centers

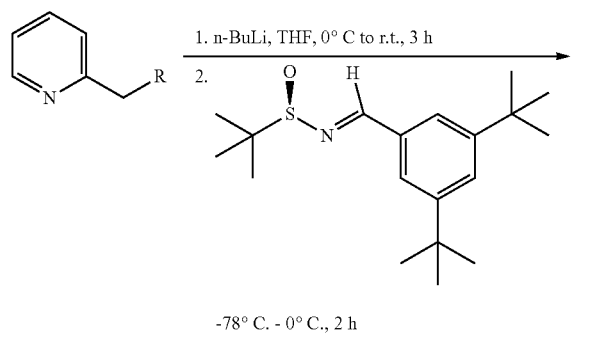

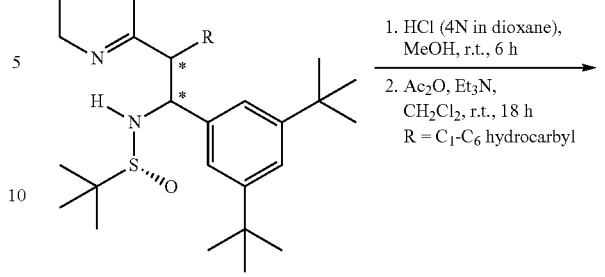

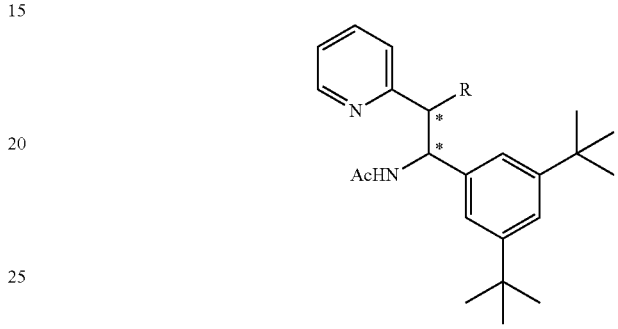

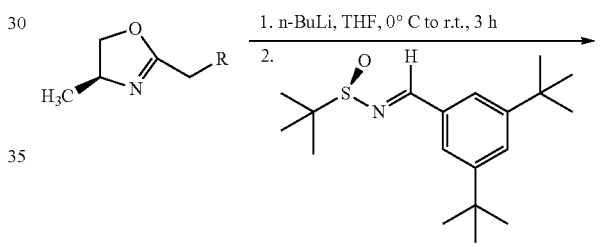

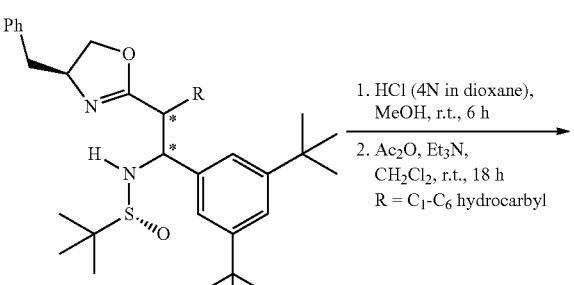

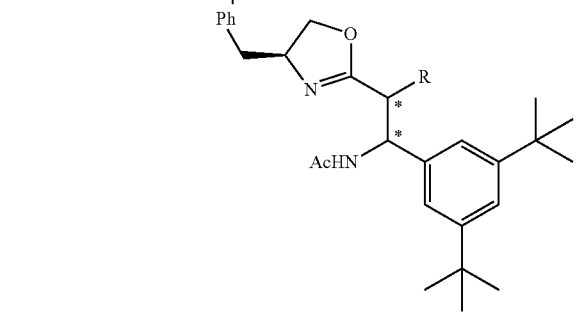

Preparation of Mono-N-Protected Aminomethyl Oxazoline Ligands

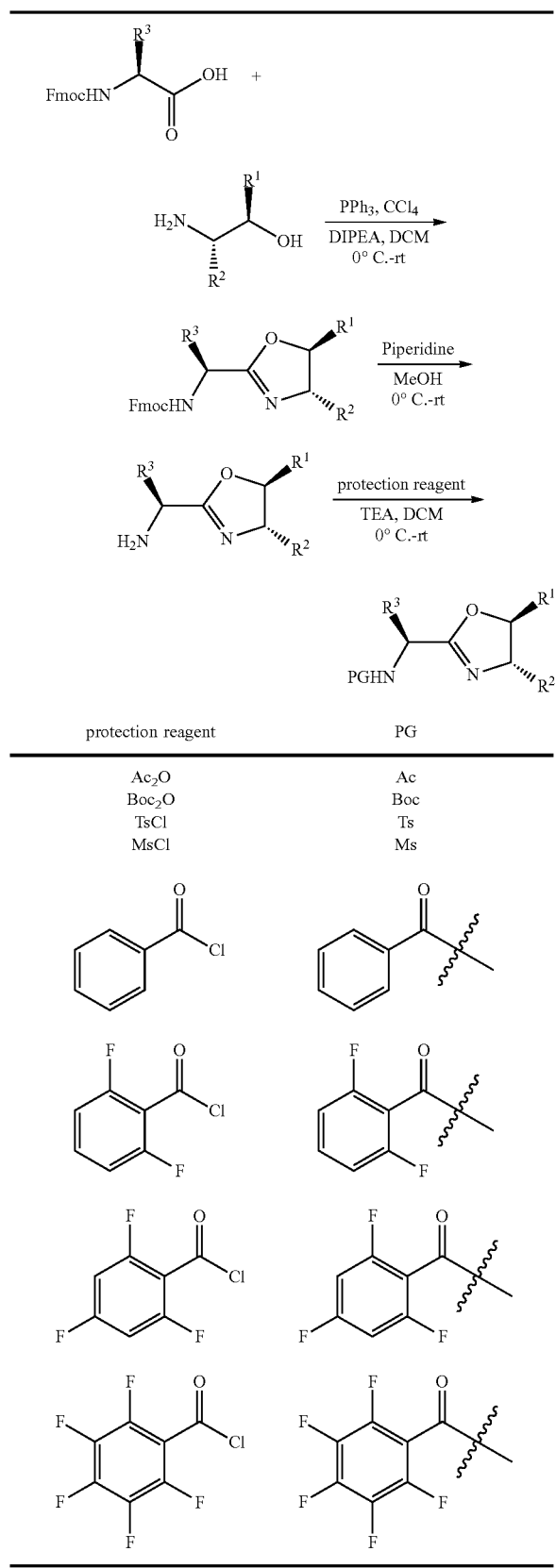

| protection reagent | PG |
|---|---|
| Ac$_2$O | Ac |
| Boc$_2$O | Boc |
| TsCl | Ts |
| MsCl | Ms |

General Procedure for the Preparation of Oxazoline Ligands [Lee et al., Org. Lett. 2005, 7:1837-1839]:

Synthesis of Fmoc Protected Oxazoline

To a solution of N-Fmoc-protected amino acid (10.0 mmol) in DCM (200 mL), amino alcohol (10.0 mmol), PPh$_3$ (30.0 mmol) and N,N-diisopropylethylamine (DIPEA) (30.0 mmol) were added at 0° C. CCl$_4$ (50.0 mmol) was added dropwise over three hours via a syringe pump. The ice bath was removed after the addition, and the reaction mixture was stirred at room temperature for 24 hours. The solvents were then removed under reduced pressure. The residue was purified by silica gel column chromatography to afford the desired oxazoline.

Deprotection of the Fmoc Protected Oxazoline

To the solution of N-Fmoc-protected oxazoline (6.0 mmol) in MeOH (30 mL), piperidine was added dropwise at 0° C. The ice bath was removed after the addition, and the reaction was stirred at room temperature. The reaction progress was monitored by TLC. After completion, the solvents were removed under reduced pressure, and the residue was purified by silica gel column chromatography to afford the desired amine.

Protection of the Amine-Acetyl Group Illustration

Triethylamine (4.5 mmol) was added to the solution of the amine (3.0 mmol) in dry DCM (20 mL). Acetic anhydride (4.5 mmol) was added slowly in 10 minutes at 0° C. The ice bath was removed after the addition, and the reaction was stirred at room temperature. The reaction progress was monitored by TLC. After completion, the reaction was quenched at 0° C. with saturated NaHCO$_3$ (aq.). The layers were separated, and the aqueous layer was extracted with DCM. The combined organic layers were dried over anhydrous NaSO$_4$, filtered and concentrated in vacuo. The crude reaction mixture was purified by silica gel column chromatography to afford the desired oxazoline ligand.

Note: When racemic amino alcohol was used for the ligand synthesis, the two diastereomers can be separated at the final step by silica gel column chromatography.

Full Characterization of Ligands

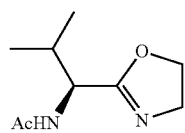

N-((1S,2S)-1-(4,5-dihydrooxazol-2-yl)-2-methyl-butyl)acetamide (L63)

L63 was prepared following the general procedure and was purified by silica gel column chromatography to give a white solid.

$^1$H NMR (600 MHz, CDCl$_3$): δ 6.29 (br, 1H, N—H), 4.66 (dd, J=9.0, 4.8 Hz, 1H), 4.35-4.27 (m, 2H), 3.84 (t, J=9.6 Hz, 2H), 2.16-2.11 (m, 1H), 2.03 (s, 3H), 0.94 (d, J=6.6 Hz, 3H), 0.92 (d, J=7.2 Hz, 3H);

$^{13}$C NMR (150 MHz, CDCl$_3$): 169.75, 167.70, 68.02, 53.75, 52.31, 31.35, 23.24, 18.72, 17.70;

HRMS (ESI-TOF): m/z calculated for C$_9$H$_{17}$N$_2$O$_2$$^+$ [M+H]$^+$ 185.1285, found 185.1288.

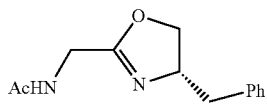 [SMILES: CC(=O)NCC1=N[C@@H](Cc2ccccc2)CO1]

(S)—N-((4-benzyl-4,5-dihydrooxazol-2-yl)methyl)acetamide (L64)

L64 was prepared following the general procedure and was purified by silica gel column chromatography to give a pale yellow oil.

$^1$H NMR (600 MHz, CDCl$_3$): δ 7.32-7.29 (m, 2H), 7.25-7.22 (m, 1H), 7.20-7.19 (m, 2H), 6.24 (br, 1H, N—H), 4.43-4.37 (m, 1H), 4.27 (t, J=9.0 Hz, 18H), 4.06-4.02 (m, 3H), 3.08 (dd, J=13.8, 5.4 Hz, 1H), 2.67 (dd, J=13.8, 8.4 Hz, 1H), 2.04 (s, 3H);

$^{13}$C NMR (150 MHz, CDCl$_3$): 169.97, 164.62, 137.48, 129.13, 128.57, 126.65, 72.59, 66.88, 41.55, 37.03, 22.98;

HRMS (ESI-TOF): m/z calculated for C$_{13}$H$_{17}$N$_2$O$_2^+$ [M+H]$^+$ 233.1285, found 233.1285.

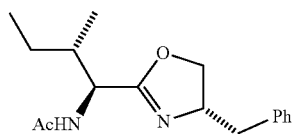 [SMILES: CC[C@H](C)[C@H](NC(C)=O)C1=N[C@@H](Cc2ccccc2)CO1]

N-((1S,2)-1-((S)-4-benzyl-4,5-dihydrooxazol-2-yl)-2-methylbutyl)acetamide (L62)

L62 was prepared following the general procedure and was purified by silica gel column chromatography to give a white solid.

$^1$H NMR (600 MHz, acetone-d$^6$): δ 7.30-7.25 (m, 4H), 7.21-7.18 (m, 1H), 7.12 (br, 1H, N—H), 4.58 (dd, J=9.6, 7.8 Hz, 1H), 4.38-4.33 (m, 1H), 4.23 (t, J=8.4 Hz, 1H), 3.98 (dd, J=7.8, 7.2 Hz, 1H), 2.91 (dd, J=13.8, 6.0 Hz, 1H), 2.70 (dd, J=13.8, 7.2 Hz, 1H), 1.94 (s, 3H), 1.79-1.75 (m, 1H), 1.52-1.46 (m, 1H), 1.21-1.15 (m, 1H), 0.89-0.87 (m, 6H);

$^{13}$C NMR (150 MHz, acetone-d$^6$): 169.53, 166.81, 139.33, 130.30, 129.09, 127.05, 72.43, 67.97, 52.14, 42.30, 38.74, 25.80, 22.85, 15.80, 11.78;

HRMS (ESI-TOF): m/z calculated for C$_{17}$H$_{25}$N$_2$O$_2^+$ [M+H]$^+$ 289.1911, found 289.1906.

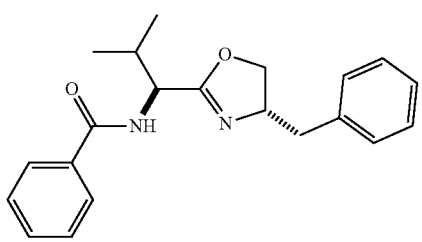 [SMILES: CC(C)[C@H](NC(=O)c1ccccc1)C1=N[C@@H](Cc2ccccc2)CO1]

N—((S)-1-((S)-4-benzyl-4,5-dihydrooxazol-2-yl)-2-methylpropyl)benzamide (L65)

L65 was prepared following the general procedure and was purified by silica gel column chromatography to give a white solid.

$^1$H NMR (600 MHz, CDCl$_3$): δ 7.85-7.83 (m, 2H), 7.53 (tt, J=7.2, 1.8 Hz, 1H), 7.48-7.45 (m, 2H), 7.27-7.25 (m, 2H), 7.21 (tt, J=7.2, 1.8 Hz, 1H), 7.18-7.16 (m, 2H), 6.83 (br, 1H, N—H), 4.81 (dd, J=8.4, 4.8 Hz, 1H), 4.42-4.37 (m, 1H), 4.27 (t, J=8.4 Hz, 1H), 4.07 (dd, J=8.4, 7.2 Hz, 1H), 3.01 (dd, J=13.8, 6.0 Hz, 1H), 2.68 (dd, J=13.8, 7.8 Hz, 1H), 2.26-2.20 (m, 1H), 1.00 (d, J=7.2 Hz, 3H), 0.98 (d, J=6.6 Hz, 3H);

$^{13}$C NMR (150 MHz, CDCl$_3$): 166.99, 166.93, 137.60, 134.38, 131.58, 129.28, 128.56, 128.47, 127.09, 126.56, 72.45, 66.82, 52.83, 41.76, 31.79, 18.82, 17.90;

HRMS (ESI-TOF): m/z calculated for C$_{21}$H$_{25}$N$_2$O$_2^+$ [M+H]$^+$ 337.1911, found 337.1911.

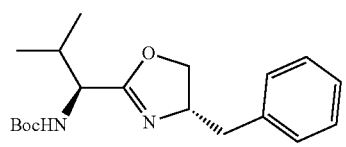 [SMILES: CC(C)[C@H](NC(=O)OC(C)(C)C)C1=N[C@@H](Cc2ccccc2)CO1]

tert-butyl ((S)-1-((S)-4-benzyl-4,5-dihydrooxazol-2-yl)-2-methylpropyl)carbamate (L66)

L66 was prepared following the general procedure and was purified by silica gel column chromatography to give a white solid.

$^1$H NMR (600 MHz, CDCl$_3$): δ 7.30-7.28 (m, 2H), 7.23-7.18 (m, 3H), 5.08 (br, 1H, N—H), 4.40-4.35 (m, 1H), 4.26 (dd, J=9.0, 4.8 Hz, 1H), 4.20-4.17 (m, 1H), 4.02 (t, J=8.4 Hz, 1H), 3.07 (dd, J=13.8, 5.4 Hz, 1H), 2.65 (dd, J=13.8, 8.4 Hz, 1H), 2.09-2.03 (m, 1R), 1.46 (s, 9H), 0.95 (d, J=6.6 Hz, 3H), 0.89 (d, J=6.6 Hz, 3H);

$^{13}$C NMR (150 MHz, CDCl$_3$): 167.11, 155.61, 137.67, 129.24, 128.49, 126.52, 79.51, 72.04, 66.94, 53.96, 41.63, 31.45, 28.32, 18.86, 17.54;

HRMS (ESI-TOF): m/z calculated for C$_{19}$H$_2$N$_{29}$N$_2$O$_3^+$ [M+H]$^+$ 333.2173, found 333.2175.

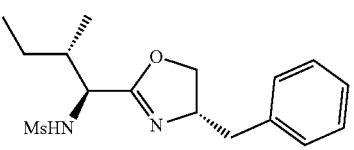

N-((1S,2S)-1-((S)-4-benzyl-4,5-dihydrooxazol-2-yl)-2-methylbutyl)methanesulfonamide (L67)

L67 was prepared following the general procedure and was purified by silica gel column chromatography to give a white solid.

$^1$H NMR (600 MHz, CDCl$_3$): δ 7.32-7.30 (m, 2H), 7.25-7.23 (m, 1H), 7.20-7.19 (m, 2H), 4.99 (br, 1H, N—H), 4.45-4.40 (m, 1H), 4.30 (dt, J=8.4, 1.2 Hz, 1H), 4.08 (dd, J=8.4, 7.2 Hz, 1H), 4.01 (dd, J=9.6, 5.4 Hz, 1H), 3.04 (dd, J=13.8, 6.0 Hz, 1H), 2.91 (s, 3H), 2.69 (dd, J=13.8, 8.4 Hz, 1H), 1.87-1.81 (m, 1H), 1.50-1.44 (m, 1H), 1.19-1.12 (m, 1H), 0.98 (d, J=7.2 Hz, 3H), 0.91 (t, J=7.8 Hz, 3H);

$^{13}$C NMR (150 MHz, CDCl$_3$): 166.52, 137.36, 129.17, 128.63, 126.73, 72.78, 66.90, 56.28, 41.57, 40.96, 38.32, 24.34, 15.44, 11.46;

HRMS (ESI-TOF): m/z calculated for C$_{16}$H$_{25}$FN$_2$O$_3$S$^+$ [M+H]$^+$ 325.1580, found 325.1580.

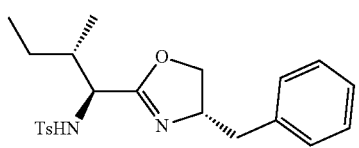

N-((1S,2S)-1-((S)-4-benzyl-4,5-dihydrooxazol-2-yl)-2-methylbutyl)-4-methylbenzenesulfonamide (L68)

L68 was prepared following the general procedure and was purified by silica gel column chromatography to give a white solid.

$^1$H NMR (600 MHz, CDCl$_3$): δ 7.77-7.75 (m, 2H), 7.29-7.27 (m, 4H), 7.23-7.21 (m, 1i), 7.07-7.06 (m, 2H), 5.17 (br, 1H, N—H), 4.08-4.03 (m, 1H), 3.93-3.88 (m, 2H), 3.72 (dd, J=8.4, 7.2 Hz, 1H), 2.73 (dd, J=13.8, 6.0 Hz, 1H), 2.41 (s, 3H), 2.09 (dd, J=13.8, 8.4 Hz, 1H), 1.77-1.70 (m, 1H), 1.51-1.45 (m, 1H), 1.20-1.13 (m, 1H), 0.92 (d, J=6.6 Hz, 3H), 0.88 (t, J=7.8 Hz, 3H);

$^{13}$C NMR (150 MHz, CDCl$_3$): 165.57, 143.30, 137.61, 137.31, 129.46, 128.92, 128.60, 127.50, 126.61, 72.37, 66.84, 55.92, 41.37, 38.71, 24.56, 21.51, 15.24, 11.30;

HRMS (ESI-TOF): m/z calculated for C$_{22}$H$_{29}$N$_2$O$_3$S$^+$ [M+H]$^+$ 401.1893, found 401.1895.

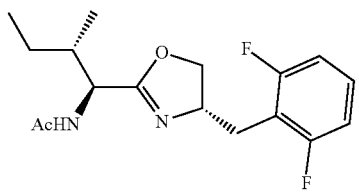 [SMILES: CC[C@H](C)[C@H](NC(C)=O)C1=N[C@@H](Cc2c(F)cccc2F)CO1]

N-((1S,2S)-1-((S)-4-(2,6-difluorobenzyl)-4,5-dihydrooxazol-2-yl)-2-methylbutyl)acetamide (L69)

L69 was prepared following the general procedure and was purified by silica gel column chromatography to give a white solid.

$^1$H NMR (600 MHz, CDCl$_3$): δ 7.21-7.17 (m, 1H), 6.89-6.85 (m, 2H), 6.12 (br, 1H, N—H), 4.63 (dd, J=8.4, 5.4 Hz, 1H), 4.41-4.36 (m, 1H), 4.25 (t, J=9.0 Hz, 1H), 4.11 (dd, J=9.0, 6.0 Hz, 1H), 2.98 (dd, J=13.8, 6.0 Hz, 1H), 2.83 (dd, J=13.8, 7.2 Hz, 1H), 2.03 (s, 3H), 1.86-1.81 (m, 1H), 1.51-1.44 (m, 1H), 1.18-1.10 (m, 1H), 0.91 (t, J=7.8 Hz, 3H), 0.88 (d, J=6.6 Hz, 3H);

$^{13}$C NMR (150 MHz, CDCl$_3$): 169.48, 167.24, 161.68 (dd, J=245.0, 8.7 Hz), 128.37 (t, J=8.7 Hz), 113.55 (t, J=19.8 Hz), 111.19 (d, J=21.9 Hz), 72.36, 65.23, 51.73, 38.21, 28.43, 25.14, 23.28, 15.04, 11.66;

$^{19}$F NMR (376 MHz, CDCl$_3$): δ −114.36 (s, 2F);

HRMS (ESI-TOF): m/z calculated for C$_{17}$H$_{23}$F$_2$N$_2$O$_2^+$ [M+H]$^+$ 325.1722, found 325.1729.

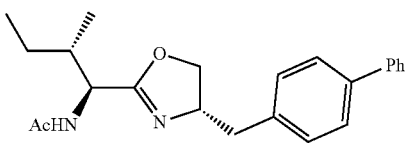 [SMILES: CC[C@H](C)[C@H](NC(C)=O)C1=N[C@@H](Cc2ccc(-c3ccccc3)cc2)CO1]

N-((1S,2S)-1-((S)-4-([1,1'-biphenyl]-4-ylmethyl)-4,5-dihydrooxazol-2-yl)-2-methylbutyl)acetamide (L70)

L70 was prepared following the general procedure and was purified by silica gel column chromatography to give a pale yellow oil.

$^1$H NMR (600 MHz, CDCl$_3$): δ 7.58 (d, J=9.0 Hz, 2H), 7.53 (d, J=8.4 Hz, 2H), 7.43 (t, J=7.8 Hz, 2H), 7.34 (t, J=7.2 Hz, 1H), 7.26 (d, J=8.4 Hz, 2H), 6.13 (br, 1H, N—H), 4.68 (dd, J=8.4, 5.4 Hz, 1H), 4.43-4.38 (m, 1R), 4.25 (t, J=8.4 Hz, 1H), 4.07 (dd, J=9.0, 6.6 Hz, 1H), 3.08 (dd, J=13.8, 6.0 Hz, 1H), 2.71 (dd, J=13.8, 7.2 Hz, 1H), 2.04 (s, 3H), 1.88-1.84 (m, 1H), 1.52-1.45 (m, 1H), 1.19-1.12 (m, 1H), 0.93-0.90 (m, 6H);

$^{13}$C NMR (150 MHz, CDCl$_3$): 169.51, 166.90, 140.78, 139.55, 136.71, 129.62, 128.75, 127.26, 127.19, 126.98, 72.30, 66.83, 51.78, 41.38, 38.09, 25.09, 23.34, 15.18, 11.68;

HRMS (ESI-TOF): m/z calculated for C$_{23}$H$_{29}$N$_2$O$_2^+$ [M+H]$^+$ 365.2224, found 365.2225.

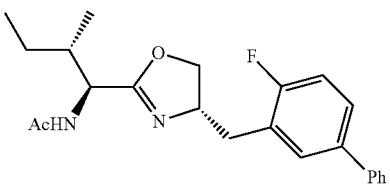 [SMILES: CC[C@H](C)[C@H](NC(C)=O)C1=N[C@@H](Cc2cc(-c3ccccc3)ccc2F)CO1]

((1S,2s)-1-((S)-4-((4-fluoro-[1,1'-biphenyl]-3-yl)methyl)-4,5-dihydrooxazol-2-yl)-2-methylbutyl)-acetamide (L71)

L71 was prepared following the general procedure and was purified by silica gel column chromatography to give a white solid.

$^1$H NMR (600 MHz, CDCl$_3$): δ 7.52 (d, J=8.4 Hz, 2H), 7.44-7.39 (m, 4H), 7.34 (t, J=7.2 Hz, 1H), 7.10 (t, J=9.0 Hz, 1H), 6.12 (br, 1H, N—H), 4.65 (dd, J=8.4, 4.8 Hz, 1H), 4.46-4.41 (m, 1H), 4.28 (t, J=9.0 Hz, 1H), 4.10 (dd, J=9.0, 6.6 Hz, 1H), 3.03 (dd, J=13.8, 6.0 Hz, 1H), 2.84 (dd, J=13.8, 7.2 Hz, 1H), 1.93 (s, 3H), 1.86-1.80 (m, 1H), 1.50-1.43 (m, 1H), 1.17-1.10 (m, 1H), 0.90 (t, J=7.2 Hz, 3H), 0.88 (d, J=7.2 Hz, 3H);

$^{13}$C NMR (150 MHz, CDCl$_3$): 169.48, 167.15, 160.84 (d, J=242.9 Hz), 140.09, 137.34, 130.56 (d, J=4.4 Hz), 128.81, 127.30, 127.11 (d, J=8.9 Hz), 126.95, 124.79 (d, J=17.6 Hz), 115.70 (d, J=24.0 Hz), 72.39, 65.65, 51.75, 38.12, 35.16, 25.12, 23.12, 15.09, 11.66;

$^{19}$F NMR (376 MHz, CDCl$_3$): δ −120.61 (s, 1F);

HRMS (ESI-TOF): m/z calculated for C$_{23}$H$_{28}$FN$_2$O$_2^+$ [M+H]$^+$ 383.2129, found 383.2130.

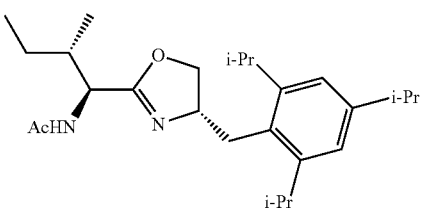 [SMILES: CC[C@H](C)[C@H](NC(C)=O)C1=N[C@@H](Cc2c(C(C)C)cc(C(C)C)cc2C(C)C)CO1]

N-((1S,2S)-2-methyl-1-((S)-4-(2,4,6-triisopropyl-benzyl)-4,5-dihydrooxazol-2-yl)butyl)acetamide (L72)

L72 was prepared following the general procedure and was purified by silica gel column chromatography to give a white solid.

$^1$H NMR (600 MHz, CDCl$_3$): δ 6.99 (s, 2H), 6.21 (br, 1H, N—H), 4.74 (dd, J=8.4, 4.2 Hz, 1H), 4.28 (t, J=8.4 Hz, 1H), 4.25-4.20 (m, 1H), 4.04 (dd, J=8.4, 6.6 Hz, 1H), 3.22-3.15 (m, 2H), 2.98 (dd, J=14.4, 7.8 Hz, 1H), 2.88-2.84 (m, 1H), 2.79 (dd, J=14.4, 6.6 Hz, 1H), 2.01 (s, 3H), 1.91-1.86 (m, 1H), 1.50-1.44 (m, 1H), 1.25-1.22 (m, 18H), 1.18-1.12 (m, 1H), 0.92 (t, J=7.2 Hz, 3H), 0.89 (d, J=6.6 Hz, 3H);

$^{13}$C NMR (150 MHz, CDCl$_3$): 169.34, 166.49, 147.09, 147.05, 128.79, 121.18, 72.42, 67.37, 51.87, 38.39, 34.08, 32.98, 29.42, 25.11, 24.48, 24.22, 23.98, 23.39, 15.09, 11.79;

HRMS (ESI-TOF): m/z calculated for C$_{26}$H$_{43}$N$_2$O$_2^+$ [M+H]$^+$ 415.3319, found 415.3319.

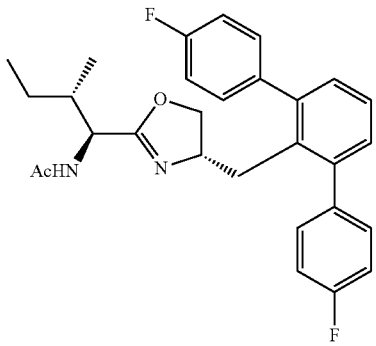 [SMILES: CC[C@H](C)[C@H](NC(C)=O)C1=N[C@@H](Cc2c(-c3ccc(F)cc3)cccc2-c2ccc(F)cc2)CO1]

N-((1S,2S)-1-((S)-4-((4,4''-difluoro-[1,1':3',1''-terphenyl]-2'-yl)methyl)-4,5-dihydrooxazol-2-yl)-2-methylbutyl)acetamide (L73)

L73 was prepared following the general procedure and was purified by silica gel column chromatography to give a white solid.

$^1$H NMR (600 MHz, CDCl$_3$): δ 7.34-7.30 (m, 5H), 7.20 (d, J=7.2 Hz, 2H), 7.13-7.10 (m, 4H), 5.90 (br, 1H, N—H), 4.51 (dd, J=8.4, 4.8 Hz, 1H), 3.76 (t, J=9.0 Hz, 1H), 3.70-3.65 (m, 1H), 3.44 (t, J=7.8 Hz, 1H), 3.02 (dd, J=14.4, 7.2 Hz, 1H), 2.78 (dd, J=14.4, 7.2 Hz, 1H), 1.96 (s, 3H), 1.71-1.63 (m, 1H), 1.31-1.25 (m, 1H), 1.03-0.96 (m, 1H), 0.82 (t, J=7.2 Hz, 3H), 0.71 (d, J=7.2 Hz, 3H);

$^{13}$C NMR (150 MHz, CDCl$_3$): 169.18, 165.76, 162.01 (d, J=245.0 Hz), 142.31, 137.95 (d, J=4.4 Hz), 133.27, 130.94 (d, J=6.6 Hz), 130.13, 126.30, 115.32 (d, J=19.7 Hz), 72.09, 65.20, 51.64, 38.12, 35.48, 24.90, 23.27, 14.96, 11.57;

$^{19}$F NMR (376 MHz, CDCl$_3$): δ −115.42 (s, 2F);

HRMS (ESI-TOF): m/z calculated for C$_{29}$H$_{31}$F$_2$N$_2$O$_2^+$ [M+H]$^+$ 477.2348, found 477.2345.

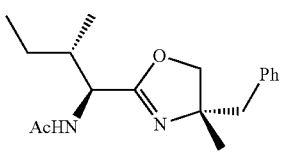 [SMILES: CC[C@H](C)[C@H](NC(C)=O)C1=N[C@@](C)(Cc2ccccc2)CO1]

N-((1S,2S)-1-((S)-4-benzyl-d-methyl-4,5-dihydrooxazol-2-yl)-2-methylbutyl)acetamide (L74)

L74 was prepared using the general procedure and was purified by silica gel column chromatography to give a white solid.

$^1$H NMR (600 MHz, CDCl$_3$): δ 7.28-7.22 (m, 3H), 7.15 (d, J=7.8 Hz, 2H), 6.11 (br, 1H, N—H), 4.53 (dd, J=8.4, 4.8 Hz, 1H), 4.20 (d, J=8.4 Hz, 1H), 3.82 (d, J=8.4 Hz, 1H), 2.85 (d, J=13.2 Hz, 1H), 2.78 (d, J=13.8 Hz, 1H), 2.05 (s, 3H), 1.84-1.79 (m, 1H), 1.47-1.41 (m, 1H), 1.32 (s, 3H), 1.16-1.08 (m, 1H), 0.90 (t, J=7.8 Hz, 3H), 0.87 (d, J=6.6 Hz, 3H);

$^{13}$C NMR (150 MHz, CDCl$_3$): 169.35, 165.37, 136.81, 130.40, 128.08, 126.66, 76.84, 70.29, 51.49, 46.66, 38.16, 27.19, 25.08, 23.33, 15.02, 11.70;

HRMS (ESI-TOF): m/z calculated for C$_{18}$H$_{27}$N$_2$O$_2^+$ [M+H]$^+$ 303.2067, found 303.2068.

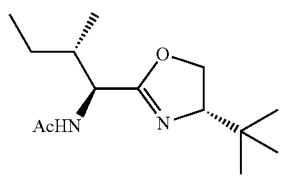 [SMILES: CC[C@H](C)[C@H](NC(C)=O)C1=N[C@@H](C(C)(C)C)CO1]

N-((1S,2S)-1-((S)-4-(tert-butyl)-4,5-dihydrooxazol-2-yl)-2-methylbutyl)acetamide (L75)

L75 was prepared following the general procedure and was purified by silica gel column chromatography to give a white solid.

$^1$H NMR (600 MHz, CDCl$_3$): δ 6.14 (br, 1H, N—H), 4.67-4.64 (m, 1H), 4.22-4.18 (m, 1H), 4.13-4.09 (m, 1H), 3.85-3.82 (m, 1H), 4.01 (t, J=7.8 Hz, 1H), 3.92-3.88 (m, 1H), 2.03 (s, 3H), 1.88-1.84 (m, 1H), 1.54-1.47 (m, 1H), 1.20-1.13 (m, 1H), 0.94-0.90 (m, 6H), 0.87 (s, 9H);

$^{13}$C NMR (150 MHz, CDCl$_3$): δ 169.47, 166.06, 75.18, 69.07, 51.87, 38.13, 33.58, 25.74, 25.15, 23.30, 15.16, 11.68;

HRMS (ESI-TOF): m/z calculated for C$_{14}$H$_{27}$N$_2$O$_2^+$ [M+H]$^+$ 255.2067, found 255.2068.

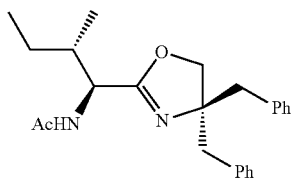

N-((1S,2S)-1-(4,4-dibenzyl-4,5-dihydrooxazol-2-yl)-2-methylbutyl)acetamide (L76)

L76 was prepared following the general procedure and was purified by silica gel column chromatography to give a pale yellow oil.

$^1$H NMR (600 MHz, CDCl$_3$): δ 7.28-7.15 (m, 10H), 5.86 (br, 1H, N—H), 4.38 (dd, J=9.0, 5.4 Hz, 1H), 4.10-4.04 (m, 2H), 3.10 (d, J=13.8 Hz, 1H), 3.03 (d, J=13.8 Hz, 1H), 2.83 (dd, J=13.2, 10.8 Hz, 2H), 2.01 (s, 3H), 1.59-1.54 (m, 1H), 1.20-1.15 (m, 1H), 0.94-0.86 (m, 1H), 0.76 (t, J=7.8 Hz, 3H), 0.60 (d, J=6.6 Hz, 3H);

$^{13}$C NMR (150 MHz, CDCl$_3$): 169.10, 165.84, 136.51, 136.39, 130.92, 130.70, 128.09, 128.05, 126.72, 126.56, 73.66, 72.67, 51.55, 46.18, 45.51, 38.03, 24.79, 23.30, 14.83, 11.41;

HRMS (ESI-TOF): m/z calculated for C$_{24}$H$_{31}$N$_2$O$_2^+$ [M+H]$^+$ 379.2380, found 379.2383.

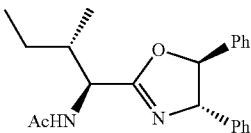 [SMILES: CC[C@H](C)[C@H](NC(C)=O)C1=N[C@@H](c2ccccc2)[C@H](c2ccccc2)O1]

N-((1S,2S)-1-((4S,5S)-4,5-diphenyl-4,5-dihydrooxazol-2-yl)-2-methylbutyl)acetamide (L77)

L77 was prepared following the general procedure and was purified by silica gel column chromatography to give a white solid.

$^1$H NMR (600 MHz, CDCl$_3$): δ 7.42-7.26 (m, 8H), 7.20 (d, J=7.8 Hz, 2H), 6.26 (br, 1H, N—H), 5.29 (d, J=8.4 Hz, 1H), 5.04 (d, J=8.4 Hz, 1H), 4.94 (dd, J=8.4, 4.2 Hz, 1H), 2.06-1.99 (m, 1H), 2.03 (s, 3H), 1.67-1.62 (m, 1H), 1.30-1.22 (m, 1H), 1.05 (d, J=6.6 Hz, 3H), 0.99 (t, J=7.2 Hz, 3H);

$^{13}$C NMR (150 MHz, CDCl$_3$): 169.79, 167.08, 141.20, 139.66, 128.94, 128.89, 128.60, 127.92, 126.68, 125.79, 89.92, 77.93, 52.00, 38.16, 24.99, 23.31, 15.54, 11.76;

HRMS (ESI-TOF): m/z calculated for C$_{22}$H$_{27}$N$_2$O$_2^+$ [M+H]$^+$ 351.2067, found 351.2067.

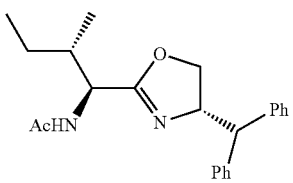 [SMILES: CC[C@H](C)[C@H](NC(C)=O)C1=N[C@@H](C(c2ccccc2)c2ccccc2)CO1]

N-((1S,2S)-1-((S)-4-benzhydryl-4,5-dihydrooxazol-2-yl)-2-methylbutyl)acetamide (L78)

L78 was prepared following the general procedure and was purified by silica gel column chromatography to give a pale yellow oil.

$^1$H NMR (600 MHz, CDCl$_3$): δ 7.31-7.18 (m, 10H), 6.02 (br, 1H, N—H), 4.90-4.86 (m, 1H), 4.56 (dd, J=9.0, 4.8 Hz, 1H), 4.31 (t, J=9.0 Hz, 1H), 4.02 (dd, J=9.0, 7.2 Hz, 1H), 3.92 (d, J=9.0 Hz, 1H), 2.10-2.04 (m, 1H), 1.99 (s, 3H), 1.67-1.57 (m, 2H), 0.91 (t, J=7.2 Hz, 3H), 0.87 (d, J=7.2 Hz, 3H);

$^{13}$C NMR (150 MHz, CDCl$_3$): 169.77, 167.19, 142.05, 141.57, 128.69, 128.63, 128.54, 128.30, 126.84, 126.56, 71.98, 69.23, 56.95, 52.45, 31.41, 23.28, 18.82, 17.83;

HRMS (ESI-TOF): m/z calculated for C$_{23}$H$_{29}$N$_2$O$_2^+$ [M+H]$^+$ 365.2224, found 365.2224.

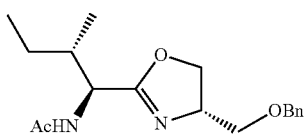 [SMILES: CC[C@H](C)[C@H](NC(C)=O)C1=N[C@@H](COCc2ccccc2)CO1]

N-((1S,2S)-1-((S)-4-(benzyloxy)methyl)-4,5-dihydrooxazol-2-yl)-2-methylbutyl)acetamide (L79)

L79 was prepared following the general procedure and was purified by silica gel column chromatography to give a white solid.

$^1$H NMR (600 MHz, CDCl$_3$): δ 7.36-7.27 (m, 5H), 6.17 (br, 1H, N—H), 4.68 (dd, J=9.0, 5.4 Hz, 1H), 4.56-4.52 (m, 2H), 4.33-4.29 (m, 2H), 4.18 (t, J=6.0 Hz, 1H), 3.61 (dd, J=9.6, 4.8 Hz, 1H), 3.39 (dd, J=9.6, 6.6 Hz, 1H), 2.00 (s, 3H), 1.87-1.81 (m, 1H), 1.52-1.45 (m, 1H), 1.19-1.11 (m, 1H), 0.91 (t, J=7.8 Hz, 3H), 0.89 (d, J=7.2 Hz, 3H);

$^{13}$C NMR (150 MHz, CDCl$_3$): 169.41, 167.64, 137.86, 128.41, 127.76, 127.70, 73.38, 71.91, 70.89, 65.51, 51.78, 38.16, 25.09, 23.30, 15.04, 11.65;

HRMS (ESI-TOF): m/z calculated for C$_{18}$H$_{27}$N$_2$O$_2^+$ [M+H]$^+$ 319.2016, found 319.2017.

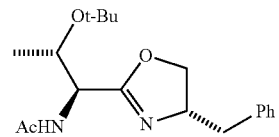 [SMILES: CC(=O)N[C@H](C1=N[C@@H](Cc2ccccc2)CO1)[C@H](C)OC(C)(C)C]

N-((1S,2S)-1-((S)-4-benzyl-4,5-dihydrooxazol-2-yl)-2-(tert-butoxy)propyl)acetamide (L80)

L80 was prepared following the general procedure and was purified by silica gel column chromatography to give a white solid.

$^1$H NMR (600 MHz, CDCl$_3$): δ 7.29 (t, J=7.8 Hz, 2H), 7.22 (t, J=7.8 Hz, 1H), 7.18 (d, J=7.2 Hz, 2H), 6.31 (br, 1H, N—H), 4.58 (d, J=9.0 Hz, 1H), 4.37-4.32 (m, 1H), 4.18 (t, J=8.4 Hz, 1H), 4.10 (dd, J=12.0, 6.6 Hz, 1H), 4.02 (t, J=8.4 Hz, 1H), 3.11 (dd, J 13.2, 5.4 Hz, 1H), 2.65 (dd, J=13.8, 9.0 Hz, 1H), 2.10 (s, 3H), 1.17 (d, J=12.6 Hz, 2H), 1.13 (s, 9H);

$^{13}$C NMR (150 MHz, CDCl$_3$): 170.26, 166.13, 137.75, 129.18, 128.56, 126.56, 74.04, 72.44, 67.36, 66.78, 52.88, 41.84, 28.23, 23.31, 20.88;

HRMS (ESI-TOF): m/z calculated for C$_{19}$H$_{29}$N$_2$O$_3^+$ [M+H]$^+$ 333.2173, found 333.2171.

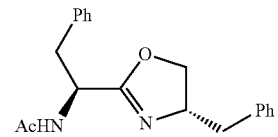 [SMILES: CC(=O)N[C@@H](Cc1ccccc1)C1=N[C@@H](Cc2ccccc2)CO1]

N—((S)-1-((S)-4-benzyl-4,5-dihydrooxazol-2-yl)-2-phenylethyl)acetamide (L81)

L81 was prepared following the general procedure and was purified by silica gel column chromatography to give a pale yellow oil.

$^1$H NMR (600 MHz, CDCl$_3$): δ 7.30-7.21 (m, 6H), 7.15 (d, J=9.0 Hz, 2H), 7.09 (d, J=9.6 Hz, 2H), 6.06 (br, 1H, N—H), 4.95-4.92 (m, 1H), 4.29-4.22 (m, 2H), 4.04 (dd, J=7.8, 6.0 Hz, 1H), 3.15 (dd, J=13.8, 6.0 Hz, 1H), 3.05 (dd, J=13.8, 4.8 Hz, 1H), 2.99 (dd, J=13.8, 4.8 Hz, 1H), 2.59 (dd, J=13.8, 7.8 Hz, 1H), 1.99 (s, 31H);

$^{13}$C NMR (150 MHz, CDCl$_3$): 169.35, 166.22, 137.54, 136.01, 129.48, 129.17, 128.53, 128.31, 126.91, 126.62, 72.52, 66.94, 48.43, 41.57, 37.99, 23.21;

HRMS (ESI-TOF): m/z calculated for $C_{20}H_{23}N_2O_2^+$ [M+H]$^+$ 323.1754, found 323.1749.

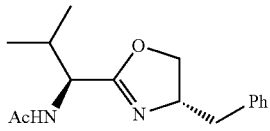 [SMILES: CC(=O)N[C@H](C1=N[C@@H](Cc2ccccc2)CO1)C(C)C]

N—((S)-1-((S)-4-benzyl-4,5-dihydrooxazol-2-yl)-2-methylpropyl)acetamide (L82)

L82 was prepared following the general procedure and was purified by silica gel column chromatography to give a white solid.

$^1$H NMR (600 MHz, acetone-d$^6$): δ 7.29-7.25 (m, 4H), 7.21-7.18 (m, 1H), 7.13 (br, 1H, N—H), 4.52 (dd, J=9.0, 6.0 Hz, 1H), 4.38-4.33 (m, 1H), 4.24 (t, J=9.0 Hz, 1H), 3.98 (t, J=9.0 Hz, 1H), 2.92 (dd, J=13.8, 6.0 Hz, 1H), 2.70 (dd, J=13.8, 7.2 Hz, 1H), 2.04-1.99 (m, 1H), 1.95 (s, 3H), 0.90 (t, J=7.2 Hz, 6H);

$^{13}$C NMR (150 MHz, acetone-d$^6$): 169.68, 166.94, 139.30, 130.29, 129.08, 127.05, 72.47, 67.95, 53.06, 42.28, 32.09, 22.83, 19.40, 18.33;

HRMS (ESI-TOF): m/z calculated for $C_{14}H_{23}N_2O_2^+$ [M+H]$^+$ 275.1754, found 275.1757.

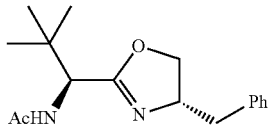 [SMILES: CC(=O)N[C@H](C1=N[C@@H](Cc2ccccc2)CO1)C(C)(C)C]

N—((S)-1-((S)-4-benzyl-4,5-dihydrooxazol-2-yl)-2,2-dimethylpropyl)acetamide (L61)

L61 was prepared following the general procedure and was purified by silica gel column chromatography to give a white solid.

$^1$H NMR (600 MHz, acetone-d$^6$): δ 7.29-7.26 (m, 4H), 7.21-7.18 (m, 1H), 7.08 (br, 1H, N—H), 4.53 (dd, J=9.0, 2.4 Hz, 1H), 4.39-4.34 (m, 1H), 4.21 (t, J=9.0 Hz, 1H), 3.98 (t, J=8.4 Hz, 1f), 2.91 (dd, J=13.8, 6.6 Hz, 1i), 2.70 (dd, J=13.8, 7.2 Hz, 1H), 1.96 (s, 3H), 0.96 (s, 9H);

$^{13}$C NMR (150 MHz, acetone-d$^6$): δ 169.55, 166.47, 139.31, 130.30, 129.08, 127.05, 72.06, 67.98, 55.82, 42.33, 35.40, 27.00, 22.85;

HRMS (ESI-TOF): m/z calculated for $C_{17}H_{25}N_2O_2^+$ [M+H]$^+$ 289.1911, found 289.1917.

The structure of L61 was confirmed by X-ray crystallography. Metrical parameters for the structure are available free of charge from the Cambridge Crystallographic Data Centre under reference number CCDC 1518967.

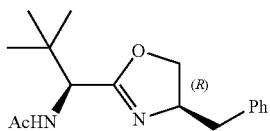

N—((S)-1-((R)-4-benzyl-4,5-dihydrooxazol-2-yl)-2,2-dimethylpropyl)acetamide (L83)

L83 was prepared following the general procedure and was purified by silica gel column chromatography to give a white solid.

$^1$H NMR (600 MHz, CDCl$_3$): δ 7.30 (t, J=7.2 Hz, 2H), 7.23 (t, J=7.2 Hz, 1H), 7.20 (d, J=7.2 Hz, 2H), 6.03 (br, 1H, N—H), 4.57 (d, J=9.6 Hz, 1H), 4.42-4.37 (m, 1H), 4.23 (t, J=9.0 Hz, 1H), 3.97 (t, J=8.4 Hz, 1H), 3.07 (dd, J=14.4, 5.4 Hz, 1H), 2.66 (dd, J=13.8, 8.4 Hz, 1H), 2.02 (s, 3H), 0.97 (s, 9H);

$^{13}$C NMR (150 MHz, CDCl$_3$): δ 169.40, 166.70, 137.54, 129.26, 128.56, 126.57, 71.74, 67.05, 54.88, 41.82, 35.05, 26.44, 23.39;

HRMS (ESI-TOF): m/z calculated for $C_{17}H_{25}N_2O_2^+$ [M+H]$^+$ 289.1911, found 289.1914.

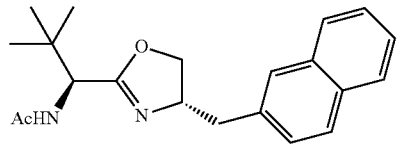 [SMILES: CC(=O)N[C@H](C1=N[C@@H](Cc2ccc3ccccc3c2)CO1)C(C)(C)C]

N—((S)-2,2-dimethyl-1-((S)-4-(naphthalen-2-ylmethyl)-4,5-dihydrooxazol-2-yl)propyl)acetamide (L84)

L84 was prepared following the general procedure and was purified by silica gel column chromatography to give a white solid.

$^1$H NMR (600 MHz, CDCl$_3$): δ 7.81 (d, J=7.8 Hz, 1H), 7.78 (d, J=8.4 Hz, 2H), 7.62 (s, 1H), 7.48-7.43 (m, 2H), 7.32 (d, J=8.4 Hz, 1H), 6.06 (br, 1H, N—H), 4.58 (d, J=9.6 Hz, 1H), 4.50-4.44 (m, 1H), 4.17 (t, J=9.0 Hz, 1H), 4.08 (t, J=8.4 Hz, 1H), 3.22 (dd, J=13.8, 5.4 Hz, 1H), 2.80 (dd, J=13.8, 8.4 Hz, 1H), 2.04 (s, 3H), 0.98 (s, 9H);

$^{13}$C NMR (150 MHz, CDCl$_3$): δ 169.44, 166.70, 135.18, 133.47, 132.25, 128.18, 127.64, 127.51, 127.45, 126.14, 125.55, 71.79, 66.83, 55.18, 41.85, 35.04, 26.54, 23.37;

HRMS (ESI-TOF): m/z calculated for $C_{21}H_{27}N_2O_2^+$ [M+H]$^+$ 339.2067, found 339.2068.

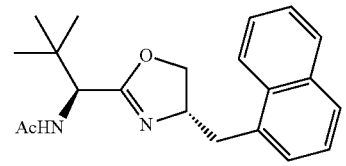 [SMILES: CC(=O)N[C@H](C1=N[C@@H](Cc2cccc3ccccc23)CO1)C(C)(C)C]

N—((S)-2,2-dimethyl-1-((S)-4-(naphthalen-1-ylmethyl)-4,5-dihydrooxazol-2-yl)propyl)acetamide (L85)

L85 was prepared following the general procedure and was purified by silica gel column chromatography to give a white solid.

$^1$H NMR (600 MHz, CDCl$_3$): δ 8.10 (d, J=8.4 Hz, 1H), 7.87 (d, J=7.8 Hz, 1H), 7.76 (d, J=8.4 Hz, 1H), 7.55-7.48 (m, 2H), 7.41 (t, J=7.2 Hz, 1H), 7.31 (d, J=6.6 Hz, 1H), 6.07 (br, 1H, N—H), 4.60 (d, J=9.0 Hz, 1H), 4.59-4.54 (m, 1H), 4.13-4.08 (m, 2H), 3.62 (dd, J=13.8, 5.4 Hz, 1H), 2.95 (dd, J=13.8, 9.6 Hz, 1H), 2.04 (s, 3H), 0.99 (s, 9H);
$^{13}$C NMR (150 MHz, CDCl$_3$): δ 169.48, 166.76, 133.95, 133.76, 131.99, 128.86, 127.51, 127.07, 126.09, 125.71, 125.42, 123.73, 71.98, 66.06, 55.23, 38.93, 35.10, 26.57, 23.43;
HRMS (ESI-TOF): m/z calculated for C$_{21}$H$_{27}$N$_2$O$_2$$^+$[M+H]$^+$ 339.2067, found 339.2067.

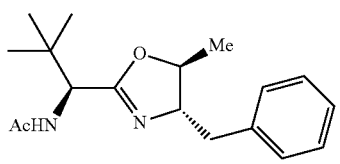 [SMILES: CC(=O)N[C@H](C1=N[C@@H](Cc2ccccc2)[C@H](C)O1)C(C)(C)C]

N—((S)-1-((4S,5S)-4-benzyl-5-methyl-4,5-dihydro-oxazol-2-yl)-2,2-dimethylpropyl)acetamide (L86)

L86 was prepared following the general procedure and was purified by silica gel column chromatography to give a white solid.
$^1$H NMR (600 MHz, CDCl$_3$): δ 7.29 (t, J=7.2 Hz, 2H), 7.22 (t, J=7.2 Hz, 1H), 7.17 (d, J=7.2 Hz, 2H), 6.15 (br, 1H, N—H), 4.51 (d, J=9.0 Hz, 1H), 4.36-4.32 (m, 1H), 3.85 (dt, J=8.4, 6.0 Hz, 1H), 3.05 (dd, J=7.8, 5.4 Hz, 1H), 2.59 (dd, J=13.8, 8.4 Hz, 1H), 2.05 (s, 3H), 1.10 (d, J=6.0 Hz, 3H), 0.98 (s, 9H);
$^{13}$C NMR (150 MHz, CDCl$_3$): δ 169.42, 165.88, 137.37, 129.25, 129.21, 128.49, 126.56, 80.89, 73.62, 55.06, 41.54, 35.23, 26.61, 23.40, 21.01;
HRMS (ESI-TOF): m/z calculated for C$_{18}$H$_{27}$N$_2$O$_2$$^+$ [M+H]$^+$ 303.2067, found 303.2068.

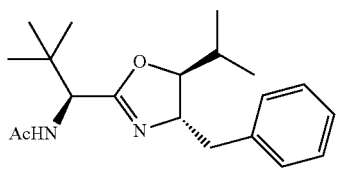 [SMILES: CC(=O)N[C@H](C1=N[C@@H](Cc2ccccc2)[C@H](C(C)C)O1)C(C)(C)C]

N—((S)-1-((4S,5S)-4-benzyl-5-isopropyl-4,5-dihydro-oxazol-2-yl)-2,2-dimethylpropyl)acetamide (L87)

L87 was prepared following the general procedure and was purified by silica gel column chromatography to give a white solid.
$^1$H NMR (600 MHz, CDCl$_3$): δ 7.29 (tt, J=7.2, 1.8 Hz, 2H), 7.22 (tt, J=7.2, 1.2 Hz, 1H), 7.18 (dd, J=7.2, 1.8 Hz, 2H), 6.13 (br, 1H, N—H), 4.52 (d, J=9.0 Hz, 1H), 3.98-3.62 (m, 2H), 2.97 (dd, J=13.8, 5.4 Hz, 1H), 2.63 (dd, J=13.8, 7.2 Hz, 1H), 2.05 (s, 3H), 1.57-1.52 (m, 1H), 0.99 (s, 9H), 0.84 (d, J=6.6 Hz, 3H), 0.64 (d, J=6.6 Hz, 3H);
$^{13}$C NMR (150 MHz, CDCl$_3$) δ 169.38, 165.95, 137.47, 129.59, 128.40, 126.56, 89.71, 69.98, 55.28, 42.51, 35.01, 32.04, 26.61, 23.40, 18.06, 17.30;
HRMS (ESI-TOF): m/z calculated for C$_{20}$H$_{31}$N$_2$O$_2$$^+$ [M+H]$^+$ 331.2380, found 331.2380.

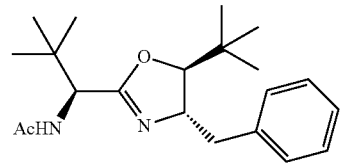 [SMILES: CC(=O)N[C@H](C1=N[C@@H](Cc2ccccc2)[C@H](C(C)(C)C)O1)C(C)(C)C]

N—((S)-1-((4S,5S)-4-benzyl-5-(tert-butyl)-4,5-dihydrooxazol-2-yl)-2,2-dimethylpropyl)acetamide (L88)

L88 was prepared following the general procedure and was purified by silica gel column chromatography to give a pale yellow oil.
$^1$H NMR (600 MHz, CDCl$_3$): δ 7.30-7.28 (m, 2H), 7.24-7.20 (m, 3H), 5.95 (br, 1H, N—H), 4.39 (d, J=9.0 Hz, 1H), 3.51 (dd, J=13.8, 3.0 Hz, 1H), 2.79 (d, J=3.0 Hz, 1H), 2.62 (dt, J=9.6, 3.0 Hz, 1H), 2.19 (dd, J=13.8, 9.6 Hz, 1H), 2.02 (s, 3H), 1.08 (s, 9H), 0.90 (s, 9H);
$^{13}$C NMR (150 MHz, CDCl$_3$) δ 181.43, 169.87, 138.43, 128.99, 128.48, 126.54, 60.98, 53.73, 41.21, 36.86, 34.01, 30.93, 26.76, 26.53, 23.21;
HRMS (ESI-TOF): m/z calculated for C$_{21}$H$_{33}$N$_2$O$_2$$^+$ [M+H]$^+$ 345.2537, found 345.2533.

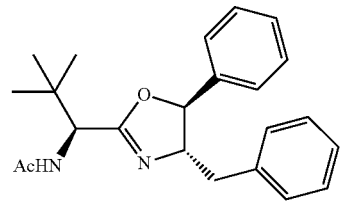 [SMILES: CC(=O)N[C@H](C1=N[C@@H](Cc2ccccc2)[C@H](c2ccccc2)O1)C(C)(C)C]

N—((S)—N-((4S,5S)-4-benzyl-5-phenyl-4,5-dihydro-oxazol-2-yl)-2,2-dimethylpropyl)acetamide (L89)

L89 was prepared following the general procedure and was purified by silica gel column chromatography to give a white solid.
$^1$H NMR (600 MHz, CDCl$_3$): δ 7.29-7.25 (m, 5H), 7.24-7.21 (m, 1H), 7.20-7.18 (m, 2H), 6.98-6.96 (m, 2H), 6.09 (br, 1H, N—H), 5.11 (d, J=7.2 Hz, 1H), 4.67 (d, J=9.6 Hz, 1H), 4.30 (dt, J=7.8, 6.0 Hz, 1H), 3.16 (dd, J=13.8, 6.0 Hz, 1H), 2.81 (dd, J=13.8, 7.8 Hz, 1H), 2.07 (s, 3H), 1.03 (s, 9H);
$^{13}$C NMR (150 MHz, CDCl$_3$) δ 169.47, 165.52, 140.10, 137.04, 129.61, 128.66, 128.51, 128.23, 126.70, 125.73, 85.88, 75.39, 55.47, 41.91, 35.09, 26.72, 23.39;
HRMS (ESI-TOF): m/z calculated for C$_{23}$H$_{29}$N$_2$O$_2$$^+$ [M+H]$^+$ 365.2224, found 365.2222.

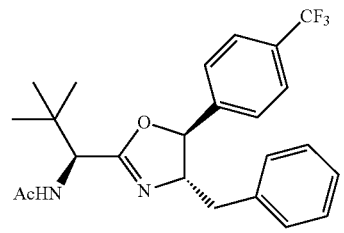 [SMILES: CC(=O)N[C@H](C1=N[C@@H](Cc2ccccc2)[C@H](c2ccc(C(F)(F)F)cc2)O1)C(C)(C)C]

N—((S)-1-((4,5S)-4-benzyl-5-(4-(trifluoromethyl)-phenyl)-4,5-dihydrooxazol-2-yl)-2,2-dimethylpropyl-1)acetamide (L90)

L90 was prepared following the general procedure and was purified by silica gel column chromatography to give a white solid.

$^1$H NMR (600 MHz, CDCl$_3$): δ 7.49 (d, J=8.4 Hz, 2H), 7.32-7.29 (m, 2H), 7.27-7.24 (m, 1H), 7.20-7.18 (m, 2H), 6.96 (d, J=7.8 Hz, 2H), 6.05 (br, 1H, N—H), 5.16 (d, J=7.2 Hz, 1H), 4.69 (d, J=9.6 Hz, 1H), 4.26 (ddd, J=9.0, 7.2, 5.4 Hz, 1H), 3.27 (dd, J=13.8, 5.4 Hz, 1H), 2.76 (dd, J=13.8, 9.0 Hz, 1H), 2.08 (s, 3H), 1.05 (s, 9H);

$^{13}$C NMR (150 MHz, CDCl$_3$) δ 169.49, 165.46, 144.15, 136.65, 130.27 (q, J=32.9 Hz), 129.58, 128.70, 126.94, 125.74, 125.59 (q, J=3.3 Hz), 123.85 (q, J=271.2 Hz), 84.81, 75.94, 55.45, 42.03, 34.98, 26.71, 23.37;

$^{19}$F NMR (376 MHz, CDCl$_3$): δ −62.94 (s, 3F);

HRMS (ESI-TOF): m/z calculated for C$_{24}$H$_{28}$F$_3$N$_2$O$_2{}^+$ [M+H]$^+$ 433.2097, found 433.2097.

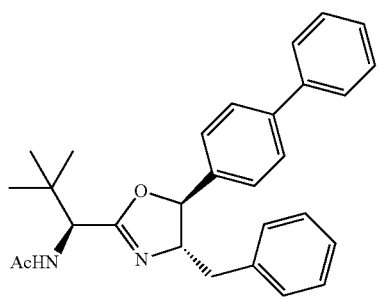 [SMILES: CC(=O)N[C@H](C1=N[C@@H](Cc2ccccc2)[C@H](c2ccc(-c3ccccc3)cc2)O1)C(C)(C)C]

N—((S)-1-((4S,5S)-5-([1,1'-biphenyl]-4-yl)-4-benzyl-4,5-dihydrooxazol-2-yl)-2,2-dimethylpropyl)acetamide (L91)

L91 was prepared following the general procedure and was purified by silica gel column chromatography to give a white solid.

$^1$H NMR (600 MHz, CDCl$_3$): δ 7.55-7.53 (m, 2H), 7.49 (dt, J=8.4, 1.8 Hz, 2H), 7.44-7.41 (m, 2H), 7.35-7.33 (m, 1H), 7.31-7.28 (m, 2H), 7.25-7.21 (m, 3H), 7.03-7.02 (m, 2H), 6.13 (br, 1H, N—H), 5.16 (d, J=7.2 Hz, 1H), 4.69 (d, J=10.2 Hz, 1H), 4.35 (ddd, J=7.8, 7.2, 6.0 Hz, 1H), 3.20 (dd, J=13.8, 6.0 Hz, 1H), 2.82 (dd, J=13.8, 7.8 Hz, 1H), 2.08 (s, 3H), 1.05 (s, 9H);

$^{13}$C NMR (150 MHz, CDCl$_3$) δ 169.47, 165.56, 141.15, 140.40, 139.05, 137.00, 129.63, 128.78, 128.54, 127.48, 127.36, 127.02, 126.73, 126.18, 85.63, 75.41, 55.48, 41.93, 35.10, 26.74, 23.39;

HRMS (ESI-TOF): m/z calculated for C$_{29}$H$_{33}$N$_2$O$_2{}^+$ [M+H]$^+$ 441.2537, found 441.2534.

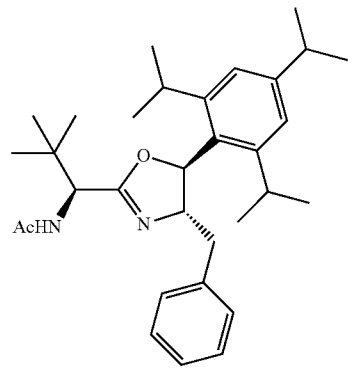 [SMILES: CC(=O)N[C@H](C1=N[C@@H](Cc2ccccc2)[C@H](c2c(C(C)C)cc(C(C)C)cc2C(C)C)O1)C(C)(C)C]

N—((S)-1-((4S,5)-4-benzyl-5-(2,4,6-triisopropylphenyl)-4,5-dihydrooxazol-2-yl)-2,2-dimethylpropyl)-acetamide (L92)

L92 was prepared following the general procedure and was purified by silica gel column chromatography to give a white solid.

$^1$H NMR (600 MHz, CDCl$_3$): δ 7.17-7.15 (m, 2H), 7.12-7.09 (m, 2H), 7.01-6.99 (m, 3H), 6.38 ((br, 1H, N—H), 5.92 (d, J=9.0 Hz, 1H), 5.64 (d, J=11.4 Hz, 1H), 5.00-4.94 (m, 1H), 4.22 (d, J=9.6 Hz, 1H), 3.85 (sep, J=6.6 Hz, 1H), 3.30 (sep, J=6.6 Hz, 1H), 2.88 (sep, J=6.6 Hz, 1H), 2.59 (dd, J=13.8, 3.6 Hz, 1H), 2.50 (dd, J=14.4, 11.4 Hz, 1H), 1.92 (s, 3H), 1.38 (d, J=7.2 Hz, 3H), 1.36 (d, J=6.6 Hz, 3H), 1.29 (d, J=6.0 Hz, 3H), 1.27-1.25 (m, 9H), 0.99 (s, 9H);

$^{13}$C NMR (151 MHz, CDCl$_3$) δ 170.65, 169.51, 149.21, 146.04, 137.38, 129.31, 129.12, 128.18, 126.32, 124.01, 121.07, 60.77, 60.02, 55.98, 38.68, 34.52, 34.09, 30.01, 29.54, 26.49, 25.10, 24.99, 24.37, 23.86, 23.85, 23.38, 23.11;

HRMS (ESI-TOF): m/z calculated for C$_{32}$H$_{47}$N$_2$O$_2{}^+$ [M+H]$^+$ 491.3632, found 491.3634.

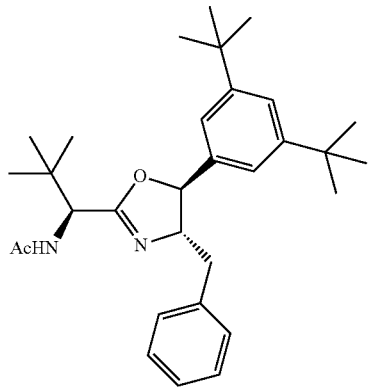 [SMILES: CC(=O)N[C@H](C1=N[C@@H](Cc2ccccc2)[C@H](c2cc(C(C)(C)C)cc(C(C)(C)C)c2)O1)C(C)(C)C]

N—((S)-1-((4S,5S)-4-benzyl-5-(3,5-di-tert-butylphenyl)-4,5-dihydrooxazol-2-yl)-2,2-dimethylpropyl)acetamide (L93)

L93 was prepared following the general procedure and was purified by silica gel column chromatography to give a white solid.

$^1$H NMR (600 MHz, CDCl$_3$): δ 7.31-7.29 (m, 3H), 7.24-7.21 (m, 3H), 6.78 (d, J=1.8 Hz, 2H), 6.15 ((br, 1H,

N—H), 5.16 (d, J=6.6 Hz, 1H), 4.69 (d, J=9.6 Hz, 1H), 4.31-4.27 (m, 1H), 3.20 (dd, J=13.8, 6.0 Hz, 1H), 2.76 (dd, J=13.2, 8.4 Hz, 1H), 2.07 (s, 3H), 1.22 (s, 18H), 1.06 (s, 9H);

$^{13}$C NMR (151 MHz, CDCl$_3$) δ 169.34, 165.70, 151.12, 139.52, 137.18, 129.67, 128.59, 126.75, 122.15, 119.70, 86.51, 75.66, 55.43, 42.49, 35.30, 34.80, 31.34, 26.77, 23.43;

HRMS (ESI-TOF): m/z calculated for $C_{31}H_{45}N_2O_2^+$ [M+H]$^+$ 477.3476, found 477.3475.

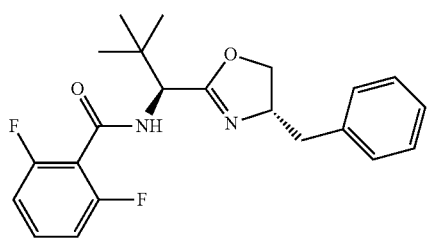 [SMILES: CC(C)(C)[C@H](NC(=O)c1c(F)cccc1F)C1=N[C@@H](Cc2ccccc2)CO1]

N—((S)-1-((S)-4-benzyl-4,5-dihydrooxazol-2-yl)-2,2-dimethylpropyl)-2,6-difluorobenzamide (L94)

L94 was prepared following the general procedure and was purified by silica gel column chromatography to give a white solid.

$^1$H NMR (600 MHz, CDCl$_3$): δ 7.40-7.35 (m, 1H), 7.29-7.27 (m, 2H), 7.23-7.18 (m, 3H), 6.98-6.94 (m, 2H), 6.62 (br, 1H, N—H), 4.78 (d, J=9.6 Hz, 1H), 4.41-4.37 (m, 1H), 4.20 (t, J=9.0 Hz, 1H), 4.07 (dd, J=9.0, 6.6 Hz, 1H), 3.04 (dd, J=13.8, 5.4 Hz, 1H), 2.67 (dd, J=13.8, 8.4 Hz, 1H), 1.05 (s, 9H);

$^{13}$C NMR (150 MHz, CDCl$_3$): 166.12, 159.98 (dd, J=250.5, 6.5 Hz), 159.72, 137.51, 131.67 (t, J=9.9 Hz), 129.27, 128.51, 126.57, 114.42 (t, J=19.7 Hz), 111.97 (dd, J=20.7, 3.2 Hz), 71.82, 66.89, 55.66, 41.55, 35.54, 26.53;

$^{19}$F NMR (376 MHz, CDCl$_3$): δ −112.16 (s, 2F);

HRMS (ESI-TOF): m/z calculated for $C_{22}H_{25}F_2N_2O_2^+$ [M+H]$^+$ 387.1879, found 387.1879.

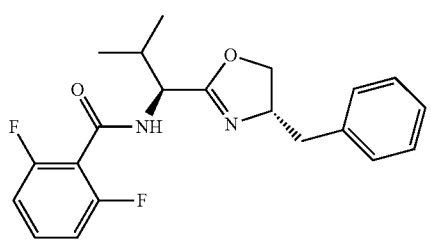 [SMILES: CC(C)[C@H](NC(=O)c1c(F)cccc1F)C1=N[C@@H](Cc2ccccc2)CO1]

N—((S)-1-((S)-4-benzyl-4,5-dihydrooxazol-2-yl)-2-methylpropyl)-2,6-difluorobenzamide (L95)

L95 was prepared following the general procedure and was purified by silica gel column chromatography to give a white solid.

$^1$H NMR (600 MHz, CDCl$_3$): δ 7.40-7.35 (m, 1H), 7.30-7.26 (m, 2H), 7.23-7.18 (m, 3H), 6.98-6.94 (m, 2H), 6.62 (br, 1H, N—H), 4.84 (dd, J=9.0, 4.8 Hz, 1H), 4.41-4.36 (m, 1H), 4.25 (t, J=9.0 Hz, 1H), 4.08 (dd, J=9.0, 7.2 Hz, 1H), 3.01 (dd, J=13.8, 5.4 Hz, 1H), 2.71 (dd, J=13.8, 7.8 Hz, 1H), 2.27-2.20 (m, 1H), 1.03 (d, J=6.6 Hz, 3H), 0.96 (d, J=7.2 Hz, 3H);

$^{13}$C NMR (150 MHz, CDCl$_3$): 166.28, 160.01 (dd, J=250.5, 6.5 Hz), 159.86, 137.45, 131.67 (t, J=11.0 Hz), 129.35, 128.48, 126.59, 114.33 (t, J=20.7 Hz), 111.97 (dd, J=21.8, 4.4 Hz), 72.35, 66.83, 52.85, 41.60, 31.67, 18.77, 17.59;

$^{19}$F NMR (376 MHz, CDCl$_3$): δ −112.24 (s, 2F);

HRMS (ESI-TOF): m/z calculated for $C_{21}H_{23}F_2N_2O_2^+$ [M+H]$^+$ 373.1722, found 373.1726.

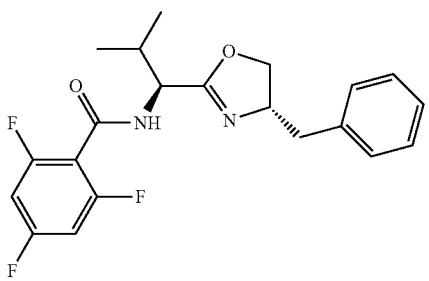 [SMILES: CC(C)[C@H](NC(=O)c1c(F)cc(F)cc1F)C1=N[C@@H](Cc2ccccc2)CO1]

N—((S)-1-((S)-4-benzyl-4,5-dihydrooxazol-2-yl)-2-methylpropyl)-2,4,6-trifluorobenzamide (L96)

L96 was prepared following the general procedure and was purified by silica gel column chromatography to give a pale yellow oil.

$^1$H NMR (600 MHz, CDCl$_3$): δ 7.30-7.27 (m, 2H), 7.23-7.20 (m, 1H), 7.19-7.18 (m, 2H), 6.75-6.71 (m, 2H), 6.62 (br, 1H, N—H), 4.8.1 (dd, J=9.0, 4.8 Hz, 1H), 4.40-4.38 (m, 1H), 4.26 (t, J=9.0 Hz, 1H), 4.08 (dd, J=8.4, 7.2 Hz, 1H), 3.01 (dd, J=13.8, 6.0 Hz, 1H), 2.70 (dd, J=14.4, 7.2 Hz, 1H), 2.27-2.19 (m, 1H), 1.02 (d, J=7.2 Hz, 3H), 0.95 (d, J=7.2 Hz, 3H);

$^{13}$C NMR (150 MHz, CDCl$_3$): 166.23, 163.44 (dt, J=251.6, 15.3 Hz), 160.59 (ddd, J=252.6, 15.3, 9.8 Hz), 159.04, 137.40, 129.30, 128.48, 126.60, 111.00 (dt, J=20.7, 4.4 Hz), 100.94 (tt, J=25.2, 2.3 Hz), 72.40, 66.80, 52.91, 41.58, 31.60, 18.74, 17.55;

$^{19}$F NMR (376 MHz, CDCl$_3$): δ −104.17 (t, J=8.6 Hz, 1F), −108.79 (d, J=7.1 Hz, 2F);

HRMS (ESI-TOF): m/z calculated for $C_{21}H_{22}F_3N_2O_2^+$ [M+H]$^+$ 391.1628, found 391.1628.

N-((5)-1-((S)-4-benzyl-4,5-dihydrooxazol-2-yl)-2-methylpropyl)-2,3,4,5,6-pentafluorobenzamide (L97)

L97 was prepared following the general procedure and was purified by silica gel column chromatography to give a pale yellow oil.

¹H NMR (600 MHz, CDCl₃): δ 7.31-7.28 (m, 2H), 7.24-7.21 (m, 1H), 7.19-7.18 (m, 2H), 6.70 (br, 1H, N—H), 4.79 (dd, J=9.0, 4.8 Hz, 1H), 4.42-4.37 (m, 1H), 4.29 (t, J=9.0 Hz, 1H), 4.09 (dd, J=9.0, 7.2 Hz, 1H), 2.99 (dd, J=13.8, 6.0 Hz, 1H), 2.72 (dd, J=13.8, 7.8 Hz, 1H), 2.28-2.20 (m, 1H), 1.01 (d, J₁=7.2 Hz, 3H), 0.94 (d, J=7.2 Hz, 3H);

¹³C NMR (150 MHz, CDCl₃): 165.97, 156.90, 137.34, 129.29, 128.51, 126.67, 72.66, 66.77, 53.26, 41.61, 31.55, 18.72, 17.47;

¹⁹F NMR (376 MHz, CDCl₃): δ −140.41−−140.49 (m, 2F), −150.99 (t, J=20.7 Hz, 1F), −160.22−−160.37 (m, 2F);

HRMS (ESI-TOF): m/z calculated for $C_{21}H_{20}F_5N_2O_2^+$ [M+H]⁺ 427.1439, found 427.1439.

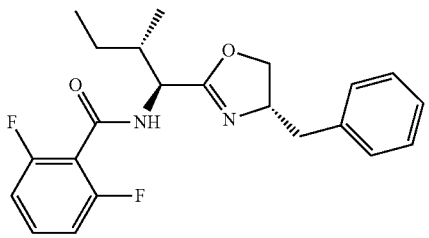 [SMILES: CC[C@H](C)[C@H](NC(=O)c1c(F)cccc1F)C1=N[C@@H](Cc2ccccc2)CO1]

N-((1S,2S)-1-((S)-4-benzyl-4,5-dihydrooxazol-2-yl)-2-methylbutyl)-2,6-difluorobenzamide (L98)

L98 was prepared following the general procedure and was purified by silica gel column chromatography to give a white solid.

¹H NMR (600 MHz, CDCl₃): δ 7.40-7.35 (m, 1H), 7.30-7.27 (m, 2H), 7.23-7.18 (m, 3H), 6.98-6.94 (m, 2H), 6.68 (br, 1H, N—H), 4.87 (dd, J=8.4, 4.8 Hz, 1H), 4.41-4.36 (m, 1H), 4.25 (t, J=9.0 Hz, 1H), 4.07 (dd, J=9.0, 4.8 Hz, 1H), 3.01 (dd, J=13.8, 7.8 Hz, 1H), 2.70 (dd, J=13.8, 7.8 Hz, 1H), 2.03-1.97 (m, 1H), 1.57-1.51 (m, 1H), 1.25-1.18 (m, 1H), 0.98 (d, J=6.6 Hz, 3H), 0.95 (t, J=7.8 Hz, 3H);

¹³C NMR (150 MHz, CDCl₃): 166.20, 160.04 (dd, J=251.6, 6.5 Hz), 159.69, 137.46, 131.66 (t, J=11.0 Hz), 129.34, 128.48, 126.59, 114.30 (t, J=19.8 Hz), 111.97 (dd, J=21.8, 4.4 Hz), 72.31, 66.79, 52.27, 41.58, 38.21, 25.00, 15.15, 11.68;

¹⁹F NMR (376 MHz, CDCl₃): δ −112.27 (s, 2F);

HRMS (ESI-TOF): m/z calculated for $C_{22}H_{25}F_2N_2O_2^+$ [M+H]⁺ 387.1879, found 387.1872.

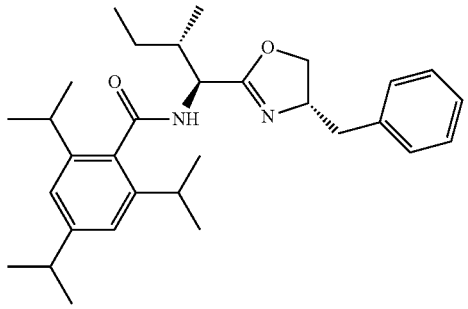 [SMILES: CC[C@H](C)[C@H](NC(=O)c1c(C(C)C)cc(C(C)C)cc1C(C)C)C1=N[C@@H](Cc2ccccc2)CO1]

N-((1S,2S)-1-((S)-4-benzyl-4,5-dihydrooxazol-2-yl)-2-methylbutyl)-2,4,6-triisopropylbenzamide (L99)

L99 was prepared following the general procedure and was purified by silica gel column chromatography to give a white solid.

¹H NMR (600 MHz, CDCl₃): δ 7.30-7.28 (m, 2H), 7.23-7.20 (m, 1H), 7.19-7.18 (m, 2H), 7.01 (s, 2H), 6.35 (br, 1H, N—H), 4.91 (dd, J=8.4, 4.8 Hz, 1H), 4.40-4.34 (m, 1H), 4.18 (t, J=8.4 Hz, 1H), 4.03 (dd, J=8.4, 7.2 Hz, 1H), 3.10 (dd, J=13.8, 5.4 Hz, 1H), 3.06-3.02 (m, 2H), 2.91-2.86 (m, 1H), 2.56 (dd, J=13.8, 8.4 Hz, 1H), 2.01-1.94 (m, 1H), 1.59-1.52 (m, 1H), 1.29-1.19 (m, 19H), 0.98-0.95 (m, 6H);

¹³C NMR (150 MHz, CDCl₃): 170.03, 166.31, 149.72, 145.03, 144.93, 137.68, 133.40, 129.10, 128.59, 126.58, 121.04, 120.87, 72.09, 67.02, 51.97, 41.67, 38.25, 34.39, 30.91, 30.75, 25.35, 24.78, 24.40, 23.98, 23.96, 15.29, 11.74;

HRMS (ESI-TOF): m/z calculated for $C_{31}H_{45}N_2O_2^+$ [M+H]⁺ 477.3476, found 477.3479.

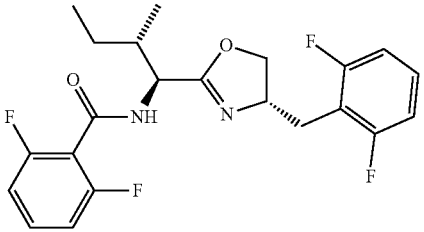 [SMILES: CC[C@H](C)[C@H](NC(=O)c1c(F)cccc1F)C1=N[C@@H](Cc2c(F)cccc2F)CO1]

N-((1S,2S)-1-((S)-4-(2,6-difluorobenzyl)-4,5-dihydrooxazol-2-yl)-2-methylbutyl)-2,6-difluorobenzamide (L100)

L100 was prepared following the general procedure and was purified by silica gel column chromatography to give a white solid.

¹H NMR (600 MHz, CDCl₃): δ 7.39-7.34 (m, 1H), 7.20-7.15 (m, 1H), 6.97-6.93 (m, 2H), 6.87-6.82 (m, 2H), 6.68 (br, 1H, N—H), 4.88 (dd, J=8.4, 4.8 Hz, 1H), 4.44-4.39 (m, 1H), 4.27 (t, J=9.0 Hz, 1H), 4.14 (dd, J=9.0, 7.2 Hz, 1H), 3.00 (dd, J=13.8, 6.0 Hz, 1H), 2.83 (dd, J=13.8, 7.8 Hz, 1H), 2.05-1.98 (m, 1H), 1.58-1.51 (m, 1H), 1.27-1.19 (m, 1H), 0.98 (d, J=6.6 Hz, 3H), 0.96 (t, J=7.2 Hz, 3H);

¹³C NMR (150 MHz, CDCl₃): 166.42, 161.67 (dd, J=245.1, 7.7 Hz), 160.07 (dd, J=251.6, 6.6 Hz), 159.63, 131.63 (t, J=9.9 Hz), 128.34 (t, J=9.9 Hz), 114.28 (t, J=19.7 Hz), 113.45 (t, J=20.7 Hz), 111.94 (dd, J=20.7, 3.3 Hz), 111.17 (dd, J=20.7, 4.4 Hz), 72.51, 65.30, 52.28, 38.27, 28.31, 25.07, 15.05, 11.68;

¹⁹F NMR (376 MHz, CDCl₃): δ −112.13 (s, 2F), −114.28 (s, 2F);

HRMS (ESI-TOF): m/z calculated for $C_{22}H_{23}F_4N_2O_2^+$ [M+H]⁺ 423.1690, found 423.1698.

Optimization of the Reaction Conditions Screening of the Pd Source for the Arylation of Isobutyric Amide*,†

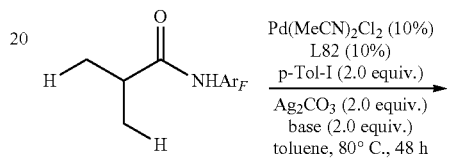

Pd (10%)
L82 (20%)
p-Tol-I (2.0 equiv.)
Ag$_2$CO$_3$ (2.0 equiv.)
toluene, 80° C., 48 h

3

4b

4b'

| entry | Pd | yield (%) | 4b/4b' | er |
|---|---|---|---|---|
| 1 | Pd(OAc)$_2$ | 51 | 5.0/1 | 75:25 |
| 2 | Pd(TFA)$_2$ | 30 | 5.2/1 | 76:24 |
| 3 | Pd$_2$(η$^3$-C$_3$H$_5$)$_2$Cl$_2$ | 50 | 3.1/1 | 69:31 |
| 4 | Pd(MeCN)$_2$Cl$_2$ | 55 | 4.2/1 | 82:18 |
| 5 | Pd(PPh$_3$)$_2$Cl$_2$ | NR | — | — |
| 6 | Pd(PhCN)$_2$Cl$_2$ | 66 | 3.0/1 | 71:29 |
| 7 | Pd(OTf)$_2$(MeCN)$_4$ | 15 | 5.8/1 | 73:27 |
| 8 | Pd$_2$(dba)$_3$ | 25 | 5.7/1 | 79:21 |

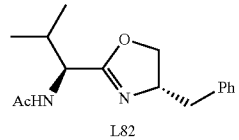

L82

*Conditions:
0.1 mmol of 1, 2.0 equiv. of 4-iodotoluene, 10 mol % of Pd, 10 mol % of L22, 2.0 equiv. of Ag$_2$CO$_3$, 0.5 mL of toluene, 80° C., 48 hours.
†The yield and the ratio of 4b/4b' were determined by $^1$H NMR analysis of the crude product using CH$_2$Br$_2$ as the internal standard, enantiomeric ratios (er) were determined by chiral high-performance liquid chromatography.

Screening of the Oxidant for the Arylation of Isobutyric Amide*,†

| entry | oxidant | yield (%) | 4b/4b' | er |
|---|---|---|---|---|
| 1 | Ag$_2$CO$_3$ | 55 | 4.2/1 | 82:18 |
| 2 | AgOAc | 26 | 8.6/1 | 70:30 |
| 3 | Ag$_2$O | 50 | 3.5/1 | 76:24 |
| 4 | AgO | 60 | 4.2/1 | 76:24 |
| 5 | AgNO$_3$ | NR | — | — |
| 6 | AgF | 30 | 4.6/1 | 77:23 |
| 7 | AgOTf | NR | — | — |
| 8 | AgBF$_4$ | NR | — | — |
| 9 | AgCN | NR | — | — |
| 10 | AgTFA | NR | — | — |
| 11 | AgOTs | NR | — | — |
| 12 | AgOBz | NR | — | — |
| 13 | AdCO$_2$Ag | NR | — | — |
| 14 | AgOPiv | 10 | >20/1 | 62:48 |
| 15 | PhI(OAc)$_2$ | NR | — | — |
| 16 | Oxone | NR | — | — |
| 17 | K$_2$S$_2$O$_8$ | NR | — | — |

*Conditions: 0.1 mmol of 1, 2.0 equiv. of 4-iodotoluene, 10 mol % of Pd(MeCN)$_2$Cl$_2$, 10 mol % of L82, 2.0 equiv. of oxidant, 0.5 mL of toluene, 80° C., 48 hours.
†The yield and the ratio of 4b/4b' were determined by $^1$H NMR analysis of the crude product using CH$_2$Br$_2$ as the internal standard, enantiomeric ratios (er) were determined by chiral high-performance liquid chromatography.

Screening of the Base for the Arylation of Isobutyric Amide*,†

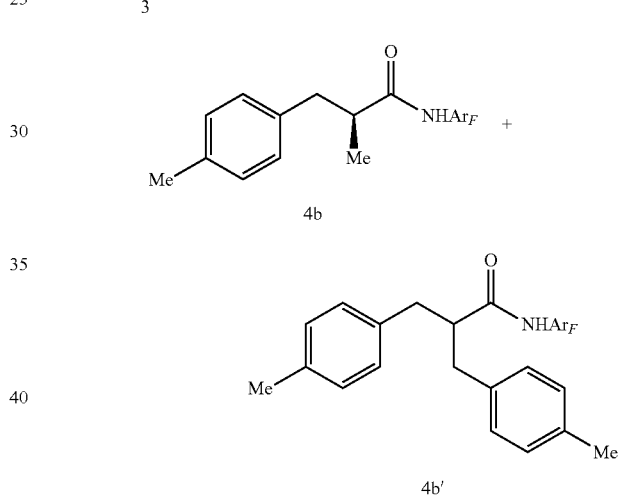

Pd(MeCN)$_2$Cl$_2$ (10%)
L82 (10%)
p-Tol-I (2.0 equiv.)
Ag$_2$CO$_3$ (2.0 equiv.)
base (2.0 equiv.)
toluene, 80° C., 48 h

3

4b

4b'

| entry | base | yield (%) | 4b/4b' | er |
|---|---|---|---|---|
| 1 | Li$_3$PO$_4$ | 80 | 3.0/1 | 76:24 |
| 2 | Na$_3$PO$_4$ | 75 | 2.1/1 | 77:23 |
| 3 | K$_3$PO$_4$ | 68 | 4.7/1 | 65:35 |
| 4 | LiH$_2$PO$_4$ | 80 | 2.1/1 | 77:23 |
| 5 | Na$_2$HPO$_4$ | 80 | 2.3/1 | 75:25 |
| 6 | NaH$_2$PO$_4$ | 80 | 2.0/1 | 75:25 |
| 7 | KH$_2$PO$_4$ | 88 | 2.8/1 | 73:27 |
| 8 | K$_2$HPO$_4$ | 75 | 2.3/1 | 75:25 |
| 9 | Li$_2$CO$_3$ | 70 | 3.1/1 | 71:29 |
| 10 | Na$_2$CO$_3$ | 80 | 2.0/1 | 71:29 |
| 11 | K$_2$CO$_3$ | 75 | 3.1/1 | 70:30 |
| 12 | Cs$_2$CO$_3$ | 50 | 4.6/1 | 69:31 |
| 13 | NaHCO$_3$ | 78 | 3.1/1 | 71:29 |
| 14 | KHCO$_3$ | 80 | 2.0/1 | 74:26 |
| 15 | LiOAc | 90 | 2.1/1 | 76:24 |
| 16 | NaOAc | 85 | 1.5/1 | 77:23 |
| 17 | KOAc | 91 | 1.5/1 | 77:23 |
| 18 | CsOAc | 50 | 3.7/1 | 72:28 |
| 19 | NaTFA | 92 | 1.1/1 | 79:21 |
| 20 | KTFA | 93 | 1.5/1 | 74:26 |
| 21 | — | 55 | 4.2/1 | 82:18 |
| 22‡ | NaTFA | 82 | 2.1/1 | 70:30 |
| 23‡,§ | NaTFA | 90 | 3.2/1 | 76:24 |
| 24‡,§,‖ | NaTFA | 92 | 3.1/1 | 79:21 |

-continued

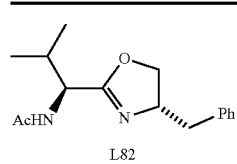

L82

*Conditions:

0.1 mmol of 3, 2.0 equiv. of 4-iodotoluene, 10 mol % of Pd(MeCN)₂Cl₂, 10 mol % of L82, 2.0 equiv. of Ag₂CO₃, 2.0 equiv. base, 0.5 mL of toluene, 80° C., 48 hours.

†The yield and the ratio of 4b/4b' were determined by ¹H NMR analysis of the crude product using CH₂Br₂ as the internal standard, enantiomeric ratios (er) were determined by chiral high-performance liquid chromatography.

‡The reaction temperature was 60° C. §20 mol % of L82 was used. ‖Reaction under N₂.

Preliminary Screening of the Ligand for the Arylation of Isobutyric Amide*'†

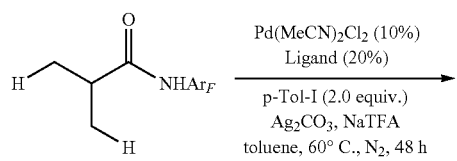

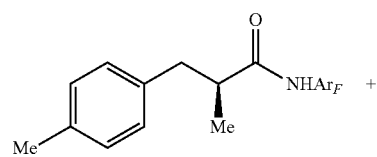

4b

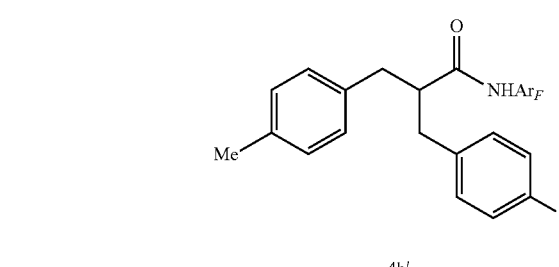

4b'

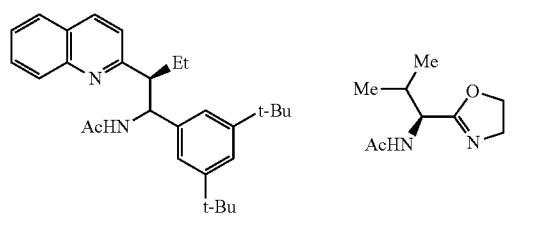

L1, 46% yield
4b/4b' = 3.0/1, 51:49 er

L63, 50% yield
4b/4b' = 5.3/1, 52:48 er

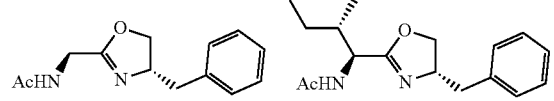

L64, 15% yield
4b/4b' = 10.1/1, 51:49 er

L62, 78% yield
4b/4b' = 3.0/1, 80:20 er

-continued

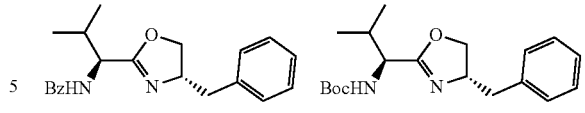

L65, NR

L66, 30% yield
4b/4b' = 8.1/1, 55:45 er

L67, NR

L68, NR

*Conditions:
0.1 mol of 3, 2.0 equiv. of 4-iodotoluene, 10 mol % of Pd(MeCN)₂Cl₂, 20 mol % of Ligand, 2.0 equiv. of Ag₂CO₃, 2.0 equiv. NaTFA, 0.5 mL of toluene, 60° C., N₂, 48 hours.

†The yield and the ratio of 4b/4b¢ were determined by ¹H NMR analysis of the crude product using CH₂Br₂ as the internal standard, enantiomeric ratios (er) were determined by chiral high-performance liquid chromatography.

Further Screening of the Ligand for the Arylation of Isobutyric Amide*'†

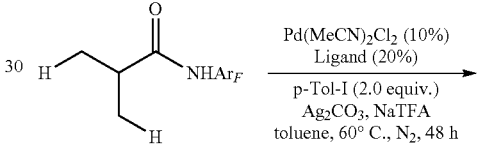

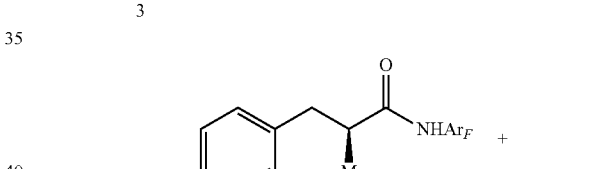

4b

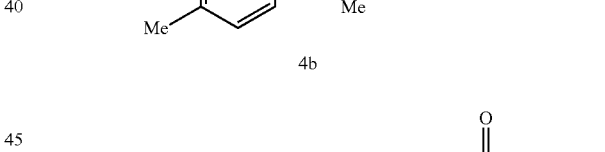

4b'

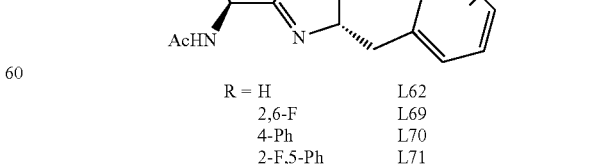

| R = | |
|---|---|
| H | L62 |
| 2,6-F | L69 |
| 4-Ph | L70 |
| 2-F,5-Ph | L71 |
| 2,4,6-i-Ph | L72 |
| 2,6-(4-F—Ph) | L73 |

-continued
Further Screening of the Ligand for the Arylation of Isobutyric Amide*, †
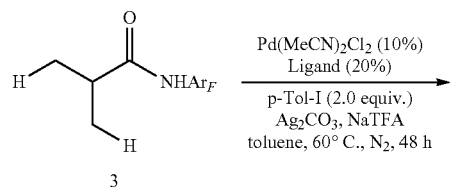
3
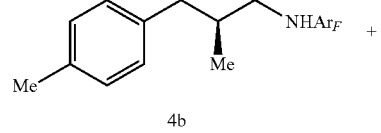
4b  +
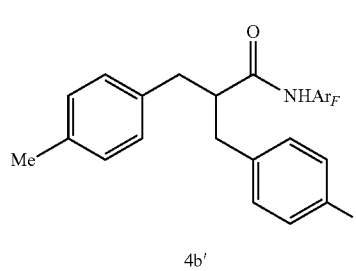
4b′
| | |
|---|---|
| 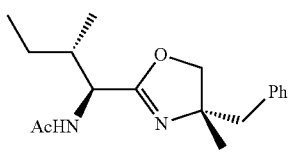 | L74 |
| 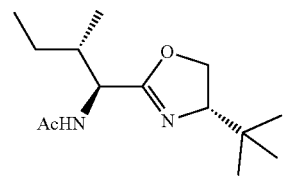 | L75 |
| 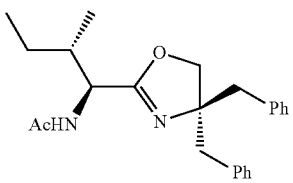 | L76 |
| 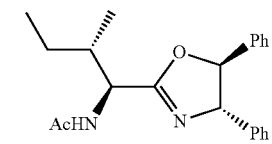 | L77 |
| 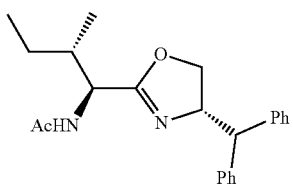 | L78 |
-continued
Further Screening of the Ligand for the Arylation of Isobutyric Amide*, †
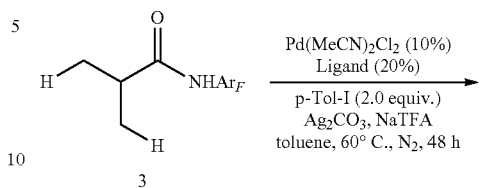
3
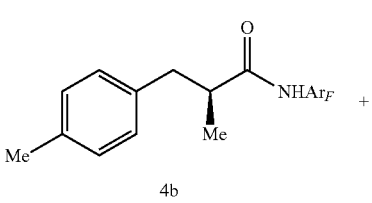
4b  +
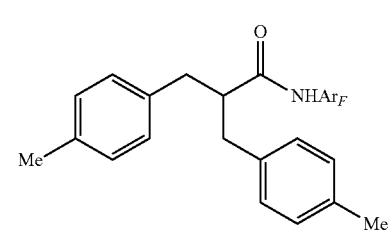
4b′
| | |
|---|---|
| 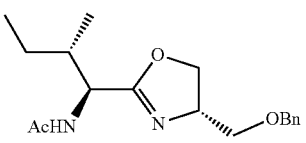 | L79 |
| 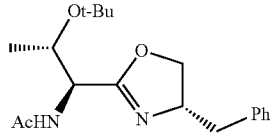 | L80 |
| 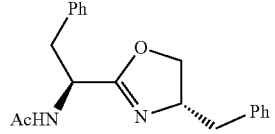 | L81 |
| 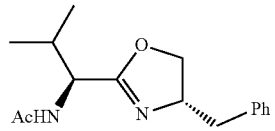 | L82 |
| | L61 |
| 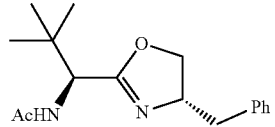 | L83 |

Further Screening of the Ligand for the Arylation of Isobutyric Amide*,†
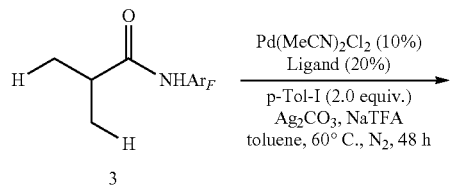
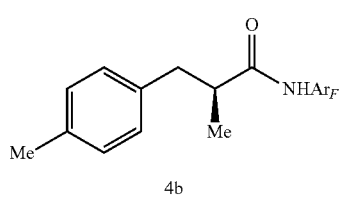
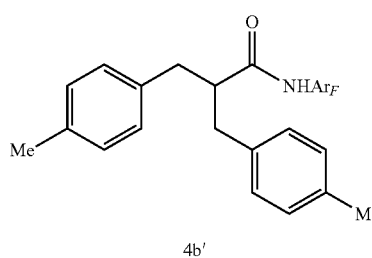
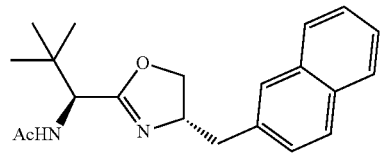 [SMILES: CC(=O)N[C@H](C1=N[C@@H](Cc2ccc3ccccc3c2)CO1)C(C)(C)C]
L84
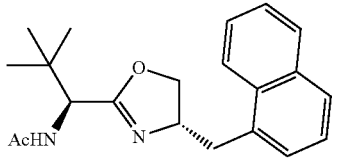 [SMILES: CC(=O)N[C@H](C1=N[C@@H](Cc2cccc3ccccc23)CO1)C(C)(C)C]
L85
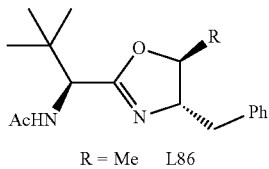
R = Me  L86
i-Pr  L87
t-Bu  L88
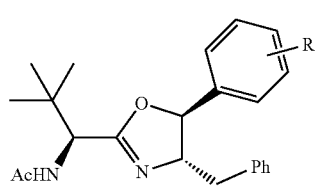
R = H  L89
4-CF3  L90
4-Ph  L91
2,4,6-i-Pr  L92
3,5-t-Bu  L93
Further Screening of the Ligand for the Arylation of Isobutyric Amide*,†
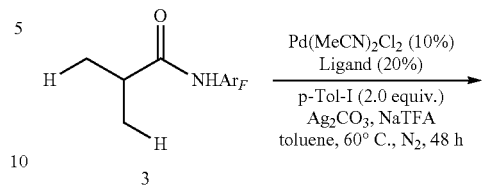
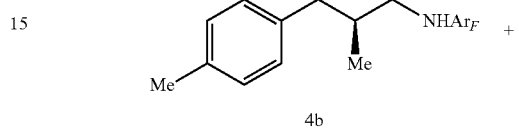
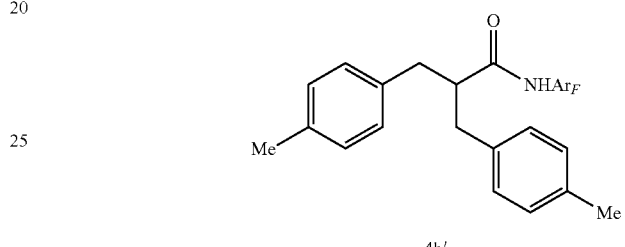
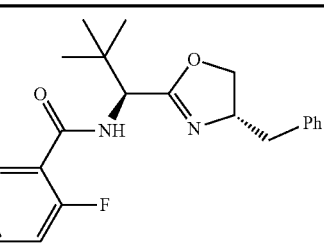
L94
| entry | ligand | yield (%) | 4b/4b' | er |
|---|---|---|---|---|
| 1 | L62 | 78 | 3.0/1 | 80:20 |
| 2 | L69 | 60 | 4.2:1 | 75:25 |
| 3 | L70 | 70 | 2.2:1 | 78:22 |
| 4 | L71 | 60 | 2.6:1 | 75:25 |
| 5 | L72 | 70 | 3.5:1 | 80:20 |
| 6 | L73 | 60 | 3.1/1 | 78:22 |
| 7 | L74 | 85 | 2.2/1 | 76:24 |
| 8 | L75 | 84 | 3.8:1 | 66:34 |
| 9 | L76 | 30 | 4.9/1 | 50:50 |
| 10 | L77 | 50 | 3.6/1 | 68:32 |
| 11 | L78 | 62 | 3.2/1 | 86:14 |
| 12 | L79 | 40 | 3.1/1 | 78:22 |
| 13 | L80 | 65 | 2.2/1 | 77:23 |
| 14 | L81 | 70 | 2.8/1 | 64:36 |
| 15 | L82 | 92 | 3.1/1 | 79:21 |
| 16 | L61 | 83 | 4.0/1 | 84:16 |
| 17 | L83 | 65 | 4.1:1 | 51:49 |
| 18 | L84 | 80 | 2.1:1 | 71:29 |
| 19 | L85 | 70 | 2.3/1 | 66:34 |
| 20 | L61 | 80 | 3.0/1 | 88:12 |
| 21 | L61 | 85 | 4.1/1 | 93:7 |
| 22‡ | L61 | 98 (70)¶ | 3.1/1 | 98:2 |
| 23‡,§ | L86 | 85 | 3.2/1 | 94:6 |
| 24‡,§,∥ | L87 | 75 | 5.1/1 | 91:9 |
| 25‡,§,∥ | L88 | 40 | 5.2/1 | 91:9 |
| 26‡,§,∥ | L89 | 95 | 3.3/1 | 96:4 |
| 27‡,§,∥ | L90 | 84 | 5.0/1 | 93:7 |
| 28‡,§,∥ | L91 | 65 | 8.2/1 | 92:8 |
| 29‡,§,∥ | L92 | 50 | 8.2/1 | 92:8 |

Further Screening of the Ligand for the Arylation of Isobutyric Amide*, †

[Scheme: Isobutyric amide 3 (H-CH2-C(CH2-H)(C(O)NHArF)) + p-Tol-I (2.0 equiv.) with Pd(MeCN)2Cl2 (10%), Ligand (20%), Ag2CO3, NaTFA, toluene, 60 °C, N2, 48 h → products 4b (mono-arylated, Me-C6H4-CH2-CH(Me)-C(O)NHArF) and 4b' (bis-arylated)]

| | Ligand | Yield | 4b/4b' | er |
|---|---|---|---|---|
| 30[‡,§,‖] | L93 | 67 | 7.1/1 | 93:7 |
| 31[‡,§,‖] | L94 | 50 | 6.3/1 | 80:20 |

*Conditions:
0.1 mmol of 3, 2.0 equiv. of 4-iodotoluene, 10 mol % of Pd(MeCN)2Cl2, 20 mol % of Ligand, 2.0 equiv. of Ag2CO3, 2.0 equiv. NaTFA, 0.5 mL of toluene, 60° C., N2, 48 hours.
†The yield and the ratio of 4b/4b' were determined by 1H NMR analysis of the crude product using CH2Br2 as the internal standard, enantiomeric ratios (er) were determined by chiral high-performance liquid chromatography.
[‡]3.0 equiv. of 4-iodotoluene was used.
[§]0.25 mL of toluene was used.
[‖]The reaction time was 72 hours.
[¶]The isolated yield of 4b.

General Procedure for the Pd(II)-Catalyzed Arylation of Isobutyric Amide

Method A

[Scheme: amide 3 (ArF = 4-(CF3)C6F4) + Ar(Het)–I (3.0 equiv.) with Pd(MeCN)2Cl2 (10%), L61 (20%), Ag2CO3 (2.0 equiv), NaTFA (2.0 equiv.), toluene [0.4M], 60° C., N2, 72 h → product 4]

[Structure L61: AcHN-CH(t-Bu)-oxazoline-CH2Ph]

A reaction tube (10 mL) with magnetic stir bar was charged with the amide 3 (0.1 mmol), aryl iodide (0.30 mmol), Pd(MeCN)2Cl2 (0.01 mmol, 2.6 mg), L61 (0.02 mmol, 5.8 mg), Ag2CO3 (0.20 mmol, 55.2 mg), NaTFA (0.2 mmol, 27.2 mg). The reaction tube was evacuated and backfilled with nitrogen (x3). Toluene (0.25 mL) was added to the tube and the tube was sealed and heated to 60° C. for 72 hours. The crude reaction mixture was filtrated with Celite® and washed with EtOAc. The solvents were removed under reduced pressure and the residue was purified by preparative TLC to afford the desired product.

Method B

[Scheme: amide 3 (ArF = 4-(CF3)C6F4) + Ar(Het)–I (3.0 equiv.) with Pd(OAc)2 (10%), L89 (20%), Ag2CO3 (2.0 equiv), toluene [0.4 M], 50° C., 72 h → product 4]

[Structure L89: AcHN-CH(t-Bu)-oxazoline-CH(Ph)-CH(Ph)]

A reaction tube (10 mL) with magnetic stir bar was charged with the amide 3 (0.1 mmol), aryl iodide (0.30 mmol), Pd(OAc)2 (0.01 mmol, 2.3 mg), L89 (0.02 mmol, 7.3 mg), Ag2CO3 (0.20 mmol, 55.2 mg). Toluene (0.25 mL) was added to the tube and the tube was sealed and heated to 50° C. for 72 hours. The crude reaction mixture was filtrated with Celite® and washed with EtOAc. The solvents were removed under reduced pressure and the residue was purified by preparative TLC to afford the desired product.

Gram Scale Arylation of Isobutyric Amide

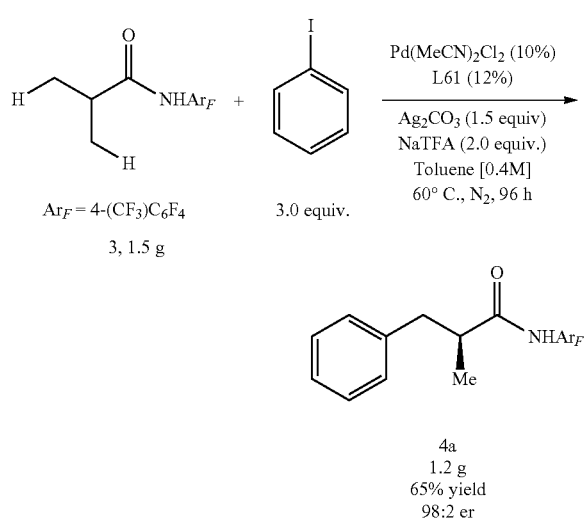

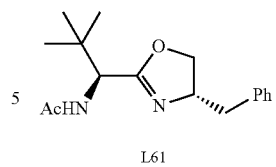

A reaction tube (50 mL) with magnetic stir bar was charged with the amide 3 (5.0 mmol, 1.5 g), iodobenzene (15.0 mmol, 3.0 g), Pd(MeCN).C$_2$ (0.5 mmol, 128.9 mg), L61 (0.6 mmol, 172.9 mg), Ag$_2$CO$_3$ (10.0 mmol, 2.8 g), NaTFA (10.0 mmol, 1.2 g). The reaction tube was evacuated and back-filled with nitrogen (×3). Toluene (12.5 mL) was added to the tube and the tube was sealed and heated to 60° C. for 96 hours. The crude reaction mixture was filtrated with Celite® and washed with EtOAc. The solvents were removed under reduced pressure and the residue was purified by silica gel column chromatography to afford the desired product as white solid in 65% yield (1.2 g).

Pd(II)-Catalyzed Arylation of Quaternary Amino Acid

Optimization of the Reaction Condition Initial Optimization of Pd(II)-Catalyzed Arylation of Quaternary Amino Acid*, †

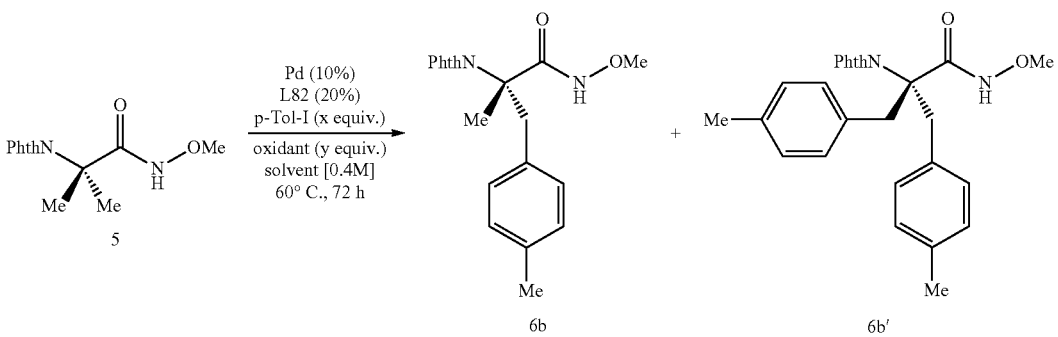

| entry | Pd | solvent | ArI (x) | oxidant | oxidant (y) | yield (%) | 6b/6b' | er |
|---|---|---|---|---|---|---|---|---|
| 1 | Pd(OAc)$_2$ | HFIP | 2.0 | Ag$_2$CO$_3$ | 2.0 | 62 | 3.2/1 | 80/20 |
| 2 | Pd(TFA)$_2$ | HFIP | 2.0 | Ag$_2$CO$_3$ | 2.0 | 60 | 2.9/1 | 75/25 |
| 3 | Pd(MeCN)$_2$Cl$_2$ | HFIP | 2.0 | Ag$_2$CO$_3$ | 2.0 | 50 | 3.8/1 | 78/22 |
| 4 | Pd$_2$(η$^3$-C$_3$H$_5$)$_2$Cl$_2$ | HFIP | 2.0 | Ag$_2$CO$_3$ | 2.0 | 60 | 3.3/1 | 75/25 |
| 5 | Pd(OTf)$_2$(MeCN)$_4$ | HFIP | 2.0 | Ag$_2$CO$_3$ | 2.0 | 65 | 3.1/1 | 67/33 |
| 7 | Pd(OAc)$_2$ | (t-Amyl-OH) | 2.0 | Ag$_2$CO$_3$ | 2.0 | 20 | 5.2/1 | 90/10 |
| 8 | Pd(OAc)$_2$ | t-Bu—OH | 2.0 | Ag$_2$CO$_3$ | 2.0 | 22 | 7.8/1 | 90/10 |
| 9 | Pd(OAc)$_2$ | toluene | 2.0 | Ag$_2$CO$_3$ | 2.0 | 30 | 4.2/1 | 83/17 |
| 10 | Pd(OAc)$_2$ | DCE | 2.0 | Ag$_2$CO$_3$ | 2.0 | 20 | 5.9/1 | 81/19 |
| 11 | Pd(OAc)$_2$ | C$_5$F$_5$ | 2.0 | Ag$_2$CO$_3$ | 2.0 | 15 | 3.8/1 | 81/19 |
| 12 | Pd(OAc)$_2$ | HFIP | 2.0 | AgOAc | 2.0 | 86 | 2.1/1 | 81/19 |
| 13 | Pd(OAc)$_2$ | HFIP | 2.0 | AgTFA | 2.0 | NR | — | — |
| 14 | Pd(OAc)$_2$ | HFIP | 2.0 | AgOPiv | 2.0 | 55 | 1.2/1 | 75/25 |
| 15 | Pd(OAc)$_2$ | HFIP | 2.0 | Ag$_2$O | 2.0 | NR | — | — |
| 16 | Pd(OAc)$_2$ | HFIP | 2.0 | AgF | 2.0 | NR | — | — |
| 17 | Pd(OAc)$_2$ | HFIP | 2.0 | AgOAc | 3.0 | 85 | 2.0/1 | 81/19 |
| 18 | Pd(OAc)$_2$ | HFIP | 3.0 | AgOAc | 2.0 | 95 | 1.2/1 | 86/14 |

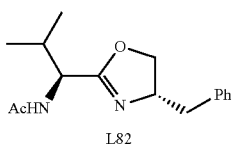 [SMILES: CC(=O)N[C@H](C1=N[C@@H](Cc2ccccc2)CO1)C(C)C]

*Conditions:
0.1 mmol of 3, x equiv. of p-Tol-I, 10 mol % of Pd, 20 mol % of L82, y equiv. of oxidant, 0.25 mL of solvent, 60° C., 72 hours.
†The yield and the ratio of 6b/6b' were determined by $^1$H NMR analysis of the crude product using CH$_2$Br$_2$ as the internal standard, enantiomeric ratios (er) were determined by chiral high-performance liquid chromatography Screening the Ligand of Pd(II)-Catalyzed Arylation of Quaternary Amino Acid*,†
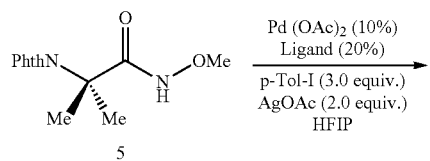
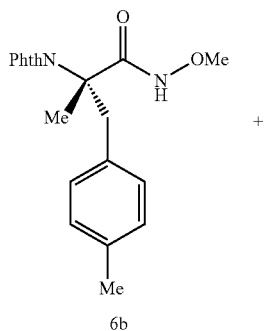
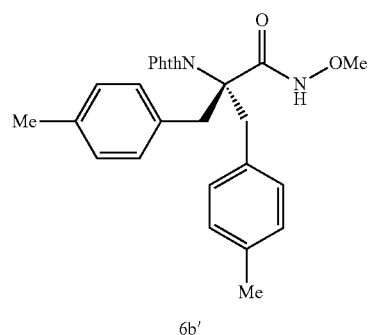
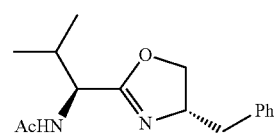 [SMILES: CC(=O)N[C@H](C1=N[C@@H](Cc2ccccc2)CO1)C(C)C] L82
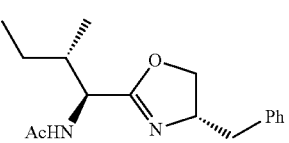 [SMILES: CC[C@H](C)[C@H](NC(C)=O)C1=N[C@@H](Cc2ccccc2)CO1] L62
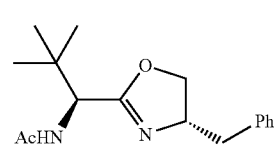 [SMILES: CC(=O)N[C@H](C1=N[C@@H](Cc2ccccc2)CO1)C(C)(C)C] L61
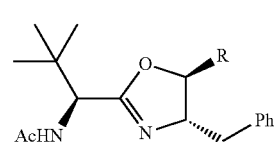
R= Me  L86
    Ph  L89
-continued
Screening the Ligand of Pd(II)-Catalyzed Arylation of Quaternary Amino Acid*,†
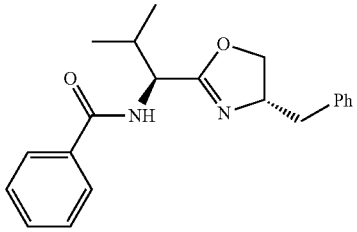 [SMILES: CC(C)[C@H](NC(=O)c1ccccc1)C1=N[C@@H](Cc2ccccc2)CO1] L65
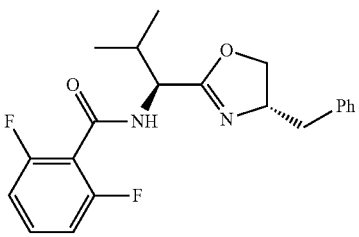 [SMILES: CC(C)[C@H](NC(=O)c1c(F)cccc1F)C1=N[C@@H](Cc2ccccc2)CO1] L95
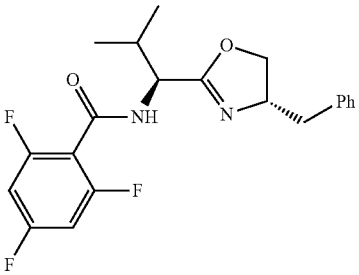 [SMILES: CC(C)[C@H](NC(=O)c1c(F)cc(F)cc1F)C1=N[C@@H](Cc2ccccc2)CO1] L96
L97
L98
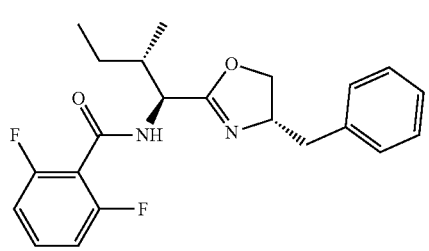 [SMILES: CC[C@H](C)[C@H](NC(=O)c1c(F)cccc1F)C1=N[C@@H](Cc2ccccc2)CO1]

Screening the Ligand of Pd(II)-Catalyzed Arylation of Quaternary Amino Acid*, †

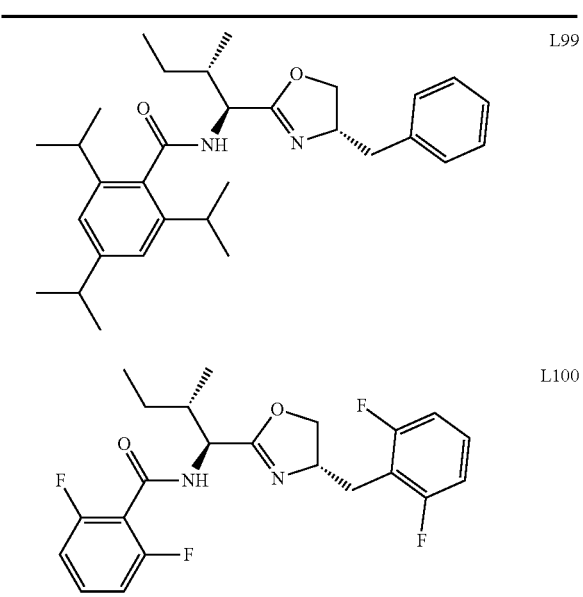

| entry | ligand | M (mol/L) | T (° C.) | yield (%) | 6b/6b' | er |
|---|---|---|---|---|---|---|
| 1 | L82 | 0.4 | 60 | 95 | 1.2/1 | 86/14 |
| 2 | L62 | 0.4 | 60 | 85 | 1.5/1 | 87/13 |
| 3 | L61 | 0.4 | 60 | 72 | 2.9/1 | 80/20 |
| 4 | L86 | 0.4 | 60 | 70 | 2.1/1 | 81/19 |
| 5 | L89 | 0.4 | 60 | 66 | 2.4/1 | 80/20 |
| 6 | L62 | 0.4 | 35 | 80 | 3.1/1 | 90/10 |
| 7 | L62 | 0.8 | 35 | 95 | 1.1/1 | 95/5 |
| 8 | L61 | 0.8 | 35 | 73 | 1.2/1 | 91/9 |
| 9 | L65 | 0.8 | 35 | NR | — | — |
| 10 | L95 | 0.8 | 35 | 94 | 1.3/1 | 95/5 |
| 11 | L96 | 0.8 | 35 | 95 | 1.3/1 | 94/6 |
| 12 | L97 | 0.8 | 35 | 60 | 3.3/1 | 86/14 |
| 13 | L98 | 0.8 | 35 | 95 | 2.5/1 | 96/4 |
| 14 | L99 | 0.8 | 35 | 45 | 4.2/1 | 79/21 |
| 15 | L100 | 0.8 | 35 | 98 (75)‡ | 3.3/1 | 96/4 |

*Conditions:
0.2 mmol of 5, 3.0 equiv. of p-Tol-I, 10 mol % of Pd (OAc)₂, 20 mol % of Ligand, 2.0 equiv. of AgOAc, 72 hours.
†The yield and the ratio of 6b/6b' were determined by ¹H NMR analysis of the crude product using CH₂Br₂ as the internal standard, enantiomeric ratios (er) were determined by chiral high-performance liquid chromatography.
‡The isolated yield of the mono product 6b.

General Procedure for the Pd(II)-Catalyzed Arylation of Quaternary Amino Acid

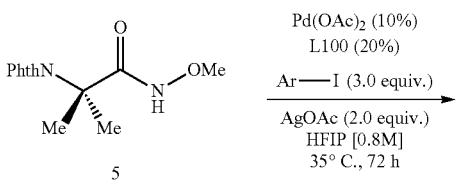

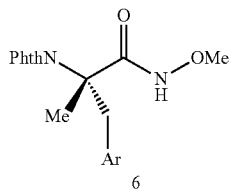

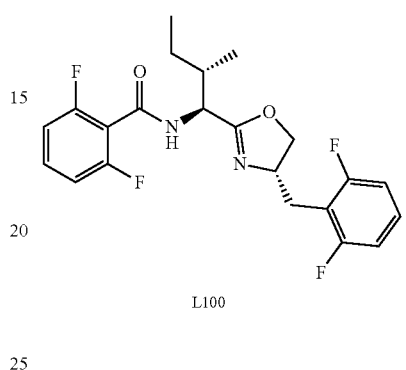

A reaction tube (10 mL) with magnetic stir bar was charged with 5 (0.2 mmol), aryl iodide (0.60 mmol), Pd(OAc)₂ (0.02 mmol, 4.5 mg), L100 (0.04 mmol, 16.9 mg), AgOAc (0.40 mmol, 66.8 mg). 1,1,1,3,3,3-Hexafluoro-2-propanol (0.25 mL) was added to the tube and the tube was sealed and heated to 35° C. for 72 hours. The crude reaction mixture was filtered through Celite® and washed with EtOAc. The solvents were removed under reduced pressure and the residue was purified by preparative TLC to afford the desired product.

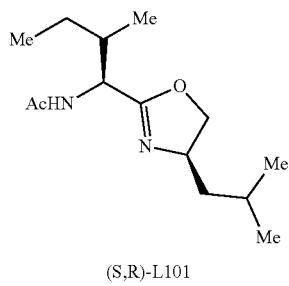 [SMILES: CCC(C)[C@H](NC(C)=O)C1=N[C@H](CC(C)C)CO1]

N-((1S,2S)-1-((R)-4-Isobutyl-4,5-dihydrooxazol-2-yl)-2-methylbutyl)acetamide [(S,R)-L101]

¹H NMR (600 MHz, CDCl₃) δ 6.22 (d, J=7.8 Hz, 1H), 4.66-4.63 (m, 1H), 4.38-4.35 (m, 1H), 4.14-4.09 (m, 1H), 3.86-3.84 (m, 1H), 2.02 (s, 3H), 1.89-1.82 (m, 1H), 1.76-1.69 (m, 1H), 1.60-1.56 (m, 1H), 1.53-1.47 (m, 1H), 1.29-1.24 (m, 1H), 1.20-1.13 (m, 1R), 0.95-0.92 (m, 9H), 0.90 (d, J=7.2 Hz, 3H); ¹³C NMR (150 MHz, CDCl₃) δ 169.4, 166.1, 73.4, 64.2, 51.6, 45.7, 38.2, 25.4, 25.2, 23.3, 22.9, 22.5, 14.9, 11.7; HRMS (ESI-TOF) Calcd for C₁₄H₂₇N₂O₂⁺ [M+H]⁺: 255.2067; found: 255.2068.

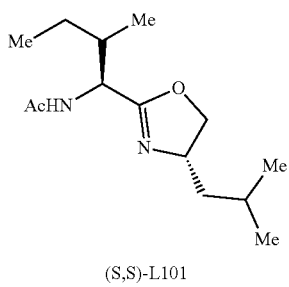 [SMILES: CCC(C)[C@H](NC(C)=O)C1=N[C@@H](CC(C)C)CO1]

(S,S)-L101

N-((1S,2S)-1-((S)-4-Isobutyl-4,5-dihydrooxazol-2-yl)-2-methylbutyl)acetamide [(S,S)-L101]

$^1$H NMR (600 MHz, CDCl$_3$) δ 6.66 (d, J=8.4 Hz, 1H), 4.68-4.65 (m, 1H), 4.33-4.30 (m, 1H), 4.10-4.04 (m, 1H), 3.85-3.83 (m, 1H), 1.97 (s, 3H), 1.86-1.78 (m, 1H), 1.70-1.63 (m, 1H), 1.57-1.52 (m, 1H), 1.47-1.40 (m, 1H), 1.28-1.23 (m, 1H), 1.16-1.08 (m, 1H), 0.92-0.83 (m, 12H); $^{13}$C NMR (150 MHz, CDCl$_3$) δ 169.6, 166.3, 73.3, 64.1, 51.7, 45.4, 38.0, 25.3, 25.0, 23.2, 22.8, 22.4, 15.1, 11.6; HRMS (ESI-TOF) Calcd for C$_{14}$H$_{27}$N$_2$O$_2^+$ [M+H]$^+$: 255.2067; found: 255.2066.

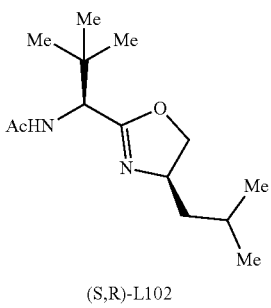 [SMILES: CC(=O)N[C@H](C1=N[C@H](CC(C)C)CO1)C(C)(C)C]

(S,R)-L102

N—((S)-1-((R)-4-Isobutyl-4,5-dihydrooxazol-2-yl)-2,2-dimethylpropyl)acetamide [(S,R)-L102]

$^1$H NMR (600 MHz, CDCl$_3$) δ 6.13 (d, J=9.6 Hz, 1H), 4.56-4.54 (m, 1H), 4.36-4.33 (m, 1H), 4.16-4.10 (m, 1H), 3.83-3.81 (m, 1H), 2.03 (s, 3H), 1.75-1.68 (m, 1H), 1.60-1.55 (m, 1H), 1.29-1.25 (m, 1H), 0.98 (s, 9H), 0.95 (d, J=6.6 Hz, 3H), 0.93 (d, J=6.6 Hz, 3H); $^{13}$C NMR (150 MHz, CDCl$_3$) δ 169.4, 166.0, 73.1, 64.3, 54.8, 45.8, 35.1, 26.4, 25.4, 23.4, 22.9, 22.5; HRMS (ESI-TOF) Calcd for C$_{14}$H$_{27}$N$_2$O$_2^+$ [M+H]$^+$: 255.2067; found: 255.2067.

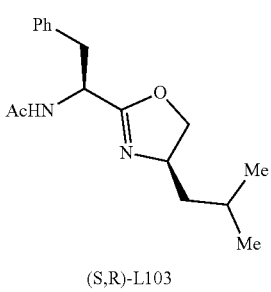 [SMILES: CC(=O)N[C@@H](Cc1ccccc1)C1=N[C@H](CC(C)C)CO1]

(S,R)-L103

N—((S)-1-((R)-4-Isobutyl-4,5-dihydrooxazol-2-yl)-2-phenylethyl)acetamide [(S,R)-L103]

$^1$H NMR (600 MHz, CDCl$_3$) δ 7.28-7.25 (m, 2H), 7.25-7.21 (m, 1H), 7.11-7.08 (m, 2H), 6.17 (d, J=7.2 Hz, 1H), 4.93-4.90 (m, 1H), 4.40-4.37 (m, 1H), 4.08-4.03 (m, 1H), 3.87-3.84 (m, 1H), 3.18 (dd, J$_1$=13.8 Hz, J$_2$=6.0 Hz, 1H), 3.07 (dd, J$_1$=13.8 Hz, J$_2$=4.8 Hz, 0.1H), 2.00 (s, 3H), 1.64-1.57 (m, 1H), 1.38-1.34 (m, 1H), 1.14-1.09 (m, 1H), 0.89 (d, J=6.6 Hz, 3H), 0.85 (d, J=6.6 Hz, 3H); $^{13}$C NMR (150 MHz, CDCl$_3$) δ 169.3, 165.4, 136.0, 129.7, 128.2, 126.8, 73.8, 64.1, 48.3, 45.4, 37.8, 25.2, 23.2, 22.60, 22.58; HRMS (ESI-TOF) Calcd for C$_{17}$H$_{25}$N$_2$O$_2^+$ [M+H]$^+$: 289.1910; found: 289.1910.

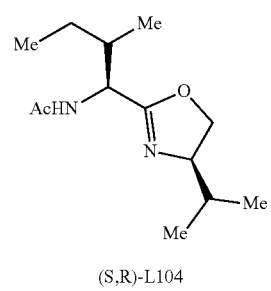 [SMILES: CCC(C)[C@H](NC(C)=O)C1=N[C@H](C(C)C)CO1]

(S,R)-L104

N-((1S,2S)-1-((R)-4-Isopropyl-4,5-dihydrooxazol-2-yl)-2-methylbutyl)acetamide [(S,R)-L104]

$^1$H NMR (600 MHz, CDCl$_3$) δ 6.18 (d, J=8.4 Hz, 1H), 4.65-4.63 (m, 1H), 4.28 (dd, J$_1$=9.6 Hz, J$_2$=8.4 Hz, 1H), 3.99-3.96 (m, 1H), 3.93-3.89 (m, 1H), 2.02 (s, 3H), 1.88-1.82 (m, 1H), 1.78-1.73 (m, 1H), 1.55-1.49 (m, 1H), 1.20-1.13 (m, 1H), 0.96 (d, J=7.2 Hz, 3H), 0.94-0.88 (m, 9H); $^{13}$C NMR (150 MHz, CDCl$_3$) δ 169.3, 166.1, 71.7, 70.3, 51.7, 38.2, 32.4, 25.3, 23.4, 18.9, 18.1, 15.0, 11.7; HRMS (ESI-TOF) Calcd for C$_{13}$H$_{25}$N$_2$O$_2^+$ [M+H]$^+$: 241.1911; found: 241.1911.

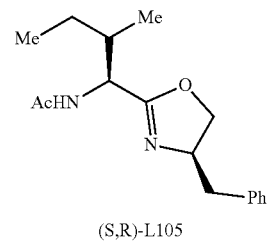 [SMILES: CCC(C)[C@H](NC(C)=O)C1=N[C@H](Cc2ccccc2)CO1]

(S,R)-L105

N-((1S,2S)-1-((R)-4-Benzyl-4,5-dihydrooxazol-2-yl)-2-methylbutyl)acetamide [(S,R)-L105]

$^1$H NMR (600 MHz, CDCl$_3$) δ 7.32-7.29 (m, 2H), 7.24-7.22 (m, 1H), 7.20-7.17 (m, 2H), 6.15 (d, J=8.4 Hz, 1H), 4.67-4.65 (m, 1H), 4.42-4.37 (m, 1H), 4.25-4.22 (m, 1H), 4.02-3.99 (m, 1H), 3.09 (dd, J$_1$=13.8 Hz, J$_2$=4.8 Hz, 1H), 2.65 (dd, J$_1$=13.8 Hz, J$_2$=9.0 Hz, 1H), 2.02 (s, 3H), 1.87-1.81 (m, 1H), 1.51-1.44 (m, 1H), 1.19-1.11 (m, 1H), 0.92 (t, J=7.5 Hz, 3H), 0.89 (d, J=7.2 Hz, 3H); $^{13}$C NMR (150 MHz, CDCl$_3$) δ 169.4, 166.9, 137.5, 129.2, 128.5, 126.6, 72.2, 66.8, 51.6, 41.7, 38.2, 25.1, 23.3, 15.0, 11.7; HRMS (ESI-TOF) Calcd for C$_{17}$H$_{25}$N$_2$O$_2^+$ [M+H]$^+$: 289.1910; found: 289.1911.

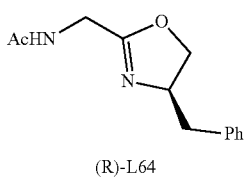 [SMILES: CC(=O)NCC1=N[C@H](Cc2ccccc2)CO1]

(R)-L64

(R)—N-((4-Benzyl-4,5-dihydrooxazol-2-yl)methyl)-acetamide [(R)-L64]

$^1$H NMR (600 MHz, CDCl$_3$) δ 7.32-7.30 (m, 2H), 7.25-7.22 (m, 1H), 7.20-7.18 (m, 2H), 6.39 (br s, 1H), 4.43-4.37 (m, 1H), 4.27 (t, J=9.0 Hz, 1H), 4.06-4.01 (m, 3H), 3.07 (dd, J$_1$=13.8 Hz, J$_2$=6.0 Hz, 1H), 2.68 (dd, J$_1$=13.8 Hz, J$_2$=8.1 Hz, 1H), 2.03 (s, 3H); $^{13}$C NMR (150 MHz, CDCl$_3$) δ 170.1, 164.7, 137.4, 129.1, 128.5, 126.6, 72.6, 66.8, 41.5, 37.0, 22.9; HRMS (ESI-TOF) Calcd for C$_{13}$H$_{17}$N$_2$O$_2^+$ [M+H]J: 233.1285; found: 233.1285.

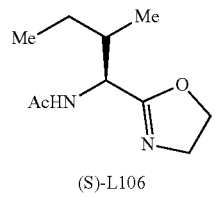

(S)-L106

N-((1S,2S)-1-(4,5-Dihydrooxazol-2-yl)-2-methylbutyl)-acetamide [(S)-L106]

$^1$H NMR (600 MHz, CDCl$_3$) δ 6.43 (d, J=8.4 Hz, 1H), 4.73-4.69 (m, 1H), 4.35-4.27 (m, 2H), 3.86-3.82 (m, 2H), 2.01 (s, 3H), 1.90-1.83 (m, 1H), 1.52-1.45 (m, 1H), 1.20-1.13 (m, 1H), 0.94-0.90 (m, 6H); $^{13}$C NMR (150 MHz, CDCl$_3$) δ 169.6, 167.8, 68.0, 53.6, 51.7, 38.1, 25.1, 23.2, 15.2, 11.7; HRMS (ESI-TOF) Calcd for C$_{10}$H$_{19}$N$_2$O$_2^+$ [M+H]$^+$: 199.1441; found: 199.1441.

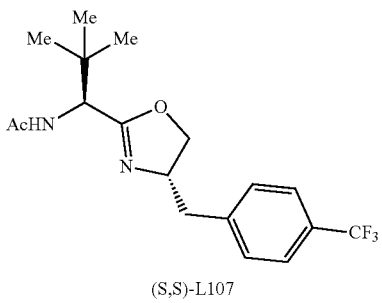 [SMILES: CC(=O)N[C@H](C1=N[C@@H](Cc2ccc(C(F)(F)F)cc2)CO1)C(C)(C)C]

(S,S)-L107

N—((S)-2,2-Dimethyl-1-((S)-4-(4-(trifluoromethyl)-benzyl)-4,5-dihydrooxazol-2-yl)propyl)acetamide [(S,S)-L107]

$^1$H NMR (600 MHz, CDCl$_3$) δ 7.56-7.55 (m, 2H), 7.32-7.30 (m, 2H), 6.03 (d, J=9.6 Hz, 1H), 4.56 (d, J=9.6 Hz, 1H), 4.40-4.34 (m, 1H), 4.23-4.20 (m, 1H), 4.00 (dd, J$_1$=9.0 Hz, J$_2$=7.2 Hz, 1H), 3.04 (dd, J$_1$=13.8 Hz, J$_2$=6.0 Hz, 1H), 2.74 (dd, J$_1$=13.8 Hz, J$_2$=7.8 Hz, 1H), 2.05 (s, 3H), 0.97 (s, 9H); $^{13}$C NMR (150 MHz, CDCl$_3$) δ 169.4, 166.9, 141.9, 129.5, 129.0 (q, J$_{FC}$=32.2 Hz), 125.4 (q, J$_{FC}$=3.6 Hz), 124.2 (q, J$_{FC}$=270.2 Hz), 71.7, 66.6, 55.2, 41.6, 34.9, 26.5, 23.4; HRMS (ESI-TOF) Calcd for C$_{17}$H$_{25}$N$_2$O$_2^+$ [M+H]$^+$: 357.1784; found: 357.1787.

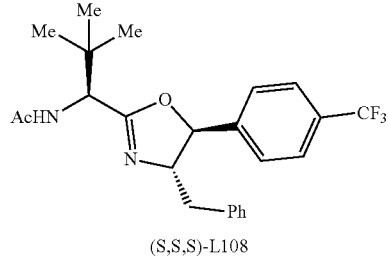 [SMILES: CC(=O)N[C@H](C1=N[C@@H](Cc2ccccc2)[C@H](c2ccc(C(F)(F)F)cc2)O1)C(C)(C)C]

(S,S,S)-L108

N—((S)-1-((4S,5S)-4-Benzyl-5-(4-(trifluoromethyl)-phenyl)-4,5-dihydrooxazol-2-yl)-2,2-dimethylpropyl)-acetamide [(S,S)-L108]

$^1$H NMR (600 MHz, CDCl$_3$) δ 7.49 (d, J=7.8 Hz, 2H), 7.31-7.29 (m, 2H), 7.26-7.24 (m, 1H), 7.20-7.18 (m, 2H), 6.97 (d, J=7.8 Hz, 2H), 6.17 (br s, 1H), 5.17 (d, J=7.2 Hz, 1H), 4.70 (d, J=9.6 Hz, 1H), 4.28-4.25 (m, 1H), 3.26 (dd, J$_1$=13.8 Hz, J$_2$=5.4 Hz, 1H), 2.76 (dd, J$_1$=13.8 Hz, J$_2$=9.0 Hz, 1H), 2.08 (s, 3H), 1.05 (s, 9H); $^{13}$C NMR (150 MHz, CDCl$_3$) δ 169.5, 165.4, 144.1, 136.6, 130.2 (q, J$_{FC}$=32.0 Hz), 129.5, 128.6, 126.9, 125.7, 125.5 (q, J$_{FC}$=3.5 Hz), 123.8 (q, J$_{FC}$=270.5 Hz), 84.7, 75.9, 55.4, 42.0, 34.9, 26.7, 23.3;

HRMS (ESI-TOF) Calcd for C$_{24}$H$_{28}$F$_3$N$_2$O$_2^+$ [M+H]$^+$: 433.2097; found: 433.2098.

Each of the patents, patent applications and articles cited herein is incorporated by reference.

The foregoing description and the examples are intended as illustrative and are not to be taken as limiting. Still other variations within the spirit and scope of this invention are possible and will readily present themselves to those skilled in the art.

The invention claimed is:

1. A method for carrying out a Pd(II)-catalyzed chiral insertion of an aryl or heteroaryl substituent at the β-carbon of a protected prochiral carboxylic acid substrate to provide an insertion product whose enantiomeric ratio is greater for one enantiomer than the other that comprises the steps of
a) heating a reaction mixture containing a solvent having dispersed or dissolved therein (i) a protected carboxylic acid substrate molecule of Formula I, (ii) an excess of an aromatic or

I $$R^c \underset{R^b}{\overset{R^a}{|}} CO-X$$

heteroaromatic iodide reactant relative to said substrate, (iii) a catalytic amount of a Pd(II) catalyst, (iv) a chiral acyl-protected ligand (L) of Formula A present in an amount of about 5 to about 20 mole percent based on the amount of protected carboxylic acid substrate molecule of Formula I, and (v) an excess of silver compound oxidant relative to said protected carboxylic acid substrate at a temperature of about 70° to about 120° C. in a sealed pressure vessel; and b) maintaining said reaction mixture for a time and at a temperature sufficient to carry out said insertion and form an insertion product;

wherein in a compound of Formula I, i) $R^a$ is hydrido, a protected amino group (NPG), or a $C_1$-$C_6$ hydrocarbyl straight or branched chain substituent, and one or two of $R^b$ and $R^c$ is hydrido, and when other than hydrido, a $R^b$ and $R^c$ group is a $C_1$-$C_{13}$ hydrocarbyl straight or branched chain or cyclic aliphatic group; or a (methyl) $C_6$-$C_{10}$ aromatic or heteroaromatic group containing up to three heteroatoms that can each be nitrogen, or can be two nitrogens and an oxygen, and wherein the ring of a (methyl)$C_6$-$C_{10}$ aromatic or heteroaromatic group is unsubstituted or substituted with up to three substituents that are independently selected from one or more of the group consisting of halogen other than iodo, $C_1$-$C_6$ hydrocarbyl, $C_1$-$C_6$ hydrocarbyloxy, carboxy $C_1$-$C_6$ hydrocarbyl, trifluoromethyl, $C_1$-$C_6$ hydrocarboyl, $C_1$-$C_6$ hydrocarbyl carboxylate, nitro, $C_1$-$C_6$ hydrocarbylthiooxy, cyano and protected amino; and (ii) X of a molecule of Formula I is a $NHR^2$ group, in which $R^2$ is a perfluorinated p-tolyl group [4-($CF_3$)$C_6F_4$], OH, or —O—$C_1$-$C_{12}$ hydrocarbyl group so that X is NH[4-($CF_3$)$C_6F_4$], NOH or NH—O—$C_1$-$C_{12}$ hydrocarbyl group;

said aromatic or heteroaromatic iodide reactant is unsubstituted, or contains up to three substituents in addition to the iodo group, wherein the additional substituents are independently selected from one or more of the group consisting of halogen other than iodo, $C_1$-$C_6$ hydrocarbyl, $C_1$-$C_6$ hydrocarbyloxy, trifluoromethyl, trifluoromethoxy, $C_1$-$C_6$ hydrocarboyl, $C_1$-$C_6$ hydrocarbyl carboxylate, hydrocarbylthiooxy, nitro, cyano, methylene dioxy, $C_1$-$C_6$ vicinyl dioxy alkyl group, and $C_1$-$C_6$ hydrocarbyl di-$C_1$-$C_6$ alkyl phosphonate; and said protected ligand, L, is a compound of Formula A

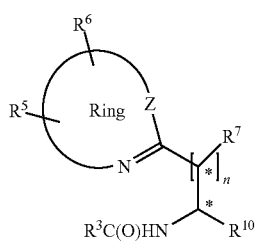

A wherein:
$R^3$ is a C1-C4 alkyl group or a fluoro-substituted benzoyl group;
the depicted cyclic moiety (Ring) on which $R^5$ and $R^6$ can be substituents is a cyclic ring structure containing one ring or two fused rings that each contains 5 or 6 atoms in the ring;
Z is oxygen (O) or CH when part of a double bond;
$R^5$ and $R^6$ are the same or different and are independently selected from the group consisting of a hydrido, halogen other than iodo, straight chain, branched chain and cyclic $C_1$-$C_7$ hydrocarbyl, $C_1$-$C_7$ hydrocarbyloxy, carboxy $C_1$-$C_6$ hydrocarbyl, trifluoromethyl, $C_1$-$C_6$ hydrocarboyl, nitro, $C_1$-$C_6$ hydrocarbylthiooxy, and a cyano group, or a benzyl group whose ring is substituted by 1 through five fluoro groups;

$R^7$ is a straight chain, branched chain or cyclic $C_1$-$C_6$ hydrocarbyl group, or a $C_1$-$C_6$ hydrocarbyloxy group;

"n" is zero or one, such that when n is zero, the carbon atom bearing $R^7$ and $R^7$ itself are absent, and the depicted Ring is bonded directly to the carbon atom bearing the $R^3C(O)HN$ group;

$R^{10}$ is a straight chain, branched chain or cyclic $C_1$-$C_7$ hydrocarbyl group, or a $C_1$-$C_7$ hydrocarbyloxy group that is unsubstituted, or $R^{10}$ is an optionally substituted cyclic $C_5$-$C_7$ hydrocarbyl group, or an optionally substituted $C_5$-$C_7$ hydrocarbyloxy group whose optional substituent is one or two groups, $R^8$ and $R^9$, that are the same or different and are independently selected from the group consisting of straight chain, branched chain and cyclic $C_1$-$C_7$ hydrocarbyl group, and a $C_1$-$C_7$ hydrocarbyloxy group; and an atom with an adjacent asterisk is chiral.

2. The method according to claim 1, wherein Z is CH that is part of a double bond.

3. The method according to claim 2, wherein n is one.

4. The method according to claim 3, wherein said Ring contains two fused rings that each contains 6 atoms.

5. The method according to claim 1, wherein Z is oxygen.

6. The method according to claim 5, wherein n is zero.

7. The method according to claim 6, wherein said Ring contains one ring that contains five ring atoms.

8. The method according to claim 1, $R^7$ is a straight chain $C_1$-$C_3$ hydrocarbyl group, or a $C_1$-$C_3$ hydrocarbyloxy group.

9. The method according to claim 1, wherein $R^{10}$ is phenyl, $R^8$ and $R^9$ are the same substituent, and are bonded a) in the 3- and 5-positions or b) in the 2- and 6-positions.

10. The method according to claim 9, wherein R7 and the phenyl ring containing $R^8$ and $R^9$ substituents are in a syn or anti relationship.

11. The method according to claim 1, including the further step of recovering said reaction product.

12. The method according to claim 1, wherein Z is CH that is part of a double bond.

13. The method according to claim 12, wherein n is one.

14. The method according to claim 12, wherein said Ring contains two fused rings that each contains 6 atoms.

15. The method according to claim 1, wherein Z is oxygen.

16. The method according to claim 15, wherein n is zero.

17. The method according to claim 16, wherein said Ring contains one ring that contains five ring atoms.

18. The method according to claim 1, $R^7$ is a straight chain $C_1$-$C_3$ hydrocarbyl group, or a $C_1$-$C_3$ hydrocarbyloxy group.

19. The method according to claim 1, wherein $R^{10}$ is phenyl, $R^8$ and $R^9$ are the same substituent, and are bonded a) in the 3- and 5-positions or b) in the 2- and 6-positions.

20. The method according to claim 1, wherein $R^7$ and the phenyl ring containing $R^8$ and $R^9$ substituents are in a syn or anti relationship.

21. The method according to claim 1, wherein n is one, Z is CH and said compound corresponds in structure to Formula A1 or A2

A-1

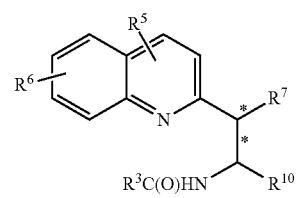

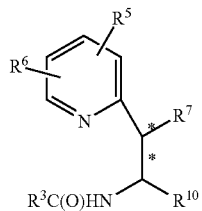

A-2

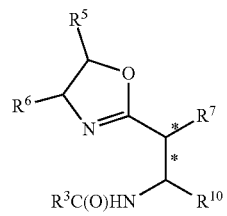

A-3

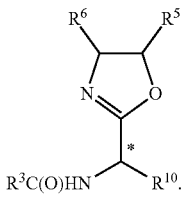

A-4

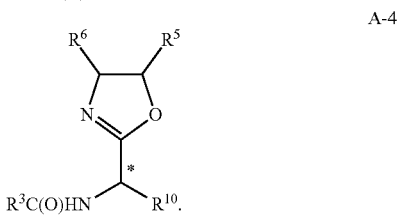

wherein *, $R^3$, $R^5$, $R^6$, $R^7$ and $R^{10}$ are as previously defined.

22. The method according to claim 21, wherein $R^{10}$ is phenyl, $R^8$ and $R^9$ are the same substituent, and are bonded a) in the 3- and 5-positions or b) in the 2- and 6-positions.

23. The method according to claim 22, wherein $R^7$ and the phenyl ring containing $R^8$ and $R^9$ substituents are in a syn or anti relationship.

24. The method according to claim 23, wherein $R^8$ and $R^9$ are t-butyl.

25. The method according to claim 24, wherein said compound corresponds in structure to Formula A-1.

26. The method according to claim 25, wherein one of $R^5$ and $R^6$ is hydrido.

27. The method according to claim 25, wherein $R^5$ and $R^6$ are both hydrido.

28. The method according to claim 25, wherein $R^3C(O)$ is acetyl.

29. The method according to claim 1, wherein n is one, Z is oxygen and said compound corresponds in structure to Formula A-3, or wherein n is zero, Z is oxygen and said compound corresponds in structure to Formula A-4, and *, $R^3$, $R^5$, $R^6$, $R^7$ and $R^{10}$ are as previously defined 30. The method according to claim 29, wherein one of $R^5$ and $R^6$ is hydrido.

31. The compound according to claim 29 that corresponds in structure to Formula A-4.

32. The method according to claim 31, wherein $R^3$ is $C_1$ (methyl) or a fluoro-substituted benzoyl group.

33. The method according to claim 31, wherein $R^5$ is hydrido.

34. The method according to claim 33, wherein $R^6$ is a benzyl group whose ring is substituted by 1 through five fluoro groups.

35. The method according to claim 31, wherein $R^{10}$ a straight chain or branched chain $C_1$-$C_6$ hydrocarbyl group.

* * * * *